(12) United States Patent
Wang et al.

(10) Patent No.: US 11,701,345 B2
(45) Date of Patent: Jul. 18, 2023

(54) CAR ACTIVATOR AGENTS FOR CYCLOPHOSPHAMIDE-BASED TREATMENTS OF CANCER

(71) Applicant: UNIVERSITY OF MARYLAND, BALTIMORE, Baltimore, MD (US)

(72) Inventors: Hongbing Wang, Ellicot City, MD (US); Fengtian Xue, Potomac, MD (US); Dongdong Liang, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/623,453

(22) PCT Filed: Jun. 19, 2018

(86) PCT No.: PCT/US2018/038265
§ 371 (c)(1),
(2) Date: Dec. 17, 2019

(87) PCT Pub. No.: WO2018/236856
PCT Pub. Date: Dec. 27, 2018

(65) Prior Publication Data
US 2020/0352915 A1 Nov. 12, 2020

Related U.S. Application Data

(60) Provisional application No. 62/588,965, filed on Nov. 21, 2017, provisional application No. 62/521,614, filed on Jun. 19, 2017.

(51) Int. Cl.
*A61K 31/429* (2006.01)
*A61P 35/00* (2006.01)
*A61K 31/424* (2006.01)
*A61K 31/475* (2006.01)
*A61K 31/519* (2006.01)
*A61K 31/573* (2006.01)
*A61K 31/704* (2006.01)
*C07D 487/04* (2006.01)
*C07D 498/04* (2006.01)
*C07D 513/04* (2006.01)

(52) U.S. Cl.
CPC .......... *A61K 31/429* (2013.01); *A61K 31/424* (2013.01); *A61K 31/475* (2013.01); *A61K 31/519* (2013.01); *A61K 31/573* (2013.01); *A61K 31/704* (2013.01); *A61P 35/00* (2018.01); *C07D 487/04* (2013.01); *C07D 498/04* (2013.01); *C07D 513/04* (2013.01)

(58) Field of Classification Search
CPC .. A61K 31/429; A61K 31/573; A61K 31/519; A61K 31/704; A61K 31/475; A61K 31/424; C07D 513/04; C07D 498/04; C07D 487/04; A61P 35/00

USPC ............................................... 514/34
See application file for complete search history.

(56) References Cited

U.S. PATENT DOCUMENTS

| | | | |
|---|---|---|---|
| 7,351,481 B2 | 4/2008 | Lee et al. | |
| 7,501,430 B2 | 3/2009 | Pierre et al. | |
| 7,790,741 B2 | 9/2010 | Calderwood et al. | |
| 2012/0010188 A1* | 1/2012 | Nilsson | A61P 1/00 514/210.18 |
| 2013/0059845 A1* | 3/2013 | Song | A61P 3/10 514/233.2 |
| 2017/0114056 A1 | 4/2017 | Mitchell et al. | |

OTHER PUBLICATIONS

Hedrich et al. Activation of the Constitutive Androstane Receptor Increases the Therapeutic Index of CHOP in Lymphoma Treatment. Mol Cancer Ther 2016;15:392-401. Published Online First Jan. 28, 2016. (Year: 2016).*
Maddry et al. Discovery of Novel Benzoquinazolinones and Thiazoloimidazoles, Inhibitors of Influenza H5N1 and H1N1 Viruses, from a Cell-Based High-Throughput Screen. Journal of Biomolecular Screening 16(1):73-81, 2011. (Year: 2011).*
Belyuga et al. Preparation of 6-aryl-5-(acylamino)imidazo[2,1-b]thiazoles and their 1,3,4-thiadiazole analogs on the basis of amidophenacylating reagents. Zhurnal Organichnoi ta Farmatsevtichnoi Khimii (2005), 3(4), 38-42 (4-page summary is deposited in STN) (Year: 2005).*
PUBCHEM-CID 4792020 Create Date: Sep. 17, 2005, pp. 1-11; p. 3.
Hedrich et al., "Activation of the Constitutive Androstane Receptor Increases the Therapeutic Index of CHOP in Lymphoma Treatment" Mol Cancer Ther; 15(3) Mar. 2016.
Wang et al. "The constitutive androstane receptor is a novel therapeutic target facilitating cyclophosphamide-based treatment of hematopoietic malignancies" Blood, 2013 121: 329-338.
International Search Report dated Sep. 6, 2018 (PCT International Application No. PCT/US2018/038265).

* cited by examiner

*Primary Examiner* — Yih-Horng Shiao
(74) *Attorney, Agent, or Firm* — Morgan, Lewis & Bockius LLP

(57) ABSTRACT

The invention relates to selective small molecule human constitutive androstane receptor (hCAR) activators of Formula (I) or (II), pharmaceutical compositions thereof, and use thereof for the treatment of hematologic malignancies and other cancers. The small molecule hCAR activator in combination with CPA based chemotherapy regimen provides a synergistic effect to help promote cytoxicity of the cyclophosphamide (CPA) based anticancer treatments including CHOP regimen (CPA, doxorubicin, vincristine, and prednisone) by preferential induction of CYP2B6 over CYP3A4 and promoting the formation of therapeutically active CPA metabolite 4-OH-CPA.

17 Claims, 30 Drawing Sheets
Specification includes a Sequence Listing.

DL5016

CITCO

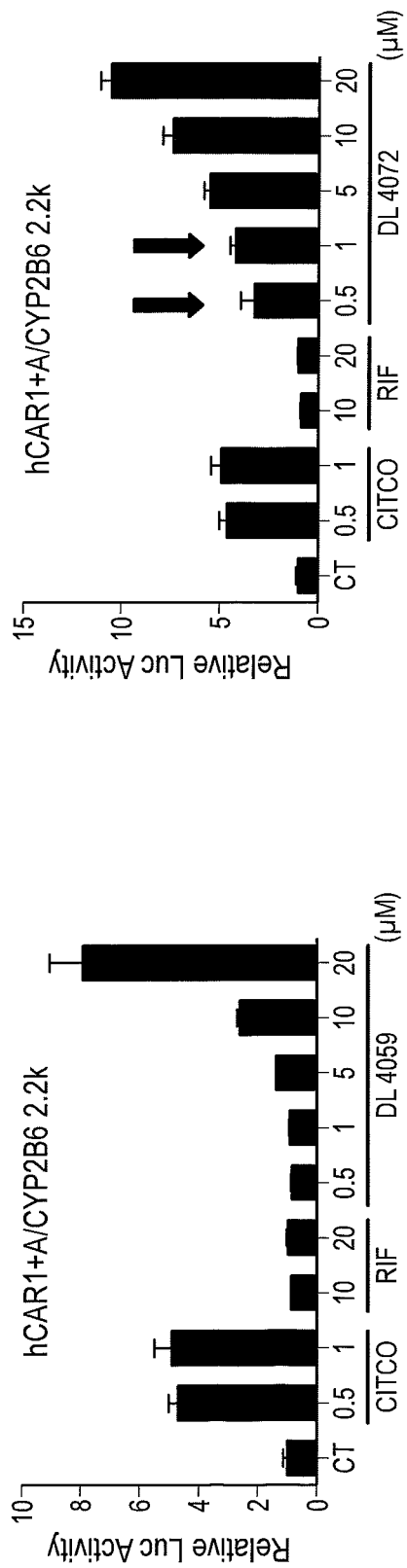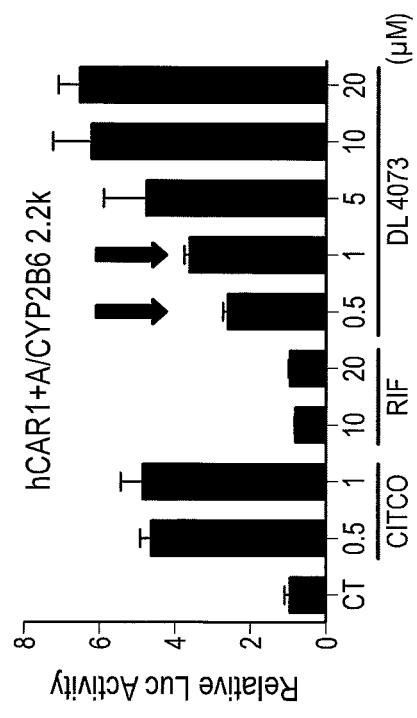
FIG. 3E
FIG. 3F
FIG. 3G

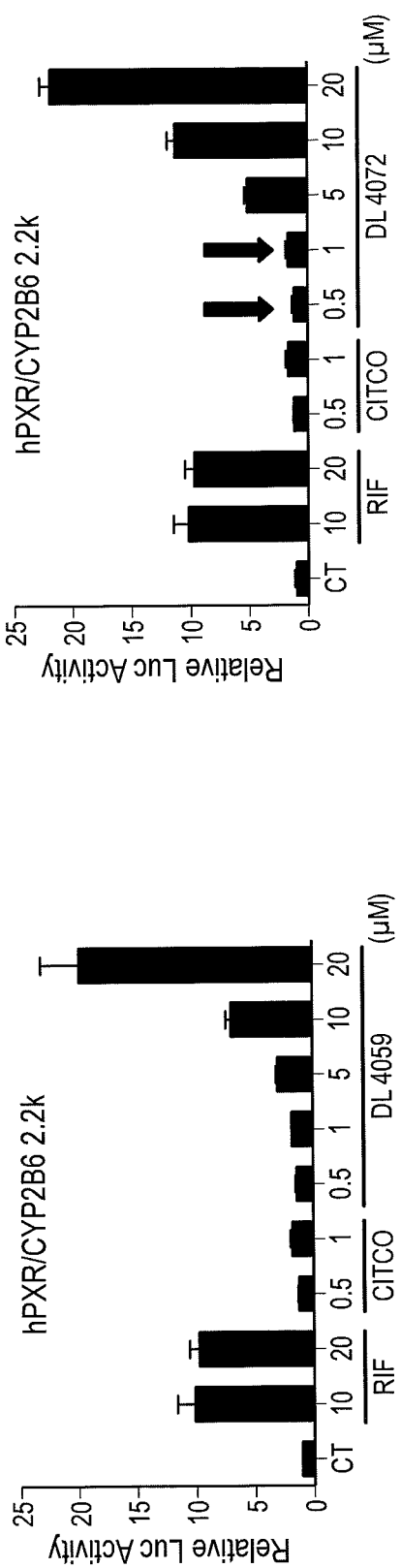
FIG. 3H
FIG. 3I
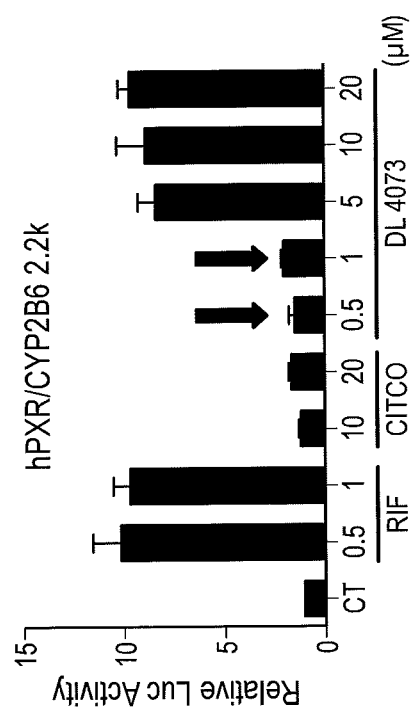
FIG. 3J

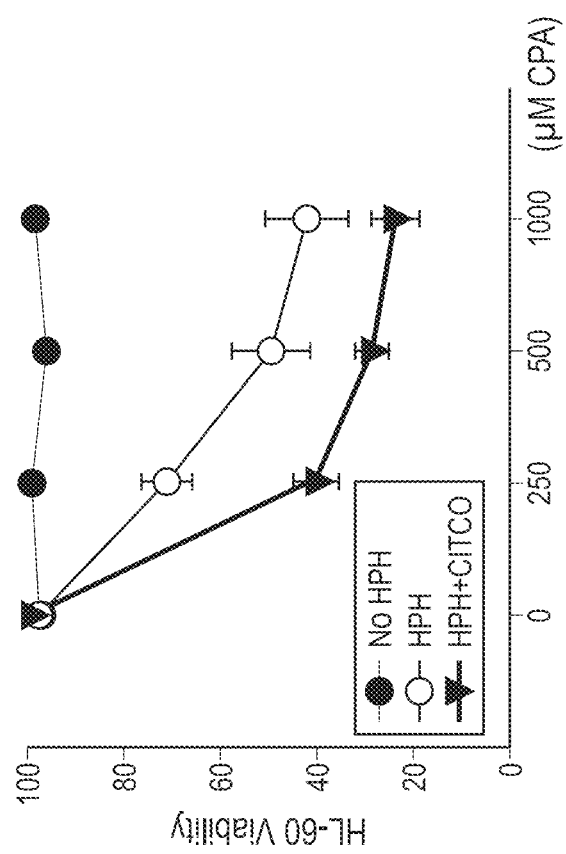

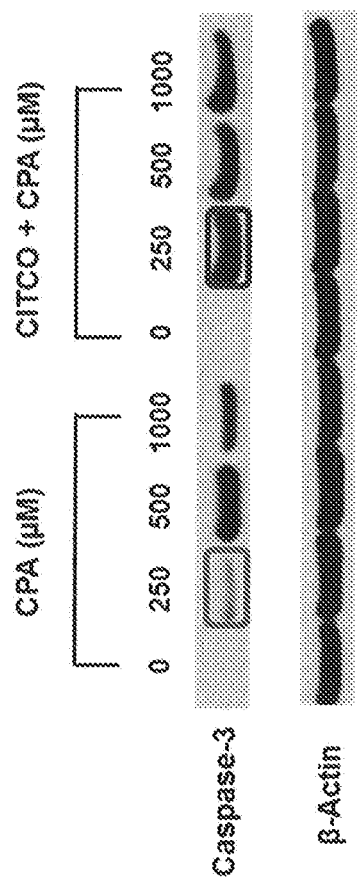
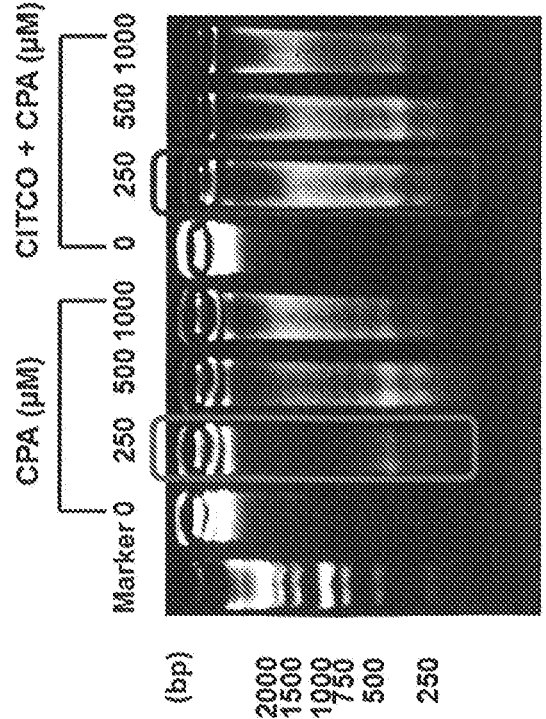
Figure 15A
Figure 15B

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer: CYP2B6

<400> SEQUENCE: 1
agacgccttc aatcctgacc                                             20

<210> SEQ ID NO 2
<211> LENGTH: 21
<212> TYPE: DNA
<213> ORGANISM: Artificial Sequence
<220> FEATURE:
<223> OTHER INFORMATION: Synthetic primer: CYP2B6

<400> SEQUENCE: 2
ccttcaccaa gacaaatccg c                                           21

<210> SEQ ID NO 3
<211> LENGTH: 21
<212> TYPE: DNA
<213> ORGANISM: Artificial Sequence
<220> FEATURE:
<223> OTHER INFORMATION: Synthetic primer: CYP3A4

<400> SEQUENCE: 3
gtggggcttt tatgatggtc a                                           21
```

```
<210> SEQ ID NO 4
<211> LENGTH: 23
<212> TYPE: DNA
<213> ORGANISM: Artificial Sequence
<220> FEATURE:
<223> OTHER INFORMATION: Synthetic primer: CYP3A4

<400> SEQUENCE: 4
gcgtcagatt tctcaccaac aca                                           23
```

CAR ACTIVATOR AGENTS FOR CYCLOPHOSPHAMIDE-BASED TREATMENTS OF CANCER

CROSS-REFERENCE TO RELATED APPLICATIONS

This application is a U.S. National Phase Application under 35 U.S.C. § 371 of International Application PCT/US18/38265, filed Jun. 19, 2018, which claims the benefit of U.S. Provisional Patent Applications Nos. 62/521,614, filed Jun. 19, 2017, and 62/588,965, filed Nov. 21, 2017, each of which is incorporated by reference herein in its entirety.

STATEMENT OF GOVERNMENT SUPPORT

This invention was made with government support under Grant No. GM107058 awarded by the National Institutes of Health. The Government has certain rights in the invention.

FIELD OF THE INVENTION

The invention relates generally to the field of medicine, cancer biology, and in particular novel compounds/agents which can enhance the therapeutic efficacy of cyclophosphamide-based chemotherapy, pharmaceutical compositions comprising such novel compounds/agents, and methods of making and use thereof.

BACKGROUND OF THE INVENTION

Cyclophosphamide (CPA), an alkylating prodrug, has been used extensively in the treatment of various types of cancers. CPA is a mainstay of numerous drug combinations, including the CHOP regimen (CPA, doxorubicin, vincristine, and prednisone), which is the first-line chemotherapy for non-Hodgkin's lymphoma and a number of other hematologic malignancies. To date, CPA continues to be used as an important component in the front-line regiments for a number of cancers such as breast cancer, non-Hodgkin lymphoma, and chronic lymphocytic leukemia. Unfortunately, a significant number of patients remain uncured due to development of drug resistance and/or intolerable toxicities. There is a need for further optimization of current treatment regimens.

SUMMARY OF THE INVENTION

In one embodiment, the disclosure provides a compound of Formula (II), or a pharmaceutically acceptable salt, solvate, hydrate, cocrystal, or prodrug thereof:

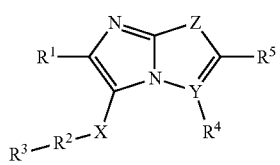

Formula (II)

wherein in Formula (II): Z is O, S, or N; Y is C, N, or —CH═CH—, with the proviso that when Y is N, $R^4$ is null, and when Y is C, $R^4$ is H or $C_{1-6}$-alkyl; $R^1$ is linear or branched $C_{1-6}$-alkyl, substituted or non-substituted aryl, or substituted or non-substituted heteroaryl, wherein the substituted aryl or heteroaryl group is optionally substituted with one or more substituents selected from hydrogen, linear or branched $C_{1-6}$-alkyl, $C_{2-6}$-alkenyl, $C_{2-6}$-alkynyl, $C_{3-8}$-cycloalkyl, $C_{3-8}$-heterocycloalkyl, aryl, arylalkyl, heteroaryl, heteroarylalkyl, hydroxy, halogen, cyano, trifluoromethyl, trifluoromethoxy, nitro, trimethylsilanyl, —$OR^a$, $SO_nR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$; X is a linker moiety selected from the group consisting of —$(CR^6R^7)_m$—O—, —C(O)—$R^8$—, —$CH_2$—NH—C(O)—, —CH═N—, —CH═N—O—, —$R^{10}$—NH—, —$R^{10}$—$NR^{11}$—, and —NH—C(O)—; $R^2$ is selected from a group consisting of a bond, —C(O)—, $C_{1-6}$-alkenyl, and $C_{3-8}$-heterocycloalkylamine; $R^3$ is selected from the group consisting of aryl, heteroaryl, $C_{3-8}$-cycloalkyl substituted with one or more substituents selected from substituted or non-substituted aryl, substituted or non-substituted heteroaryl, and $C_{3-8}$-heterocycloalkyl group substituted with one or more substituents selected from substituted or non-substituted aryl, substituted or non-substituted heteroaryl, wherein the substituent of the substituted aryl or heteroaryl is selected from hydroxy, halo, cyano, trifluoromethyl, trifluoromethoxy, nitro, trimethylsilanyl, —$OR^a$, —$SR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$; $R^5$ is selected from the group consisting of hydrogen, halogen, $C_{1-6}$-alkyl, —$C(O)R^a$, —$C(O)OR^a$, and —$C(O)N(R^a)R^b$; $R^6$ and $R^7$ are each independently selected from the group consisting of hydrogen, fluoro, and $C_{1-3}$-alkyl; $R^8$ is a bond, $C_{1-3}$-alkenyl, O, —NH—, —NH—O—; $R^{10}$ and $R^{11}$ are each independently substituted or non-substituted $C_{1-3}$-alkyl or $C_{1-3}$-alkenyl; $R^a$ and $R^b$ are each independently selected from the group consisting of hydrogen, alkyl, fluoroalkyl, cycloalkyl, carbocyclyl, carbocyclylalkyl, aryl, aralkyl, heterocycloalkyl, heterocycloalkylalkyl, heteroaryl, heteroarylalkyl, halogen, —O-alkyl, —O-aryl, cyano, nitro, —OH, —$NH_2$, —NH-alkyl, and —NH-aryl; m is an integer from 1-3; n is 0, 1 or 2; and t is 1 or 2. In one embodiment, Z is O, Y is C, and $R^4$ is H. In one embodiment, Z is S, Y is C, and $R^4$ is H. In one embodiment, X is —CH═N—, —CH═N—O—, —$CH_2$—NH—, —$CH_2$—O—, —C(O)—, —C(O)—NH—, or —NH—C(O)—.

In one embodiment, $R^1$ is selected from the group consisting of:

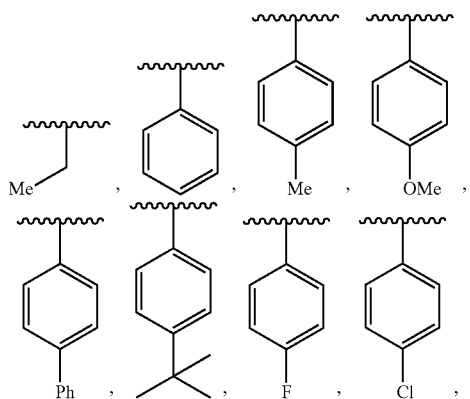

In one embodiment, —R²-R³ is selected from the group consisting of:
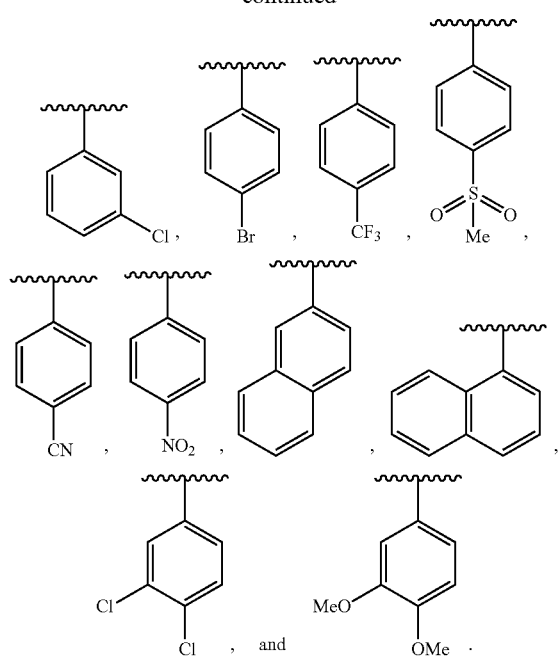

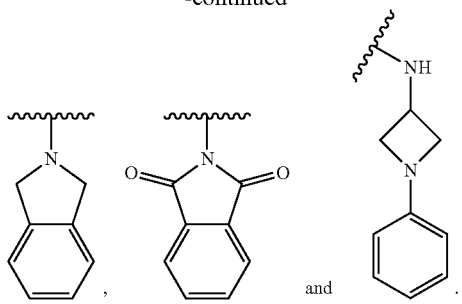

In one embodiment, the disclosure provides compounds as described in Table 1, selected from the group consisting of DL5016, DL5024, DL5012, DL4181, DL4073, DL5016L, DL5016M, DL5016N, DL5016O, DL5016P, DL5016Q, DL5016R, DL5043, DL5054, DL5098-3, DL5096-3, DL5096-2, DL5081, DL5090, DL5098-4, DL5096-1, DL5098-2, DL5098-1, DL4059, DL5043, DL4072, D4073, DL4082, DL4094, DL4095, DL4100, DL4102, DL4103, DL4104, DL4113, DL4173, DL4170, DL4153, DL4175, DL4179, DL5002, DL5026, DL4107, DL5028, DL4171, DL4143, DL5020, DL4129, DL4130, DL4132, DL4133, DL4141, YY1008, DL4142, YY1017, DL5058, DL5067, DL5045, DL5064, DL5061, DL5063, DL5068, DL5069, DL5059, DL5060, DL6065, DL5044, DL5066, DL5009, DL5013, DL5071, DL4073, DL4108, D5039, DL4181, YY1045, DL4167, DL5016D, YY1036, DL6077, DL5001, DL4097, DL5174, DL5166, DL6018, DL6037, DL6016, DL6037, DL6017, DL6030, DL6072, DL6068, DL6070, DL6061, DL6056, DL6071, DL6038, DL5014, DL5065, DL5096-4, DL5016A, DL5016B, DL5016C, DL5016D, DL5161, DL5016E, DL5055A, DL5055B, DL5055C, DL5113, DL5121, DL5118, 6000, 6001, 6002, 6003, DL4120, DL4177, and DL5055.

In one embodiment, the disclosure provides a pharmaceutical composition including a compound as described herein, or a pharmaceutically acceptable salt, solvate, hydrate, cocrystal, or prodrug thereof, and a physiologically compatible carrier medium.

In one embodiment, the disclosure provides a method of treating a disease alleviated by activating hCAR in a patient in need thereof, the method including administering to the patient a therapeutically effective amount of a compound as described herein, or a pharmaceutically acceptable salt, solvate, hydrate, cocrystal, or prodrug thereof.

In one embodiment, the disclosure provides a method of treating a disease alleviated by selective induction of CYP2B6 in a patient in need thereof, the method including administering to the patient a therapeutically effective amount of a compound as described herein, or a pharmaceutically acceptable salt, solvate, hydrate, cocrystal, or prodrug thereof.

In one embodiment, the disclosure provides a method of treating a disease alleviated by selective induction of CYP2B6 over CYP3A4 in a patient in need thereof, the method including administering to the patient a therapeutically effective amount of a compound as described herein, or a pharmaceutically acceptable salt, solvate, hydrate, cocrystal, or prodrug thereof.

In one embodiment, the disclosure provides a method of treating a disease alleviated by one or more of 1) activating hCAR in a patient in need thereof; 2) selective induction of CYP2B6 in a patient in need thereof; and/or 3) selective induction of CYP2B6 over CYP3A4 in a patient in need thereof, the method including a) administering to the patient a therapeutically effective amount of a compound as described herein, or a pharmaceutically acceptable salt, solvate, hydrate, cocrystal, or prodrug thereof; and b) administering to the patient a therapeutically effective amount of CPA, or a pharmaceutically acceptable salt, solvate, hydrate, cocrystal, or prodrug thereof. In one embodiment, CPA is administered as part of the CHOP regimen (CPA, doxorubicin, vincristine, and prednisone). In one embodiment, co-administration of a compound as described herein, or a pharmaceutically acceptable salt, solvate, hydrate, cocrystal, or prodrug thereof, and CPA, promotes the formation of therapeutically active CPA metabolite 4-OH-CPA.

In one embodiment, the disclosure provides methods of treatment as described herein, including administering one or more compounds as described herein, or pharmaceutically acceptable salts, solvates, hydrates, cocrystals, or prodrugs thereof, the compounds being administered in a dosage unit form. In one embodiment, the dosage unit form includes a physiologically compatible carrier medium.

In one embodiment, the disclosure provides methods of treating cancer, the methods including administering one or more compounds as described herein, or pharmaceutically acceptable salts, solvates, hydrates, cocrystals, or prodrugs thereof. In some embodiments, the cancer is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thymoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus induced cancer, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In one embodiment, the compounds of Formula (I) and/or (II), and a pharmaceutically acceptable salt, solvate, hydrate, or cocrystal thereof, can be used in an anticancer pharmaceutical composition. A preferred aspect of this disclosure is provided by combining a small molecule hCAR activator having formula (I) and salts thereof with a CPA based therapy regimen. The present invention features a pharmaceutical composition comprising a compound of the present invention. The present invention features a compound of the present invention for use as an active therapeutic substance. The present invention features a compound of the present invention for use in the treatment of hematological malignancy and other type cancers. The present invention features a compound of the present invention for use in the treatment of a number of cancers such as breast cancer, non-Hodgkin lymphoma, and chronic lymphocytic leukemia. The present invention features the use of a compound of the present invention in the manufacture of a medicament for use in the treatment of hematological malignancy and other type cancers. The present invention features the use of a compound of the present invention in the manufacture of a medicament for use in the treatment of a number of cancers such as breast cancer, non-Hodgkin lymphoma, and chronic lymphocytic leukemia. The present invention features a method for the treatment of hematological malignancy and other type cancers, comprising the administration of a compound of the present invention. The present invention features a method for the treatment of a number of cancers such as breast cancer, non-Hodgkin lymphoma, and chronic lymphocytic leukemia comprising the administration of a compound of the present invention.

BRIEF DESCRIPTION OF THE DRAWINGS

FIGS. 3E-3J. Compounds DL4072 and DL4073 activated hCAR but not hPXR at concentrations under 1 μm. DL4059 exhibited low activity for both hCAR and hPXR at the same concentrations.

FIGS. 5A-5B: induction of CYP2B6 and CYP3A4 mRNA analyzed with RT-PCR in HPHs from liver donors (HL #23, HL #24, and HL #35). FIG. 5C: representative immunoblots of CYP2B6 and CYP3A4 proteins in HPHs from liver donors (HL #23, and HL #24). RT-PCR data obtained from 3 independent experiments were expressed as mean±SD normalized against vehicle control.

FIGS. 6A-6B. Activation of CAR enhances CPA anticancer activity in the human primary hepatocyte-HL-60 cell coculture system. The anticancer activity of CPA was analyzed in a unique hepatocyte-cancer cell coculture model. FIG. 6A: illustration of the HPH-HL-60 coculture model and experimental scheme. FIG. 6B: effects of CAR activation on the concentration-dependent anticancer activity of CPA in HL-60 cell.

FIGS. 15A-15D. Activation of CAR promotes CPA-mediated apoptosis of HL-60 cells in the HPH-HL-60 coculture model. FIG. 15A: DNA extracted from treated cells was loaded on an agarose gel to illustrate CPA-induced DNA fragmentation. FIG. 15B: caspase 3 activity was analyzed with Western blotting to detect the large fragment (17/19 kDa) of activated caspase 3 in HL-60 cells. β-actin was used to normalize protein loading. FIGS. 15C-15D: effects of CAR activation on CPA-mediated membrane translocation of phosphatidylserine during apoptosis were analyzed using flow cytometry.

DETAILED DESCRIPTION OF THE INVENTION

Figure 1:
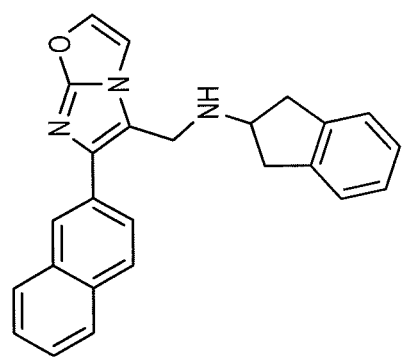
FIG. 1. Chemical structures for compounds CITCO and DL5016.
Figure 1:
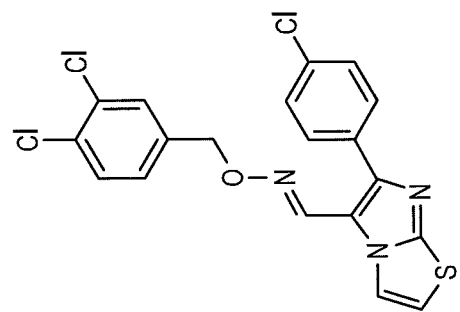

The CYP2B6 and CYP3A4 are two primary enzymes in the human cytochrome P450 super family responsible for xenobiotic metabolism. The CYP2B6 is responsible for the metabolic conversion of CPA, a prodrug, to the pharmacologically active 4-hydroxylcyclophosphamide (4-OH-CPA). On the other hand, CYP3A4 can convert CPA to its inactive metabolite N-dechloroethyl-CPA (N-DCE-CPA) and the toxic byproduct chloroacetaldehyde. The human constitutive androstane receptor (hCAR, NR113) and the pregnane X receptor (PXR, NR112) are key modulators governing the inductive expression of CYP2B6. The selective activation of hCAR over PXR preferentially induces the expression of hepatic CYP2B6 over CYP3A4 and increases the formation of 4-OH-CPA without concomitant increasing the non-therapeutic metabolites. The selective transcription of CYP2B6 over CYP3A4 by hCAR may have clinical relevance with respect to drugs that are predominantly metabolized by CYP2B6. The activators of hCAR may function as co-administrated facilitators for such biotransformation. CYP2B6 selectively upregulated by hCAR, provides an attractive approach for improving CPA-based therapeutics.

The process of enhancement of the anticancer activity is synergetic when the anticancer activity of the combination is in excess of the simple addition of the activity of the two separate substances. The hCAR activity induction component of the mixture is a synergist.

A New Chemical Entity (NCE), DL5016 that acts as a selective hCAR activator to facilitate CPA-based chemotherapy for hematologic malignancies was developed. CPA, a DNA-alkylating prodrug, is extensively used in the treatment of various solid cancers and hematologic malignancies. However, its harsh side effects contribute significantly to patient morbidity and mortality. DL5016 is a useful addition to CPA-containing regimens, as hCAR activation potentiates the benefits of CPA, without altering its side effect profile. CPA is a mainstay of numerous drug combinations, most importantly the CHOP (CPA, doxorubicin, vincristine, and prednisone) regimen, which is the first-line chemotherapy for non-Hodgkin's lymphoma and a number of other hematologic malignancies. Mechanistically, the CYP2B6 enzyme expressed in hepatocytes converts CPA to pharmacologically active 4-hydroxyl-CPA (4-OH-CPA). CYP2B6 is selectively upregulated by hCAR, providing an attractive approach for improving CPA-based therapeutics.

CPA-based chemotherapy continues to be the mainstay of many front-line chemotherapeutic regimens for the CI treatment of non-Hodgkin lymphoma, chronic lymphocytic leukemia, triple negative breast cancers, and other solid tumors. As a prodrug, CPA relies heavily on hepatic CYP2B6-mediated bioactivation to generate the active alkylating moiety before exhibiting chemotherapeutic effects. Alternatively, CYP3A4 can convert CPA to its inactive metabolite N-dechloroethyl-CPA (N-DCE-CPA) and the toxic byproduct chloroacetaldehyde. It is shown that activation of hCAR preferentially induces the expression of CYP2B6 in the liver, without concurrent augmentation of its nontherapeutic metabolites.

Definitions

As used in the preceding sections and throughout the rest of this specification, unless defined otherwise, all technical and scientific terms used herein have the same meaning as is commonly understood by one of skill in the art to which this invention belongs. All patents and publications referred to herein are incorporated by reference in their entireties.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —$N(R^a)$C(O)O$R^a$, —$N(R^a)$C(O)$R^a$, —$N(R^a)$C(O)N($R^a$)$_2$, $N(R^a)$C(N-$R^a$)N($R^a$)$_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or PO$_3$($R^a$)$_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —$N(R^a)$C(O)O$R^a$, —$N(R^a)$C(O)$R^a$, —$N(R^a)$C(O)N($R^a$)$_2$, $N(R^a)$C(N$R^a$)N($R^a$)$_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., ($C_{2-10}$)alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a ($C_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]

pyridazinyl, thiazolyl, thiadiazolyl, thiapyranyl, triazolyl, tetrazolyl, triazinyl, thieno[2,3-d]pyrimidinyl, thieno[3,2-d] pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

The terms "substituted" or "optionally substituted" refer to chemical moieties, wherein one or more hydrogen atoms may be replaced by a halogen atom, a $NH_2$, SH, $NO_2$ or OH group, or by an alkyl, alkenyl, alkanoyl, heteroalkyl, aryl, heteroaryl, cycloalkyl or heterocycle group as defined herein. The last-mentioned groups may be optionally substituted.

In some embodiments, compound (E)-6-(4-chlorophenyl)imidazo[2,1-b]thiazole-5-carbaldehyde O-(3,4-dichlorobenzyl) oxime (CITCO) (FIG. 1) is excluded from the compounds of Formula (I) or (II).

The terms "subject" and "patient" are used interchangeably herein to refer to a warm blooded animal such as a mammal, preferably a human, or a human child, which is afflicted with, or has the potential to be afflicted with one or more diseases and/or conditions described herein.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

As used herein, the terms "treat," "treatment," and/or "treating" may refer to the management of a disease, disorder, or pathological condition, or symptom thereof with the intent to cure, ameliorate, stabilize, prevent, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "combination" or "pharmaceutical combination" refers to the combined administration of the anticancer agents. Combinations of the disclosure include a CYP2B6 activator, e.g., a compound of Formula (I) and at least one anti-cancer agent cyclophosphamide (CPA, an alkylating prodrug) based chemotherapy regimen, e.g. CHOP regimen (CPA, doxorubicin, vincristine, and prednisone); which anti-cancer agents may be administered to a subject in need thereof, e.g., concurrently or sequentially.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, ALL, CLL, SLL, acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "synergistic," or "synergistic effect" or "synergism" as used herein, generally refers to an effect such that the one or more effects of the combination of compositions is greater than the one or more effects of each component alone, or they can be greater than the sum of the one or more effects of each component alone. The synergistic effect can be greater than about 10%, 20%, 30%, 40%, 50%, 60%, 75%, 100%, 110%, 120%, 150%, 200%, 250%, 350%, or 500% or more than the effect on a subject with one of the components alone, or the additive effects of each of the components when administered individually. The effect can be any of the measurable effects described herein. Advantageously, such synergy between the agents when combined, may allow for the use of smaller doses of one or both agents, may provide greater efficacy at the same doses, and may prevent or delay the build-up of multi-drug resistance and/or toxicity. The combination index (CI) method of Chou and Talalay may be used to determine the synergy, additive or antagonism effect of the agents used in combination. When the CI value is less than 1, there is synergy between the compounds used in the combination; when the CI value is equal to 1, there is an additive effect between the compounds used in the combination and when CI value is more than 1, there is an antagonistic effect. The synergistic effect may be attained by co-formulating the agents of the pharmaceutical combination. The synergistic effect may be attained by administering two or more agents as separate formulations administered simultaneously or sequentially.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof "crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Pharmaceutically acceptable" refers to those compounds, materials, compositions, and/or dosage forms which are, within the scope of sound medical judgment, suitable for contact with the tissues of human beings and non-human animals without excessive toxicity, irritation, allergic response, or other adverse complications commensurate with a reasonable benefit/risk ratio.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic compounds such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included within the scope of this invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvates can be from the solvent of crystallization, inherent in the solvent of preparation or crystallization, or adventitious to such solvent. Such solvates are also within the scope of the present invention.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

All other terms used in the description of the present invention have their art recognized meanings.

As will be apparent to anyone skilled in the art, the compounds of the present invention may have one or more chiral centers, and in that case, exist in various stereoisomeric forms. The compounds of the present invention encompass all such optical isomers, diastereomers and enantiomers. The compounds are normally prepared as a racemic mixture or racemate and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms from a mixture of enantiomers. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. Stereochemistry of Organic Compounds; Wiley: New York, 1994, and Jacques, J, et al. Enantiomers, Racemates, and Resolutions; Wiley: New York, 1981, each incorporated by reference herein in their entireties.

"Solvate" refers to a compound in physical association with one or more molecules of a pharmaceutically acceptable solvent.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization.

A specific example of phenol-keto tautomerization is the interconversion of pyridin-4-ol and pyridin-4(1H)-one tautomers.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Novel Selective Small Molecule hCAR Activators

In one aspect, the disclosure relates to a compound of Formula (I):

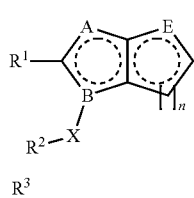

Formula (I)

wherein in Formula (I):

A is C or N;
B is C or N;
E is C, O, S or N;

$R^1$ is linear or branched $C_{1-6}$-alkyl, substituted or non-substituted aryl, or substituted or non-substituted heteroaryl, wherein the substituted aryl or heteroaryl group is optionally substituted with one or more substituents including hydrogen, linear or branched $C_{1-6}$-alkyl, $C_{2-6}$-alkenyl, $C_{2-6}$-alkynyl, $C_{3-8}$-cycloalkyl, $C_{3-8}$-heterocycloalkyl, aryl, arylalkyl, heteroaryl, heteroarylalkyl, hydroxy, halogen, cyano, trifluoromethyl, trifluoromethoxy, nitro, trimethylsilanyl, —$OR^a$, $SO_pR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$;

$R^2$ is selected from a group consisting of a bond, hydrogen, —C(O)—, $C_{1-6}$-alkenyl, and $C_{3-8}$-heterocycloalkylamine;

$R^3$ is selected from the group consisting of $C_{3-8}$-cycloalkyl, aryl, heteroaryl, and $C_{3-8}$-heterocycloalkyl group optionally substituted with one or more substituents selected from substituted or non-substituted aryl, substituted or non-substituted heteroaryl, wherein the substituent of the substituted aryl or heteroaryl is selected from hydroxy, halo, cyano, trifluoromethyl, trifluoromethoxy, nitro, trimethylsilanyl, —$OR^a$, —$SR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$;

X is a linker moiety selected from the group consisting of —$(CR^6R^7)_m$—O—, —$C(O)$—$R^8$—, —$CH_2$—NH—$C(O)$—, —CH=N—, —CH=N—O—, —$R^{10}$—NH—, and —NH—C(O)—;

$R^6$ and $R^7$ are each independently selected from the group consisting of hydrogen, fluoro, and $C_{1-3}$-alkyl;

$R^8$ is a bond, $C_{1-3}$-alkenyl, O, —NH—, —NH—O—;

$R^{10}$ is substituted or non-substituted $C_{1-3}$-alkenyl;

$R^a$ and $R^b$ are each independently selected from the group consisting of hydrogen, alkyl, fluoroalkyl, cycloalkyl, carbocyclyl, carbocyclylalkyl, aryl, aralkyl, heterocycloalkyl, heterocycloalkylalkyl, heteroaryl, heteroarylalkyl, halogen, —O-alkyl, —O-aryl, cyano, nitro, —OH, —$NH_2$, —NH-alkyl, and —NH-aryl;

m is an integer from 1-3;
n is 1 or 2;
p is 0, 1 or 2; and
t is 1 or 2, or a pharmaceutically acceptable salt, solvate, hydrate, or cocrystal thereof.

In another aspect, the disclosure relates to a compound of Formula (I), wherein the bicyclic core is selected from the group consisting of:

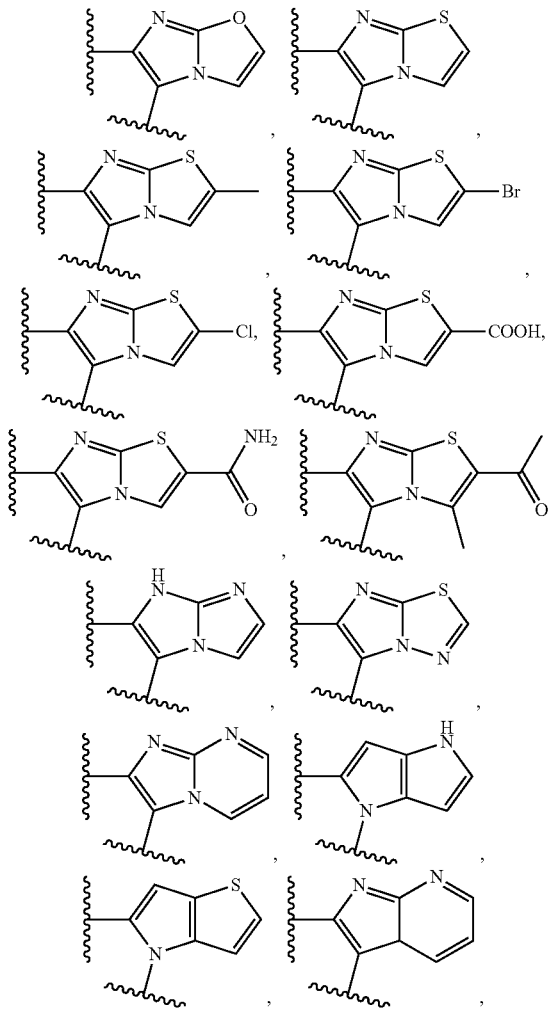

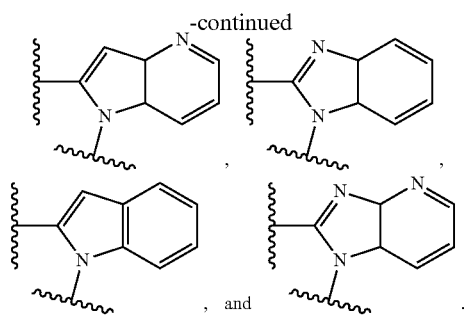
, and .

In another aspect, the disclosure relates to a compound of Formula (II):

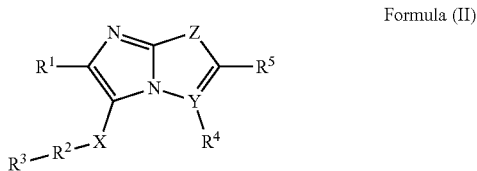

Formula (II)

wherein in Formula (II):

Z is O, S, or N;

Y is C, N, or —CH=CH—, with the proviso that when Y is N, $R^4$ is null, and when Y is C, $R^4$ is H or $C_{1-6}$-alkyl;

$R^1$ is linear or branched $C_{1-6}$-alkyl, substituted or non-substituted aryl, or substituted or non-substituted heteroaryl, wherein the substituted aryl or heteroaryl group is optionally substituted with one or more substituents selected from hydrogen, linear or branched $C_{1-6}$-alkyl, $C_{2-6}$-alkenyl, $C_{2-6}$-alkynyl, $C_{3-8}$-cycloalkyl, $C_{3-8}$-heterocycloalkyl, aryl, arylalkyl, heteroaryl, heteroarylalkyl, hydroxy, halogen, cyano, trifluoromethyl, trifluoromethoxy, nitro, trimethylsilanyl, —$OR^a$, $SO_nR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$;

X is a linker moiety selected from the group consisting of —$(CR^6R^7)_m$—O—, —$C(O)$—$R^8$—, —$CH_2$—NH—$C(O)$—, —CH=N—, —CH=N—O—, —$R^{10}$—NH—, —$R^{10}$—$NR^{11}$—, and —NH—$C(O)$—;

$R^2$ is selected from a group consisting of a bond, —$C(O)$—, $C_{1-6}$-alkenyl, and $C_{3-8}$-heterocycloalkylamine;

$R^3$ is selected from the group consisting of aryl, heteroaryl, $C_{3-8}$-cycloalkyl substituted with one or more substituents selected from substituted or non-substituted aryl, substituted or non-substituted heteroaryl, and $C_{3-8}$-heterocycloalkyl group substituted with one or more substituents selected from substituted or non-substituted aryl, substituted or non-substituted heteroaryl, wherein the substituent of the substituted aryl or heteroaryl is selected from hydroxy, halo, cyano, trifluoromethyl, trifluoromethoxy, nitro, trimethylsilanyl, —$OR^a$, —$SR^a$, —$OC(O)R^a$, —$N(R^a)R^b$, —$C(O)R^a$, —$C(O)OR^a$, —$OC(O)N(R^a)R^b$, —$C(O)N(R^a)R^b$, —$N(R^a)C(O)OR^a$, —$N(R^a)C(O)R^a$, —$N(R^a)C(O)N(R^a)R^b$, —$N(R^a)C(NR^a)N(R^a)R^b$, —$N(R^a)S(O)_tR^a$, —$S(O)_tOR^a$, —$S(O)_tN(R^a)R^b$, or —$P(O)(OR^a)(OR^b)$;

$R^5$ is selected from the group consisting of hydrogen, halogen, $C_{1-6}$-alkyl, —$C(O)R^a$, —$C(O)OR^a$, and —$C(O)N(R^a)R^b$;

$R^6$ and $R^7$ are each independently selected from the group consisting of hydrogen, fluoro, and $C_{1-3}$-alkyl;

$R^8$ is a bond, $C_{1-3}$-alkenyl, O, —NH—, —NH—O—;

$R^{10}$ and R11 are each independently substituted or non-substituted $C_{1-3}$-alkyl or $C_{1-3}$-alkenyl;

$R^a$ and $R^b$ are each independently selected from the group consisting of hydrogen, alkyl, fluoroalkyl, cycloalkyl, carbocyclyl, carbocyclylalkyl, aryl, aralkyl, heterocycloalkyl, heterocycloalkylalkyl, heteroaryl, heteroarylalkyl, halogen, —O-alkyl, —O-aryl, cyano, nitro, —OH, —$NH_2$, —NH-alkyl, and —NH-aryl;

m is an integer from 1-3;

n is 0, 1 or 2; and t is 1 or 2;

or a pharmaceutically acceptable salt, solvate, hydrate, or cocrystal thereof.

In another aspect, the disclosure relates to a compound of Formula (I) or Formula (II) having an alternate bicyclic core

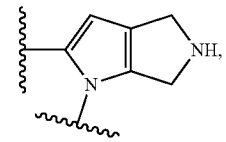 [SMILES: *c1cc2c(n1*)CNC2]

or an alternate heterocyclic core

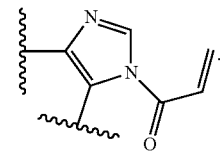 [SMILES: *c1ncn(C(=O)C=C)c1*]

In one aspect, the disclosure relates to a compound of Formula (II), wherein $R^1$ is selected from the group consisting of:

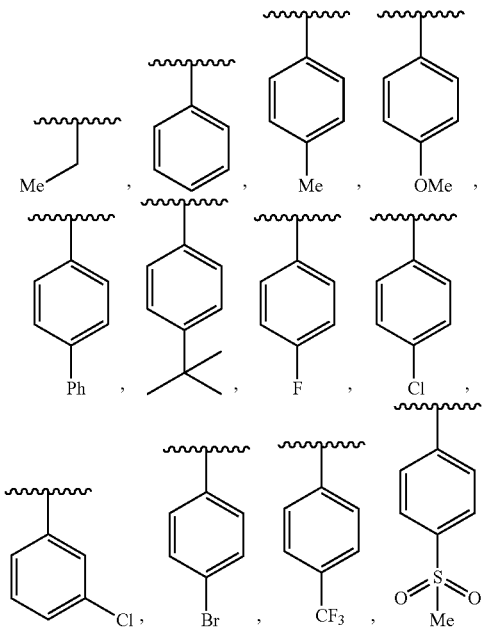

-continued
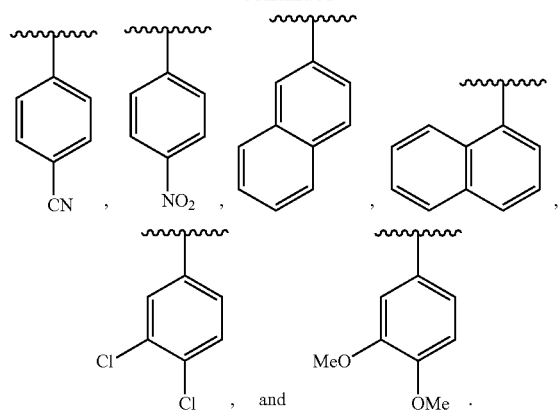
In another aspect, the disclosure relates to compounds of Formula (II) wherein —$R^2$-$R^3$ in Formula (II), is selected from the group consisting of:
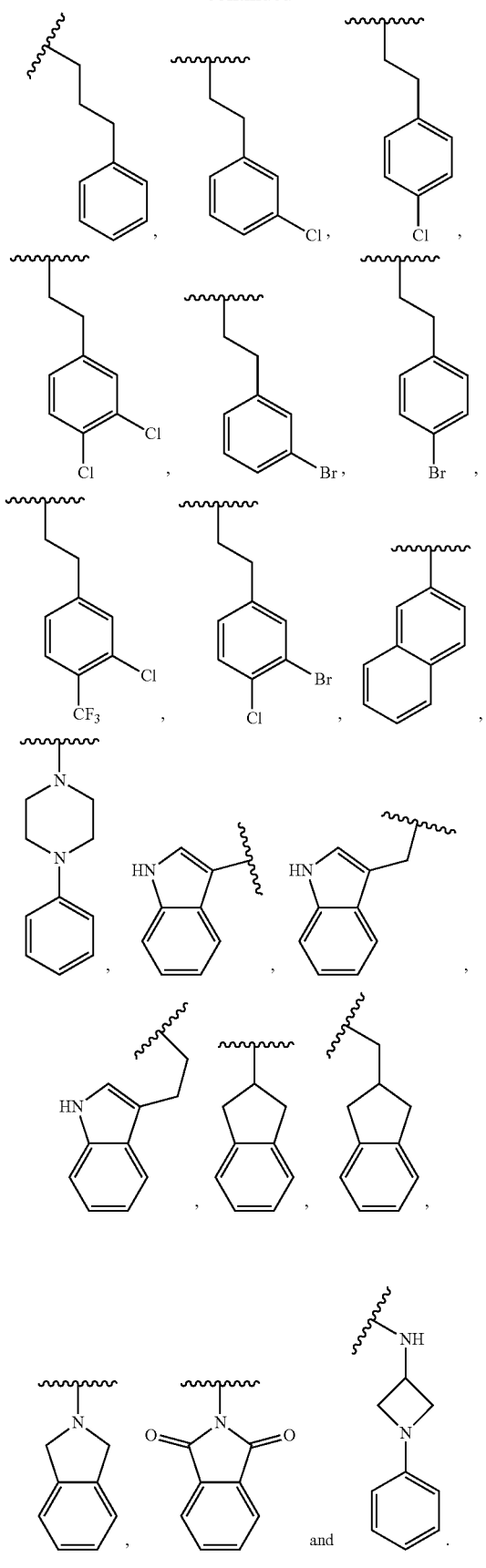

In one aspect, the present invention provides the compounds included in Table 1.

TABLE 1

| Entry No. | Compound No. | Compound | Chemical Name |
|---|---|---|---|
| 1 | CITCO | | (E)-6-(4-chlorophenyl)imidazo[2,1-b]thiazole-5-carbaldehyde O-(3,4-dichlorobenzyl) oxime |
| 2 | DL5016 | | N-((6-(naphthalen-2-yl)imidazo[2,1-b]oxazol-5-yl)methyl)-2,3-dihydro-1H-inden-2-amine |
| 3 | DL5016M | | N-((6-(naphthalen-2-yl)imidazo[2,1-b]thiazol-5-yl)methyl)-2,3-dihydro-1H-indene-2-carboxamide |
| 4 | DL5024 | | N-((6-(naphthalen-1-yl)imidazo[2,1-b]thiazol-5-yl)methyl)-2,3-dihydro-1H-inden-2-amine |

TABLE 1-continued

| Entry No. | Compound No. | Compound | Chemical Name |
|---|---|---|---|
| 5 | DL5012 | | N-((6-(naphthalen-2-yl)imidazo[2,1-b]thiazol-5-yl)methyl)-2-phenylpropan-1-amine |
| 6 | DL4181 | | N-((6-(4-chlorophenyl)imidazo[2,1-b]oxazol-5-yl)methyl)-2,3-dihydro-1H-inden-2-amine |
| 7 | DL5016L | | N-((2,3-dihydro-1H-inden-2-yl)methyl)-6-(naphthalen-2-yl)imidazo[2,1-b]oxazole-5-carboxamide |
| 8 | DL5016E | | 6-(naphthalen-2-yl)-N-(3-phenylpropyl)imidazo[2,1-b]oxazole-5-carboxamide |
| 9 | DL5016F | | N-((3,4-dichlorobenzyl)oxy)-6-(naphthalen-2-yl)imidazo[2,1-b]oxazole-5-carboxamide |

TABLE 1-continued
| Entry No. | Compound No. | Compound | Chemical Name |
|---|---|---|---|
| 10 | DL5016G | 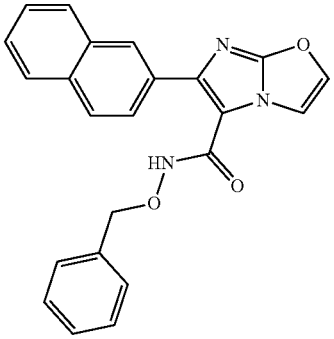 [SMILES: O=C(NOCc1ccccc1)c1c(-c2ccc3ccccc3c2)nc2occn12] | N-(benzyloxy)-6-(naphthalen-2-yl)imidazo[2,1-b]oxazole-5-carboxamide |
| 11 | DL5016H | 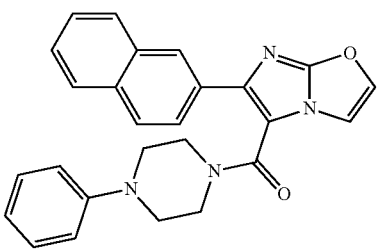 [SMILES: O=C(c1c(-c2ccc3ccccc3c2)nc2occn12)N1CCN(c2ccccc2)CC1] | (6-(naphthalen-2-yl)imidazo[2,1-b]oxazol-5-yl)(4-phenylpiperazin-1-yl)methanone |
| 12 | DL5016I | 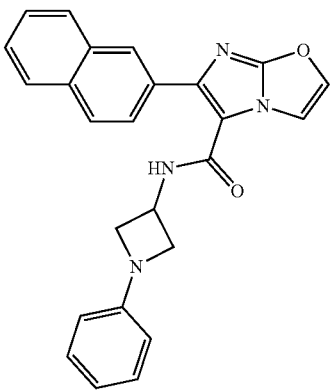 [SMILES: O=C(NC1CN(c2ccccc2)C1)c1c(-c2ccc3ccccc3c2)nc2occn12] | 6-(naphthalen-2-yl)-N-(1-phenylazetidin-3-yl)imidazo[2,1-b]oxazole-5-carboxamide |
| 13 | DL5016J | 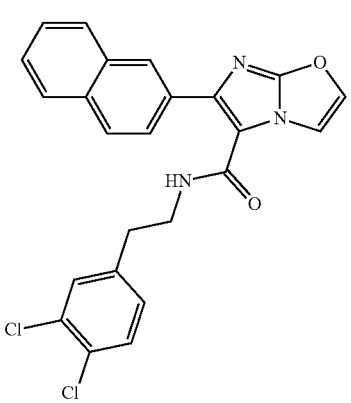 | N-(3,4-dichlorophenethyl)-6-(naphthalen-2-yl)imidazo[2,1-b]oxazole-5-carboxamide |

TABLE 1-continued
| Entry No. | Compound No. | Compound | Chemical Name |
|---|---|---|---|
| 14 | DL5016K | 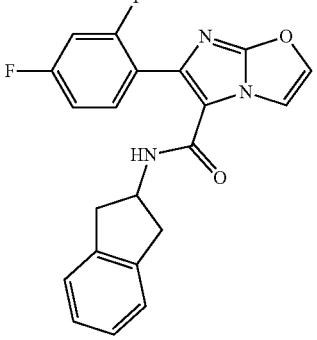 | 6-(2,4-difluorophenyl)-N-(2,3-dihydro-1H-inden-2-yl)imidazo[2,1-b]oxazole-5-carboxamide |
| 15 | DL4073 | 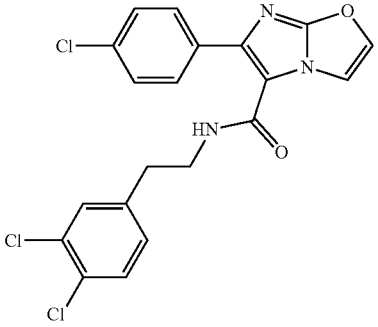 | 6-(4-chlorophenyl)-N-(3,4-dichlorophenethyl)imidazo[2,1-b]oxazole-5-carboxamide |
| 16 | DL5016L | 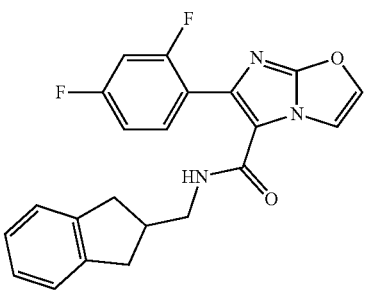 [SMILES: O=C(NCC1Cc2ccccc2C1)c1c(-c2ccc(F)cc2F)nc2occn12] | 6-(2,4-difluorophenyl)-N-((2,3-dihydro-1H-inden-2-yl)methyl)imidazo[2,1-b]oxazole-5-carboxamide |
| 17 | DL5016M | 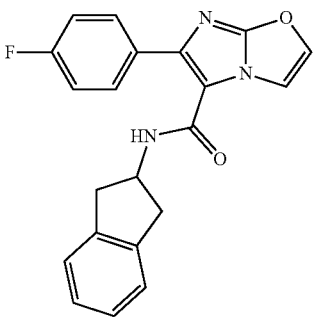 [SMILES: O=C(NC1Cc2ccccc2C1)c1c(-c2ccc(F)cc2)nc2occn12] | N-(2,3-dihydro-1H-inden-2-yl)-6-(4-fluorophenyl)imidazo[2,1-b]oxazole-5-carboxamide |

TABLE 1-continued
| Entry No. | Compound No. | Compound | Chemical Name |
|---|---|---|---|
| 18 | DL5016N | 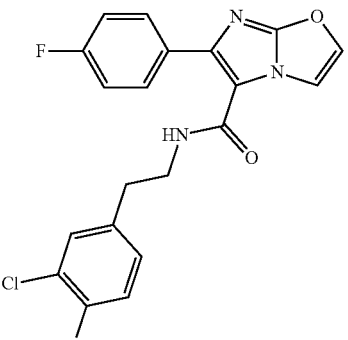 | N-(3,4-dichlorophenethyl)-6-(4-fluorophenyl)imidazo[2,1-b]oxazole-5-carboxamide |
| 19 | DL5016O | 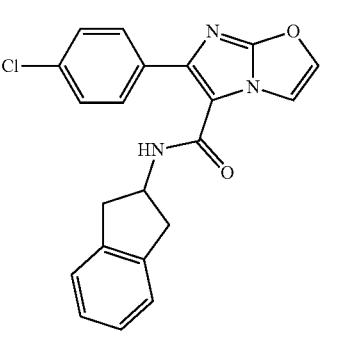 [SMILES: O=C(NC1Cc2ccccc2C1)c1c(-c2ccc(Cl)cc2)nc2occn12] | 6-(4-chlorophenyl)-N-(2,3-dihydro-1H-inden-2-yl)imidazo[2,1-b]oxazole-5-carboxamide |
| 20 | DL5016P | 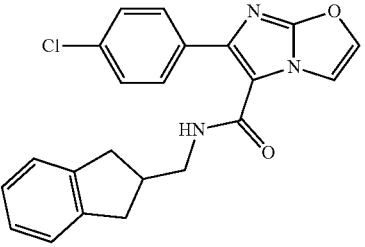 [SMILES: O=C(NCC1Cc2ccccc2C1)c1c(-c2ccc(Cl)cc2)nc2occn12] | 6-(4-chlorophenyl)-N-((2,3-dihydro-1H-inden-2-yl)methyl)imidazo[2,1-b]oxazole-5-carboxamide |
| 21 | DL5016Q | 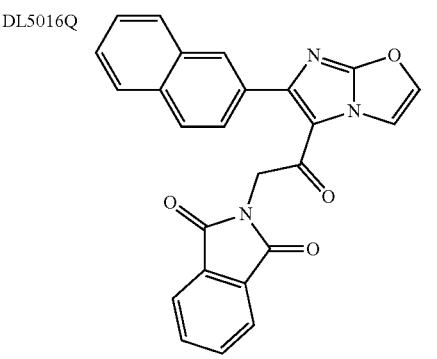 | 2-(2-(6-(naphthalen-2-yl)imidazo[2,1-b]oxazol-5-yl)-2-oxoethyl)isoindoline-1,3-dione |

TABLE 1-continued

| Entry No. | Compound No. | Compound | Chemical Name |
|---|---|---|---|
| 22 | DL5016R | | N-(6-(naphthalen-2-yl)imidazo[2,1-b]oxazol-5-yl)-2,3-dihydro-1H-indene-2-carboxamide |
| 23 | DL5043 | | (E)-6-(4-chlorophenyl)imidazo[2,1-b]oxazole-5-carbaldehyde O-(3,4-dichlorobenzyl) oxime |
| 24 | DL5054 | | (E)-6-(naphthalen-2-yl)imidazo[2,1-b]oxazole-5-carbaldehyde O-(3,4-dichlorobenzyl) oxime |
| 25 | DL5098-3 | | (E)-6-(naphthalen-2-yl)imidazo[2,1-b]oxazole-5-carbaldehyde O-benzyl oxime |

TABLE 1-continued
| Entry No. | Compound No. | Compound | Chemical Name |
|---|---|---|---|
| 26 | DL5096-3 | 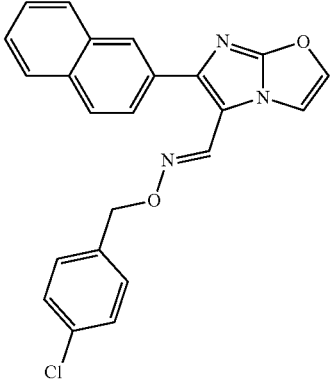 [SMILES: Clc1ccc(CO/N=C/c2c(-c3ccc4ccccc4c3)nc3occn23)cc1] | (E)-6-(naphthalen-2-yl)imidazo[2,1-b]oxazole-5-carbaldehyde O-(4-chlorobenzyl) oxime |
| 27 | DL5096-2 | 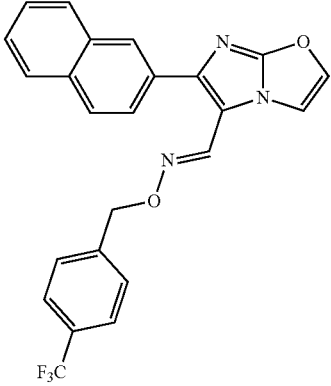 [SMILES: FC(F)(F)c1ccc(CO/N=C/c2c(-c3ccc4ccccc4c3)nc3occn23)cc1] | (E)-6-(naphthalen-2-yl)imidazo[2,1-b]oxazole-5-carbaldehyde O-(4-(trifluoromethyl)benzyl) oxime |
| 28 | DL5081 | 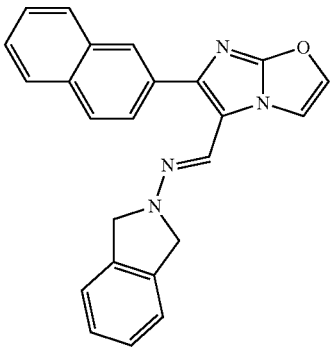 [SMILES: C(=N\N1Cc2ccccc2C1)/c1c(-c2ccc3ccccc3c2)nc2occn12] | (E)-N-(isoindolin-2-yl)-1-(6-(naphthalen-2-yl)imidazo[2,1-b]oxazol-5-yl)methanimine |
| 29 | DL5090 | 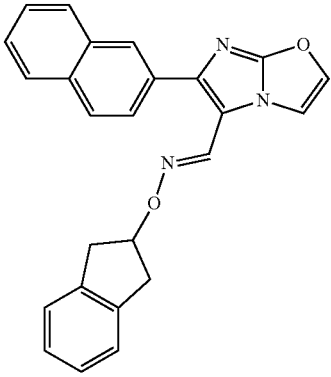 [SMILES: C(=N\OC1Cc2ccccc2C1)/c1c(-c2ccc3ccccc3c2)nc2occn12] | (E)-6-(naphthalen-2-yl)imidazo[2,1-b]oxazole-5-carbaldehyde O-(2,3-dihydro-1H-inden-2-yl) oxime |

TABLE 1-continued

| Entry No. | Compound No. | Compound | Chemical Name |
|---|---|---|---|
| 30 | DL5098-4 | | (E)-6-(naphthalen-2-yl)imidazo[2,1-b]oxazole-5-carbaldehyde O-(4-methoxybenzyl) oxime |
| 31 | DL5096-1 | | (E)-6-(naphthalen-2-yl)imidazo[2,1-b]oxazole-5-carbaldehyde O-(2,4-dichlorobenzyl) oxime |
| 32 | DL5098-2 | | (E)-6-(naphthalen-2-yl)imidazo[2,1-b]oxazole-5-carbaldehyde O-(2-chlorobenzyl) oxime |
| 33 | DL5098-1 | | (E)-6-(naphthalen-2-yl)imidazo[2,1-b]oxazole-5-carbaldehyde O-((perfluorophenyl)methyl) oxime |

TABLE 1-continued

| Entry No. | Compound No. | Compound | Chemical Name |
|---|---|---|---|
| 34 | DL4059 | 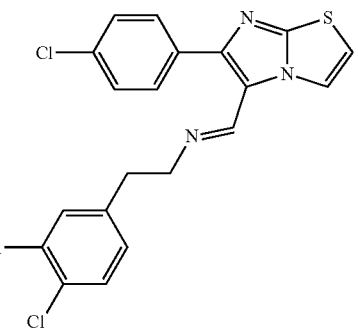 | (E)-1-(6-(4-chlorophenyl)imidazo[2,1-b]thiazol-5-yl)-N-(3,4-dichlorophenethyl)methanimine |
| 35 | DL5043 | 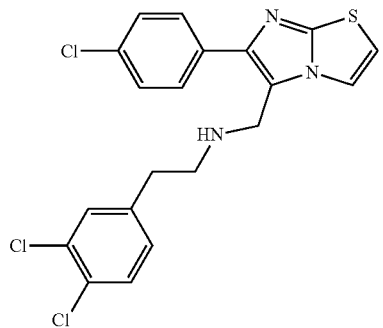 | N-((6-(4-chlorophenyl)imidazo[2,1-b]thiazol-5-yl)methyl)-2-(3,4-dichlorophenyl)ethan-1-amine |
| 36 | DL4072 | 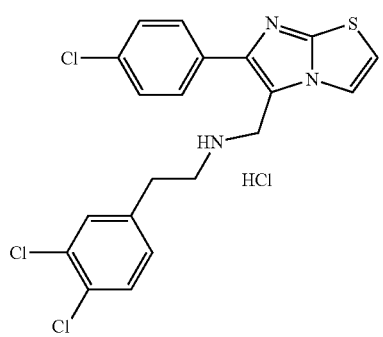 [SMILES: Clc1ccc(-c2nc3sccn3c2CNCCc2ccc(Cl)c(Cl)c2)cc1 ; Cl] | N-((6-(4-chlorophenyl)imidazo[2,1-b]thiazol-5-yl)methyl)-2-(3,4-dichlorophenyl)ethan-1-amine hydrochloride |
| 37 | D4073 | 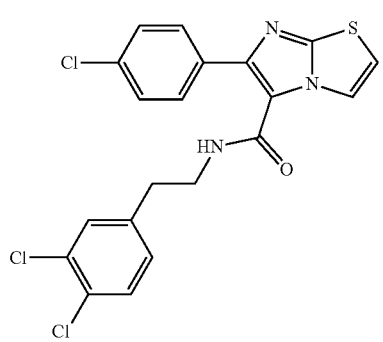 [SMILES: O=C(NCCc1ccc(Cl)c(Cl)c1)c1c(-c2ccc(Cl)cc2)nc2sccn12] | 6-(4-chlorophenyl)-N-(3,4-dichlorophenethyl)imidazo[2,1-b]thiazole-5-carboxamide |

TABLE 1-continued
| Entry No. | Compound No. | Compound | Chemical Name |
|---|---|---|---|
| 38 | DL4082 | 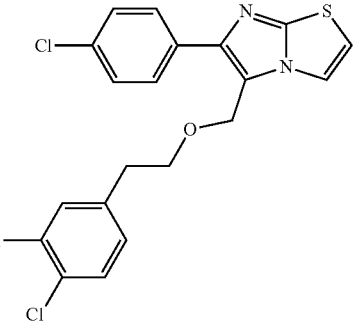 | 6-(4-chlorophenyl)-5-((3,4-dichlorophenethoxy)methyl)imidazo[2,1-b]thiazole |
| 39 | DL4094 | 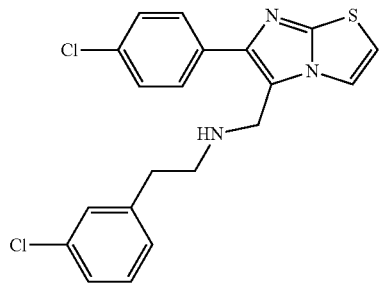 [SMILES: Clc1ccc(-c2nc3sccn3c2CNCCc2cccc(Cl)c2)cc1] | 2-(3-chlorophenyl)-N-((6-(4-chlorophenyl)imidazo[2,1-b]thiazol-5-yl)methyl)ethan-1-amine |
| 40 | DL4095 | 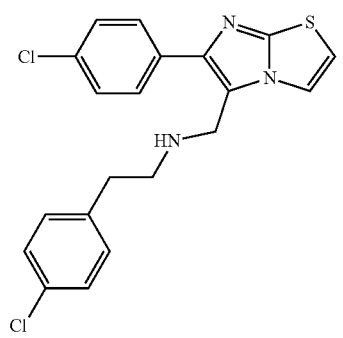 | 2-(4-chlorophenyl)-N-((6-(4-chlorophenyl)imidazo[2,1-b]thiazol-5-yl)methyl)ethan-1-amine |
| 41 | DL4100 | 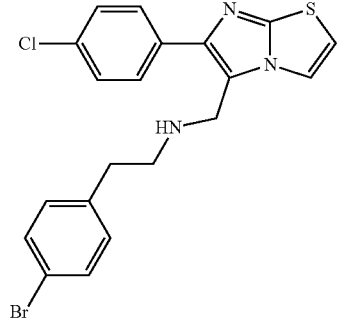 [SMILES: Clc1ccc(CCNCc2c(-c3ccc(Cl)cc3)nc3sccn23)cc1] | 2-(4-bromophenyl)-N-((6-(4-chlorophenyl)imidazo[2,1-b]thiazol-5-yl)methyl)ethan-1-amine |

TABLE 1-continued

| Entry No. | Compound No. | Compound | Chemical Name |
|---|---|---|---|
| 42 | DL4102 | 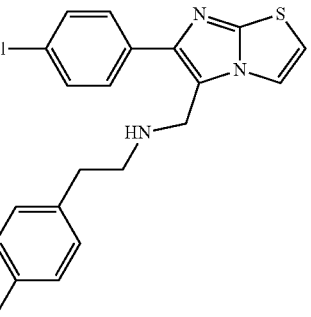 | 2-(3-bromo-4-chlorophenyl)-N-((6-(4-chlorophenyl)imidazo[2,1-b]thiazol-5-yl)methyl)ethan-1-amine |
| 43 | DL4103 | 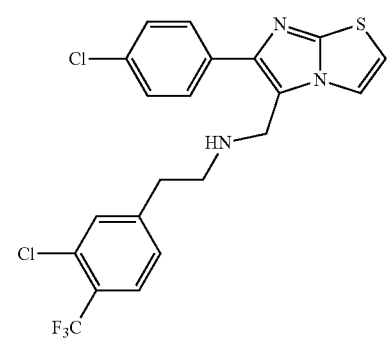 [SMILES: FC(F)(F)c1ccc(CCNCc2c(-c3ccc(Cl)cc3)nc3sccn23)cc1Cl] | 2-(3-chloro-4-(trifluoromethyl)phenyl)-N-((6-(4-chlorophenyl)imidazo[2,1-b]thiazol-5-yl)methyl)ethan-1-amine |
| 44 | DL4104 | 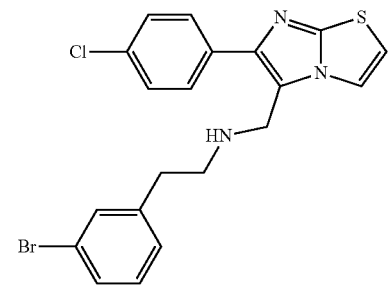 | 2-(3-bromophenyl)-N-((6-(4-chlorophenyl)imidazo[2,1-b]thiazol-5-yl)methyl)ethan-1-amine |
| 45 | DL4113 | 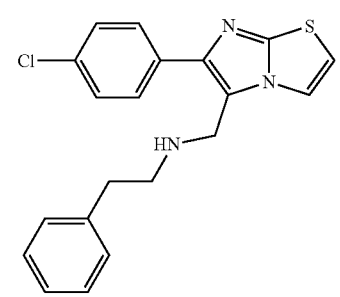 [SMILES: Clc1ccc(-c2nc3sccn3c2CNCCc2ccccc2)cc1] | N-((6-(4-chlorophenyl)imidazo[2,1-b]thiazol-5-yl)methyl)-2-phenylethan-1-amine |
| 46 | DL4173 | 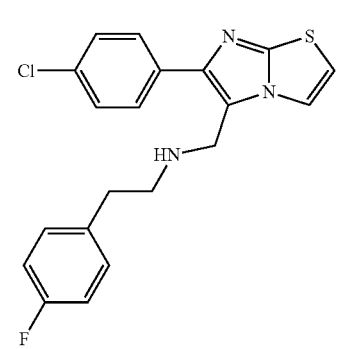 [SMILES: Fc1ccc(CCNCc2c(-c3ccc(Cl)cc3)nc3sccn23)cc1] | N-((6-(4-chlorophenyl)imidazo[2,1-b]thiazol-5-yl)methyl)-2-(4-fluorophenyl)ethan-1-amine |

TABLE 1-continued

| Entry No. | Compound No. | Compound | Chemical Name |
|---|---|---|---|
| 47 | DL4170 | | 4-(2-(((6-(4-chlorophenyl)imidazo[2,1-b]thiazol-5-yl)methyl)amino)ethyl)phenol |
| 48 | DL4153 | | N-((6-(4-chlorophenyl)imidazo[2,1-b]thiazol-5-yl)methyl)-2-(1H-indol-3-yl)ethan-1-amine |
| 49 | DL4175 | | N-((6-(4-chlorophenyl)imidazo[2,1-b]thiazol-5-yl)methyl)-2,3-dihydro-1H-inden-2-amine |
| 50 | DL4179 | | N-((6-(4-chlorophenyl)imidazo[2,1-b]thiazol-5-yl)methyl)naphthalen-2-amine |
| 51 | DL5002 | | N-benzyl-1-(6-(4-chlorophenyl)imidazo[2,1-b]thiazol-5-yl)methanamine |
| 52 | DL5026 | | N-((6-(4-chlorophenyl)imidazo[2,1-b]thiazol-5-yl)methyl)-2-(3,4-dichlorophenyl)-N-methylethan-1-amine |

TABLE 1-continued

| Entry No. | Compound No. | Compound | Chemical Name |
|---|---|---|---|
| 53 | DL4107 | 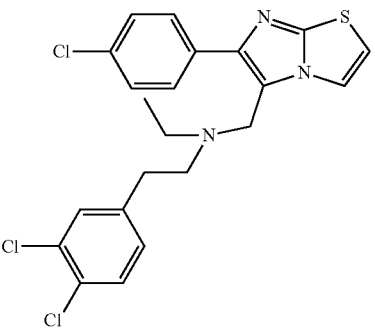 [SMILES: CCN(CCc1ccc(Cl)c(Cl)c1)Cc1c(-c2ccc(Cl)cc2)nc2sccn12] | N-((6-(4-chlorophenyl)imidazo[2,1-b]thiazol-5-yl)methyl)-2-(3,4-dichlorophenyl)-N-ethylethan-1-amine |
| 54 | DL5028 | 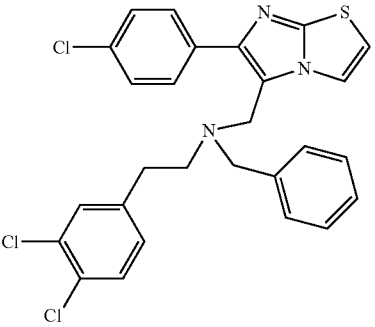 [SMILES: Clc1ccc(-c2nc3sccn3c2CN(CCc2ccc(Cl)c(Cl)c2)Cc2ccccc2)cc1] | N-benzyl-N-((6-(4-chlorophenyl)imidazo[2,1-b]thiazol-5-yl)methyl)-2-(3,4-dichlorophenyl)ethan-1-amine |
| 55 | DL4171 | 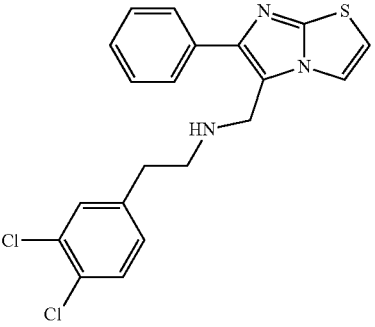 [SMILES: Clc1ccc(CCNCc2c(-c3ccccc3)nc3sccn23)cc1Cl] | 2-(3,4-dichlorophenyl)-N-((6-phenylimidazo[2,1-b]thiazol-5-yl)methyl)ethan-1-amine |
| 56 | DL4143 | 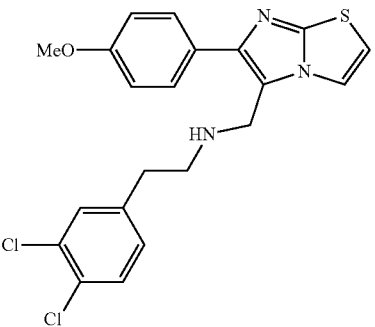 [SMILES: COc1ccc(-c2nc3sccn3c2CNCCc2ccc(Cl)c(Cl)c2)cc1] | 2-(3,4-dichlorophenyl)-N-((6-(4-methoxyphenyl)imidazo[2,1-b]thiazol-5-yl)methyl)ethan-1-amine |

TABLE 1-continued
| Entry No. | Compound No. | Compound | Chemical Name |
|---|---|---|---|
| 57 | DL5020 | 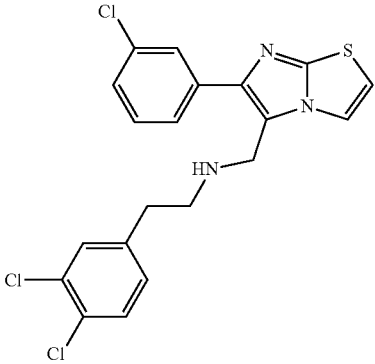 [SMILES: Clc1cccc(-c2nc3sccn3c2CNCCc2ccc(Cl)c(Cl)c2)c1] | N-((6-(3-chlorophenyl)imidazo[2,1-b]thiazol-5-yl)methyl)-2-(3,4-dichlorophenyl)ethan-1-amine |
| 58 | DL4129 | 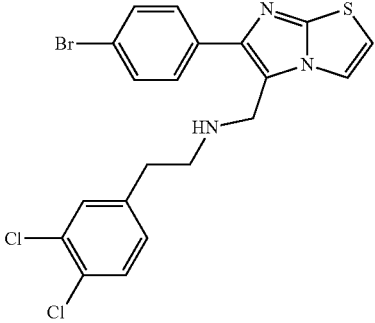 | N-((6-(4-bromophenyl)imidazo[2,1-b]thiazol-5-yl)methyl)-2-(3,4-dichlorophenyl)ethan-1-amine |
| 59 | DL4130 | 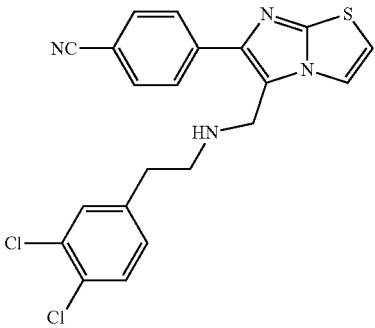 | 2-(3,4-dichlorophenyl)-N-((6-(4-isocyanophenyl)imidazo[2,1-b]thiazol-5-yl)methyl)ethan-1-amine |
| 60 | DL4132 | 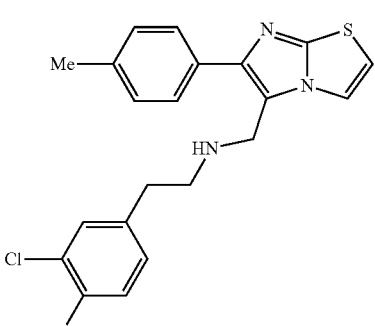 | 2-(3,4-dichlorophenyl)-N-((6-(p-tolyl)imidazo[2,1-b]thiazol-5-yl)methyl)ethan-1-amine |

TABLE 1-continued

| Entry No. | Compound No. | Compound | Chemical Name |
|---|---|---|---|
| 61 | DL4133 | 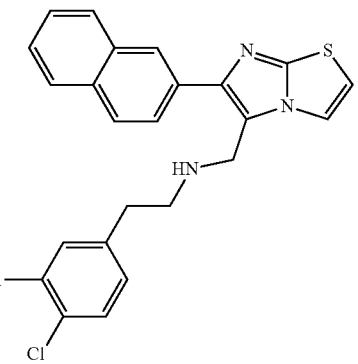 | 2-(3,4-dichlorophenyl)-N-((6-(naphthalen-2-yl)imidazo[2,1-b]thiazol-5-yl)methyl)ethan-1-amine |
| 62 | DL4141 | 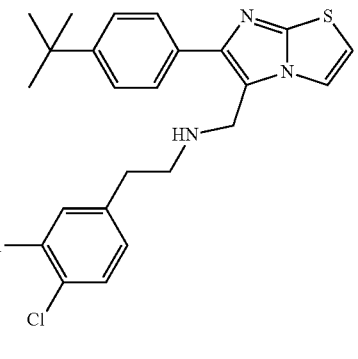 | N-((6-(4-(tert-butyl)phenyl)imidazo[2,1-b]thiazol-5-yl)methyl)-2-(3,4-dichlorophenyl)ethan-1-amine |
| 63 | YY1008 | 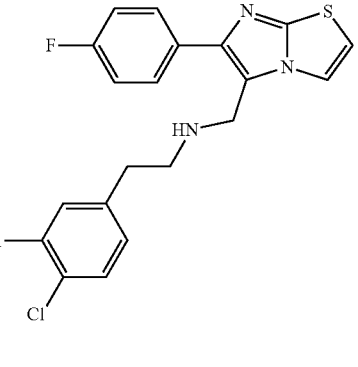 | 2-(3,4-dichlorophenyl)-N-((6-(4-fluorophenyl)imidazo[2,1-b]thiazol-5-yl)methyl)ethan-1-amine |
| 64 | DL4142 | 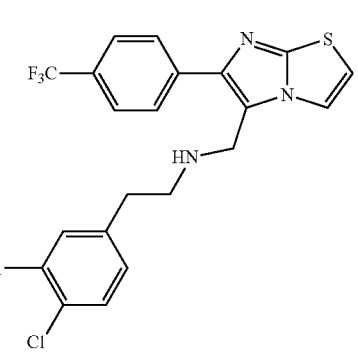 | 2-(3,4-dichlorophenyl)-N-((6-(4-(trifluoromethyl)phenyl)imidazo[2,1-b]thiazol-5-yl)methyl)ethan-1-amine |

TABLE 1-continued
| Entry No. | Compound No. | Compound | Chemical Name |
|---|---|---|---|
| 65 | YY1017 | 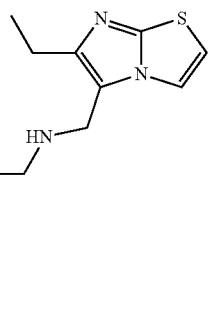 | 2-(3,4-dichlorophenyl)-N-((6-ethylimidazo[2,1-b]thiazol-5-yl)methyl)ethan-1-amine |
| 66 | DL5058 | 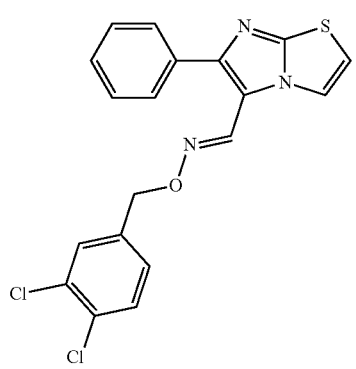 [SMILES: Clc1ccc(CO/N=C/c2c(-c3ccccc3)nc3sccn23)cc1Cl] | (E)-6-phenylimidazo[2,1-b]thiazole-5-carbaldehyde O-(3,4-dichlorobenzyl) oxime |
| 67 | DL5067 | 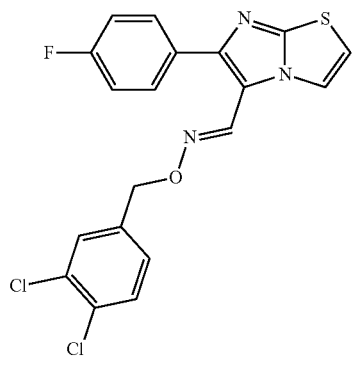 [SMILES: Fc1ccc(-c2nc3sccn3c2/C=N/OCc2ccc(Cl)c(Cl)c2)cc1] | (E)-6-(4-fluorophenyl)imidazo[2,1-b]thiazole-5-carbaldehyde O-(3,4-dichlorobenzyl) oxime |
| 68 | DL5045 (CITCO) | 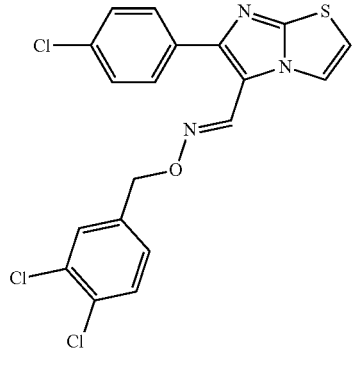 [SMILES: Clc1ccc(-c2nc3sccn3c2/C=N/OCc2ccc(Cl)c(Cl)c2)cc1] | (E)-6-(4-chlorophenyl)imidazo[2,1-b]thiazole-5-carbaldehyde O-(3,4-dichlorobenzyl) oxime |

TABLE 1-continued

| Entry No. | Compound No. | Compound | Chemical Name |
|---|---|---|---|
| 69 | DL5064 | | (E)-6-(4-bromophenyl)imidazo[2,1-b]thiazole-5-carbaldehyde O-(3,4-dichlorobenzyl) oxime |
| 70 | DL5061 | | (E)-6-(4-isocyanophenyl)imidazo[2,1-b]thiazole-5-carbaldehyde O-(3,4-dichlorobenzyl) oxime |
| 71 | DL5063 | | (E)-6-(4-(trifluoromethyl)phenyl)imidazo[2,1-b]thiazole-5-carbaldehyde O-(3,4-dichlorobenzyl) oxime |
| 72 | DL5068 | | (E)-6-(p-tolyl)imidazo[2,1-b]thiazole-5-carbaldehyde O-(3,4-dichlorobenzyl) oxime |

TABLE 1-continued

| Entry No. | Compound No. | Compound | Chemical Name |
|---|---|---|---|
| 73 | DL5069 | 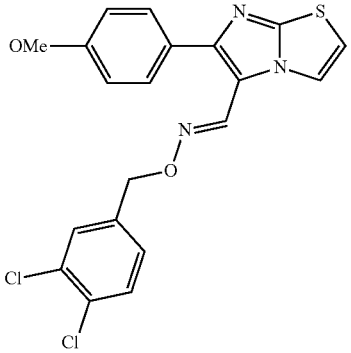 [SMILES: COc1ccc(-c2nc3sccn3c2/C=N/OCc2ccc(Cl)c(Cl)c2)cc1] | (E)-6-(4-methoxyphenyl)imidazo[2,1-b]thiazole-5-carbaldehyde O-(3,4-dichlorobenzyl) oxime |
| 74 | DL5059 | 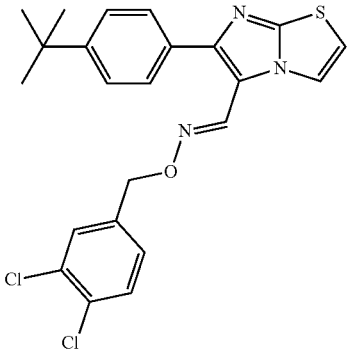 [SMILES: CC(C)(C)c1ccc(-c2nc3sccn3c2/C=N/OCc2ccc(Cl)c(Cl)c2)cc1] | (E)-6-(4-(tert-butyl)phenyl)imidazo[2,1-b]thiazole-5-carbaldehyde O-(3,4-dichlorobenzyl) oxime |
| 75 | DL5060 | 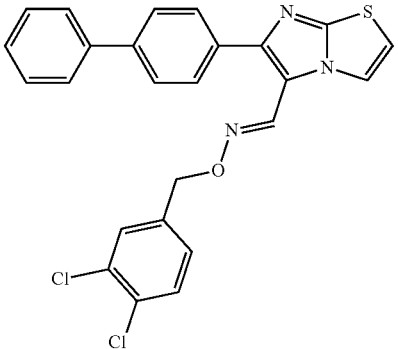 [SMILES: Clc1ccc(CO/N=C/c2c(-c3ccc(-c4ccccc4)cc3)nc3sccn23)cc1Cl] | (E)-6-([1,1'-biphenyl]-4-yl)imidazo[2,1-b]thiazole-5-carbaldehyde O-(3,4-dichlorobenzyl) oxime |
| 76 | DL6065 | 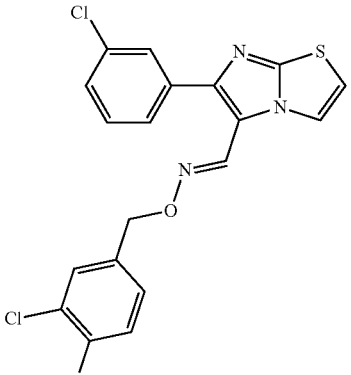 | (E)-6-(3-chlorophenyl)imidazo[2,1-b]thiazole-5-carbaldehyde O-(3,4-dichlorobenzyl) oxime |

TABLE 1-continued

| Entry No. | Compound No. | Compound | Chemical Name |
|---|---|---|---|
| 77 | DL5044 | | (E)-6-(naphthalen-2-yl)imidazo[2,1-b]thiazole-5-carbaldehyde O-(3,4-dichlorobenzyl) oxime |
| 78 | DL5066 | | (E)-6-(naphthalen-1-yl)imidazo[2,1-b]thiazole-5-carbaldehyde O-(3,4-dichlorobenzyl) oxime |
| 79 | DL5009 | | (E)-6-(naphthalen-2-yl)imidazo[2,1-b]thiazole-5-carbaldehyde O-benzyl oxime |
| 80 | DL5013 | | (E)-6-(4-chlorophenyl)imidazo[2,1-b]thiazole-5-carbaldehyde oxime |

TABLE 1-continued
| Entry No. | Compound No. | Compound | Chemical Name |
|---|---|---|---|
| 81 | DL5071 | 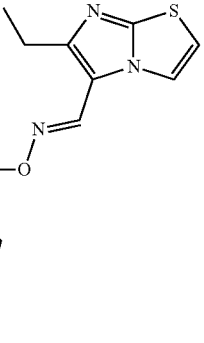 | (E)-6-ethylimidazo[2,1-b]thiazole-5-carbaldehyde O-(3,4-dichlorobenzyl) oxime |
| 82 | DL4073 | 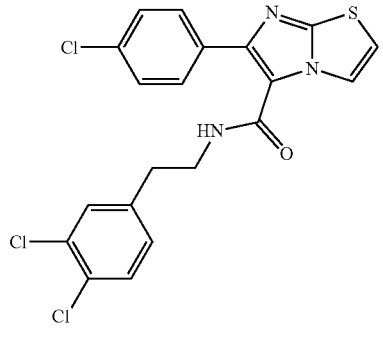 | 6-(4-chlorophenyl)-N-(3,4-dichlorophenethyl)imidazo[2,1-b]thiazole-5-carboxamide |
| 83 | DL4108 | 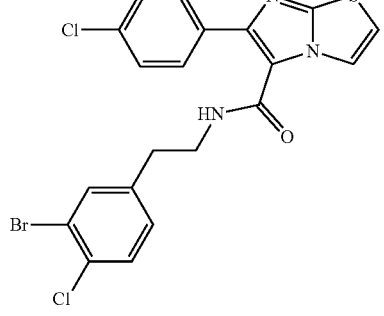 | N-(3-bromo-4-chlorophenethyl)-6-(4-chlorophenyl)imidazo[2,1-b]thiazole-5-carboxamide |
| 84 | D5039 | 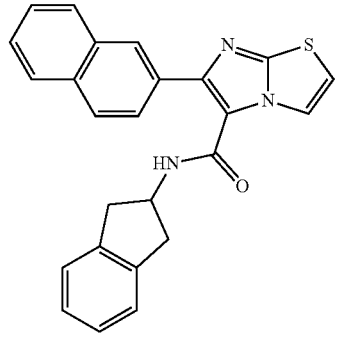 [SMILES: O=C(NC1Cc2ccccc2C1)c1c(-c2ccc3ccccc3c2)nc2sccn12] | N-(2,3-dihydro-1H-inden-2-yl)-6-(naphthalen-2-yl)imidazo[2,1-b]thiazole-5-carboxamide |

TABLE 1-continued
| Entry No. | Compound No. | Compound | Chemical Name |
|---|---|---|---|
| 85 | DL4181 | 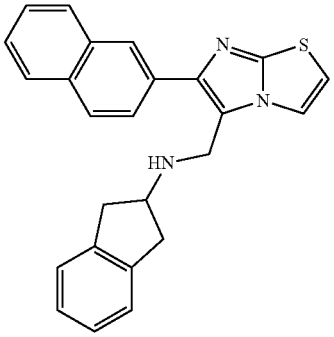 [SMILES: c1ccc2c(c1)CC(NCc1c(-c3ccc4ccccc4c3)nc3sccn13)C2] | N-((6-(naphthalen-2-yl)imidazo[2,1-b]thiazol-5-yl)methyl)-2,3-dihydro-1H-inden-2-amine |
| 86 | YY1045 | 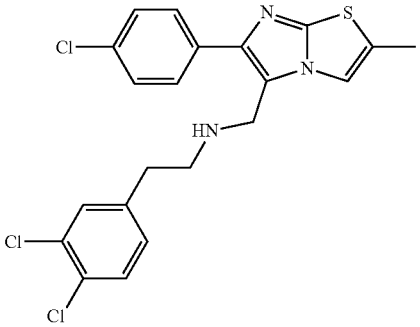 [SMILES: Cc1cn2c(CNCCc3ccc(Cl)c(Cl)c3)c(-c3ccc(Cl)cc3)nc2s1] | N-((6-(4-chlorophenyl)-2-methylimidazo[2,1-b]thiazol-5-yl)methyl)-2-(3,4-dichlorophenyl)ethan-1-amine |
| 87 | DL4167 | 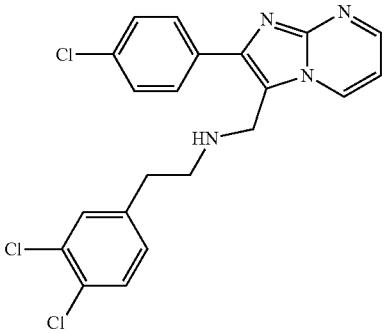 [SMILES: Clc1ccc(-c2nc3ncccn3c2CNCCc2ccc(Cl)c(Cl)c2)cc1] | N-(2-(4-chlorophenyl)imidazo[1,2-α]pyrimidin-3-yl)methyl)-2-(3,4-dichlorophenyy)ethan-1-amine |
| 88 | DL5016D | 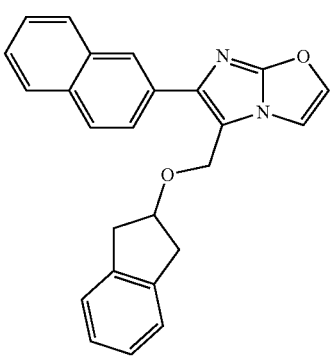 [SMILES: c1ccc2c(c1)CC(OCc1c(-c3ccc4ccccc4c3)nc3occn13)C2] | 5-(((2,3-dihydro-1H-inden-2-yl)oxy)methyl)-6-(naphthalen-2-yl)imidazo[2,1-b]oxazole |

TABLE 1-continued

| Entry No. | Compound No. | Compound | Chemical Name |
|---|---|---|---|
| 89 | YY1036 | | N-((6-(4-chlorophenyl)imidazo[2,1-b]oxazol-5-yl)methyl)-2-(3,4-dichlorophenyl)ethan-1-amine |
| 90 | DL6077 | | 1-(2,3-dihydro-1H-inden-2-yl)-N-((6-(naphthalen-2-yl)imidazo[2,1-b]oxazol-5-yl)methyl)methanamine |
| 91 | DL5001 | | N-((6-(naphthalen-2-yl)imidazo[2,1-b]thiazol-5-yl)methyl)-2,3-dihydro-1H-inden-2-amine |
| 92 | DL4097 | | N-((6-(4-chlorophenyl)imidazo[2,1-b]thiazol-5-yl)methyl)-2-(3,4-dichlorophenyl)ethan-1-amine |
| 93 | DL5174 | | N-((6-(naphthalen-2-yl)imidazo[2,1-b]oxazol-5-yl)methyl)-2,3-dihydro-1H-indene-2-carboxamide |

TABLE 1-continued
| Entry No. | Compound No. | Compound | Chemical Name |
|---|---|---|---|
| 94 | DL5166 | 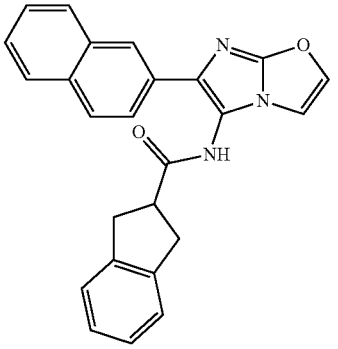 [SMILES: O=C(Nc1c(-c2ccc3ccccc3c2)nc2occn12)C1Cc2ccccc2C1] | N-(6-(naphthalen-2-yl)imidazo[2,1-b]oxazol-5-yl)-2,3-dihydro-1H-indene-2-carboxamide |
| 95 | DL6018 | 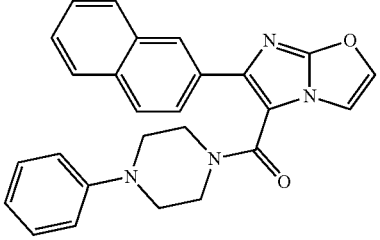 [SMILES: O=C(c1c(-c2ccc3ccccc3c2)nc2occn12)N1CCN(c2ccccc2)CC1] | (6-(naphthalen-2-yl)imidazo[2,1-b]oxazol-5-yl)(4-phenylpiperazin-1-yl)methanone |
| 96 | DL6031 | 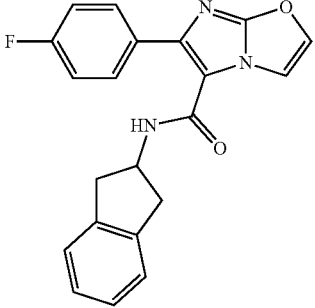 [SMILES: O=C(NC1Cc2ccccc2C1)c1c(-c2ccc(F)cc2)nc2occn12] | N-(2,3-dihydro-1H-inden-2-yl)-6-(4-fluorophenyl)imidazo[2,1-b]oxazole-5-carboxamide |
| 97 | DL6016 | 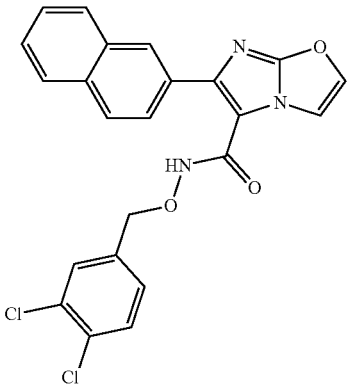 | N-((3,4-dichlorobenzyl)oxy)-6-(naphthalen-2-yl)imidazo[2,1-b]oxazole-5-carboxamide |

TABLE 1-continued
| Entry No. | Compound No. | Compound | Chemical Name |
|---|---|---|---|
| 98 | DL6037 | 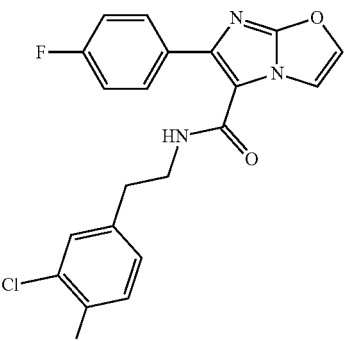 | N-(3,4-dichlorophenethyl)-6-(4-fluorophenyl)imidazo[2,1-b]oxazole-5-carboxamide |
| 99 | DL6017 | 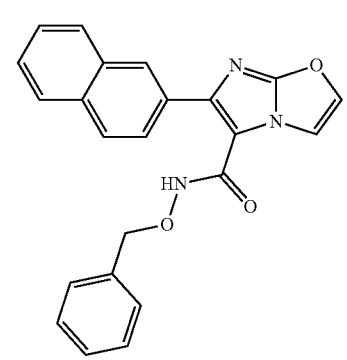 [SMILES: O=C(NOCc1ccccc1)c1c(-c2ccc3ccccc3c2)nc2occn12] | N-(benzyloxy)-6-(naphthalen-2-yl)imidazo[2,1-b]oxazole-5-carboxamide |
| 100 | DL6030 | 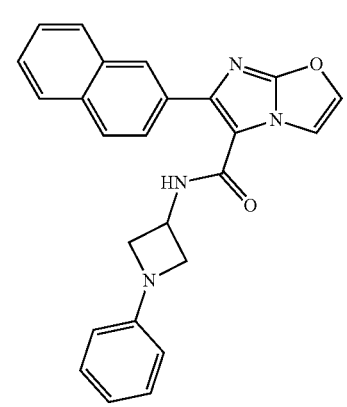 [SMILES: O=C(NC1CN(c2ccccc2)C1)c1c(-c2ccc3ccccc3c2)nc2occn12] | 6-(naphthalen-2-yl)-N-(1-phenylazetidin-3-yl)imidazo[2,1-b]oxazole-5-carboxamide |
| 101 | DL6072 | 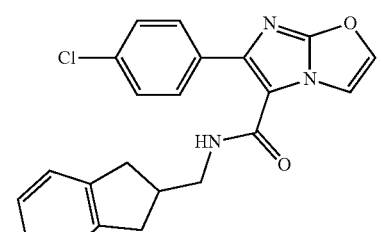 | 6-(4-chlorophenyl)-N-((2,3-dihydro-1H-inden-2-yl)methyl)imidazo[2,1-b]oxazole-5-carboxamide |

TABLE 1-continued

| Entry No. | Compound No. | Compound | Chemical Name |
|---|---|---|---|
| 102 | DL6068 | 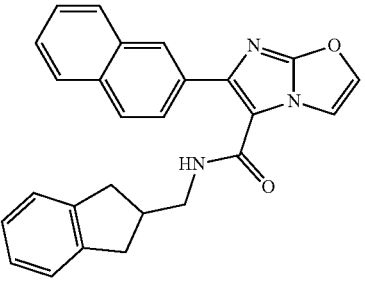 [SMILES: O=C(NCC1Cc2ccccc2C1)c1c(-c2ccc3ccccc3c2)nc2occn12] | N-((2,3-dihydro-1H-inden-2-yl)methyl)-6-(naphthalen-2-yl)imidazo[2,1-b]oxazole-5-carboxamide |
| 103 | DL6070 | 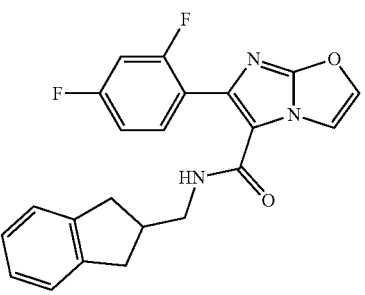 [SMILES: O=C(NCC1Cc2ccccc2C1)c1c(-c2ccc(F)cc2F)nc2occn12] | 6-(2,4-difluorophenyl)-N-((2,3-dihydro-1H-inden-2-yl)methyl)imidazo[2,1-b]oxazole-5-carboxamide |
| 104 | DL6061 | 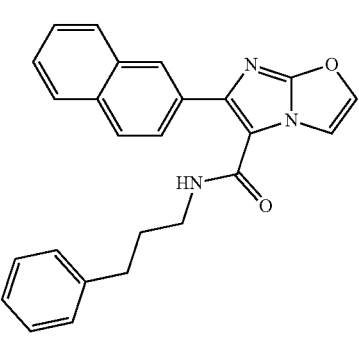 [SMILES: O=C(NCCCc1ccccc1)c1c(-c2ccc3ccccc3c2)nc2occn12] | 6-(naphthalen-2-yl)-N-(3-phenylpropyl)imidazo[2,1-b]oxazole-5-carboxamide |
| 105 | DL6056 | 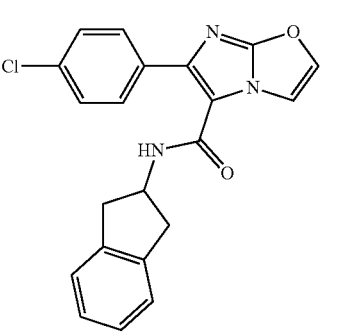 [SMILES: O=C(NC1Cc2ccccc2C1)c1c(-c2ccc(Cl)cc2)nc2occn12] | 6-(4-chlorophenyl)-N-(2,3-dihydro-1H-inden-2-yl)imidazo[2,1-b]oxazole-5-carboxamide |
| 106 | DL6071 | 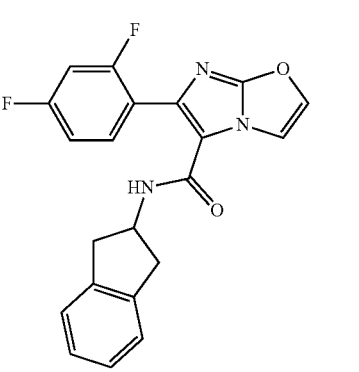 [SMILES: O=C(NC1Cc2ccccc2C1)c1c(-c2ccc(F)cc2F)nc2occn12] | 6-(2,4-difluorophenyl)-N-(2,3-dihydro-1H-inden-2-yl)imidazo[2,1-b]oxazole-5-carboxamide |

TABLE 1-continued

| Entry No. | Compound No. | Compound | Chemical Name |
|---|---|---|---|
| 107 | DL6038 | | N-(3,4-dichlorophenethyl)-6-(naphthalen-2-yl)imidazo[2,1-b]oxazole-5-carboxamide |
| 108 | DL5014 | | (E)-6-(naphthalen-2-yl)imidazo[2,1-b]thiazole-5-carbaldehyde O-(3,4-dichlorobenzyl) oxime |
| 109 | DL5065 | | (E)-6-(3-chlorophenyl)imidazo[2,1-b]thiazole-5-carbaldehyde O-(3,4-dichlorobenzyl) oxime |
| 110 | DL5096-4 | | (E)-6-(naphthalen-2-yl)imidazo[2,1-b]oxazole-5-carbaldehyde O-(4-methoxybenzyl) oxime |

TABLE 1-continued

| Entry No. | Compound No. | Compound | Chemical Name |
|---|---|---|---|
| 111 | DL5016A | | 2-(isoindolin-2-yl)-1-(6-(naphthalen-2-yl)imidazo[2,1-b]oxazol-5-yl)ethan-1-one |
| 112 | DL5016B | | 5-(1,1-difluoro-2-(isoindolin-2-yl)ethyl)-6-(naphthalen-2-yl)imidazo[2,1-b]oxazole |
| 113 | DL5016C | | N-(6-(naphthalen-2-yl)imidazo[2,1-b]oxazol-5-yl)isoindoline-2-carboxamide |
| 114 | DL5161 | | 5-(((2,3-dihydro-1H-inden-2-yl)oxy)methyl)-6-(naphthalen-2-yl)imidazo[2,1-b]oxazole |

TABLE 1-continued

| Entry No. | Compound No. | Compound | Chemical Name |
|---|---|---|---|
| 115 | DL5016E | | 5-(((2,3-dihydro-1H-inden-2-yl)oxy)difluoromethyl)-6-(naphthalen-2-yl)imidazo[2,1-b]oxazole |
| 116 | DL5113 | | 2,3-dihydro-1H-inden-2-yl 6-(naphthalen-2-yl)imidazo[2,1-b]oxazole-5-carboxylate |
| 117 | DL5121 | | N-(2,3-dihydro-1H-inden-2-yl)-6-(naphthalen-2-yl)imidazo[2,1-b]oxazole-5-carboxamide |
| 118 | DL5118 | | N-((2,3-dihydro-1H-inden-2-yl)oxy)-6-(naphthalen-2-yl)imidazo[2,1-b]oxazole-5-carboxamide |

TABLE 1-continued

| Entry No. | Compound No. | Compound | Chemical Name |
|---|---|---|---|
| 119 | 6000 | 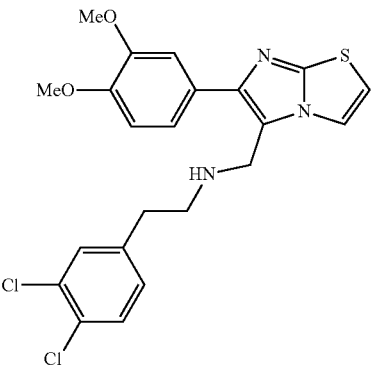 [SMILES: COc1ccc(-c2nc3sccn3c2CNCCc2ccc(Cl)c(Cl)c2)cc1OC] | 2-(3,4-dichlorophenyl)-N-((6-(3,4-dimethoxyphenyl)imidazo[2,1-b]thiazol-5-yl)methyl)ethan-1-amine |
| 120 | 6001 | 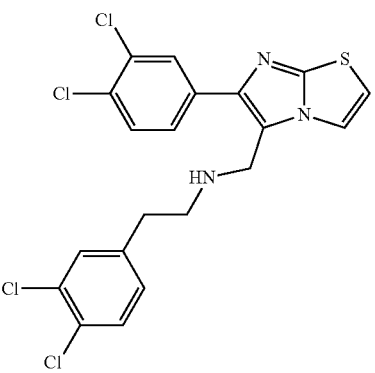 [SMILES: Clc1ccc(CCNCc2c(-c3ccc(Cl)c(Cl)c3)nc3sccn23)cc1Cl] | 2-(3,4-dichlorophenyl)-N-((6-(3,4-dichlorophenyl)imidazo[2,1-b]thiazol-5-yl)methyl)ethan-1-amine |
| 121 | 6002 | 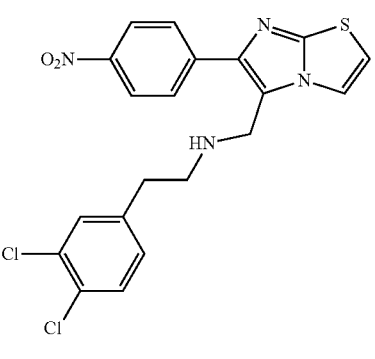 [SMILES: O=[N+]([O-])c1ccc(-c2nc3sccn3c2CNCCc2ccc(Cl)c(Cl)c2)cc1] | 2-(3,4-dichlorophenyl)-N-((6-(4-nitrophenyl)imidazo[2,1-b]thiazol-5-yl)methyl)ethan-1-amine |
| 123 | 6003 | 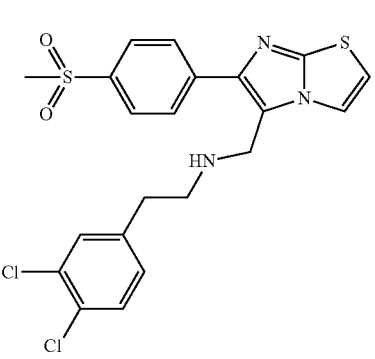 [SMILES: CS(=O)(=O)c1ccc(-c2nc3sccn3c2CNCCc2ccc(Cl)c(Cl)c2)cc1] | 2-(3,4-dichlorophenyl)-N-((6-(4-(methylsulfonyl)phenyl)imidazo[2,1-b]thiazol-5-yl)methyl)ethan-1-amine |

TABLE 1-continued

| Entry No. | Compound No. | Compound | Chemical Name |
|---|---|---|---|
| 124 | DL4120 | | 5-((chloro(3,4-dichlorophenethyl)-l5-azanyl)methyl)-6-(4-chlorophenyl)imidazo[2,1-b]thiazole |
| 125 | DL4177 | | N-((6-(naphthalen-2-yl)imidazo[2,1-b]thiazol-5-yl)methyl)-2-phenylethan-1-amine |
| 126 | DL5055 | | N-(2,3-dihydro-1H-inden-2-yl)-6-(naphthalen-2-yl)imidazo[2,1-b]oxazole-5-carboxamide |

Pharmaceutical Compositions and Routes of Administration

In one embodiment, the disclosure provides a pharmaceutical composition for use in the treatment of the diseases and conditions described herein. In a preferred embodiment, the disclosure provides pharmaceutical compositions, including those described below, for use in the treatment of hematological malignancy. In one embodiment, the disclosure provides a pharmaceutical composition comprising a compound of Formula (I). In one embodiment, the disclosure provides a pharmaceutical composition comprising a compound of Formula (II). In one embodiment, the disclosure provides a pharmaceutical composition comprising a compound included in Table 1.

Any compound disclosed herein, for example a compound included in Table 1, may be administered to a subject by itself, or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients, or auxiliaries which facilitate processing of the compounds into preparations which can be used pharmaceutically. A specific formulation method will be dependent upon the route of administration chosen.

The pharmaceutical compositions are typically formulated to provide a therapeutically effective amount of a novel hCAR activator as described herein, for example in Table 1, or a fragment, derivative, conjugate, variant, radioisotope-labeled complex, or biosimilar thereof, or pharmaceutically acceptable salts, prodrugs, solvates, or hydrates thereof, as the active ingredients. Where desired, the pharmaceutical compositions contain a pharmaceutically acceptable salt and/or coordination complex of one or more of the active ingredients.

Where desired, other active pharmaceutical ingredient(s) may be mixed into a preparation or two or more components of the combination may be formulated into separate preparations for use in combination separately or at the same time. A kit containing the components of the combination, formulated into separate preparations for said use, is also provided by the invention.

Where desired, other active pharmaceutical ingredient(s) may be mixed into a preparation or two or more components of the combination may be formulated into separate preparations for use in combination separately or at the same time. A kit containing the components of the combination, formulated into separate preparations for said use, is also provided by the invention.

In some embodiments, the concentration of any one of the hCAR activators described herein, for example an hCAR activator included in Table 1, provided in a pharmaceutical composition of the invention, is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v of the pharmaceutical composition.

In some embodiments, the concentration of any one of the hCAR activators described herein, for example an hCAR activator included in Table 1, provided in a pharmaceutical composition of the invention, is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v of the pharmaceutical composition.

In some embodiments, the concentration of any one of the hCAR activators described herein, for example an hCAR activator included in Table 1, provided in a pharmaceutical composition of the invention, is independently in the range from about 0.0001% to about 50%, from about 0.001% to about 40%, from about 0.01% to about 30%, from about 0.02% to about 29%, from about 0.03% to about 28%, from about 0.04% to about 27%, from about 0.05% to about 26%, from about 0.06% to about 25%, from about 0.07% to about 24%, from about 0.08% to about 23%, from about 0.09% to about 22%, from about 0.1% to about 21%, from about 0.2% to about 20%, from about 0.3% to about 19%, from about 0.4% to about 18%, from about 0.5% to about 17%, from about 0.6% to about 16%, from about 0.7% to about 15%, from about 0.8% to about 14%, from about 0.9% to about 12%, or from about 1% to about 10% w/w, w/v, or v/v of the pharmaceutical composition.

In some embodiments, the concentration of any one of the hCAR activators described herein, for example an hCAR activator included in Table 1, provided in a pharmaceutical composition of the invention, is independently in the range from about 0.001% to about 10%, from about 0.01% to about 5%, from about 0.02% to about 4.5%, from about 0.03% to about 4%, from about 0.04% to about 3.5%, from about 0.05% to about 3%, from about 0.06% to about 2.5%, from about 0.07% to about 2%, from about 0.08% to about 1.5%, from about 0.09% to about 1%, from about 0.1% to about 0.9% w/w, w/v, or v/v of the pharmaceutical composition.

In some embodiments, the amount or dose of any one of the hCAR activators described herein, for example an hCAR activator included in Table 1, provided in a pharmaceutical composition of the invention, is independently equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount or dose of any one of the hCAR activators described herein, for example an hCAR activator included in Table 1, provided in a pharmaceutical composition of the invention, is independently more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5, about 3 g, about 3.5, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

Each of the hCAR activators described herein, for example an hCAR activator included in Table 1, is effective over a wide dosage range. For example, in the treatment of adult humans, dosages independently ranging from about 0.01 to about 1000 mg, from about 0.5 to about 100 mg, from about 1 to about 50 mg per day, and from about 5 to about 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Cyclophosphamide (CPA), an alkylating prodrug, has been used extensively in the treatment of various types of cancers. CPA is a mainstay of numerous drug combinations, most importantly the CHOP regimen. CHOP is named after the initials of the drugs used which are CPA, doxorubicin, Oncovin (vincristine), and prednisone. CHOP consists of CAP, an alkylating agent which damages DNA by binding to it and causing the formation of cross-links hydroxydaunorubicin (also called doxorubicin or adriamycin), an intercalating agent which damages DNA by inserting itself between DNA bases Oncovin (vincristine), which prevents cells from duplicating by binding to the protein tubulin prednisone or prednisolone, which are corticosteroids. CHOP is the first-line chemotherapy for non-Hodgkin's lymphoma and a number of other hematologic malignancies. A unit dose of CHOP consists of 750-1200 mg/m$^2$ of CPA, 50-75 mg mg/m$^2$ of doxorubicin, 1.4 mg/m$^2$ (maximum 2 mg) of vincristine and 40-100 mg/m$^2$ of prednisone.

In one aspect, the disclosure relates generally to novel compounds/agents which can enhance the therapeutic efficacy of cyclophosphamide-based chemotherapy, pharmaceutical compositions comprising such novel compounds/agents and methods of use thereof.

In another aspect, the disclosure provides combination therapies for the treatment of cancer. In particular, the disclosure provides combination therapies of known CYP2B6 substrate anticancer agent e.g. cyclophosphamide for treating cancer. In one aspect the disclosure provides compositions and methods for treating cancer with a human constitutively active receptor (hCAR) activator that induces the expression of CYP2B6, e.g., DL5016 in combination with a cyclophosphamide-based chemotherapy. Such combination provides sensitization effects in the treatment of cancers and particularly treatment of hematologic malignancies.

In another aspect the disclosure provides novel compounds of hCAR activator, such as DL5016 from Table 1 acting as a selective hCAR activator that potentiates the efficacy: toxicity ratio of CPA-based chemotherapy to facilitate cyclophosphamide (CPA)-based chemotherapy for hematologic malignancies. DL5016 induced hCAR activation potentiates the benefits of CPA, without altering its side effect profile. These new class of hCAR activator compounds have utility as novel therapeutic agents sensitizing CPA-based chemotherapy in clinics.

In another aspect the disclosure provides the methods for synthesis of these new molecules, including DL5016 and DL5055. In a further aspect the disclosure provides biological effects of compounds, e.g., DL5016 on the selective induction of CYP2B6 over CYP3A4 at both mRNA and protein levels.

A further embodiment of the pharmaceutical composition comprises the hCAR activators described herein, for example the hCAR activators included in Table 1, a pharmaceutically acceptable salt, solvate, hydrate, cocrystal, or prodrug thereof, at least one oxazaphosphorine class of antineoplastic agent based chemotherapy, and a physiologically compatible carrier.

In a further embodiment, the disclosure provides pharmaceutical compositions comprising the combination of novel hCAR activators from Table 1 with cyclophosphamide for the treatment of non-Hodgkin lymphoma, chronic lymphocytic leukemia, triple negative breast cancers, and other solid tumors.

In one embodiment, the disclosure provides pharmaceutical compositions including the combination of novel hCAR activators from Table 1 with cyclophosphamide for the treatment of hematologic malignancies. In one embodiment, the disclosure provides pharmaceutical compositions including the combination of novel hCAR activators from Table 1 with cyclophosphamide-based chemotherapy regimen (e.g. CHOP) for the treatment of non-Hodgkin lymphoma, chronic lymphocytic leukemia, triple negative breast cancers, and other solid tumors. In one embodiment, the disclosure provides the combination of an hCAR activator of Table 1, a pharmaceutically acceptable salt, solvate, hydrate, cocrystal, or prodrug thereof, and a CPA based chemotherapy. In one embodiment, the disclosure provides the combination of an hCAR activator of Table 1, a pharmaceutically acceptable salt, solvate, hydrate, cocrystal, or prodrug thereof and the CHOP treatment regimen.

Described below are non-limiting pharmaceutical compositions and methods for preparing the same.

Pharmaceutical Compositions for Oral Administration

In preferred embodiments, the invention provides a pharmaceutical composition for oral administration containing one or more hCAR activators described herein, for example an hCAR activator included in Table 1, and a pharmaceutical excipient suitable for administration. In other embodiments, the invention provides a pharmaceutical composition for oral administration containing one or more hCAR activators of Table 1 according to the invention, a pharmaceutical excipient suitable for administration, and one or more additional active pharmaceutical ingredient.

In some embodiments, the pharmaceutical composition may be a solid pharmaceutical composition suitable for oral consumption. In some embodiments, the pharmaceutical composition may be a liquid pharmaceutical composition suitable for oral consumption.

Pharmaceutical compositions of the invention suitable for oral administration can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the hCAR activators described herein, for example the hCAR activators included in Table 1, used as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of about 10%, about 25%, about 50%, about 100%, or up to about 200% by weight, based on the combined weight of the drug, and other excipients. If desired, very small amounts of solubilizer may also be used, such as about 5%, about 2%, about 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not be limited to, sodium, potassium, lithium, magnesium, calcium, and/or ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the invention provides a pharmaceutical composition for injection containing an hCAR activator described herein, for example an hCAR activator included in Table 1, according to the invention, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating an hCAR activator described herein, for example an hCAR activator included in Table 1, according to the invention, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, the invention provides a pharmaceutical composition for transdermal delivery containing an hCAR activator described herein, for example an hCAR activator included in Table 1, according to the invention, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the compounds of the invention, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

In some embodiments, the invention provides a pharmaceutical composition for inhalation or insufflation delivery containing an hCAR activator described herein, for example an hCAR activator included in Table 1, according to the invention. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of an hCAR activator described herein, for example an hCAR activator included in Table 1, according to the invention, or pharmaceutical compositions of these compounds, can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The compounds or compositions thereof can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include each of an hCAR activator described herein, for example an hCAR activator included in Table 1, according to the invention, or pharmaceutical compositions thereof, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient.

Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, the invention provides a kit comprising a composition comprising a therapeutically effective amount of an hCAR activator described herein, for example an hCAR activator included in Table 1, according to the invention, or a fragment, derivative, conjugate, variant, radioisotope-labeled complex, biosimilar, pharmaceutically acceptable salt, solvate, hydrate, cocrystal, or prodrug thereof. These compositions are typically pharmaceutical compositions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery system may be employed. Liposomes and emulsions are well known examples of delivery vehicles that may be used to deliver the compounds of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. A variety of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed. As the compounds of the invention may contain charged side chains or termini, they may be included in any of the above-described formulations as the free acids or bases or as pharmaceutically acceptable salts. Pharmaceutical salts tend to be more soluble in aqueous and other protic solvents than are the corresponding free acid or base forms.

The methods of the present invention will normally include medical follow-up to determine the therapeutic or prophylactic effect brought about in the patient undergoing treatment with the compound(s) and/or composition(s) described herein. Efficacy of the methods may be assessed on the basis of tumor regression, e.g., reducing the size and/or number of neoplasms, inhibition of tumor metastasis, decrease in a serological marker of disease, or other indicator of an inhibitory or remedial effect.

Dosages and Dosing Regimens

The amount of the hCAR activator described herein, for example an hCAR activator included in Table 1, to be administered, will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day. The dosage of the hCAR activator may be provided in units of mg/kg of body mass, or in mg/m$^2$ of body surface area.

In some embodiments, the hCAR activator described herein, for example an hCAR activator included in Table 1, is administered in a single dose. Such administration may be by injection, e.g., intravenous injection, in order to introduce the hCAR activator quickly. However, other routes, including the oral route, may be used as appropriate. A single dose of the hCAR activator may also be used for treatment of an acute condition.

In some embodiments, the hCAR activator described herein, for example an hCAR activator included in Table 1, is administered in multiple doses. In a preferred embodiment, the hCAR activator is administered in multiple doses. Dosing may be once, twice, three times, four times, five times, six times, or more than six times per day. Dosing may be once a month, once every two weeks, once a week, or once every other day. In other embodiments, the hCAR activator described herein, for example an hCAR activator included in Table 1, is administered about once per day to about 6 times per day. In some embodiments, the hCAR activator described herein, for example an hCAR activator included in Table 1, is administered once daily, while in other embodiments, the hCAR activator described herein, for example an hCAR activator included in Table 1, is administered twice daily, and in other embodiments the hCAR activator described herein, for example an hCAR activator included in Table 1, is administered three times daily.

Administration of the active pharmaceutical ingredients of the invention may continue as long as necessary. In some embodiments, the hCAR activator described herein, for example an hCAR activator included in Table 1, is administered for more than 1, 2, 3, 4, 5, 6, 7, 14, or 28 days. In some embodiments, the hCAR activator is administered for less than 28, 14, 7, 6, 5, 4, 3, 2, or 1 day. In some embodiments, the hCAR activator is administered chronically on an ongoing basis, e.g., for the treatment of chronic effects. In another embodiment the administration of the hCAR activator continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an hCAR activator described herein, for example an hCAR activator included in Table 1, is in the range of about 1 mg to about 50 mg, about 5 mg to about 45 mg, about 10 mg to about 40 mg, about 15 mg to about 35 mg, about 20 mg to about 30 mg, about 23 mg to about 28 mg, about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, about 198 to about 202 mg, or about 198 to about 207 mg.

In some embodiments, an effective dosage of an hCAR activator described herein, for example an hCAR activator included in Table 1, is about 25 mg, about 50 mg, about 75 mg, about 100 mg, about 125 mg, about 150 mg, about 175 mg, about 200 mg, about 225 mg, or about 250 mg.

In some embodiments, an effective dosage of an hCAR activator described herein, for example an hCAR activator included in Table 1, is in the range of about 0.01 mg/kg to about 0.7 mg/kg, about 0.07 mg/kg to about 0.65 mg/kg, about 0.15 mg/kg to about 0.6 mg/kg, about 0.2 mg/kg to about 0.5 mg/kg, about 0.3 mg/kg to about 0.45 mg/kg, about 0.3 mg/kg to about 0.4 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg to about 1.6 mg/kg, about 1.35 mg/kg to about 1.5 mg/kg, about 1.4 mg/kg to about 1.45 mg/kg, about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of an hCAR activator described herein, for example an hCAR activator included in Table 1, is about 0.35 mg/kg, about 0.4 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of the combination of an hCAR activator described herein, for example an hCAR activator included in Table 1, may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Methods of Treating Hematological Malignancies and Solid Tumors

In some embodiments, the invention relates to a method of treating a disease alleviated by activating hCAR enzyme in a patient in need thereof, including administering to the patient a therapeutically effective amount of one or more compounds of Formula (I) and/or Formula (II), or a pharmaceutically acceptable salt, solvate, hydrate, cocrystal, or prodrug thereof.

In some embodiments, the invention relates to a method of treating a disease alleviated by activating hCAR enzyme in a patient in need thereof, including administering to the patient a therapeutically effective amount of one or more compounds of Formula (I) and/or (II) or a pharmaceutically acceptable salt, solvate, hydrate, cocrystal, or prodrug thereof.

In some embodiments, the invention relates to a method of treating a disease alleviated by activating hCAR enzyme in a patient in need thereof, including administering to the patient a therapeutically effective amount of one or more compounds of Formulas (I) and (II), or a pharmaceutically acceptable salt, solvate, hydrate, cocrystal, or prodrug thereof.

In a preferred embodiment, the patient or subject is a mammal, such as a human. In an embodiment, the patient or subject is a human. In an embodiment, the patient or subject is a companion animal. In an embodiment, the patient or subject is a canine, feline, or equine.

In some embodiments, the invention relates to a method of treating a disease alleviated by activating hCAR enzyme, in a patient in need thereof, including administering to the patient dosage unit form including a therapeutically effective amount of one or more compounds of Formulas (I) and (II), or a pharmaceutically acceptable salt, solvate, hydrate, cocrystal, or prodrug thereof. In some embodiments, the dosage unit form includes a physiologically compatible carrier medium.

In some embodiments, the invention relates to a method of treating a cancer alleviated by activating hCAR enzyme, in a patient in need thereof, including administering to the patient a therapeutically effective amount of one or more compounds of Formulas (I) and (II), or a pharmaceutically acceptable salt, solvate, hydrate, cocrystal, or prodrug thereof.

In some embodiments, the hematological malignancies can be breast cancer, non-Hodgkin lymphoma, and chronic lymphocytic leukemia.

Combinations of hCAR Activators with CPA Based Treatment Regimen

The hCAR activator described herein can also be co-administered with additional chemotherapeutic active pharmaceutical ingredients, for example doxorubicin, vincristine, and prednisone. In a preferred embodiment, the invention provides a method of treating a hematological malignancy or a solid tumor cancer in a human including the step of administering to said human hCAR activator, and further including the step of administering a therapeutically-effective amount of gemcitabine, or a pharmaceutically acceptable salt, prodrug, cocrystal, solvate or hydrate thereof. In an embodiment, the invention provides a method of treating a hematological malignancy or a solid tumor cancer in a human including the step of administering to said human a hCAR activator described herein, or a pharmaceutically acceptable salt, prodrug, cocrystal, solvate or hydrate thereof, and further including the step of administering a therapeutically-effective amount of gemcitabine, or a pharmaceutically acceptable salt, prodrug, cocrystal, solvate or hydrate thereof. In an embodiment, the solid tumor cancer in any of the foregoing embodiments is pancreatic cancer.

As used herein, the term "combination" or "pharmaceutical combination" refers to the combined administration of therapeutic agents, for example an hCAR activator and an anticancer agent. Combinations of the disclosure include an hCAR activator described herein, for example as described in Table 1, and at least one anticancer agent, for example CPA. The term "synergistic" or "synergistic effect" or "synergism" as used herein, generally refers to an effect such that the one or more effects of the combination of compositions is greater than the one or more effects of each component alone, or they can be greater than the sum of the one or more effects of each component alone. The synergistic effect can be greater than about 10%, 20%, 30%, 50%, 75%, 100%, 110%, 120%, 150%, 200%, 250%, 350%, or 500%, or more than the effect on a subject with one of the components alone, or the additive effects of each of the components when administered individually. The effect can be any of the measurable effects described herein. Advantageously, such synergy between the agents when combined, may allow for the use of smaller doses of one or both agents, may provide greater efficacy at the same doses, and may prevent or delay the build-up of multi-drug resistance. The combination index (CI) method of Chou and Talalay may be used to determine the synergy, additive or antagonism effect of the agents used in combination. When the CI value is less than 1, there is synergy between the compounds used in the combination; when the CI value is equal to 1, there is an additive effect between the compounds used in the combination and when CI value is more than 1, there is an antagonistic effect. The synergistic effect may be attained by co-formulating the agents of the pharmaceutical combination. The synergistic effect may be attained by administering two or more agents as separate formulations administered simultaneously or sequentially.

In any of the foregoing embodiments, the chemotherapeutic active pharmaceutical ingredient, for example CPA, or combinations thereof, may be administered before, concurrently, or after administration of the hCAR activator described herein.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

I. Chemical Synthesis Methods

The compounds of this invention may be made by various methods known in the art. Such methods include those of the following reaction schemes, as well as the methods specifically exemplified below. Modifications of such methods and schemes that involve techniques commonly practiced in the art of organic synthesis may also be used. The variable numbering and structure numbering shown in the synthetic schemes are distinct from, and should not be confused with, the variables or structure numbering in the claims or other parts of the specification. The variables in the schemes are meant only to illustrate how to make certain of the compounds of this invention. General routes suitable to prepare chemical species exemplified herein are shown in the schemes 1-4 below. The reagents and starting materials are commercially available, or readily synthesized by well-known techniques by one of ordinary skill in the art. All preparative methods disclosed herein are contemplated to be implemented on any scale, including milligram, gram, multigram, kilogram, multikilogram or commercial industrial scale.

Abbreviations

The symbols and conventions used in the reaction schemes and preparative examples set forth below are consistent with those used in the contemporary scientific literature, for example, the journal of the American Chemical Society or the Journal of Biological Chemistry. Specifically, the following abbreviations may be used in the examples and throughout the specification:

g (grams);
DCM (dichloromethane);
EtOAc (ethylacetate);
$NaHCO_3$ (sodium bicarbonate);
$Na_2SO_4$ (sodium sulfate);
$POCl_3$ (phosphoryl chloride);
EtOH (ethanol);
DMF (N,N-dimethylformamide);
$CHCl_3$ (chloroform);
AcOH (acetic acid);
$H_2O$ (water);
THF (tetrahydrofuran);
EDCI (1-Ethyl-3-(3-dimethylaminopropylcarbodiimide);
DMAP (4-Dimethylaminopyridine);
$CH_3OH$ (methanol);
$K_2CO_3$ (potassium carbonate);
EA/HE (ethyl acetate/hexane);
h (hour);
mg (milligrams);
mL (milliliters);
mmol (millimole);
equiv. (equivalent);
Ac (acetyl);
Et (ethyl);
TLC (thin-layer chromatography);
HPLC (high-performance liquid chromatography);
NMR spectra (nuclear magnetic resonance spectroscopy);
$^1H$ NMR (proton nuclear magnetic resonance spectroscopy);
$^{13}C$ NMR (carbon 13 nuclear magnetic resonance spectroscopy);
UV spectra (ultra violet spectra);
HRMS (high-resolution mass spectra);
ESI (electron spray ionization);
APCI (atmospheric pressure chemical ionization);
Vilsmeier reagent (chloromethylene)dimethyliminium chloride;
Arnold's reagent, dimethylchloroformiminium chloride).

The following examples describe the invention in further detail, with reference to specific embodiments. These are representative embodiments of the invention which are provided for illustrative purposes only, and which should not be regarded as limiting the invention in any way.

Unless otherwise indicated in the examples, all temperature is expressed in Centigrade (C). All reactions were conducted under an inert atmosphere at ambient temperature unless otherwise noted. Reagents employed without synthetic details are commercially available or made according to literature procedures.

General Procedures

All reagents and solvents were of analytical grade and used without further purification. NMR spectra were obtained on a Varian INOVA 400 MHz NMR spectrometer at 25° C. Chemical shifts are reported as δ values (parts per million) using the residual solvent peak as an internal reference. Data for $^1H$ NMR are reported in the following order: chemical shift, multiplicity (s, singlet; d, doublet; t, triplet; sept, septuplet; dd, double doublet; dt, double triplet; m, multiplet), coupling constant (Hz), number of protons. Data for $^{13}C$ NMR are reported as δ values (parts per million). UV spectra were obtained on a Nanodrop 2000c spectrophotometer. High-resolution mass spectra (HRMS) were obtained on a JEOL AccuTOF with ESI/APCI ion sources coupled to an Agilent 1100 HPLC system. HPLC analysis was performed on a Shimadzu HPLC fitted with a C-18 reversed-phase column (Phenomenex: 4.6 mm×250 mm) with a flow rate of 0.5 mL/min using $CH_3OH$—$H_2O$ 3:1 with 0.1% N1140Ac mobile phase.

All reactions were monitored by thin-layer chromatography on 0.25 mm E. Merck silica gel plates (60F-254), visualized with UV light, 5% ethanolic phosphomolybdic acid, p-anisaldehyde solution, aqueous potassium permanganate or potassium iodide/platinum chloride solution in water.

1. Synthesis of Aryl Substituted imidazo[2,1-b]thiazole-5-oxime (1)

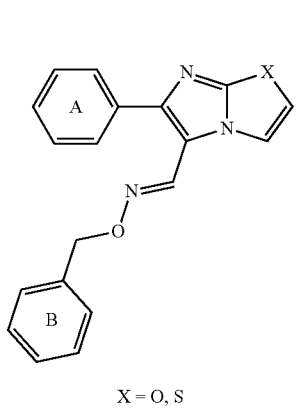

X = O, S

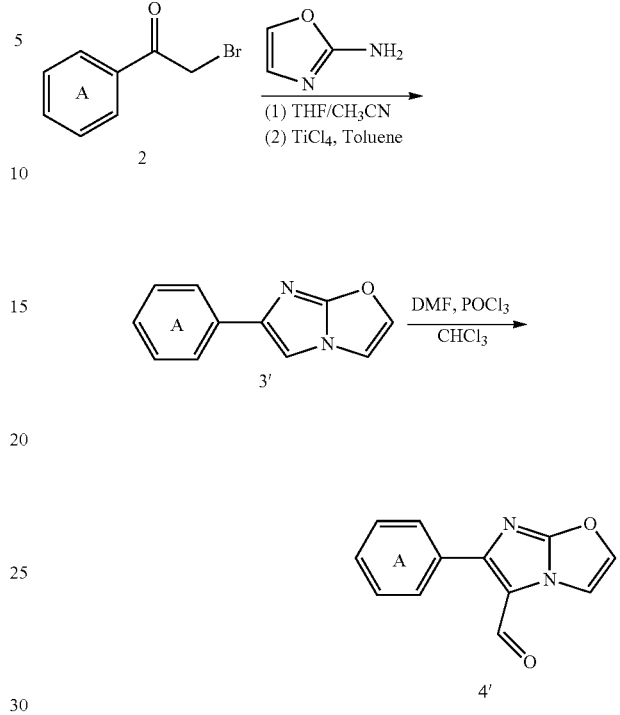

A solution of 2-aminothiazole 2 (5 mmol, 1 equiv) and bromomethylphenyl ketone (5 mmol, 1 equiv) in ethanol (30 mL) was heated under reflux for 16 h. The solvent was removed under reduced pressure, and saturated NaHCO₃ (30 mL) was added to the remaining solid. The mixture was then extracted with EtOAc (30 mL×3), and the organic layers were combined, dried over Na₂SO₄. The concentrated crude product dried overnight under vacuum to get the crude imidazothiazole 3 without purification to do next step.

The Vilsmeier reagent was prepared, under cooling and stirring, by dropping of POCl₃ (16.5 mmol, 3.3 equiv) onto the equivalent of dimethylformamide (DMF) in 5 mL of CHCl₃. The temperature was maintained between 0 and 5° C. and a solution of crude imidazothiazole 3 (5 mmol in 30 ml of CHCl₃) was added dropwise. After 1 h at room temperature, the reaction mixture was refluxed for 9 h; CHCl₃ was eliminated under reduced pressure and the residue was poured onto ice. The crude aldehyde 4 thus obtained was collected by filtration and purified from chromatographic column with a yield of 70-80%.

To a solution of aldehyde 4 (1 mmol) in EtOH (5 mL) was added hydroxylamine 5 (1 mmol) followed by AcOH (5 mmol 5 equiv). The reaction mixture was refluxed over night. After cooled to room temperature, a saturated aqueous solution of NaHCO₃ (30 mL) was added. The aqueous layer was extracted with EtOAc (3×30 mL) and the combined organics were washed with brine (45 mL), dried (Na₂SO₄). The crude material was then purified by flash column chromatography or recrystallized to give the desired product 1.

The oxazole analogs can be prepared in the similar way as those for thiazole analogs in Scheme 1.

Example 1. (E)-6-phenylimidazo[2,1-b]thiazole-5-carbaldehyde O-(3,4-dichlorobenzyl) oxime A. 6-phenylimidazo[2,1-b]thiazole-5-carbaldehyde

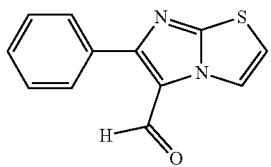 [SMILES: O=Cc1c(-c2ccccc2)nc2sccn12]

$^1$H NMR (400 MHz, CDCl$_3$): δ(ppm) 9.90 (s, 1H), 8.39 (d, J=4.0 Hz, 1H), 7.79 (d, J=6.8 Hz, 2H), 7.50 (d, J=7.2 Hz, 3H), 7.05 (d, J=4.0 Hz, 1H); $^{13}$C NMR (100 MHz, CDCl$_3$): δ(ppm) 178.1, 158.2, 155.6, 132.5, 129.7, 129.1, 128.9, 124.0, 121.5, 114.6.

B. (E)-6-phenylimidazo[2,1-b]thiazole-5-carbaldehyde O-(3,4-dichlorobenzyl) oxime

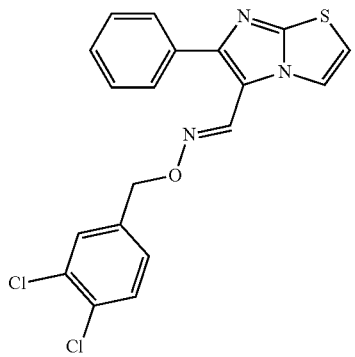
DL5058

Yield 99%, $^1$H NMR (400 MHz, CDCl$_3$): δ(ppm) 8.44 (s, 1H), 8.00 (d, J=4.8 Hz, 1H), 7.66 (d, J=6.8 Hz, 2H), 7.52-7.37 (m, 5H), 7.25 (d, J=8.4 Hz, 1H), 6.91 (d, J=4.8 Hz, 1H), 5.13 (s, 2H); $^{13}$C NMR (100 MHz, CDCl$_3$): δ(ppm) 152.6, 150.6, 140.3, 137.9, 133.3, 132.6, 132.0, 130.5, 130.1, 128.8, 128.4, 127.4, 121.6, 115.6, 112.8, 74.9. HRMS (ESI): Exact mass calcd for C$_{19}$H$_{14}$Cl$_2$N$_3$OS [M+H]$^+$ 402.0234, found 402.0227.

Example 2. (E)-6-(4-fluorophenyl)imidazo[2,1-b]thiazole-5-carbaldehyde O-(3,4-dichlorobenzyl) oxime A. 6-(4-fluorophenyl)imidazo[2,1-b]thiazole-5-carbaldehyde

$^1$H NMR (400 MHz, CDCl$_3$): δ(ppm) 9.86 (s, 1H), 8.38 (d, J=4.8 Hz, 1H), 7.78 (t, J=8.0 Hz, 2H), 7.19 (t, J=7.6 Hz, 2H), 7.07 (d, J=4.0 Hz, 1H); $^{13}$C NMR (100 MHz, CDCl$_3$): δ(ppm) 177.7, 163.8 (J=248.5 Hz), 156.6, 155.4, 130.9 (J=7.4 Hz), 128.3, 123.8, 121.5, 116.2 (J=20.8 Hz), 115.0.

B. (E)-6-(4-fluorophenyl)imidazo[2,1-b]thiazole-5-carbaldehyde O-(3,4-dichlorobenzyl) oxime

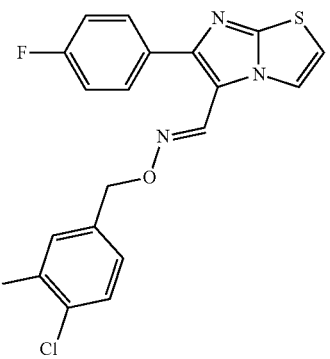
DL5067

Yield 81%. $^1$H NMR (400 MHz, CDCl$_3$): δ(ppm) 8.38 (s, 1H), 7.99 (d, J=3.6 Hz, 1H), 7.64-7.61 (m, 2H), 7.51 (s, 1H), 7.44 (t, J=4.8 Hz, 1H), 7.24 (J=8.4 Hz, 1H), 7.17-7.12 (m, 2H), 6.91 (d, J=4.8 Hz, 1H), 5.13 (s, 2H); $^{13}$C NMR (100 MHz, CDCl$_3$): δ(ppm) 162.9 (J=247 Hz), 152.6, 149.5, 140.0, 137.8, 132.6, 132.0, 130.5, 130.14, 130.06, 129.5, 127.4, 121.5, 115.8 (J=20.8 Hz), 115.5, 112.9, 74.9. HRMS (ESI): Exact mass calcd for C$_{19}$H$_{13}$Cl$_2$FN$_3$OS [M+H]$^+$ 420.0140, found 420.0137.

Example 3. (E)-6-(4-chlorophenyl)imidazo[2,1-b]thiazole-5-carbaldehyde O-(3,4-dichlorobenzyl) oxime A. 6-(4-chlorophenyl)imidazo[2,1-b]thiazole-5-carbaldehyde

$^1$H NMR (400 MHz, CDCl$_3$): δ(ppm) 9.89 (s, 1H), 8.39 (d, J=4.8 Hz, 1H), 7.74 (d, J=8.8 Hz, 2H), 7.49 (d, J=8.4 Hz, 2H), 7.08 (d, J=4.0 Hz, 1H); $^{13}$C NMR (100 MHz, CDCl$_3$): δ(ppm) 177.7, 156.8, 155.7, 136.0, 130.9, 130.2, 129.2, 124.0, 121.5, 114.9.

B. (E)-6-(4-chlorophenyl)imidazo[2,1-b]thiazole-5-carbaldehyde O-(3,4-dichlorobenzyl) oxime

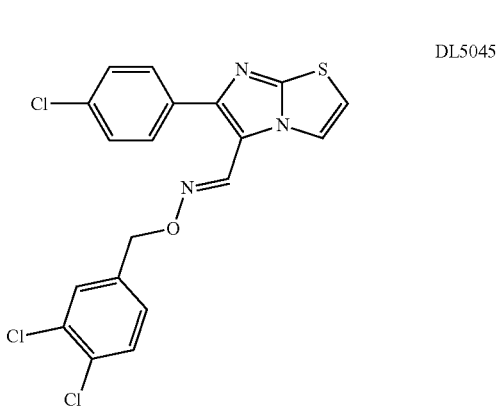 [SMILES: Clc1ccc(-c2nc3sccn3c2/C=N/OCc2ccc(Cl)c(Cl)c2)cc1]

DL5045

Yield 23%. $^1$H NMR (400 MHz, CDCl$_3$): δ(ppm) 8.39 (s, 1H), 7.99 (d, J=7.6 Hz, 1H), 7.59 (d, J=8.0 Hz, 2H), 7.51 (s, 1H), 7.46-7.42 (m, 3H), 7.24 (d, J=8.4 Hz, 1H), 6.92 (d, J=4.4 Hz, 1H), 5.13 (s, 2H); $^{13}$C NMR (100 MHz, CDCl$_3$): δ(ppm) 152.7, 149.3, 139.9, 137.7, 134.5, 132.6, 132.1, 131.9, 130.5, 130.1, 129.5, 129.0, 127.4, 121.5, 115.7, 113.0, 75.0. RMS (ESI): Exact mass calcd for C$_{19}$H$_{13}$Cl$_3$N$_3$OS [M+H]$^+$ 435.9845, found 435.9855.

Example 4. (E)-6-(4-bromophenyl)imidazo[2,1-b]thiazole-5-carbaldehyde O-(3,4-dichlorobenzyl) oxime A. 6-(4-bromophenyl)imidazo[2,1-b]thiazole-5-carbaldehyde

$^1$H NMR (400 MHz, CDCl$_3$): δ(ppm) 9.87 (s, 1H), 8.37 (d, J=4.8 Hz, 1H), 7.67-7.61 (m, 4H), 7.07 (d, J=3.6 Hz, 1H); $^{13}$C NMR (100 MHz, CDCl$_3$): δ(ppm) 177.6, 156.7, 155.7, 132.1, 131.4, 130.5, 124.3, 124.0, 121.5, 114.9.

B. (E)-6-(4-bromophenyl)imidazo[2,1-b]thiazole-5-carbaldehyde O-(3,4-dichlorobenzyl) oxime

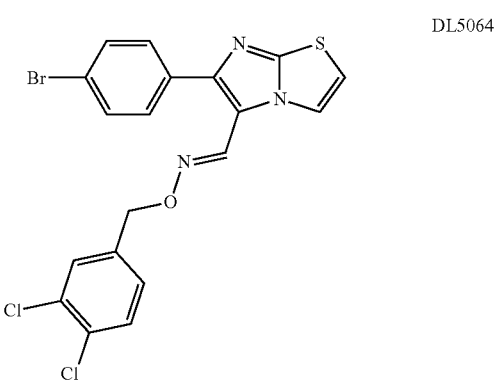 [SMILES: Clc1ccc(CO/N=C/c2c(-c3ccc(Br)cc3)nc3sccn23)cc1Cl]

DL5064

50% yield. $^1$H NMR (400 MHz, CDCl$_3$): δ(ppm) 8.39 (s, 1H), 7.98 (d, J=2.8 Hz, 1H), 7.56-7.44 (m, 6H), 7.24 (d, J=7.6 Hz, 1H), 6.92 (d, J=2.8 Hz, 1H), 5.13 (s, 2H); $^{13}$C NMR (100 MHz, CDCl$_3$): δ(ppm) 152.7, 149.2, 139.9, 137.7, 132.6, 132.5, 132.3, 131.9, 130.5, 130.1, 129.8, 127.4, 122.7, 121.5, 115.7, 113.1, 75.0. HRMS (ESI): Exact mass calcd for C$_{19}$H$_{13}$BrN$_3$OS [M+H]$^+$ 479.9340, found 479.9454.

Example 5. (E)-6-(4-isocyanophenyl)imidazo[2,1-b]thiazole-5-carbaldehyde O-(3,4-dichlorobenzyl) oxime A. 4-(5-formylimidazo[2,1-b]thiazole-6-yl)benzonitrile

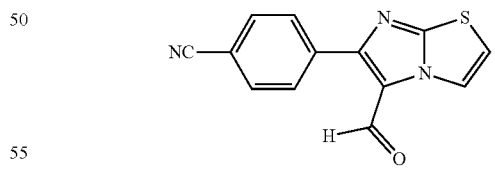

$^1$H NMR (400 MHz, CDCl$_3$): δ(ppm) 9.94 (s, 1H), 8.41 (d, J=4.0 Hz, 1H), 7.93 (d, J=8.0 Hz, 2H), 7.81 (d, J=7.6 Hz, 2H), 7.13 (d, J=4.8 Hz, 1H); $^{13}$C NMR (100 MHz, CDCl$_3$): δ(ppm) 177.3, 155.8, 155.3, 136.8, 132.7, 129.5, 124.4, 121.5, 118.3, 115.6, 113.2.

115

B. (E)-6-(4-isocyanophenyl)imidazo[2,1-b]thiazole-5-carbaldehyde O-(3,4-dichlorobenzyl) oxime

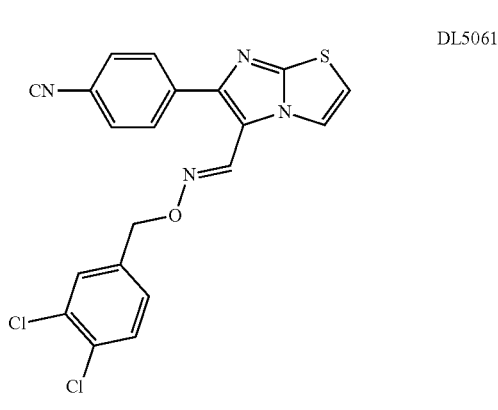

DL5061

Yield 80%. ¹H NMR (400 MHz, CDCl₃): δ(ppm) 8.41 (s, 1H), 8.00 (d, J=2.8 Hz, 1H), 7.76 (d, J=8.4 Hz, 2H), 7.71 (d, J=7.6 Hz, 2H), 7.51 (s, 1H), 7.45 (d, J=8.0 Hz, 1H), 7.24 (d, J=8.4 Hz, 1H), 6.97 (d, J=4.0 Hz, 1H), 5.15 (s, 2H); ¹³C NMR (100 MHz, CDCl₃): δ(ppm) 153.0, 147.8, 139.4, 137.9, 137.6, 132.5, 132.2, 130.6, 130.1, 128.7, 128.1, 127.4, 121.5, 118.7, 116.6, 113.7, 111.7, 75.1. HRMS (ESI): Exact mass calcd for $C_{20}H_{13}Cl_2N_4OS$ [M+H]⁺ 427.0184, found 427.0188.

Example 6. (E)-6-(4-(trifluoromethyl)phenyl)imidazo[2,1-b]thiazole-5-carbaldehyde O-(3,4-dichlorobenzyl) oxime A. 6-(4-(trifluoromethyl)phenyl)imidazo[2,1-b]thiazole-5-carbaldehyde

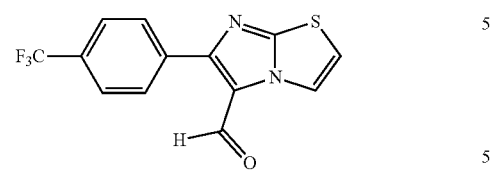

¹H NMR (400 MHz, CDCl₃): δ(ppm) 9.94 (s, 1H), 8.41 (d, J=4.0 Hz, 1H), 7.93 (d, J=8.0 Hz, 2H), 7.81 (d, J=7.6 Hz, 2H), 7.13 (d, J=4.8 Hz, 1H); ¹³C NMR (100 MHz, CDCl₃): δ(ppm) 177.3, 155.8, 155.3, 136.8, 132.7, 129.5, 124.4, 121.5, 118.3, 115.6, 113.2.

116

B. (E)-6-(4-(trifluoromethyl)phenyl)imidazo[2,1-b]thiazole-5-carbaldehyde O-(3,4-dichlorobenzyl) oxime

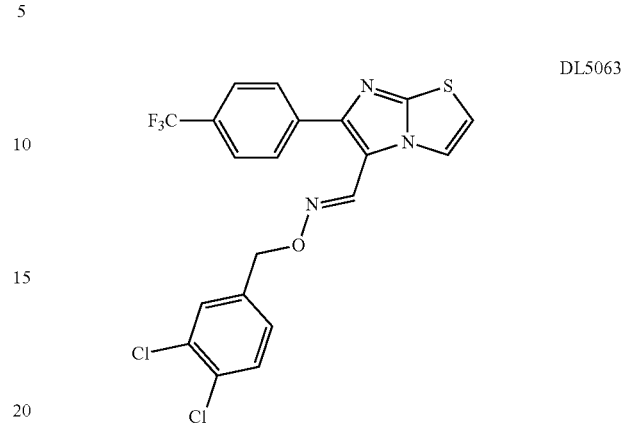

DL5063

Yield 90%. ¹H NMR (400 MHz, CDCl₃): δ(ppm) 8.42 (s, 1H), 8.00 (d, J=4.8 Hz, 1H), 7.78 (d, 1=8.8 Hz, 2H), 7.71 (d, J=8.4 Hz, 2H), 7.52 (s, 1H), 7.45 (d, J=8.8 Hz, 1H), 7.24 (d, J=7.6 Hz, 1H), 6.95 (d, J=4.8 Hz, 1H), 5.14 (s, 2H); ¹³C NMR (100 MHz, CDCl₃): δ(ppm) 152.8, 148.7, 139.7, 137.7, 136.9, 132.6, 132.1, 130.5, 130.3, 130.1, 128.5, 127.4, 126.8 (J=270.9 Hz) 125.7, 121.5, 116.3, 113.4, 75.0. HRMS (ESI): Exact mass calcd. for $C_{20}H_{13}Cl_2F_3N_3OS$ [M+H]⁺ 470.0108, found 470.0100.

Example 7. (E)-6-(p-tolyl)imidazo[2,1-b]thiazole-5-carbaldehyde O-(3,4-dichlorobenzyl) oxime A. 6-(p-tolyl)imidazo[2,1-b]thiazole-5-carbaldehyde

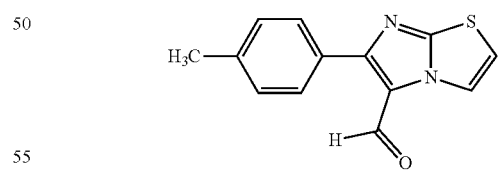

¹H NMR (400 MHz, CDCl₃): δ(ppm) 9.89 (s, 1H), 8.37 (d, J=4.8 Hz, 1H), 7.69 (d, J=8.0 Hz, 2H), 7.31 (d, J=8.0 Hz, 2H), 7.03 (d, J=4.8 Hz, 1H); ¹³C NMR (100 MHz, CDCl₃): δ(ppm) 178.1, 158.4, 155.6, 139.9, 129.7, 129.0, 123.9, 121.5, 114.4, 21.4.

117

B. (E)-6-(p-tolyl)imidazo[2,1-b]thiazole-5-carbaldehyde O-(3,4-dichlorobenzyl) oxime

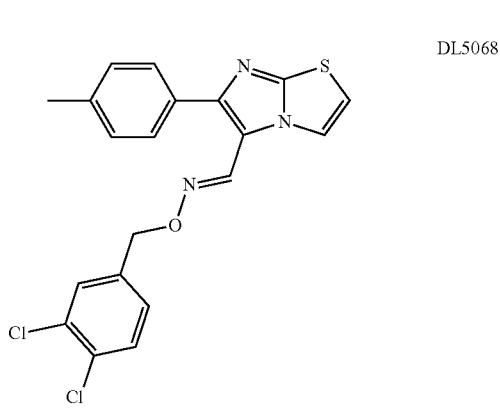

DL5068

Yield 92%, $^1$H NMR (400 MHz, CDCl$_3$): δ(ppm) 8.43 (s, 1H), 7.99 (d, J=4.0 Hz, 1H), 7.56-7.51 (m, 3H), 7.45 (d, J=8.0 Hz, 1H), 7.28-7.24 (m, 3H), 6.89 (d, J=4.0 Hz, 1H), 5.13 (s, 2H), 2.40 (s, 3H); $^{13}$C NMR (100 MHz, CDCl$_3$): δ(ppm) 152.5, 150.8, 140.4, 138.4, 137.9, 132.6, 132.0, 130.5, 130.1, 129.5, 128.3, 127.4, 121.6, 115.3, 112.6, 74.8, 21.3. HRMS (ESI): Exact mass calcd for C$_{20}$H$_{16}$Cl$_2$N$_3$OS [M+H]$^+$ 416.0391, found 416.0384.

Example 8. (E)-6-(4-methoxyphenyl)imidazo[2,1-b]thiazole-5-carbaldehyde O-(3,4-dichlorobenzyl) oxime A. 6-(4-methoxyphenyl)imidazo[2,1-b]thiazole-5-carbaldehyde

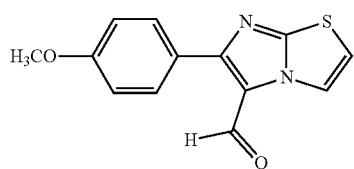 [SMILES: COc1ccc(-c2nc3sccn3c2C=O)cc1]

$^1$H NMR (400 MHz, CDCl$_3$): δ(ppm) 9.88 (s, 1H), 8.37 (d, J=4.8 Hz, 1H), 7.75 (d, J=8.8 Hz, 2H), 7.04-7.02 (m, 3H), 3.88 (s, 3H); $^{13}$C NMR (100 MHz, CDCl$_3$): δ(ppm) 178.0, 161.0, 158.0, 155.5, 130.4, 124.8, 123.6, 121.6, 114.4, 114.3, 55.4.

118

B. (E)-6-(4-methoxyphenyl)imidazo[2,1-b]thiazole-5-carbaldehyde O-(3,4-dichlorobenzyl) oxime

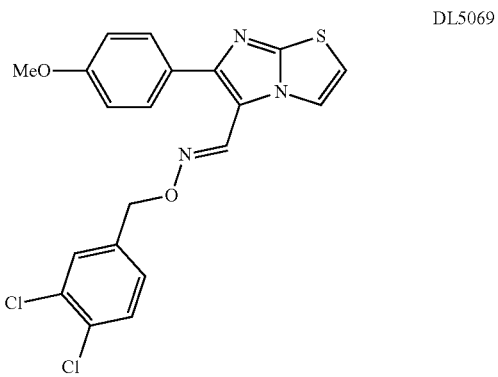 [SMILES: COc1ccc(-c2nc3sccn3c2/C=N/OCc2ccc(Cl)c(Cl)c2)cc1]

DL5069

Yield 93%, $^1$H NMR (400 MHz, CDCl$_3$): δ(ppm) 8.41 (s, 1H), 7.97 (d, J=3.2 Hz, 1H), 7.59 (d, J=8.0 Hz, 2H), 7.51 (s, 1H), 7.44 (d, J=7.6 Hz, 1H), 7.24 (d, J=8.0 Hz, 1H), 6.98 (d, J=7.6 Hz, 2H), 6.87 (d, J=3.2 Hz, 1H), 5.12 (s, 2H), 3.85 (s, 3H); $^{13}$C NMR (100 MHz, CDCl$_3$): δ(ppm) 159.9, 152.5, 150.6, 140.4, 137.9, 132.5, 132.0, 130.5, 130.1, 129.6, 127.4, 126.0, 121.6, 115.0, 114.2, 112.4, 74.8, 55.3. HRMS (ESI): Exact mass calcd for C$_{20}$H$_{16}$Cl$_2$N$_3$O$_2$S [M+H]$^+$ 432.0340, found 432.0346.

Example 9. (E)-6-(4-(tert-butyl)phenyl)imidazo[2,1-b]thiazole-5-carbaldehyde O-(3,4-dichlorobenzyl) oxime A. 6-(4-(tert-butyl)phenyl)imidazo[2,1-b]thiazole-5-carbaldehyde

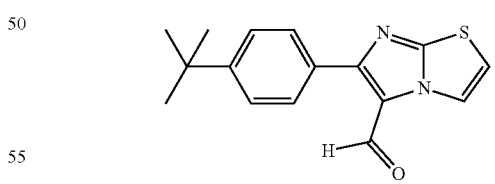

$^1$H NMR (400 MHz, CDCl$_3$): δ(ppm) 9.92 (s, 1H), 8.40 (d, J=4.4 Hz, 1H), 7.74 (d, J=8.0 Hz, 2H), 7.54 (d, J=8.8 Hz, 2H), 7.07 (d, J=4.0 Hz, 1H), 1.37 (s, 9H); $^{13}$C NMR (100 MHz, CDCl$_3$): δ(ppm) 178.2, 158.3, 155.6, 153.1, 129.5, 128.8, 125.9, 123.9, 121.5, 114.5, 34.8, 31.2.

B. (E)-6-(4-(tert-butyl)phenyl)imidazo[2,1-b]thiazole-5-carbaldehyde O-(3,4-dichlorobenzyl) oxime

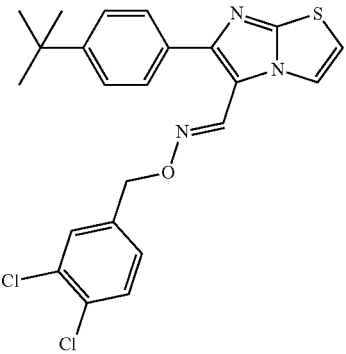

DL5059

Yield 98%, $^1$H NMR (400 MHz, CDCl$_3$): δ(ppm) 8.45 (s, 1H), 7.98 (d, J=4.4 Hz, 1H), 7.60 (d, J=8.8 Hz, 2H), 7.51-7.42 (m, 4H), 7.23 (d, J=8.0 Hz, 1H), 6.87 (d, J=4.8 Hz, 1H), 5.12 (s, 2H), 1.36 (s, 9H); $^{13}$C NMR (100 MHz, CDCl$_3$): δ(ppm) 152.5, 151.6, 150.7, 140.5, 137.9, 132.5, 131.9, 130.5, 130.0, 128.1, 127.4, 125.7, 121.6, 115.4, 112.6, 74.8, 34.7, 31.3. HRMS (ESI): Exact mass calcd. for C$_{23}$H$_{22}$C$_{12}$N$_3$OS [M+H]$^+$ 458.0860, found 458.0864.

Example 10. (E)-6-([1,1'-biphenyl]-4-yl)imidazo[2,1-b]thiazole-5-carbaldehyde O-(3,4-dichlorobenzyl) oxime

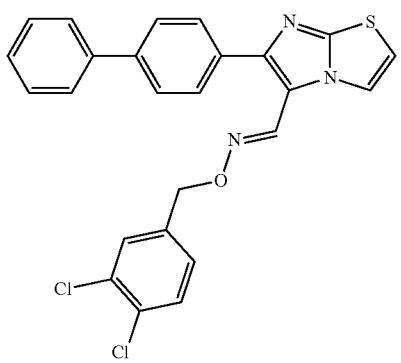

DL5060

Yield 84%. $^1$H NMR (400 MHz, CDCl$_3$): δ(ppm) 8.50 (s, 1H), 8.01 (d, J=4.0 Hz, 1H), 7.76-7.64 (m, 6H), 7.49-7.44 (m, 4H), 7.38 (t, J=7.2 Hz, 1H), 7.25 (d, J=7.6 Hz, 1H), 6.90 (d, J=4.0 Hz, 1H), 5.14 (s, 2H); $^{13}$C NMR (100 MHz, CDCl$_3$): δ(ppm) 152.7, 150.2, 141.1, 140.4, 140.3, 137.9, 132.6, 132.4, 132.0, 130.5, 130.1, 128.9, 128.7, 127.6, 127.44, 127.40, 127.1, 121.6, 115.6, 112.8.74.9. HRMS (ESI): Exact mass calcd for C$_{25}$H$_{17}$C$_{12}$N$_3$OS [M+H]$^+$ 1478.0547, found 478.0542.

Example 11. (E)-6-(3-chlorophenyl)imidazo[2,1-b]thiazole-5-carbaldehyde O-(3,4-dichlorobenzyl) oxime A. 6-(3-chlorophenyl)imidazo[2,1-b]thiazole-5-carbaldehyde

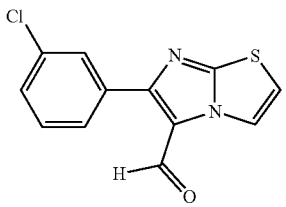 [SMILES: O=Cc1c(-c2cccc(Cl)c2)nc2sccn12]

$^1$H NMR (400 MHz, CDCl$_3$): δ(ppm) 9.89 (s, 1H), 8.37 (d, J=4.8 Hz, 1H), 7.79 (s, 1H), 7.65 (d, J=6.4 Hz, 1H), 7.43-7.39 (m, 2H), 7.07 (d, J=4.0 Hz, 1H), $^{13}$C NMR (100 MHz, CDCl$_3$): δ(ppm) 177.7, 156.2, 155.6, 135.0, 134.1, 130.2, 129.7, 129.0, 127.2, 124.1, 121.5, 115.1.

B. (E)-6-(3-chlorophenyl)imidazo[2,1-b]thiazole-5-carbaldehyde O-(3,4-dichlorobenzyl) oxime

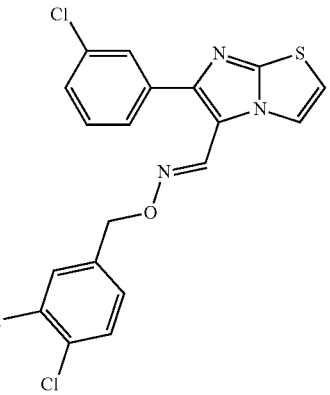

DL5065

Yield 99%. $^1$H NMR (400 MHz, CDCl$_3$): δ(ppm) 8.42 (s, 1H), 8.00 (d, J=4.0 Hz, 1H), 7.68 (s, 1H), 7.52 (s, 2H), 7.46 (d, J=8.8 Hz, 1H), 7.38 (t, J=7.6 Hz, 2H), 7.25 (d, J=8.4 Hz, 1H), 6.94 (d, J=4.0 Hz, 1H), 5.15 (s, 2H); $^{13}$C NMR (100 MHz, CDCl$_3$): δ(ppm) 152.7, 148.8, 139.8, 137.7, 135.1, 134.8, 132.6, 132.1, 130.5, 130.1, 130.0, 128.5, 128.3, 127.4, 126.4, 121.6, 115.9, 113.2, 75.0. HRMS (ESI): Exact mass calcd. for C$_{19}$H$_{13}$C$_{13}$N$_3$OS [M+H]$^+$ 435.9874, found 435.

Example 12. (E)-6-(naphthalen-2-yl)imidazo[2,1-b]thiazole-5-carbaldehyde O-(3,4-dichlorobenzyl) oxime

A. 6-(naphthalen-2-yl)imidazo[2,1-b]thiazole-5-carbaldehyde

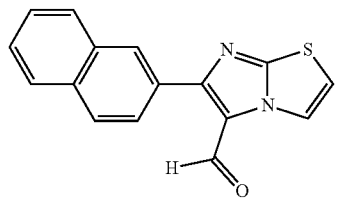

$^1$H NMR (400 MHz, CDCl$_3$): δ(ppm) 10 (s, 1H), 8.41 (d, J=4.8 Hz, 1H), 8.27 (s, 1H), 7.99-7.89 (m, 4H), 7.56-7.54 (m, 2H), 7.07 (d, J=4.4 Hz, 1H); $^{13}$C NMR (100 MHz, CDCl$_3$): δ(ppm) 178.2, 158.1, 155.7, 133.7, 133.2, 129.7, 128.9, 128.8, 128.5, 127.8, 127.1, 126.8, 126.1, 124.2, 121.6, 114.8.

B. (E)-6-(naphthalen-2-yl)imidazo[2,1-b]thiazole-5-carbaldehyde O-(3,4-dichlorobenzyl) oxime

Yield 24%. $^1$H NMR (400 MHz, CDCl$_3$): δ(ppm) 8.54 (s, 1H), 8.11 (s, 1H), 8.03 (d, J=4.4 Hz, 1H), 7.94-7.81 (m, 4H), 7.53-7.44 (m, 4H), 7.25 (d, J=6.8 Hz, 1H), 6.93 (d, J=4.4 Hz, 1H), 5.15 (s, 2H); $^{13}$C NMR (100 MHz, CDCl$_3$): δ(ppm) 152.7, 150.6, 140.4, 137.8, 133.3, 133.1, 132.0, 130.8, 130.5, 130.1, 128.5, 128.3, 127.7, 127.5, 127.4, 126.5, 126.0, 121.6, 115.8, 112.8, 74.9. HRMS (ESI): Exact mass calcd for C$_{23}$H$_{16}$C$_{12}$N$_3$OS [M+H]$^+$ 452.0391, found 425.0397.

Example 13. (E)-6-(naphthalen-2-yl)imidazo[2,1-b]thiazole-5-carbaldehyde O-benzyl oxime

A. 6-(naphthalen-2-yl)imidazo[2,1-b]thiazole-5-carbaldehyde

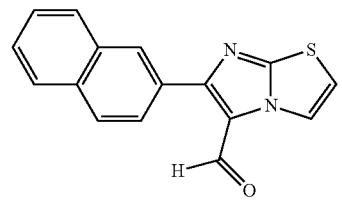

$^1$H NMR (400 MHz, CDCl$_3$): δ(ppm) 10 (s, 1H), 8.41 (d, J=4.8 Hz, 1H), 8.27 (s, 1H), 7.99-7.89 (m, 4H), 7.56-7.54 (m, 2H), 7.07 (d, J=4.4 Hz, 1H); $^{13}$C NMR (100 MHz, CDCl$_3$): δ(ppm) 178.2, 158.1, 155.7, 133.7, 133.2, 129.7, 128.9, 128.8, 128.5, 127.8, 127.1, 126.8, 126.1, 124.2, 121.6, 114.8.

B. (E)-6-(naphthalen-2-yl)imidazo[2,1-b]thiazole-5-carbaldehyde O-benzyl oxime Yield 51%, $^1$H NMR (400 MHz, CDCl$_3$): δ(ppm) 8.57 (s, 1H), 8.12 (s, 1H), 8.09 (d, J=4.8 Hz, 1H), 7.93-7.82 (m, 4H), 7.53-7.33 (m, 7H), 6.89 (d, J=4.8 Hz, 1H), 5.24 (s, 2H); $^{13}$C NMR (100 MHz, CDCl$_3$): δ(ppm) 152.5, 150.0, 139.8, 137.4, 133.3, 133.1, 130.9, 128.54, 128.47, 128.4, 128.3, 128.1, 127.7, 127.4, 126.4, 126.0, 121.8, 116.2, 112.6. HRMS (ESI): Exact mass calcd for C$_{23}$H$_{18}$N$_3$OS [M+H]$^+$ 384.1171, found 384.1177.

Example 14. (E)-6-(naphthalen-1-yl)imidazo[2,1-b]thiazole-5-carbaldehyde O-(3,4-dichlorobenzyl) oxime

A. 6-(naphthalen-1-yl)imidazo[2,1-b]thiazole-5-carbaldehyde

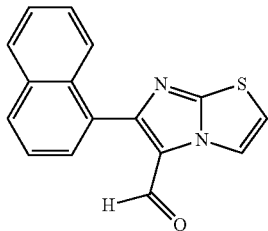 [SMILES: O=Cc1c(-c2cccc3ccccc23)nc2sccn12]

$^{1}$H NMR (400 MHz, CDCl$_3$): δ(ppm) 9.61 (s, 1H), 8.44 (d, J=3.6 Hz, 1H), 8.32-8.29 (m, 1H), 8.00-7.93 (m, 2H), 7.65 (d, 7.2 Hz, 1H), 7.60-7.54 (m, 3H), 7.12 (d, J=4.0 Hz, 1H); $^{13}$C NMR (100 MHz, CDCl$_3$): δ(ppm) 178.3, 157.9, 155.5, 133.9, 132.0, 130.2, 129.7, 129.2, 128.3, 127.1, 126.4, 125.8, 125.5, 124.9, 121.3, 114.8.

B. (E)-6-(naphthalen-1-yl)imidazo[2,1-b]thiazole-5-carbaldehyde O-(3,4-dichlorobenzyl) oxime

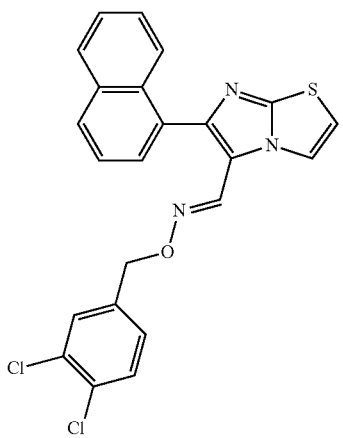

DL5066

Yield 24%. $^{1}$H NMR (400 MHz, CDCl$_3$): δ(ppm) 8.22 (t, J=5.6 Hz, 1H), 8.11 (s, 1H), 8.05 (d, J=4.0 Hz, 1H), 7.94-7.91 (m, 2H), 7.90-7.41, (m, 6H), 7.19 (d, J=7.6 Hz, 1H), 6.96 (d, J=4.0 Hz, 1H), 5.08 (s, 2H); $^{13}$C NMR (100 MHz, CDCl$_3$): δ(ppm) 152.4, 150.0, 140.2, 137.9, 133.9, 132.5, 132.1, 131.9, 130.5, 130.2, 130.0, 129.3, 128.8, 128.2, 127.3, 126.7, 126.13, 126.10, 125.0, 121.4, 112.9, 74.8. HRMS (ESI): Exact mass calcd for C$_{23}$H$_{16}$Cl$_2$N$_3$OS [M+H]$^+$ 452.0391, found 452.0399.

Example 15. (E)-6-ethylimidazo[2,1-b]thiazole-5-carbaldehyde O-(3,4-dichlorobenzyl) oxime

A. 6-ethylimidazo[2,1-b]thiazole-5-carbaldehyde

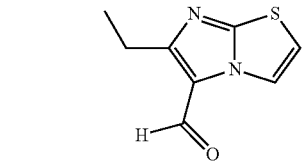

$^{1}$H NMR (400 MHz, CDCl$_3$): δ(ppm) 9.81 (s, 1H), 8.26 (d, J=3.6 Hz, 1H), 6.98 (d, J=4.8 Hz, 1H), 2.99 (q, J=8.0 Hz, 2H), 1.41 (t, J=8.0 Hz, 3H); $^{13}$C NMR (100 MHz, CDCl$_3$): δ(ppm) 175.6, 162.8, 155.6, 123.8, 121.2, 114.0, 21.7, 14.4.

B. (E)-6-ethylimidazo[2,1-b]thiazole-5-carbaldehyde O-(3,4-dichlorobenzyl) oxime

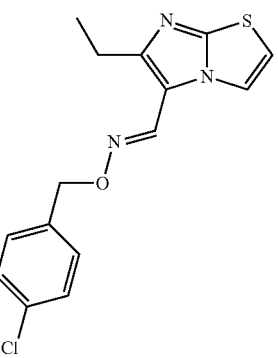

DL5071

Yield 75%, $^{1}$H NMR (400 MHz, CDCl$_3$): δ(ppm) 8.25 (s, 1H), 7.88 (d, J=4.8 Hz, 1H), 7.51 (s, 1H), 7.44 (d, J=8.4 Hz, 1H), 7.24 (d, J=7.6 Hz, 1H), 6.83 (d, J=3.6 Hz, 1H), 5.10 (s, 2H), 2.72 (q, J=7.2 Hz, 2H), 1.31 (d, J=7.6 Hz, 3H); $^{13}$C NMR (100 MHz, CDCl$_3$): δ(ppm) 154.1, 152.1, 138.9, 138.0, 132.5, 131.9, 130.4, 130.1, 127.5, 127.4, 121.2, 115.0, 112.0, 74.7, 21.3, 14.4. HRMS (ESI): Exact mass calcd for C$_{15}$H$_{14}$Cl$_2$N$_3$OS [M+H]$^+$ 354.0234, found 354.0219.

Example 16. (E)-6-(4-chlorophenyl)imidazo[2,1-b]thiazole-5-carbaldehyde oxime A. 6-(4-chlorophenyl)imidazo[2,1-b]thiazole-5-carbaldehyde

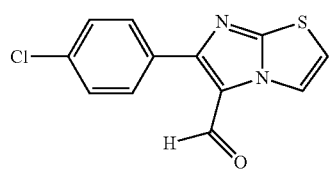 [SMILES: O=Cc1c(-c2ccc(Cl)cc2)nc2sccn12]

$^{1}$H NMR (400 MHz, CDCl$_3$): δ(ppm) 9.89 (s, 1H), 8.39 (d, J=4.8 Hz, 1H), 7.74 (d, J=8.8 Hz, 2H), 7.49 (d, J=8.4 Hz, 2H), 7.08 (d, J=4.0 Hz, 1H); $^{13}$C NMR (100 MHz, CDCl$_3$): δ(ppm) 177.7, 156.8, 155.7, 136.0, 130.9, 130.2, 129.2, 124.0, 121.5, 114.9.

B. (E)-6-(4-chlorophenyl)imidazo[2,1-b]thiazole-5-carbaldehyde oxime

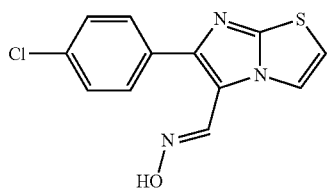

DL5013

$^1$H NMR (400 MHz, CDCl$_3$): δ(ppm) 10.44 (s, 1H), 8.37 (s, 1H), 8.09 (d, J=4.0 Hz, 1H), 7.71 (d, J=7.6 Hz, 2H), 7.53 (d, J=8.4 Hz, 2H), 7.46 (d, J=4.8 Hz, 1H), $^{13}$C NMR (100 MHz, CDCl$_3$): δ(ppm) 151.1, 143.8, 137.8, 134.7, 134.0, 133.8, 126.2, 121.8, 120.1.

Example 17. (E)-6-(4-chlorophenyl)imidazo[2,1-b]oxazole-5-carbaldehyde O-(3,4-dichlorobenzyl) oxime

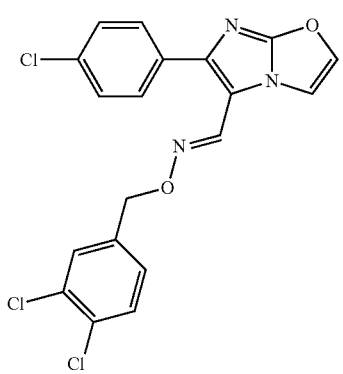

DL5043

Yield 24%, $^1$H NMR (400 MHz, CDCl$_3$): δ(ppm) 8.35 (s, 1H), 7.57 (d, J=8.4 Hz, 3H), 7.50 (s, 1H), 7.46-7.39 (m, 4H), 7.23 (d, J=8.8 Hz, 1H), 5.11 (s, 2H); $^{13}$C NMR (100 MHz, CDCl3): δ(ppm) 156.2, 146.0, 139.9, 137.9, 137.7, 134.3, 132.6, 132.0, 130.5, 130.2, 130.1, 129.3, 129.0, 127.4, 113.8, 111.7, 74.9; HRMS (ESI): Exact mass calcd for C$_{19}$H$_{12}$Cl$_3$N$_3$O$_2$ [M+H]$^+$ 420.0073.0678, found 420.0069.

Example 18. (E)-6-(naphthalen-2-yl)imidazo[2,1-b]oxazole-5-carbaldehyde O-(3,4-dichlorobenzyl) oxime

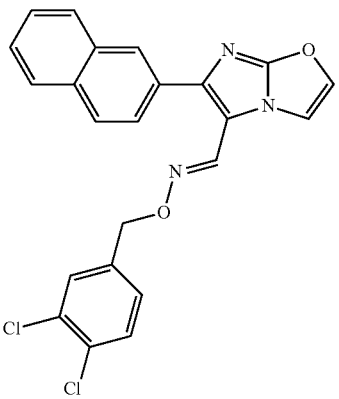

DL5054

Yield 23%, $^1$H NMR (400 MHz, CDCl$_3$): δ(ppm) 8.50 (s, 1H), 8.10 (s, 1H), 7.92-7.79 (m, 4H), 7.62 (s, 1H), 7.52-7.45 (m, 5H), 7.25 (d, J=9.2 Hz, 1H), 5.13 (s, 2H); 13C NMR (100 MHz, CDCl$_3$): δ(ppm) 156.3, 147.3, 140.4, 137.9, 133.3, 133.1, 132.6, 132.0, 131.0, 130.5, 130.1, 128.5, 128.3, 127.7, 127.4 (2C), 127.2, 126.5 (2C), 125.8, 113.9, 111.9, 74.9. HRMS (ESI): Exact mass calcd for C$_{23}$H$_{16}$Cl$_2$N$_3$O$_2$ [M+H]$^+$ 436.0619, found 436.0620.

Example 19. (E)-6-(naphthalen-2-yl)imidazo[2,1-b]oxazole-5-carbaldehyde O-benzyl oxime

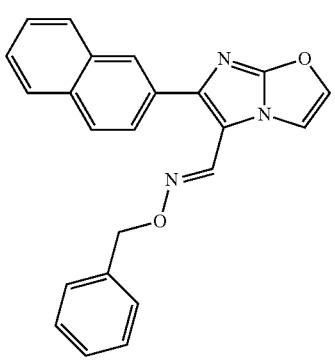

DL5098-3

Yield 71%, $^1$H NMR (400 MHz, CDCl$_3$): δ(ppm) 8.52 (s, 1H), 8.10 (s, 1H), 7.91-7.79 (m, 4H), 7.67 (s, 1H), 7.53-7.33 (m, 8H), 5.21 (s, 2H); $^{13}$C NMR (100 MHz, CDCl$_3$): δ(ppm) 156.2, 146.7, 139.8, 137.7, 137.3, 133.3, 133.0, 131.1, 128.5, 128.4, 128.3, 128.1, 127.7, 127.1, 126.41, 126.37, 125.8, 114.0, 112.2, 76.6. HRMS (ESI): Exact mass calcd for C$_{23}$H$_{18}$N$_3$O$_2$ [M+H]$^+$ 368.1399, found 368.1397.

Example 20. (E)-6-(naphthalen-2-yl)imidazo[2,1-b]oxazole-5-carbaldehyde O-(4-chlorobenzyl) oxime

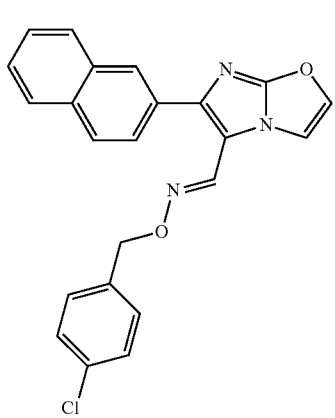

DL5096-3

Yield 44%, $^1$H NMR (400 MHz, CDCl$_3$): δ(ppm) 8.50 (s, 1H), 8.10 (s, 1H), 7.91-7.79 (m, 4H), 7.61 (s, 1H), 7.51-7.47 (m, 2H), 7.42 (s, 1H), 7.36 (s, 5H), 5.15 (s, 2H); $^{13}$C NMR (100 MHz, CDCl$_3$): δ(ppm) 156.3, 146.9, 140.1, 137.8, 136.0, 133.9, 133.3, 133.0, 131.0, 129.7, 128.7, 128.5, 128.3, 127.7, 127.2, 126.5, 126.4, 125.8, 113.9, 112.0, 75.7. HRMS (ESI): Exact mass calcd for C$_{25}$H$_{20}$N$_3$O$_2$ [M+H]$^+$ 402.1009, found 402.1000.

Example 21. (E)-6-(naphthalen-2-yl)imidazo[2,1-b]oxazole-5-carbaldehyde O-(4-(trifluoromethyl)benzyl) oxime

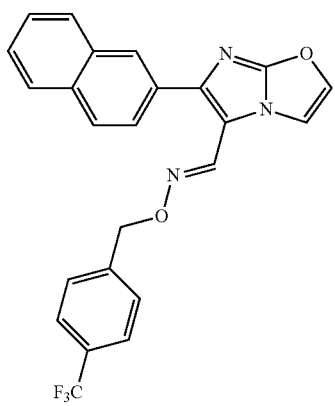

DL5096-2

Yield 33%, $^1$H NMR (400 MHz, CDCl$_3$): δ(ppm) 8.53 (s, 1H), 8.10 (s, 1H), 7.92-7.80 (m, 4H), 7.65 (d, J=8.0 Hz, 2H), 7.60 (s, 1H), 7.54-7.50 (m, 4H), 7.43 (s, 1H), 5.25 (s, 2H); $^{13}$C NMR (100 MHz, CDCl$_3$): δ(ppm) 156.3, 147.2, 141.6, 140.3, 137.8, 133.3, 133.0, 131.0, 130.1 (J=32.7 Hz), 128.5, 128.3, 128.2, 127.7, 127.2, 126.5, 125.8, 125.5, 125.4, 124.1 (J=270.8 Hz), 113.9, 111.9, 75.5. HRMS (ESI): Exact mass calcd for C$_{24}$H$_{17}$F$_3$N$_3$O$_2$ [M+H]$^+$ 436.1273, found 436.1264.

Example 22. (E)-6-(naphthalen-2-yl)imidazo[2,1-b]oxazole-5-carbaldehyde O-(4-methoxybenzyl) oxime

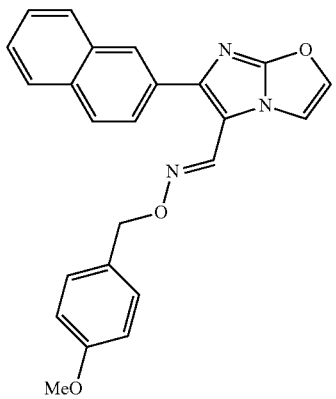

DL5096-4

Example 23. (E)-6-(naphthalen-2-yl)imidazo[2,1-b]oxazole-5-carbaldehyde O-(2-chlorobenzyl) oxime

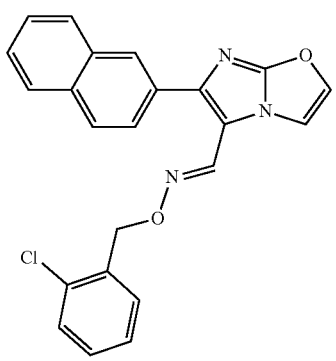

DL5098-2

Yield 41%, $^1$H NMR (400 MHz, CDCl$_3$): δ(ppm) 8.54 (s, 1H), 8.11 (s, 1H), 7.91-7.80 (m, 4H), 7.68 (d, J=1.6 Hz, 1H), 7.53-7.49 (m, 3H), 7.41 (d, J=1.6 Hz, 2H), 7.31-7.27 (m, 2H), 5.33 (s, 2H); $^{13}$C NMR (100 MHz, CDCl3): δ(ppm) 156.3, 146.9, 140.1, 137.8, 135.3, 133.5, 133.3, 133.0, 131.1, 130.2, 129.5, 129.3, 128.5, 128.3, 127.7, 127.2, 126.8, 126.44, 126.38, 125.8, 114.0, 112.1, 73.5. HRMS (ESI): Exact mass calcd for C$_{23}$H$_{17}$ClN$_3$O$_2$ [M+H]$^+$ 402.1009, found 402.1015.

Example 24. (E)-6-(naphthalen-2-yl)imidazo[2,1-b]oxazole-5-carbaldehyde O-(2,4-dichlorobenzyl) oxime

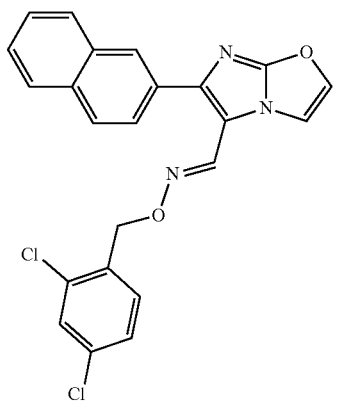

DL5096-1

Yield 46%, $^1$H NMR (400 MHz, CDCl$_3$): δ(ppm) 8.52 (s, 1H), 8.10 (s, 1H), 7.91-7.79 (m, 4H), 7.65 (s, 1H), 7.53-7.48 (m, 2H), 4.43-7.41 (m, 3H), 7.27 (d, J=8.8 Hz, 1H), 5.26 (s, 2H); $^{13}$C NMR (100 MHz, CDCl$_3$): δ(ppm) 156.3, 147.1, 140.4, 137.8, 134.3, 134.05, 133.97, 133.3, 133.0, 131.0, 130.8, 129.3, 128.5, 128.3, 127.7, 127.2, 127.16, 126.5, 126.4, 125.8, 114.0, 111.9, 72.8. HRMS (ESI): Exact mass calcd for C$_{23}$H$_{16}$Cl$_2$N$_3$O$_2$ [M+H]$^+$ 436.0619, found 436.624.

Example 25. (E)-6-(naphthalen-2-yl)imidazo[2,1-b]oxazole-5-carbaldehyde O-((perfluorophenyl)methyl) oxime

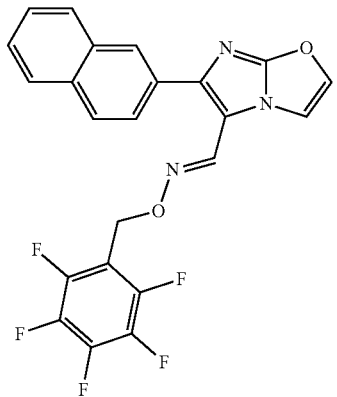

DL5098-1

Yield 35%, $^1$H NMR (400 MHz, CDCl$_3$): δ(ppm) 8.41 (s, 1H), 8.06 (s, 1H), 7.99-7.83 (m, 3H), 7.76 (d, J=7.6 Hz, 1H), 7.71 (s, 1H), 7.51-7.49 (m, 3H), 5.25 (s, 2H); $^{13}$C NMR (100 MHz, CDCl$_3$): δ(ppm) 156.4, 147.6, 147.0, 144.5, 142.8, 140.9, 138.7, 138.0, 133.3, 133.1, 130.8, 128.5, 128.3, 127.7, 127.2, 126.5, 125.7, 113.8, 111.6, 62.6. HRMS (ESI): Exact mass calcd for C$_{23}$H$_{13}$F$_5$N$_3$O$_2$ [M+H]$^+$ 458.0928, found 458.0935.

Example 26. (E)-N-(isoindolin-2-yl)-1-(6-(naphthalen-2-yl)imidazo[2,1-b]oxazol-5-yl)methanimine

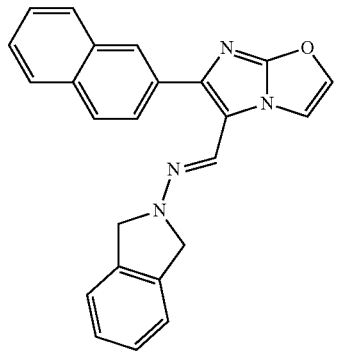

DL5081

Yield 40%, $^1$H NMR (400 MHz, CDCl$_3$): δ(ppm) 8.18 (s, 1H), 7.94-7.86 (m, 5H), 7.65 (s, 1H), 7.47 (m, 3H), 7.42 (s, 1H), 7.30 (s, 3H), 4.70 (s, 4H); $^{13}$C NMR (100 MHz, CDCl$_3$): δ(ppm) 155.5, 141.4, 137.2, 136.5, 133.6, 132.6, 132.4, 128.8, 128.3, 128.2, 127.4, 127.2, 126.5, 126.3, 125.9, 124.1, 122.7, 117.4, 113.9, 57.1. HRMS (ESI): Exact mass calcd for C$_{24}$H$_{19}$N$_4$O [M+H]$^+$ 379.1559, found 379.1556.

Example 27. (E)-6-(naphthalen-2-yl)imidazo[2,1-b]oxazole-5-carbaldehyde O-(2,3-dihydro-1H-inden-2-yl) oxime

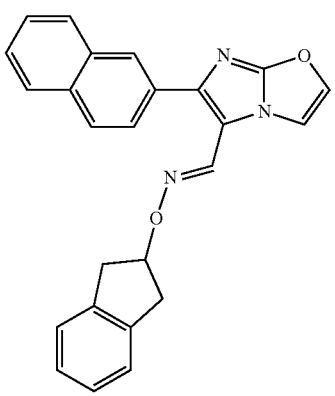

DL-5090

Yield 64%, $^1$H NMR (400 MHz, CDCl$_3$): δ(ppm) 8.41 (s, 1H), 8.08 (s, 1H), 7.87-7.77 (m, 4H), 4.9 (t, J=4.8 Hz, 2H), 7.39 (d, J=1.6 Hz, 2H), 7.28-7.20 (m, 4H), 5.16 (s, 1H), 3.37-3.23 (m, 4H); $^{13}$C NMR (100 MHz, CDCl$_3$): δ(ppm) 156.1, 146.3, 141.2, 139.7, 137.6, 133.3, 133.0, 1331.1, 128.4, 128.3, 127.7, 127.1, 126.6, 126.4, 126.3, 125.8, 124.6, 114.0, 83.4, 39.2. HRMS (ESI): Exact mass calcd for C$_{25}$H$_{20}$N$_3$O$_2$ [M+H]$^+$ 394.1555, found 394.1563.

2. Synthesis of 6-aryl Substituted imidazo[2,1-b]oxazole-5-carboxamide and 6-aryl substituted imidazo[2,1-b]thiazole-5-carboxamide analogs

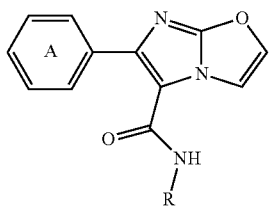

To a solution of intermediate 3 (1 mmol) in the mixture of t-butanol (10 mL) and water (10 mL) was added 2-methyl-2-butene (2 M in THF, 6.7 equiv), sodium phosphate monobasic (7.8 equiv) and sodium chlorite (80%, 10 equiv). The reaction mixture was stirred at room temperature for 24 hours. Then EtOAc (50 mL) and $H_2O$ (30 mL) was added and stirred for another 2 hours. Extracted with EtOAc (2×50 mL), Combined the EtOAc layers and washed with brine. Dried ($Na_2SO_4$), filtered, and concentrated in vacuo. Purified by silica gel chromatography and got the intermediate acid 8. The resulting acid 8 was dissolved in DMF (10 mL). To the solution was then added 1-Ethyl-3-(3-dimethylaminopropylcarbodiimide (EDCI) (1.5 equiv) and 4-Dimethylaminopyridine (DMAP) (1.5 equiv) in one portion with stirring for 30 min. Then the amine 4 (1 equiv) was added, and the reaction mixture was stirred at room temperature until TLC indicated completion of the reaction. Saturated aqueous $NaHCO_3$ (10 mL) was then added to the reaction mixture. The mixture was extracted with EtOAc (25 mL×3), and the combined organic layer was dried with anhydrous $Na_2SO_4$. The solvent was removed under vacuum, and the crude product was purified by silica gel column chromatography using EA/HE as eluent to give the final product containing amide linker.

Scheme 2A

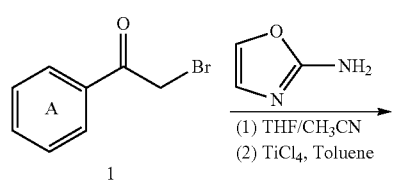

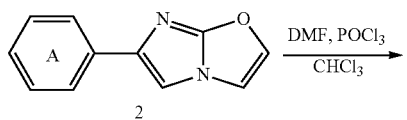

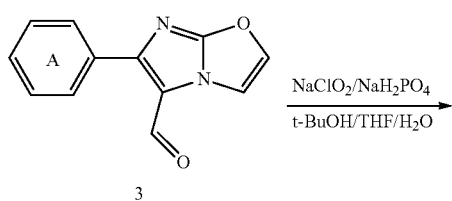

Scheme 2B

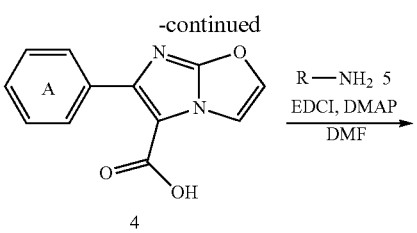

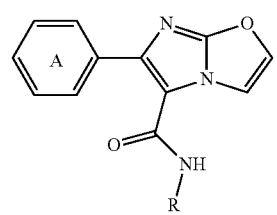

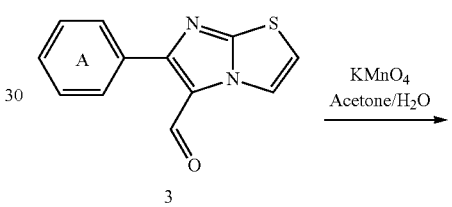

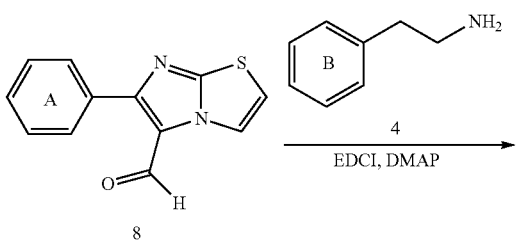

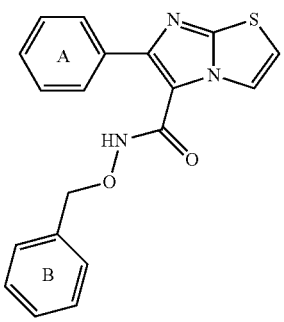

III

Example 28. N-(3,4-dichlorophenethyl)-6-(naphthalen-2-yl)imidazo[2,1-b]oxazole-5-carboxamide A. 6-(naphthalen-2-yl)imidazo[2,1-b]oxazole-5-carboxylic acid

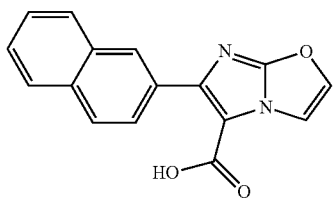 [SMILES: O=C(O)c1c(-c2ccc3ccccc3c2)nc2occn12]

$^1$H NMR (400 MHz, DMSO-d$_6$): δ(ppm) 13.24 (br s, 1H), 8.44 (s, 1H), 8.27 (d, J=3.2 Hz, 1H), 8.02-7.94 (m, 5H), 7.61-7.51 (m, 4H); $^{13}$C NMR (100 MHz, DMSO-d$_6$): δ(ppm) 165.9, 157.3, 137.9, 137.6, 136.5, 134.0, 133.5, 133.3, 132.7, 132.0, 131.7, 131.4, 127.1, 120.6.

B. N-(3,4-dichlorophenethyl)-6-(naphthalen-2-yl)imidazo[2,1-b]oxazole-5-carboxamide

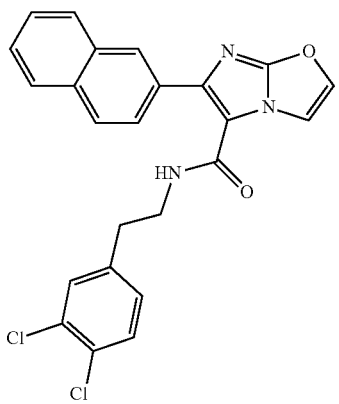

DL6038

$^1$H NMR (400 MHz, DMSO-d$_6$): δ(ppm) 8.24 (s, 1H), 8.11 (s, 1H), 7.98 (s, 1H), 7.93-7.85 (m, 3H), 7.76 (t, J=8.8 Hz, 2H), 7.55-7.51 (m, 4H), 7.22 (d, J=8.0 Hz, 1H), 3.51 (d, J=5.2 Hz, 2H), 2.84 (t, J=7.2 Hz, 2H); $^{13}$C NMR (100 MHz, DMSO-d$_6$): δ(ppm) 164.8, 159.6, 149.0, 145.9, 145.0, 138.0, 137.7, 136.0, 135.9, 135.6, 134.4, 134.0, 133.3, 132.8, 132.7, 132.5, 131.6, 131.4, 119.3, 118.7. HRMS (ESI): Exact mass calcd for C$_{24}$H$_{18}$Cl$_2$N$_3$O$_2$ [M+H]$^+$ 450.0776, found 450.0780.

Example 29. 6-(2,4-difluorophenyl)-N-(2,3-dihydro-1H-inden-2-yl)imidazo[2,1-b]oxazole-5-carboxamide

DL6071

$^1$H NMR (400 MHz, CDCl$_3$): δ(ppm) 7.91 (s, 1H), 7.48 (s, 1H), 7.37 (q, J=6.4 Hz, 1H), 7.19-7.14 (m, 4H), 6.77 (t, J=6.8 Hz, 1H), 6.65-6.61 (m, 1H), 5.66 (d, J=8.0 Hz, 1H), 4.81-4.74 (m, 1H), 3.23 (dd, J=5.2 Hz, J=10.4 Hz, 2H), 2.63 (dd, J=4.8 Hz, J=11.2 Hz, 2H); $^{13}$C NMR (100 MHz, CDCl$_3$): δ(ppm) 164.8, 164.7, 162.3, 162.2, 161.0, 160.9, 159.1, 158.5, 158.4, 155.2, 140.4, 138.4, 137.7, 132.8, 132.7, 132.6, 126.8, 124.8, 117.5, 117.3, 115.4, 113.5, 112.14, 112.11, 111.9, 104.9, 104.6, 104.4, 50.8, 40.0. HRMS (ESI): Exact mass calcd for C$_{21}$H$_{16}$F$_2$N$_3$O$_2$ [M+H]$^+$ 380.1211, found 380.1201.

Example 30. 6-(4-chlorophenyl)-N-(2,3-dihydro-1H-inden-2-yl)imidazo[2,1-b]oxazole-5-carboxamide

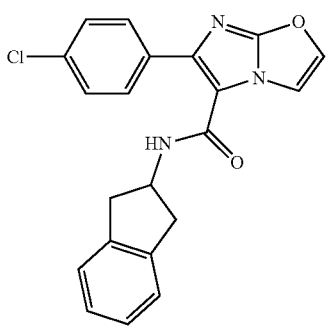

DL6056

$^1$H NMR (400 MHz, CDCl$_3$): δ(ppm) 7.92 (s, 1H), 7.46 (s, 1H), 7.39 (d, J=7.6 Hz, 2H), 7.23-7.15 (m, 6H), 5.97 (d, J=7.2 Hz, 1H), 4.78 (t, J=7.2 Hz, 1H), 3.26 (dd, J=6.4 Hz, J=10.4 Hz, 2H), 2.70 (dd, J=4.0 Hz, J=10.8 Hz, 2H); $^{13}$C NMR (100 MHz, CDCl$_3$): δ(ppm) 159.3, 155.1, 144.3, 140.4, 138.4, 135.1, 131.8, 130.3, 129.0, 127.0, 124.8, 113.7, 51.0, 39.9. HRMS (ESI): Exact mass calcd for C$_{21}$H$_{17}$ClN$_3$O$_2$ [M+H]$^+$ 378.1009, found 378.1007.

Example 31. 6-(naphthalen-2-yl)-N-(3-phenylpropyl)imidazo[2,1-b]oxazole-5-carboxamide

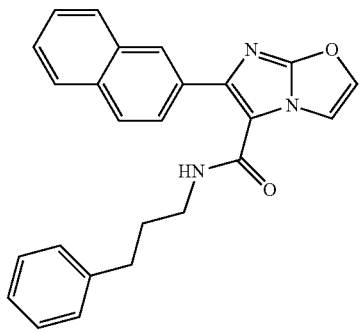

DL6061

$^1$H NMR (400 MHz, CDCl$_3$): δ(ppm) 8.17 (s, 1H), 7.98 (d, J=6.8 Hz, 1H), 7.92-7.87 (m, 2H), 7.77 (d, J=8.8 Hz, 1H), 7.59-7.53 (m, 2H), 7.48 (s, 1H), 7.19-7.13 (m, 3H), 6.93 (d, J=6.4 Hz, 2H), 5.98 (br s, 1H), 3.30 (q, J=6.4 Hz, 2H), 2.48 (t, J=7.2 Hz, 2H), 1.76-1.67 (m, 2H); $^{13}$C NMR (100 MHz, CDCl$_3$): δ(ppm) 160.0, 155.3, 145.6, 140.9, 138.2, 133.4, 133.2, 131.3, 129.0, 128.8, 128.3, 128.23, 128.19, 127.9, 127.1, 126.9, 126.6, 125.9, 113.9, 38.6, 33.0, 31.0. HRMS (ESI): Exact mass calcd for C$_{25}$H$_{22}$N$_3$O$_2$ [M+H]$^+$ 396.1712, found 396.1715.

Example 32. 6-(2,4-difluorophenyl)-N-((2,3-dihydro-1H-inden-2-yl)methyl)imidazo[2,1-b]oxazole-5-carboxamide

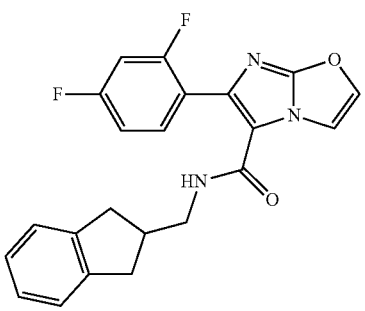

DL6070

$^1$H NMR (400 MHz, CDCl$_3$): δ(ppm) 7.95 (s, 1H), 7.59-7.53 (m, 1H), 7.50 (s, 1H), 7.16-7.13 (m, 4H), 7.02 (t, J=7.2 Hz, 1H), 6.96-6.91 (m, 1H), 5.57 (br s, 1H), 3.42 (t, J=5.2 Hz, 2H), 2.98-2.93 (m, 2H), 2.65-2.50 (m, 3H); $^{13}$C NMR (100 MHz, CDCl$_3$): δ(ppm) 165.0, 164.9, 162.5, 162.4, 161.4, 161.3, 159.5, 158.9, 158.8, 155.2, 142.1, 138.5, 137.5, 133.3, 133.2, 133.1, 126.5, 117.9, 117.7, 115.5, 113.7, 112.4, 112.23, 112.20, 105.2, 104.9, 104.7, 43.4, 39.0, 36.6. HRMS (ESI): Exact mass calcd for C$_{22}$H$_{18}$F$_2$N$_3$O$_2$ [M+H]$^+$ 394.1367, found 394.1374.

Example 33. N-((2,3-dihydro-1H-inden-2-yl)methyl)-6-(naphthalen-2-yl)imidazo[2,1-b]oxazole-5-carboxamide

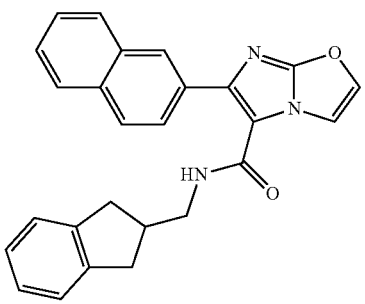

DL6068

$^1$H NMR (400 MHz, CDCl$_3$): δ(ppm) 8.17 (s, 1H), 7.97-7.87 (m, 4H), 7.76 (d, J=7.6 Hz, 1H), 7.61-7.54 (m, 2H), 7.48 (d, J=1.6 Hz, 1H), 7.16-7.04 (m, 4H), 6.08 (br s, 1H), 3.38 (t, J=6.0 Hz, 2H), 2.86 (dd, J=6.8 Hz, J=8.0 Hz, 2H), 2.57-2.46 (m, 3H); $^{13}$C NMR (100 MHz, CDCl$_3$): δ(ppm) 160.0, 155.3, 145.6, 142.1, 138.2, 133.4, 133.2, 131.3, 129.0, 128.7, 128.2, 127.9, 127.1, 126.9, 126.6, 124.5, 113.9, 43.4, 39.1, 36.7. HRMS (ESI): Exact mass calcd for C$_{26}$H$_{22}$N$_3$O$_2$ [M+H]$^+$ 408.1712, found 408.1716.

Example 34. 6-(4-chlorophenyl)-N-((2,3-dihydro-1H-inden-2-yl)methyl)imidazo[2,1-b]oxazole-5-carboxamide

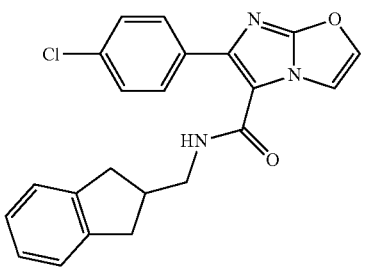

DL6072

$^1$H NMR (400 MHz, CDCl$_3$): δ(ppm) 7.92 (s, 1H), 7.57 (d, J=8.4 Hz, 2H), 7.47 (s, 1H), 7.41 (d, J=8.0 Hz, 2H), 7.19-7.13 (m, 4H), 5.92 (br s, 1H), 3.42 (t, J=6.0 Hz, 2H), 2.98 (dd, J=8.0 Hz, J=6.8 Hz, 2H), 2.65-2.54 (m, 3H); $^{13}$C NMR (100 MHz, CDCl$_3$): δ(ppm) 159.8, 155.2, 144.2, 142.1, 138.4, 135.4, 132.3, 130.6, 129.2, 126.5, 124.6, 113.8, 43.5, 39.0, 36.8. HRMS (ESI): Exact mass calcd for C$_{22}$H$_{19}$ClN$_3$O$_2$ [M+H]$^+$ 392.1166, found 392.1169.

Example 35. 6-(naphthalen-2-yl)-N-(1-phenylazetidin-3-yl)imidazo[2,1-b]oxazole-5-carboxamide

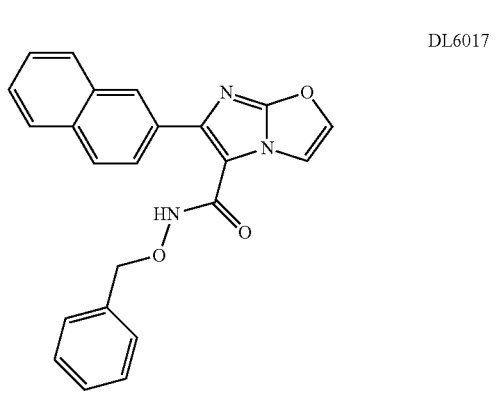 [SMILES: O=C(NOCc1ccccc1)c1c(-c2ccc3ccccc3c2)nc2occn12]

DL6017

$^1$H NMR (400 MHz, CDCl$_3$): δ(ppm) 8.18 (s, 1H), 7.93-7.77 (m, 5H), 7.56-7.50 (m, 2H), 7.47 (s, 1H), 7.18 (t, J=8.0 Hz, 2H), 6.75 (t, J=7.2 Hz, 1H), 6.45 (d, J=7.2 Hz, 1H), 6.36 (d, J=8.8 Hz, 2H), 4.90-4.86 (m, 1H), 4.18 (t, J=7.2 Hz, 2H), 3.42 (t, J=7.2 Hz, 2H); $^{13}$C NMR (100 MHz, CDCl$_3$): δ(ppm) 159.6, 155.5, 150.9, 146.4, 138.4, 133.4, 133.1, 130.9, 129.0, 128.9, 128.7, 128.1, 127.9, 127.1, 127.0, 126.3, 118.1, 113.8, 111.6, 59.1, 40.6. HRMS (ESI): Exact mass calcd for C$_{25}$H$_{21}$N$_4$O$_2$ [M+H]$^+$ 409.1665, found 409.1666.

Example 36. N-(benzyloxy)-6-(naphthalen-2-yl)imidazo[2,1-b]oxazole-5-carboxamide

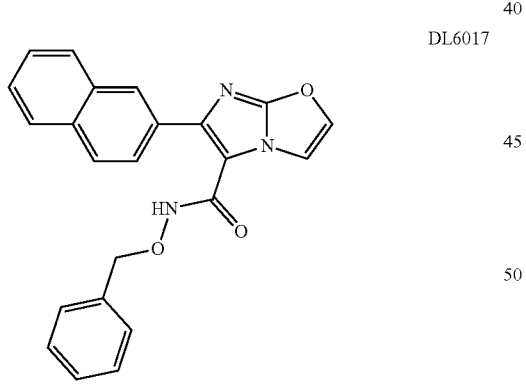

DL6017

$^1$H NMR (400 MHz, CDCl$_3$): δ(ppm) 8.43 (s, 1H), 7.98 (s, 1H), 7.92 (d, J=1.6 Hz, 1H), 7.84 (d, J=8.0 Hz, 1H), 7.74 (d, J=8.8 Hz, 2H), 7.57-7.51 (m, 3H), 7.45 (d, J=1.6 Hz, 1H), 7.26-7.22 (m, 5H), 4.92 (s, 2H); $^{13}$C NMR (100 MHz, CDCl$_3$): δ(ppm) 159.3, 155.7, 146.6, 138.4, 135.1, 133.3, 133.1, 130.8, 128.91, 128.86, 128.7, 128.5, 128.4, 127.0, 126.7, 126.0, 113.8, 111.5, 78.5. HRMS (ESI): Exact mass calcd for C$_{23}$H$_{18}$N$_3$O$_3$ [M+H]$^+$ 384.1348, found 384.1350.

Example 37. N-(3,4-dichlorophenethyl)-6-(4-fluorophenyl)imidazo[2,1-b]oxazole-5-carboxamide

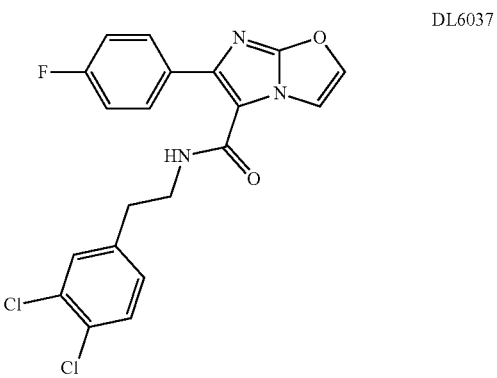 [SMILES: O=C(NCCc1ccc(Cl)c(Cl)c1)c1c(-c2ccc(F)cc2)nc2occn12]

DL6037

$^1$H NMR (400 MHz, CDCl$_3$): δ(ppm) 7.94 (s, 1H), 7.48-7.43 (m, 3H), 7.34 (d, J=8.4 Hz, 1H), 7.18 (s, 1H), 7.05 (t, J=8.4 Hz, 2H), 6.92 (d, J=7.6 Hz, 1H), 5.68 (br s, 1H), 3.56 (q, J=6.0 Hz, 2H), 2.75 (t, J=6.0 Hz, 2H); $^{13}$C NMR (100 MHz, CDCl$_3$): δ(ppm) 163.2 (J=248.6 Hz), 159.6, 154.8, 144.4, 138.6, 138.5, 132.6, 131.1 (J=7.5 Hz), 130.8, 130.5 (J=7.4 Hz), 129.9, 129.3, 127.9, 116.1 (J=22.3 Hz), 113.9, 113.5, 39.9, 34.5. HRMS (ESI): Exact mass calcd for C$_{20}$H$_{15}$FN$_3$O$_2$ [M+H]$^+$ 418.0525, found 418.0530.

Example 38. N-((3,4-dichlorobenzyl)oxy)-6-(naphthalen-2-yl)imidazo[2,1-b]oxazole-5-carboxamide

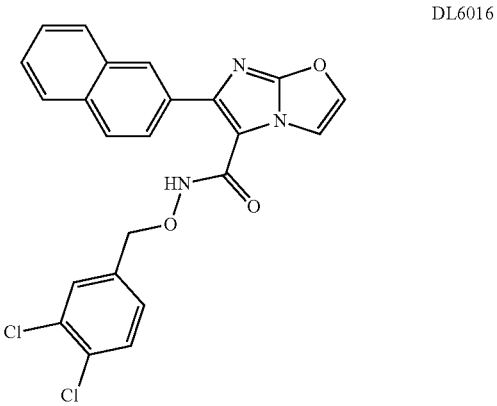 [SMILES: O=C(NOCc1ccc(Cl)c(Cl)c1)c1c(-c2ccc3ccccc3c2)nc2occn12]

DL6016

$^1$H NMR (400 MHz, CDCl$_3$): δ(ppm) 8.38 (s, 1H), 7.96-7.71 (m, 5H), 7.55-7.40 (M, 5H), 7.29 (d, J=6.4 Hz, 1H), 7.10 (d, J=6.8 Hz, 1H), 4.85 (s, 1H); $^{13}$C NMR (100 MHz, CDCl$_3$): δ(ppm) 159.6, 155.8, 147.0, 138.5, 135.6, 133.3, 132.9, 132.8, 132.7, 130.9, 130.61, 130.55, 128.9, 128.4, 128.1, 127.9, 127.8, 127.2, 127.0, 125.9, 77.3. HRMS (ESI): Exact mass calcd for C$_{23}$H$_{16}$Cl$_2$N$_3$O$_3$ [M+H]$^+$ 452.0569, found 452.0576.

Example 39. N-(2,3-dihydro-1H-inden-2-yl)-6-(4-fluorophenyl)imidazo[2,1-b]oxazole-5-carboxamide

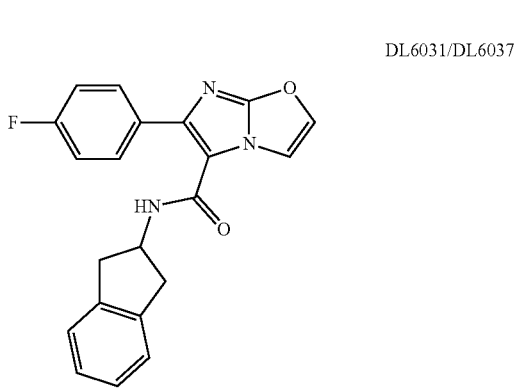 [SMILES: O=C(NC1Cc2ccccc2C1)c1c(-c2ccc(F)cc2)nc2occn12]

$^1$H NMR (400 MHz, CDCl$_3$): δ(ppm) 7.91 (s, 1H), 7.46-7.42 (m, 3H), 7.18 (s, 4H), 6.89 (t, J=8.8 Hz, 2H), 5.96 (d, J=6.8 Hz, 1H), 4.77 (t, J=3.2 Hz, 1H), 3.25 (dd, J=6.4 Hz, J=9.2 Hz, 2H), 2.67 (dd, J=3.2 Hz, J=12.8 Hz, 2H); $^{13}$C NMR (100 MHz, CDCl$_3$): δ(ppm) 163.0 (J=248.6 Hz), 159.4, 155.1, 144.7, 140.5, 138.2, 130.9 (J=7.4 Hz), 129.5, 126.9, 124.8, 115.9 (J=22.3 Hz), 113.7 (2C), 50.9, 39.9. HRMS (ESI): Exact mass calcd for C$_{21}$H$_{17}$FN$_3$O$_2$ [M+H]$^+$ 362.1305, found 362.1300.

Example 40. (6-(naphthalen-2-yl)imidazo[2,1-b]oxazol-5-yl)(4-phenylpiperazin-1-yl)methanone

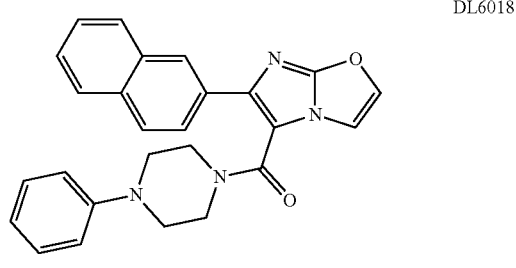 [SMILES: O=C(c1c(-c2ccc3ccccc3c2)nc2occn12)N1CCN(c2ccccc2)CC1]

$^1$H NMR (400 MHz, CDCl$_3$): δ(ppm) 8.18 (s, 1H), 7.91-7.86 (m, 3H), 7.79 (d, J=8.8 Hz, 1H), 7.66 (s, 1H), 7.52-7.49 (m, 2H), 7.18 (t, J=8.0 Hz, 2H), 6.84 (t, J=8.0 Hz, 1H), 6.71 (d, J=8.4 Hz, 2H), 3.61 (br s, 4H), 2.88 (br s, 4H); $^{13}$C NMR (100 MHz, CDCl$_3$): δ(ppm) 161.5, 155.7, 150.7, 145.0, 138.2, 133.4, 133.2, 131.5, 129.1, 128.5, 128.4, 127.8, 127.6, 126.7, 125.8, 120.6, 116.7, 112.9, 112.0, 49.3. HRMS (ESI): Exact mass calcd for C$_{26}$H$_{23}$N$_4$O$_2$ [M+H]$^+$ 423.1821, found 423.1819.

Example 41. N-(isoindolin-2-yl)-6-(naphthalen-2-yl)imidazo[2,1-b]oxazole-5-carboxamide

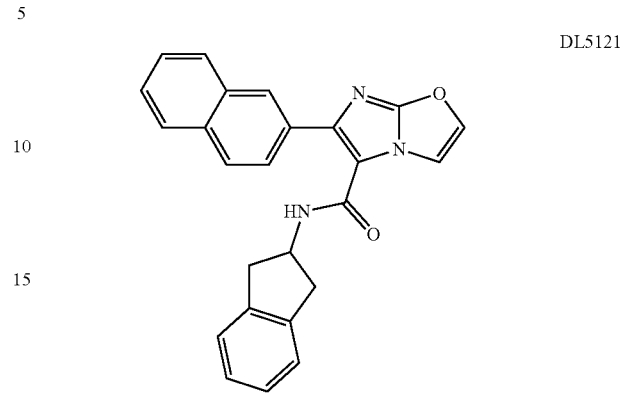

Yield 46%, $^1$H NMR (400 MHz, CDCl$_3$): δ(ppm) 8.17 (s, 1H), 7.97-7.88 (m, 4H), 7.77 (d, J=8.8 Hz, 1H), 7.57-7.55 (m, 2H), 7.49 (s, 1H), 7.16-7.11 (m, 5H), 4.25 (s, 4H); $^{13}$C NMR (100 MHz, CDCl$_3$): δ (ppm) 159.1, 155.5, 145.9, 138.3, 137.5, 133.4, 133.1, 131.0, 128.9, 128.8, 128.2, 127.9, 127.2, 127.0, 126.9, 126.4, 122.4, 113.8, 112.9. HRMS (ESI): Exact mass calcd for C$_{25}$H$_{20}$N$_3$O$_2$ [M+H]$^+$ 395.1508, found 395.1503.

Example 42. N-((2,3-dihydro-1H-inden-2-yl)oxy)-6-(naphthalen-2-yl)imidazo[2,1-b]oxazole-5-carboxamide

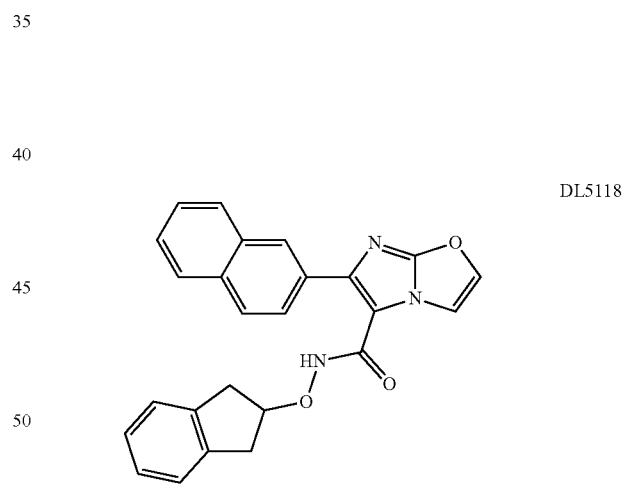

Yield 35%, $^1$H NMR (400 MHz, CDCl$_3$): δ(ppm) 8.42 (s, 1H), 8.17 (s, 1H), 7.97-7.90 (m, 4H), 7.73 (d, J=8.8 Hz, 1H), 7.60-7.59 (m, 2H), 7.58 (s, 1H), 7.13 (s, 4H), 4.97 (t, J=2.4 Hz, 1H), 3.21-3.05 (m, 4H); $^{13}$C NMR (100 MHz, CDCl$_3$): δ(ppm) 159.9, 155.8, 146.7, 140.1, 138.4, 133.5, 131.0, 129.0, 128.6, 128.3, 127.9, 127.2, 126.9, 126.7, 126.3, 124.7, 113.7, 86.2, 38.1. HRMS (ESI): Exact mass calcd for C$_{25}$H$_{20}$N$_3$O$_3$ [M+H]$^+$ 410.1504, found 410.1512.

Example 43. N-(2,3-dihydro-1H-inden-2-yl)-6-(naphthalen-2-yl)imidazo[2,1-b]oxazole-5-carboxamide

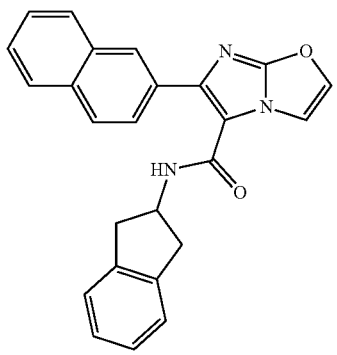

DL5055

Yield 69%, $^1$H NMR (400 MHz, CDCl$_3$): δ(ppm) 8.06 (s, 1H), 7.99 (s, 1H), 7.83 (d, J=7.2 Hz, 1H), 7.72 (t, J=6.8 Hz, 2H), 7.61 (d, J=8.4 Hz, 1H), 7.62-7.49 (m, 3H), 7.11-7.04 (m, 4H), 6.17 (d, J=7.2 Hz, 1H), 4.81-4.77 (m, 1H), 3.23 (dd, J=7.2 Hz, J=9.2 Hz, 2H), 2.60 (dd, J=4.8 Hz, J=11.6 Hz, 2H); $^{13}$C NMR (100 MHz, CDCl$_3$): δ(ppm) 159.7, 155.3, 145.7, 140.4, 138.2, 133.2, 133.0, 130.9, 128.7, 128.4, 128.2, 127.8, 126.8, 126.7 (2C), 126.2, 124.6, 113.9, 113.8, 50.8, 39.8. HRMS (ESI): Exact mass calcd for C$_{25}$H$_{20}$N$_3$O$_2$ [M+H]$^+$ 394.1555, found 394.1561.

Example 44. N-(6-(naphthalen-2-yl)imidazo[2,1-b]oxazol-5-yl)-2,3-dihydro-1H-indene-2-carboxamide

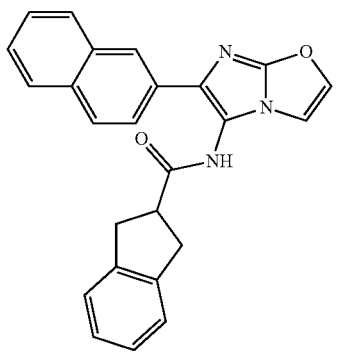

DL5166

$^1$H NMR (400 MHz, DMSO-d$_6$): δ(ppm) 10.34 (s, 1H), 8.29 (s, 1H), 7.99-7.90 (m, 5H), 7.83 (s, 1H), 7.56-7.48 (m, 2H), 7.27 (t, J=4.8 Hz, 2H), 7.18 (t, J=3.2 Hz, 2H), 3.63-3.55 (m, 1H), 3.37-3.25 (m, 4H); $^{13}$C NMR (100 MHz, DMSO-d$_6$): δ(ppm) 157.0, 146.9, 144.1, 138.8, 138.2, 137.1, 136.5, 133.1, 133.0, 132.7, 131.63, 131.58, 131.0, 129.4, 129.3, 118.6, 117.5, 49.0, 41.3. HRMS (ESI): Exact mass calcd for C$_{25}$H$_{20}$N$_3$O$_2$ [M+H]$^+$ 394.1556, found 394.1547.

Example 45. N-((6-(naphthalen-2-yl)imidazo[2,1-b]oxazol-5-yl)methyl)-2,3-dihydro-1H-indene-2-carboxamide

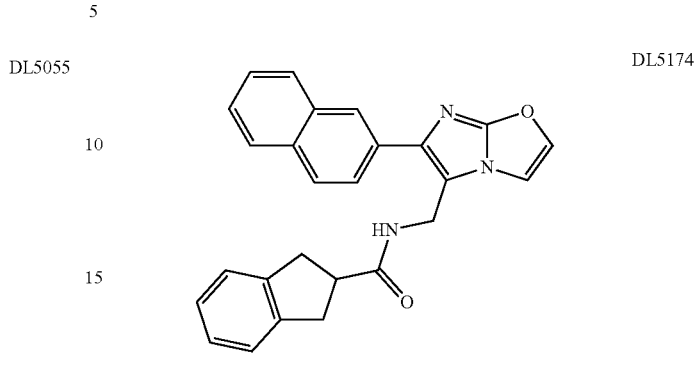

DL5174

$^1$H NMR (400 MHz, DMSO-d$_6$): δ(ppm) 8.65 (t, J=4.8 Hz, 1H), 8.11 (s, 1H), 7.88-7.81 (m, 6H), 7.45-7.38 (m, 2H), 7.10-7.01 (m, 5H), 4.59 (d, J=5.6 Hz, 2H), 3.18-3.12 (m, 1H), 3.06-2.97 (m, 4H); $^{13}$C NMR (100 MHz, DMSO-d$_6$): δ(ppm) 179.9, 159.4, 147.1, 144.6, 144.0, 138.3, 137.2, 137.1, 133.2, 133.1, 132.7, 131.5, 131.0, 130.8, 130.5, 129.3, 121.0, 117.5, 49.1, 41.6, 38.5. HRMS (ESI): Exact mass calcd for C$_{26}$H$_{22}$N$_3$O$_2$ [M+H]$^+$ 408.1712, found 408.1722.

3. Synthesis of (6-aryl-imidazo[2,1-b]thiazol-5-yl)methanamine Analogs

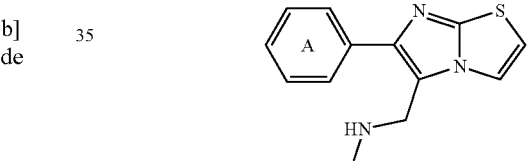

The synthetic route for the synthesis of (6-aryl-imidazo[2,1-b]thiazol-5-yl)methanamine analogs is illustrated as in Scheme 3. Condensation of bromomethyl ketone (1) with thiazol-2-amine generates imidazothiazole 2 in two steps. Vilsmeier formylation of compound 2 gave aldehyde 3 in good yields. The condensation of aldehyde 3 with amine 4 gave the imine 5, which was treated by reducing agent sodium borohydride to give (6-aryl-imidazo[2,1-b]thiazol-5-yl)methanamine analogs. The aldehydes 3 here are the same as in the previous examples above.

Scheme 3.

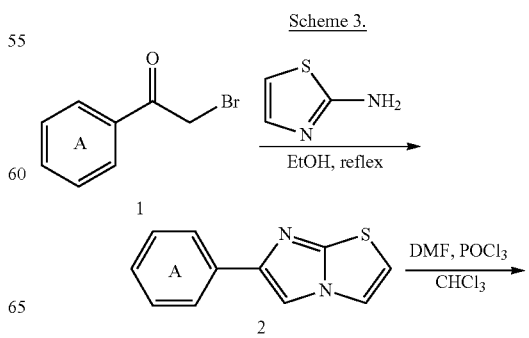

-continued

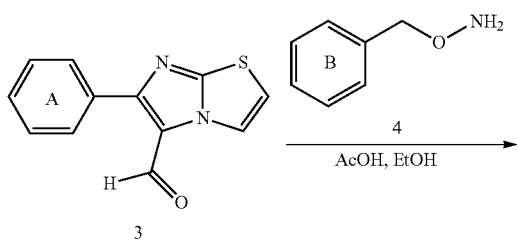

Example 46. (E)-1-(6-(4-chlorophenyl)imidazo[2,1-b]thiazol-5-yl)-N-(3,4-dichlorophenethyl)methanimine A. 6-(4-chlorophenyl)imidazo[2,1-b]thiazole-5-carbaldehyde

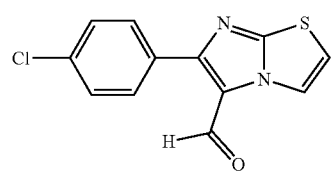 [SMILES: O=Cc1c(-c2ccc(Cl)cc2)nc2sccn12]

$^1$H NMR (400 MHz, CDCl$_3$): δ(ppm) 9.89 (s, 1H), 8.39 (d, J=4.8 Hz, 1H), 7.74 (d, J=8.8 Hz, 2H), 7.49 (d, J=8.4 Hz, 2H), 7.08 (d, J=4.0 Hz, 1H); $^{13}$C NMR (100 MHz, CDCl$_3$): δ(ppm) 177.7, 156.8, 155.7, 136.0, 130.9, 130.2, 129.2, 124.0, 121.5, 114.9.

B. (E)-1-(6-(4-chlorophenyl)imidazo[2,1-b]thiazol-5-yl)-N-(3,4-dichlorophenethyl)methanimine

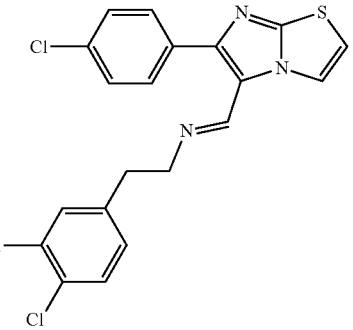

$^1$H NMR (400 MHz, CDCl$_3$): δ(ppm) 8.36 (s, 1H), 8.28 (s, 1H), 8.51 (d, J=7.2 Hz, 2H), 7.43-7.36 (m, 4H), 7.07 (d, J=7.6 Hz, 1H), 6.91 (s, 1H), 3.85 (t, J=6.8 Hz, 2H), 2.96 (t, J=6.8 Hz, 2H). $^{13}$C NMR (100 MHz, CDCl$_3$): δ(ppm) 152.8, 150.0, 140.3, 134.4, 132.2, 132.1, 131.0, 130.24, 130.17, 129.8, 128.9, 128.6, 121.8, 120.7, 112.8, 62.4, 36.9. HRMS (ESI): Exact mass calcd for C$_{20}$H$_{15}$C$_{13}$N$_3$S [M+H]$^+$ 434.0052, found 434.0037.

Example 47. N-((6-(4-chlorophenyl)imidazo[2,1-b]thiazol-5-yl)methyl)-2-(3,4-dichlorophenyl)ethan-1-amine

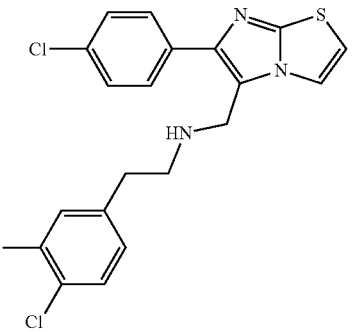

Yield 64%, $^1$H NMR (400 MHz, CDCl$_3$): δ(ppm) 7.57 (d, J=8.4 Hz, 2H), 7.48 (d, J=4.4 Hz, 1H), 7.38 (d, J=8.4 Hz, 2H), 7.32 (d, J=8.0 Hz, 1H), 7.25 (d, J=6.8 Hz, 1H), 6.96 (d, J=8.8 Hz, 1H), 6.75 (d, J=4.8 Hz, 1H), 4.12 (s, 2H), 2.87 (t, J=6.0 Hz, 2H), 2.71 (t, J=6.4 Hz, 2H); $^{13}$C NMR (100 MHz, CDCl$_3$): δ(ppm) 149.1, 143.7, 140.1, 133.1, 132.3, 130.6, 130.3, 130.2, 129.0, 128.7, 128.1, 120.3, 118.7, 111.9, 49.6, 43.7, 35.3, HRMS (ESI): Exact mass calcd for C$_{20}$H$_{17}$C$_{13}$N$_3$S [M+H]$^+$ 436.0209, found 436.0207.

Example 48. 2-(3-chlorophenyl)-N-((6-(4-chlorophenyl)imidazo[2,1-b]thiazol-5-yl)methyl)ethan-1-amine

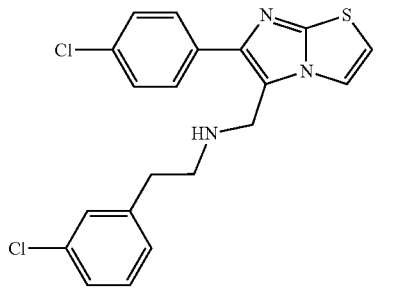

DL4094

Yield 28%, $^1$H NMR (400 MHz, CDCl$_3$): δ(ppm) 7.57-7.53 (m, 3H), 7.38 (d, J=8.4 Hz, 2H), 7.20 (d, J=8.4 Hz, 2H), 7.16 (s, 1H), 7.02 (d, J=5.6 Hz, 1H), 6.76 (d, J=4.0 Hz, 1H), 4.12 (s, 2H), 2.90 (t, J=7.2 Hz, 2H), 2.75 (t, J=6.8 Hz, 2H); 13C NMR (100 MHz, CDCl$_3$): δ(ppm) 149.1, 143.7, 141.8, 134.2, 133.1, 129.7, 129.0, 128.8, 128.7, 126.9, 126.5, 120.2, 118.8, 111.9, 49.8, 43.7, 35.7, HRMS (ESI): Exact mass calcd for C$_{20}$H$_{18}$C$_{12}$N$_3$S [M+H]$^+$ 402.0598, found 402.0599.

Example 49. 2-(4-chlorophenyl)-N-((6-(4-chlorophenyl)imidazo[2,1-b]thiazol-5-yl)methyl)ethan-1-amine

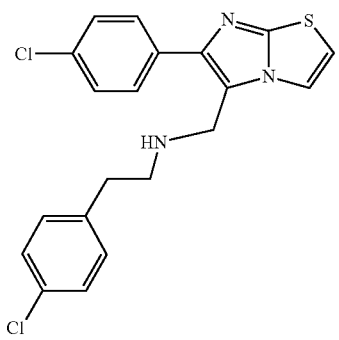

DL4095

Yield 28%, $^1$H NMR (400 MHz, CDCl$_3$): δ(ppm) 7.56 (d, J=8.8 Hz, 2H), 7.50 (d, J=4.0 Hz, 1H), 7.38 (d, J=8.8 Hz, 2H), 7.24 (d, J=8.8 Hz, 2H), 7.06 (d, J=7.6 Hz, 2H), 6.75 (d, J=4.8 Hz, 1H), 4.12 (s, 2H), 2.88 (t, J=7.2 Hz, 2H), 2.74 (t, J=7.2 Hz, 2H); $^{13}$C NMR (100 MHz, CDCl$_3$): δ(ppm) 149.1, 143.7, 138.1, 133.1, 132.0, 130.0, 129.0, 128.7, 128.6, 126.5, 120.3, 118.8, 111.9, 49.9, 43.6, 35.4, HRMS (ESI): Exact mass calcd for C$_{20}$H$_{18}$C$_{12}$N$_3$S [M+H]$^+$ 402.0598, found 402.0598.

Example 50. 2-(4-bromophenyl)-N-((6-(4-chlorophenyl)imidazo[2,1-b]thiazol-5-yl)methyl)ethan-1-amine

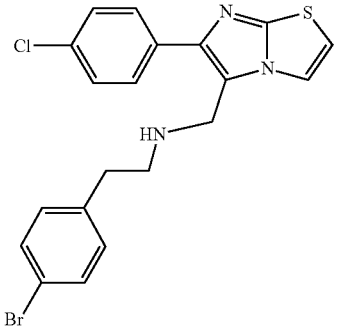

DL4100

Yield 38%, $^1$H NMR (400 MHz, CDCl$_3$): δ(ppm) 7.55 (d, J=8.8 Hz, 2H), 7.46 (d, J=4.8 Hz, 1H), 7.39-7.36 (m, 4H), 7.01 (d, J=8.0 Hz, 2H), 6.74 (d, J=8.4 Hz, 1H), 4.09 (s, 2H), 2.87 (t, J=6.8 Hz, 2H), 2.71 (t, J=6.4 Hz, 2H); $^{13}$C NMR (100 MHz, CDCl$_3$): δ(ppm) 149.0, 143.6, 138.8, 133.1, 131.5, 130.4, 129.0, 128.8, 128.6, 120.5, 120.0, 118.8, 111.9, 49.9, 43.7, 35.6. HRMS (ESI): Exact mass calcd for C$_{20}$H$_{18}$BrClN$_3$S [M+H]$^+$ 446.0093, found 446.0101.

Example 51. 2-(3-bromo-4-chlorophenyl)-N-((6-(4-chlorophenyl)imidazo[2,1-b]thiazol-5-yl)methyl)ethan-1-amine

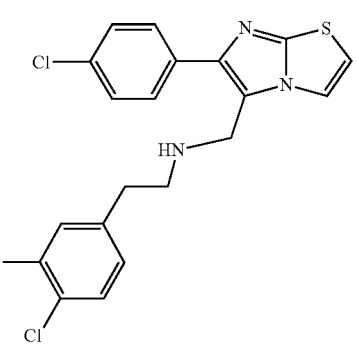

DL4102

Yield 18%, $^1$H NMR (400 MHz, CDCl$_3$): δ(ppm) 7.56 (d, J=8.8 Hz, 2H), 7.47 (d, J=4.8 Hz, 1H), 7.42-7.36 (m, 4H), 7.32 (d, J=8.0 Hz, 1H), 7.00 (d, J=8.0 Hz, 1H), 6.75 (d, J=4.8 Hz, 1H), 4.11 (s, 2H), 2.86 (t, J=6.0 Hz, 2H), 2.70 (t, J=6.4 Hz, 2H); $^{13}$C NMR (100 MHz, CDCl$_3$): δ(ppm) 149.1, 143.6, 140.3, 133.9, 133.1, 132.1, 130.2, 129.0, 128.8, 128.7, 122.3, 120.3, 118.7, 118.1, 112.0, 49.7, 43.7, 35.2, HRMS (EST): Exact mass calcd for C$_{20}$H$_{17}$BrCl$_2$N$_3$S [M+H]$^+$ 479.9704, found 479.9715.

Example 52. 2-(3-chloro-4-(trifluoromethyl)phenyl)-N-((6-(4-chlorophenyl)imidazo[2,1-b]thiazol-5-yl)methyl)ethan-1-amine

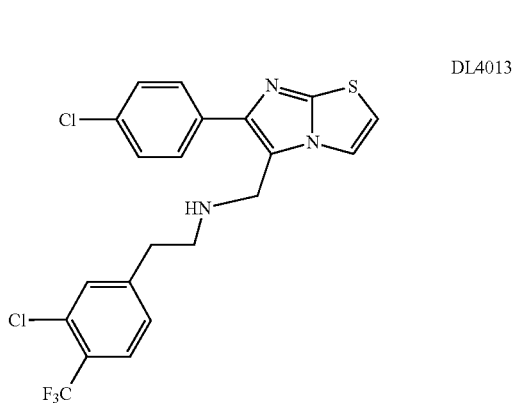 [SMILES: FC(F)(F)c1ccc(CCNCc2c(-c3ccc(Cl)cc3)nc3sccn23)cc1Cl]

DL4013

Yield 18%, $^1$H NMR (400 MHz, CDCl$_3$): δ(ppm) 7.55 (d, J=8.0 Hz, 2H), 7.42 (d, J=4.8 Hz, 1H), 7.37 (d, J=8.8 Hz, 2H), 7.29 (s, 1H), 7.09 (d, J=8.0 Hz, 1H), 6.72 (d, J=4.8 Hz, 1H), 4.11 (s, 2H), 2.89 (t, J=7.2 Hz, 2H), 2.76 (t, J=7.2 Hz, 2H); $^{13}$C NMR (100 MHz, CDCl$_3$): δ(ppm) 149.1, 145.9, 143.7, 133.1 (J=4.4 Hz), 132.1, 131.6, 129.0, 128.7, 128.6 (J=11.9 Hz), 127.5 (J=4.4 Hz), 127.0, 125.4 (J=212.8 Hz), 120.2, 118.6, 118.2, 111.9, 49.3, 43.7.

Example 53. 2-(3-bromophenyl)-N-((6-(4-chlorophenyl)imidazo[2,1-b]thiazol-5-yl)methyl)ethan-1-amine

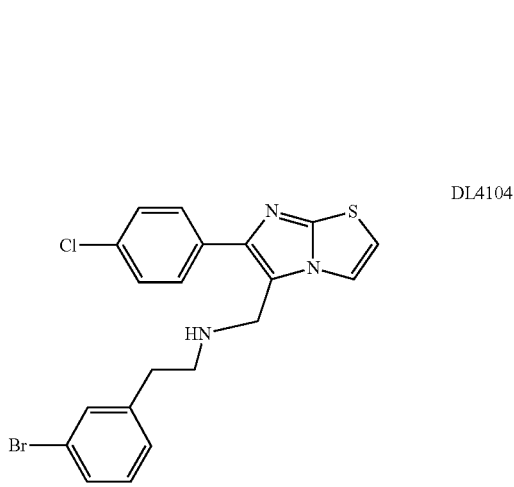 [SMILES: Clc1ccc(-c2nc3sccn3c2CNCCc2cccc(Br)c2)cc1]

DL4104

Yield 65%, $^1$H NMR (400 MHz, CDCl$_3$): δ(ppm) 7.56 (d, J=8.8 Hz, 2H), 7.51 (d, J=4.0 Hz, 1H), 7.39-7.32 (m, 3H), 7.14 (t, J=8.0 Hz, 1H), 7.06 (d, J=7.6 Hz, 1H), 6.76 (d, J=4.8 Hz, 1H), 4.11 (s, 2H), 2.89 (t, J=7.2 Hz, 2H), 2.73 (t, J=6.0 Hz, 2H); $^{13}$C NMR (100 MHz, CDCl$_3$): δ(ppm) 149.1, 143.6, 142.2, 133.1, 133.0, 131.7, 130.0, 129.4, 129.0, 128.7, 127.4, 122.5, 120.4, 118.8, 111.9, 49.8, 43.8, 35.8. HRMS' (ESI): Exact mass calcd for C$_{20}$H$_{18}$BrClN$_3$S [M+H]$^+$ 446.0093, found 446.0101.

Example 54. N-((6-(4-chlorophenyl)imidazo[2,1-b]thiazol-5-yl)methyl)-2-phenylethan-1-amine

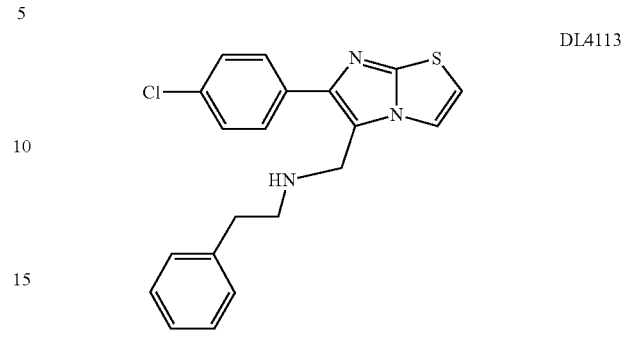

DL4113

Yield 42%, $^1$H NMR (400 MHz, CDCl$_3$): δ(ppm) 7.56 (d, J=8.8 Hz, 2H), 7.51 (d, J=8.0 Hz, 1H), 7.37 (d, J=8.8 Hz, 2H), 7.29 (t, J=8.0 Hz, 2H), 7.23 (d, J=8.0 Hz, 1H), 7.16 (d, J=7.2 Hz, 2H), 6.73 (d, J=4.0 Hz, 1H), 4.09 (s, 2H), 2.92 (t, J=6.4 Hz, 2H), 2.78 (t, J=6.0 Hz, 2H); $^{13}$C NMR (100 MHz, CDCl3): δ(ppm) 149.0, 143.5, 139.7, 133.2, 133.0, 129.0, 128.7, 128.6, 128.5, 126.3, 120.7, 118.9, 111.8, 50.2, 43.8, 36.1. HRMS (ESI): Exact mass calcd for C$_{20}$H$_{19}$ClN$_3$S [M+H]$^+$ 368.0988, found 368.0989.

Example 55. N-((6-(4-chlorophenyl)imidazo[2,1-b]thiazol-5-yl)methyl)-2-(4-fluorophenyl)ethan-1-amine

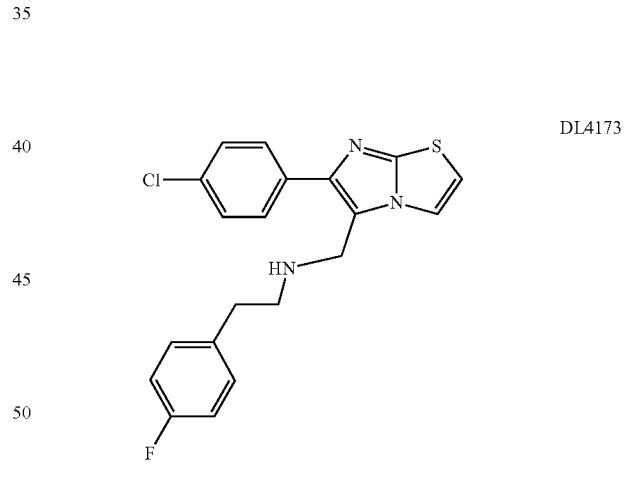

DL4173

Yield 44%, $^1$H NMR (400 MHz, CDCl$_3$): δ(ppm) 7.57 (d, J=8.4 Hz, 2H), 7.50 (d, J=4.8 Hz, 1H), 7.37 (d, J=8.8 Hz, 2H), 7.11-7.08 (m, 2H), 6.96 (t, J=8.8 Hz, 2H), 6.75 (d, J=4.8 Hz, 1H), 4.11 (s, 2H), 2.88 (t, J=6.8 Hz, 2H), 2.74 (t, J=6.4 Hz, 2H); $^{13}$C NMR (100 MHz, CDCl$_3$): δ(ppm) 161.5 (J=244.1 Hz), 149.0, 143.5, 135.4, 133.2, 133.0, 130.0 (J=7.4 Hz), 129.0, 128.6, 120.6, 118.8, 115.2 (J=22.4 Hz), 111.8, 50.2, 43.8, 35.3. HRMS (ESI): Exact mass calcd for C$_{20}$H$_{18}$ClFN$_3$S [M+H]$^+$ 386.0894, found 386.0894.

Example 56. 4-(2-(((6-(4-chlorophenyl)imidazo[2,1-b]thiazol-5yl)methyl)amino)ethyl)phenol

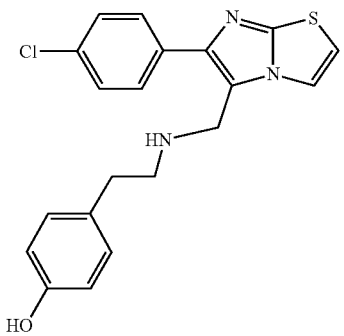

DL4170

Yield 31%, $^1$H NMR (400 MHz, CDCl$_3$): δ(ppm) 7.54-7.49 (m, 3H), 7.36 (d, J=8.8 Hz, 2H), 6.97 (d, J=8.4 Hz, 2H), 6.72 (d, J=7.2 Hz, 2H), 4.09 (s, 2H), 2.87 (t, J=6.0 Hz, 2H), 2.71 (t, J=6.4 Hz, 2H); $^{13}$C NMR (100 MHz, CDCl$_3$): δ(ppm) 154.5, 149.0, 143.4, 133.1, 132.9, 131.3, 129.7, 129.0, 128.7, 120.7, 118.8, 115.5, 112.0, 50.3, 43.7, 35.0. HRMS (ESI): Exact mass calcd for C$_{20}$H$_{19}$ClN$_3$OS [M+H]$^+$ 384.0937, found 384.0931.

Example 57. N-((6-(4-chlorophenyl)imidazo[2,1-b]thiazol-5-yl)methyl)-2-(1H-indol-3-yl)ethan-1-amine

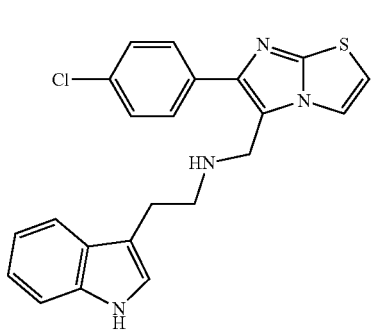

DL4153

Yield 49%, $^1$H NMR (400 MHz, CDCl$_3$): δ(ppm) 8.27 (br s, 1H), 7.59 (d, J=8.0 Hz, 1H), 7.53-7.49 (m, 3H), 7.35 (d, J=8.0 Hz, 1H), 7.28-7.20 (m, 3H), 7.12 (t, J=7.6 Hz, 1H), 6.94 (s, 1H), 6.70 (d, J=4.8 Hz, 1H), 4.08 (s, 2H), 3.01-2.95 (m, 4H); $^{13}$C NMR (100 MHz, CDCl$_3$): δ(ppm) 148.9, 143.4, 136.4, 133.1, 132.9, 128.9 (2C), 128.6, 127.3, 122.1, 119.3, 118.8, 118.7, 113.4, 111.9, 111.3, 49.1, 43.8, 25.5. HRMS (ESI): Exact mass calcd for C$_{22}$H$_{20}$ClN$_4$S [M+H]$^+$ 407.1097, found 407.1096.

Example 58. N-((6-(4-chlorophenyl)imidazo[2,1-b]thiazol-5-yl)methyl)-2,3-dihydro-1H-inden-2-amine

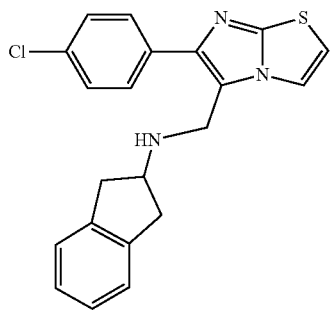

DL4175

Yield 26%, $^1$H NMR (400 MHz, CDCl$_3$): δ(ppm) 7.66 (d, J=4.4 Hz, 1H), 7.62 (d, J=8.4 Hz, 2H), 7.40 (d, J=8.0 Hz, 2H), 7.21-7.15 (m, 4H), 6.78 (d, J=4.8 Hz, 1H), 4.19 (s, 2H), 3.69-3.62 (m, 1H), 3.15 (dd, J=7.2 Hz, J=8.4 Hz, 2H), 2.89 (dd, J=5.6 Hz, J=10.0 Hz, 2H); $^{13}$C NMR (100 MHz, CDCl$_3$): δ(ppm) 149.0, 143.4, 141.4, 133.2, 133.1, 129.0, 128.7, 126.5, 124.7, 120.7, 118.9, 112.0, 59.1, 42.3, 39.9. HRMS (ESI): Exact mass calcd for C$_{21}$H$_{19}$ClN$_3$S [M+H]$^+$ 380.0988, found 380.0991.

Example 59. N-((6-(4-chlorophenyl)imidazo[2,1-b]thiazol-5-yl)methyl)naphthalen-2-amine

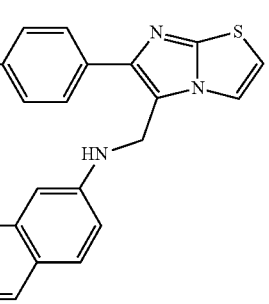

DL 4179

Yield 15%, $^1$H NMR (400 MHz, CDCl$_3$): δ(ppm) 7.73-7.66 (m, 5H), 7.62 (d, J=7.6 Hz, 1H), 7.48 (d, J=4.4 Hz, 1H), 7.43-7.28 (m, 3H), 7.26 (t, J=7.2 Hz, 1H), 6.93 (d, J=7.6 Hz, 2H), 6.84 (d, J=4.8 Hz, 1H), 4.71 (s, 2H); $^{13}$C NMR (100 MHz, CDCl$_3$): δ(ppm) 149.5, 145.0, 144.4, 134.9, 133.5, 132.6, 129.3, 128.9, 128.8, 127.9, 127.7, 126.7, 126.1, 122.7, 118.8, 117.8, 112.9, 105.0, 39.2. HRMS (ESI): Exact mass calcd for C$_{22}$H$_{17}$ClN$_3$S [M+H]$^+$ 390.0832, found 390.0839.

Example 60. N-benzyl-1-(6-(4-chlorophenyl)imidazo[2,1-b]thiazol-5-yl)methanamine

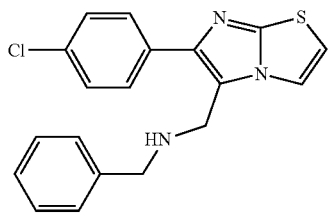

DL5002

Yield 38%, $^1$H NMR (400 MHz, CDCl$_3$): δ(ppm) 7.60 (d, J=4.8 Hz, 1H), 7.55 (d, J=8.8 Hz, 2H), 7.35-7.25 (m, 7H), 6.79 (d, J=3.6 Hz, 1H), 4.10 (s, 2H), 3.79 (s, 2H); $^{13}$C NMR (100 MHz, CDCl$_3$): δ(ppm) 149.0, 143.7, 139.6, 133.1, 133.0, 128.9, 128.6, 128.5, 128.2, 127.2, 120.6, 118.7, 112.0, 53.1, 42.8. HRMS (ESI): Exact mass calcd for C$_{19}$H$_{17}$ClN$_3$S [M+H]$^+$ 354.0832, found 354.0834.

Example 61. 2-(3,4-dichlorophenyl)-N-((6-phenylimidazo[2,1-b]thiazol-5-yl)methyl)ethan-1-amine

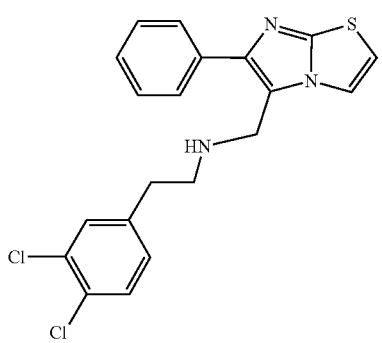

DL4171

Yield 42%, $^1$H NMR (400 MHz, CDCl$_3$): δ(ppm) 7.63 (d, J=8.0 Hz, 2H), 7.45-7.40 (m, 3H), 7.32 (t, J=7.6 Hz, 2H), 7.24 (s, 1H), 6.95 (d, J=8.0 Hz, 1H), 6.74 (d, J=4.4 Hz, 1H), 4.15 (s, 2H), 2.88 (t, J=6.4 Hz, 2H), 2.70 (t, J=6.0 Hz, 2H); $^{13}$C NMR (100 MHz, CDCl$_3$): δ(ppm) 148.9, 144.8, 140.3, 134.6, 132.2, 130.6, 130.3, 130.1, 128.5, 128.1, 127.8, 127.3, 120.2, 118.7, 111.7, 49.6, 43.7, 35.4. HRMS (ESI): Exact mass calcd for C$_{20}$H$_{18}$C$_{12}$N$_3$S [M+H]$^+$ 402.0598, found 402.0594.

Example 62. N-((6-(3-chlorophenyl)imidazo[2,1-b]thiazol-5-yl)methyl)-2-(3,4-dichlorophenyl)ethan-1-amine

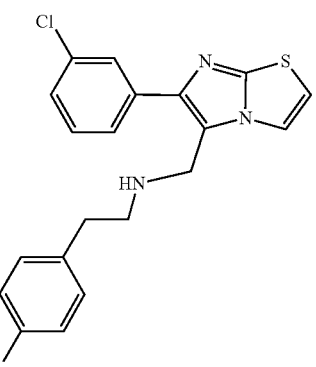

DL5020

Yield 41%, $^1$H NMR (400 MHz, CDCl$_3$): δ(ppm) 7.64 (s, 1H), 7.49 (t, J=6.8 Hz, 2H), 7.35-7.24 (m, 4H), 6.95 (d, J=8.0 Hz, 2H), 6.76 (d, J=4.8 Hz, 1H); 4.13 (s, 2H), 2.87 (t, J=6.8 Hz, 2H), 2.71 (t, J=6.8 Hz, 2H); $^{13}$C NMR (100 MHz, CDCl$_3$): δ(ppm) 149.2, 143.4, 140.0, 136.3, 134.4, 132.3, 130.6, 130.3, 130.2, 129.7, 128.1, 127.8, 127.3, 125.8, 120.4, 118.8, 112.1, 49.5, 43.6, 35.2. HRMS (ESI): Exact mass calcd for C$_{20}$H$_{17}$C$_{13}$N$_3$S [M+H]$^+$ 436.0209, found 436.0212.

Example 63. N-((6-(4-bromophenyl)imidazo[2,1-b]thiazol-5-yl)methyl)-2-(3,4-dichlorophenyl)ethan-1-amine

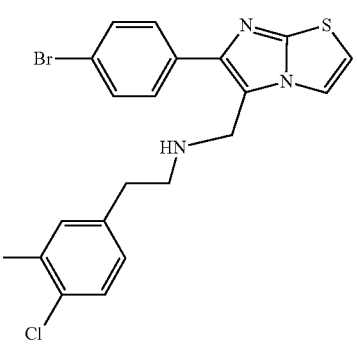

DL4129

Yield 24%, $^1$H NMR (400 MHz, CDCl$_3$): δ(ppm) 7.55-7.49 (m, 5H), 7.33 (d, J=8.8 Hz, 1H), 7.26 (d, J=8.8 Hz, 1H), 6.96 (d, J=8.0 Hz, 1H), 6.76 (d, J=4.8 Hz, 1H), 4.12 (s, 2H), 2.89 (t, J=6.8 Hz, 2H), 2.72 (t, J=6.4 Hz, 2H); $^{13}$C NMR (100 MHz, CDCl$_3$): δ(ppm) 149.1, 143.6, 140.2, 133.6, 132.2, 131.6, 130.6, 130.3, 130.2, 129.3, 128.1, 121.3, 120.4, 118.7, 111.9, 49.7, 43.7, 35.3. HRMS (ESI): Exact mass calcd for C$_{20}$H$_{17}$BrCl$_2$N$_3$S [M+H]$^+$ 479.9704, found 479.9696.

Example 64. 2-(3,4-dichlorophenyl)-N-((6-(4-isocyanophenyl)imidazo[2,1-b]thiazol-5-yl)methyl)ethan-1-amine

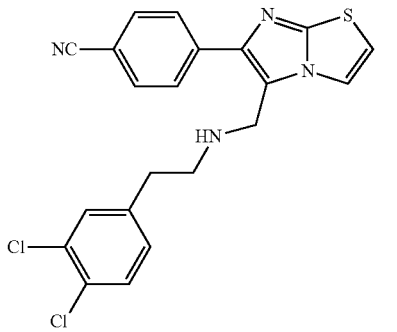

DL4130

Yield 12%, $^1$H NMR (400 MHz, CDCl$_3$): δ(ppm) 7.75 (d, J=8.4 Hz, 2H), 7.66 (d, J=8.4 Hz, 2H), 7.49 (d, J=4.4 Hz, 1H), 7.30 (d, J=7.6 Hz, 1H), 7.23 (s, 1H), 6.96 (d, J=8.8 Hz, 1H), 6.78 (d, J=4.4 Hz, 1H), 4.13 (s, 2H), 2.88 (t, J=6.0 Hz, 2H), 2.71 (t, J=6.4 Hz, 2H); $^{13}$C NMR (100 MHz, CDCl$_3$): δ(ppm) 149.5, 142.7, 140.1, 139.2, 132.3, 130.6, 130.3, 130.2, 128.1, 128.0, 121.7, 119.1, 118.7, 112.6, 110.3, 49.7, 43.9, 35.4. HRMS (ESI): Exact mass calcd for C$_{21}$H$_{17}$Cl$_2$N$_4$S [M+H]$^+$ 427.0551, found 427.0550.

Example 65. 2-(3,4-dichlorophenyl)-N-((6-(p-tolyl)imidazo[2,1-b]thiazol-5-yl)methyl)ethan-1-amine

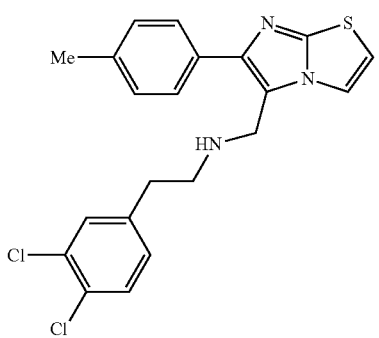

DL4132

Yield 55%, $^1$H NMR (400 MHz, CDCl$_3$): δ(ppm) 7.51 (d, J=8.0 Hz, 2H), 7.46 (d, J=4.8 Hz, 1H), 7.31 (d, J=8.8 Hz, 1H), 7.22 (d, J=7.2 Hz, 3H), 6.94 (d, J=8.0 Hz, 1H), 6.72 (d, J=4.8 Hz, 1H), 4.12 (s, 2H), 2.86 (t, J=6.0 Hz, 2H), 2.69 (t, J=6.4 Hz, 2H), 2.34 (s, 3H); $^{13}$CNMR (100 MHz, CDCl$_3$): δ(ppm) 148.8, 144.8, 140.3, 137.0, 132.2, 131.7, 130.6, 130.3, 130.1, 129.2, 128.1, 127.7, 119.9, 118.7, 111.5, 49.6, 43.7, 35.3, 21.2; HRMS (ESI): Exact mass calcd for C$_{21}$H$_{20}$Cl$_2$N$_3$S [M+H]$^+$ 416.0755, found 416.0746.

Example 66. 2-(3,4-dichlorophenyl)-N-((6-(naphthalen-2-yl)imidazo[2,1-b]thiazol-5-yl)methyl)ethan-1-amine

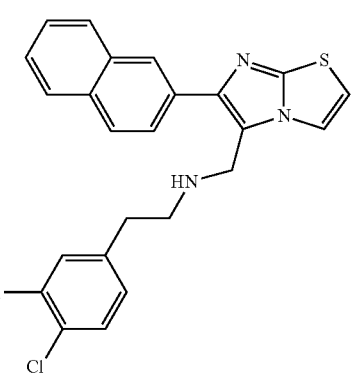

DL4133

Yield 31%, $^1$H NMR (400 MHz, CDCl$_3$): δ(ppm) 8.08 (s, 1H), 7.90-7.79 (m, 4H), 7.52-7.48 (m, 3H), 7.30-7.24 (m, 3H), 6.93 (d, J=7.6 Hz, 1H), 6.77 (d, J=4.0 Hz, 1H), 4.23 (s, 2H), 2.89 (t, J=6.0 Hz, 2H), 2.71 (t, J=6.0 Hz, 2H); $^{13}$C NMR (100 MHz, CDCl$_3$): δ(ppm) 149.1, 144.7, 140.3, 133.5, 132.6, 132.2, 132.1, 130.6, 130.3, 130.1, 128.1, 127.7, 126.5, 126.2, 126.02, 125.9, 120.6, 118.8, 111.8, 49.7, 43.8, 35.3. HRMS (ESI): Exact mass calcd for C$_{24}$H$_{20}$Cl$_2$N$_3$S [M+H]$^+$ 452.0755, found 452.0757.

Example 67. N-((6-(4-(tert-butyl)phenyl)imidazo[2,1-b]thiazol-5-yl)methyl)-2-(3,4-dichlorophenyl)ethan-1-amine

DL4141

Yield 56%, $^1$H NMR (400 MHz, CDCl$_3$): δ(ppm) 7.54 (d, J=8.0 Hz, 2H), 7.49 (d, J=4.8 Hz, 1H), 7.43 (d, J=8.4 Hz, 2H), 7.30 (d, J=7.6 Hz, 1H), 7.24 (d, J=1.6 Hz, 1H), 6.94 (d, J=8.0 Hz, 1H), 6.71 (d, J=4.8 Hz, 1H), 4.13 (s, 2H), 2.88 (t, J=6.8 Hz, 2H), 2.70 (t, J=7.2 Hz, 2H), 1.35 (s, 9H); $^{13}$C NMR (100 MHz, CDCl$_3$): δ(ppm) 150.2, 148.8, 144.8, 140.2, 132.2, 131.7, 130.6, 130.3, 130.1, 128.2, 127.5, 125.5, 119.8, 118.8, 111.5, 49.6, 43.7, 35.3, 34.6, 31.3; HRMS (ESI): Exact mass calcd for C$_{24}$H$_{26}$Cl$_2$N$_3$S [M+H]$^+$ 458.1224, found 458.1233.

Example 68. 2-(3,4-dichlorophenyl)-N-((6-(4-fluorophenyl)imidazo[2,1-b]thiazol-5-yl)methyl)ethan-1-amine

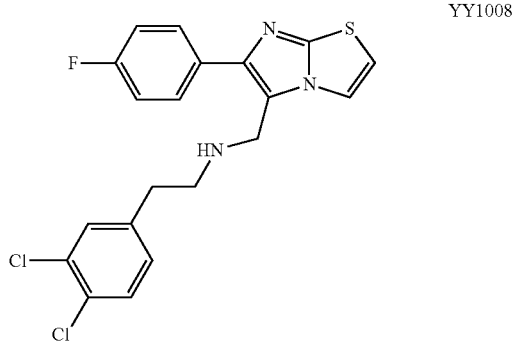 [SMILES: Fc1ccc(-c2nc3sccn3c2CNCCc2ccc(Cl)c(Cl)c2)cc1]

YY1008

Yield 34%, $^1$H NMR (400 MHz, CDCl$_3$): δ(ppm) 7.56-7.53 (m, 2H), 7.46 (d, J=4.8 Hz, 1H), 7.28 (d, J=8.0 Hz, 1H), 7.07 (t, J=8.4 Hz, 2H), 6.92 (d, J=7.6 Hz, 1H), 6.72 (d, J=4.8 Hz, HI), 4.07 (s, 2H), 2.83 (t, J=6.0 Hz, 2H), 2.67 (t, J=6.4 Hz, 2H); $^{13}$CNMR (100 MHz, CDCl$_3$): δ(ppm) 162.4 (J=245.5 Hz), 148.9, 143.8, 140.1, 132.2, 130.6, 130.3, 130.1, 129.4 (J=7.5 Hz), 128.1, 119.8, 118.7, 115.4 (J=22.3 Hz), 111.9, 49.5, 43.5, 35.2. HRMS (ESI): Exact mass calcd for C$_{20}$H$_{17}$Cl$_2$FN$_3$S [M+H]$^+$ 420.0504, found 420.0515.

Example 69. 2-(3,4-dichlorophenyl)-N-((6-(4-(trifluoromethyl)phenyl)imidazo[2,1-b]thiazol-5-yl)methyl)ethan-1-amine

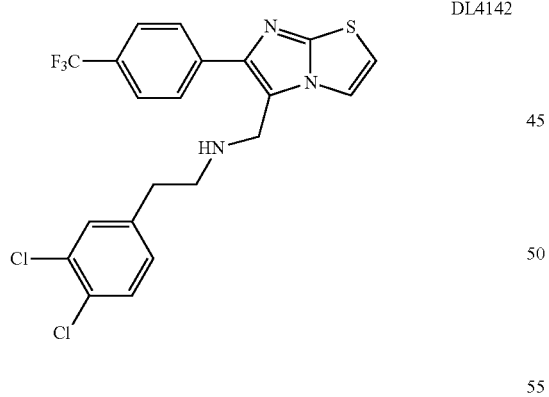

DL4142

Yield 38%, $^1$H NMR (400 MHz, CDCl$_3$): δ(ppm) 7.75 (d, J=8.8 Hz, 2H), 7.65 (d, J=8.8 Hz, 2H), 7.51 (d, J=4.8 Hz, 1H), 7.31 (d, J=8.0 Hz, 1H), 7.25 (s, 1H), 6.96 (d, J=8.8 Hz, 1H), 6.77 (d, J=4.8 Hz, 1H), 4.15 (s, 2H), 2.89 (t, J=7.2 Hz, 2H), 2.72 (t, J=7.2 Hz, 2H); $^{13}$C NMR (100 MHz, CDCl$_3$): δ(ppm) 149.4, 143.4, 140.2, 138.1, 132.3, 130.6, 130.3, 130.2, 128.1, 127.8, 126.1, 125.4, 122.9, 120.9, 118.8, 112.3, 49.6, 43.7, 35.2. HRMS (ESI): Exact mass calcd for C$_{21}$H$_{17}$C$_{12}$F$_3$N$_3$S [M+H]$^+$ 470.0472, found 470.0459.

Example 70. 2-(3,4-dichlorophenyl)-N-((6-(4-methoxyphenyl)imidazo[2,1-b]thiazol-5-yl)methyl)ethan-1-amine

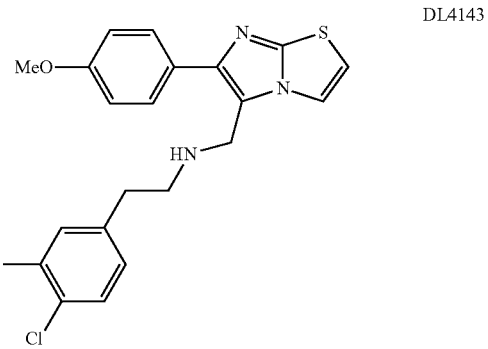

DL4143

Yield 49%, $^1$H NMR (400 MHz, CDCl$_3$): δ(ppm) 7.54-7.49 (m, 3H), 7.30 (d, J=7.6 Hz, 1H), 7.22 (d, J=1.6 Hz, 1H), 6.94 (d, J=8.8 Hz, 3H), 6.72 (d, J=4.8 Hz, 1H), 4.11 (s, 2H), 3.84 (s, 3H), 2.86 (t, J=6.8 Hz, 2H), 2.70 (t, J=7.2 Hz, 2H); $^{13}$C NMR (100 MHz, CDCl$_3$): δ(ppm) 159.0, 148.8, 144.8, 140.1, 132.2, 130.6, 130.3, 130.1, 129.0, 128.1, 127.2, 119.2, 118.7, 113.9, 111.5, 55.3, 49.5, 43.6, 35.2. HRMS (ESI): Exact mass calcd for C$_{21}$H$_{20}$Cl$_2$N$_3$OS [M+H]$^+$ 432.0704, found 432.0709.

Example 71. 2-(3,4-dichlorophenyl)-N-((6-ethylimidazo[2,1-b]thiazol-5-yl)methyl)ethan-1-amine A. 6-ethylimidazo[2,1-b]thiazole-5-carbaldehyde

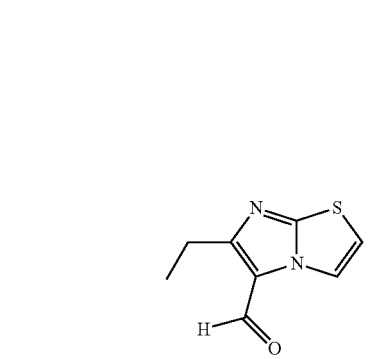

$^1$H NMR (400 MHz, CDCl$_3$): δ(ppm) 9.81 (s, 1H), 8.26 (d, J=3.6 Hz, 1H), 6.98 (d, J=4.8 Hz, 1H), 2.99 (q, J=8.0 Hz, 2H), 1.41 (t, J=8.0 Hz, 3H); $^{13}$C NMR (100 MHz, CDCl3): δ(ppm) 175.6, 162.8, 155.6, 123.8, 121.2, 114.0, 21.7, 14.4.

B. 2-(3,4-dichlorophenyl)-N-((6-ethylimidazo[2,1-b]thiazol-5-yl)methyl)ethan-1-amine

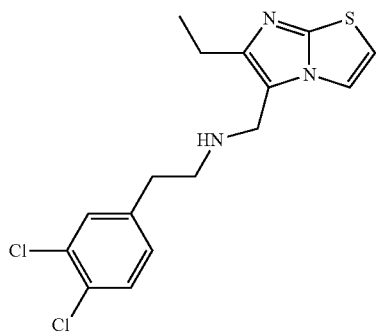

Yield 42%, $^1$H NMR (400 MHz, CDCl$_3$): δ(ppm) 7.35 (d, J=8.8 Hz, 1H), 7.32 (d, J=8.0 Hz, 1H), 7.26 (s, 1H), 6.97 (d, J=8.4 Hz, 1H), 6.67 (d, J=4.8 Hz, 1H), 3.91 (s, 2H), 2.85 (t, J=7.2 Hz, 2H), 2.71 (t, J=7.2 Hz, 2H), 2.64 (q, J=7.2 Hz, 2H), 1.26 (t, J=6.8 Hz, 3H); $^{13}$C NMR (100 MHz, CDCl$_3$): δ(ppm) 148.2, 147.2, 140.3, 132.2, 130.6, 130.3, 130.1, 128.1, 118.9, 118.3, 110.8, 49.4, 42.8, 35.4, 21.1, 14.8. HRMS (ESI): Exact mass calcd for C$_{16}$H$_{18}$Cl$_2$N$_3$S [M+H]$^+$ 354.0598, found 354.0597.

Example 72. N-((6-(4-chlorophenyl)-2-methylimidazo[2,1-b]thiazol-5-yl)methyl)-2-(3,4-dichlorophenyl)ethan-1-amine

A. 6-(4-chlorophenyl)-2-methylimidazo[2,1-b]thiazole-5-carbaldehyde

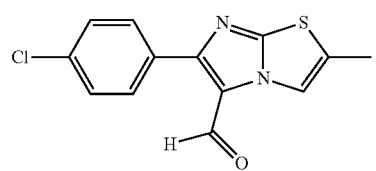 [SMILES: Cc1cn2c(C=O)c(-c3ccc(Cl)cc3)nc2s1]

$^1$H NMR (400 MHz, CDCl$_3$): δ(ppm) 9.84 (s, 1H), 8.11 (s, 1H), 7.72 (d, J=8.8 Hz, 2H), 7.48 (d, J=7.6 Hz, 2H), 2.52 (s, 3H); $^{13}$C NMR (100 MHz, CDCl$_3$): δ(ppm) 177.6, 155.7, 135.7, 131.1, 130.2, 129.3, 129.2, 123.9, 118.0, 14.0.

B. N-((6-(4-chlorophenyl)-2-methylimidazo[2,1-b]thiazol-5-yl)methyl)-2-(3,4-dichlorophenyl)ethan-1-amine

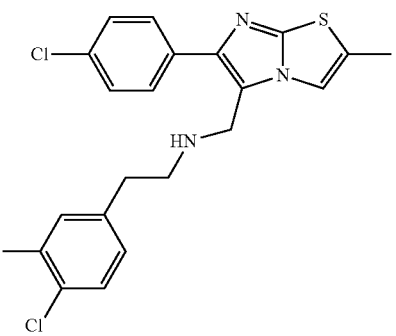

Yield 22%, $^1$H NMR (400 MHz, CDCl$_3$): δ(ppm) 7.55 (d, J=7.6 Hz, 2H), 7.38-7.32 (m, 3H), 7.26 (s, 1H), 7.10 (s, 1H), 6.96 (d, J=7.6 Hz, 1H), 4.06 (s, 2H), 2.88 (t, J=6.4 Hz, 2H), 2.71 (t, J=6.8 Hz, 2H), 2.39 (s, 3H); $^{13}$C NMR (100 MHz, CDCl$_3$): δ(ppm) 148.6, 142.4, 140.3, 133.3, 132.9, 132.2, 130.6, 130.1, 128.8, 128.7, 128.1, 126.1, 120.1, 115.0, 49.5, 43.7, 35.3, 14.1. HRMS (ESI): Exact mass calcd for C$_{21}$H$_{19}$Cl$_3$N$_3$S [M+H]$^+$ 450.0365, found 450.0363.

Example 73. N-((6-(naphthalen-2-yl)imidazo[2,1-b]thiazol-5-yl)methyl)-2-phenylethan-1-amine

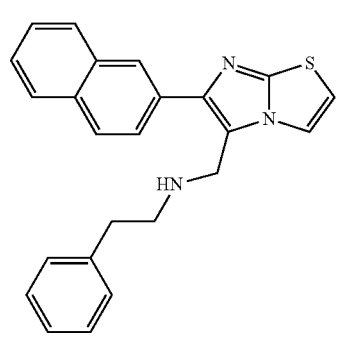

Yield 42%, $^1$H NMR (400 MHz, CDCl$_3$): δ(ppm) 8.01 (s, 1H), 7.90-7.80 (m, 4H), 7.55 (d, J=4.0 Hz, 1H), 7.51-7.48 (m, 2H), 7.29-7.17 (m, 5H), 6.75 (d, J=4.0 Hz, 1H), 4.23 (s, 2H), 2.95 (t, J=6.8 Hz, 2H), 2.80 (t, J=6.4 Hz, 2H); $^{13}$C NMR (100 MHz, CDCl$_3$): δ(ppm) 149.0, 144.6, 139.8, 133.5, 132.6, 132.2, 128.7, 128.5, 128.2, 128.1, 127.6, 126.4, 126.2, 126.13, 126.06, 125.8, 120.9, 118.9, 111.7, 50.2, 43.9, 36.1. HRMS (ESI): Exact mass calcd for C$_{24}$H$_{22}$N$_3$S [M+H]$^+$ 384.1534, found 384.1534.

Example 74. N-((6-(naphthalen-2-yl)imidazo[2,1-b]thiazol-5-yl)methyl)-2-phenylpropan-1-amine

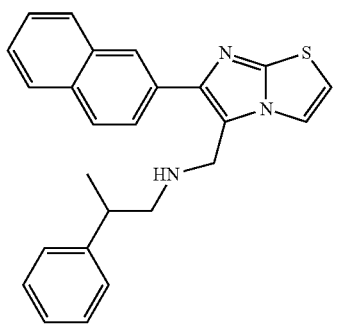

Yield 71%, $^1$H NMR (400 MHz, CDCl$_3$): δ(ppm) 8.08 (s, 1H), 7.90-7.78 (m, 4H), 7.52-7.42 (m, 3H), 7.28 (t, J=7.2 Hz, 2H), 7.26-7.18 (m, 3H), 6.69 (d, J=4.8 Hz, 1H), 4.15 (q, J=9.6 Hz, 2H), 2.93-2.79 (m, 3H), 1.24 (d, J=7.2 Hz, 3H); $^{13}$C NMR (100 MHz, CDCl$_3$): δ(ppm) 149.0, 145.1, 144.5, 133.5, 132.6, 132.2, 128.6, 128.2, 128.1, 127.7, 127.2, 126.4, 126.2, 126.1, 125.8, 121.0, 119.0, 111.5, 56.2, 43.9, 40.0, 20.0. HRMS (ESI): Exact mass calcd for C$_{25}$H$_{24}$N$_3$S [M+H]$^+$ 398.1691, found 398.1680.

Example 75. N-((6-(naphthalen-2-yl)imidazo[2,1-b]thiazol-5-yl)methyl)-2,3-dihydro-1H-inden-2-amine

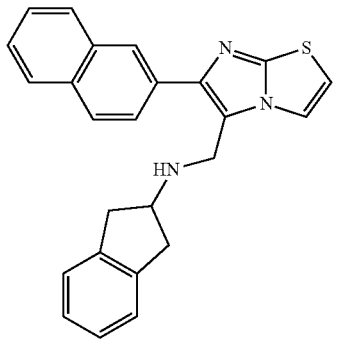

Yield 40%, $^1$H NMR (400 MHz, CDCl$_3$): δ(ppm) 8.13 (s, 1H), 7.93-7.85 (m, 4H), 7.69 (t, J=4.8 Hz, 1H), 7.53-7.47 (m, 2H), 7.21-7.15 (m, 4H), 6.78 (d, J=4.4 Hz, 1H), 4.29 (s, 2H), 3.71-3.66 (m, 1H), 3.16 (dd, J=7.2 Hz, J=8.4 Hz, 2H), 2.81 (dd, J=5.2 Hz, J=9.2 Hz, 2H); $^{13}$C NMR (100 MHz, CDCl$_3$): δ(ppm) 149.1, 144.5, 141.5, 133.5, 132.6, 132.2, 128.1, 127.7, 126.5, 126.4, 126.2, 126.0, 125.9, 124.7, 120.9, 118.9, 111.8, 59.1, 42.5, 40.0. HRMS (ESI): Exact mass calcd for C$_{25}$H$_{22}$N$_3$S [M+H]$^+$ 396.1534, found 396.1529.

Example 76. N-((6-(naphthalen-1-yl)imidazo[2,1-b]thiazol-5-yl)methyl)-2,3-dihydro-1H-inden-2-amine

A. 6-(naphthalen-1-yl)imidazo[2,1-b]thiazole-5-carbaldehyde

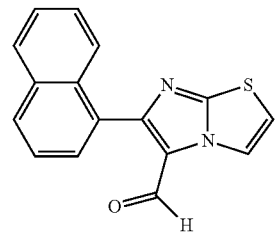 [SMILES: O=Cc1c(-c2cccc3ccccc23)nc2sccn12]

$^1$H NMR (400 MHz, CDCl$_3$): δ(ppm) 9.61 (s, 1H), 8.44 (d, J=3.6 Hz, 1H), 8.32-8.29 (m, 1H), 8.00-7.93 (m, 2H), 7.65 (d, J=7.2 Hz, 1H), 7.60-7.54 (m, 3H), 7.12 (d, J=4.0 Hz, 1H); $^{13}$C NMR (100 MHz, CDCl$_3$): δ(ppm) 178.3, 157.9, 155.5, 133.9, 132.0, 130.2, 129.7, 129.2, 128.3, 127.1, 126.4, 125.8, 125.5, 124.9, 121.3, 114.8.

B. N-((6-(naphthalen-1-yl)imidazo[2,1-b]thiazol-5-yl)methyl)-2,3-dihydro-1H-inden-2-amine

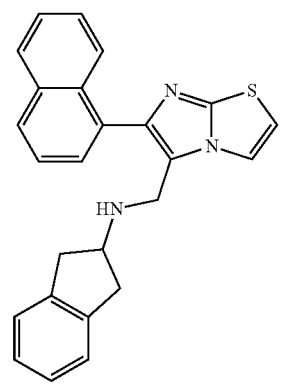

Yield 25%, $^1$H NMR (400 MHz, CDCl$_3$): δ(ppm) 8.13 (d, J=8.4 Hz, 1H), 7.91 (d, J=8.0 Hz, 2H), 7.74 (d, J=4.8 Hz, 1H), 7.55-7.44 (m, 4H), 7.13 (s, 4H), 6.83 (d, J=4.8 Hz, 1H), 4.00 (s, 2H), 3.55-3.50 (m, 1H), 3.01 (dd, J=7.2 Hz, J=8.4 Hz, 2H), 2.65 (d, J=6.4 Hz, J=9.2 Hz, 2H); $^{13}$C NMR (100 MHz, CDCl$_3$): δ(ppm) 148.9, 143.7, 141.5, 133.8, 132.5, 131.8, 128.4, 128.2, 128.1, 126.4, 126.2, 125.8, 125.1, 124.6, 122.2, 119.0, 111.7, 58.9, 42.1, 39.8. HRMS (ESI): Exact mass calcd for C$_{25}$H$_{22}$N$_3$S [M+H]$^+$ 396.1534, found 396.1539.

Example 77. N-((6-(naphthalen-2-yl)imidazo[2,1-b]oxazol-5-yl)methyl)-2,3-dihydro-1H-inden-2-amine

A. 6-(naphthalen-2-yl)imidazo[2,1-b]oxazole-5-carbaldehyde

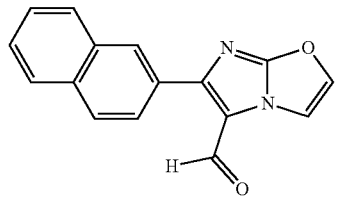 [SMILES: O=Cc1c(-c2ccc3ccccc3c2)nc2occn12]

$^1$H NMR (400 MHz, CDCl$_3$): δ(ppm) 9.98 (s, 1H), 8.28 (s, 1H), 8.00-7.89 (m, 5H), 7.58-7.55 (m, 3H); $^{13}$C NMR (100 MHz, CDCl$_3$): δ(ppm) 178.5, 156.2, 139.2, 139.0, 133.8, 133.2, 129.9, 128.8, 128.6, 127.8, 127.2, 126.8, 125.9, 121.2, 114.0, 113.9.

B. N-((6-(naphthalen-2-yl)imidazo[2,1-b]oxazol-5-yl)methyl)-2,3-dihydro-1H-inden-2-amine

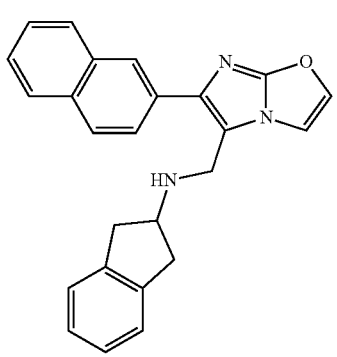

Yield 26%, $^1$H NMR (400 MHz, CDCl$_3$): δ(ppm) 8.07 (s, 1H), 7.89-7.80 (m, 5H), 7.54-7.46 (m, 3H), 7.29 (s, 1H), 7.20-7.13 (m, 5H), 4.25 (s, 2H), 3.70-3.65 (m, 1H), $^{13}$C NMR (100 MHz, CDCl$_3$): δ(ppm) 155.0, 141.3, 140.7, 137.3, 137.1, 133.5, 132.5, 132.2, 128.1, 127.7, 126.8, 126.5, 126.2, 125.9, 125.8, 124.7, 112.2, 58.9, 42.3, 39.7, 29.7. HRMS (ESI): Exact mass calcd for C$_{25}$H$_{22}$N$_3$O [M+H]$^+$ 380.1763, found 380.1767.

Example 78. N-((6-(4-chlorophenyl)imidazo[2,1-b]oxazol-5-yl)methyl)-2,3-dihydro-1H-inden-2-amine

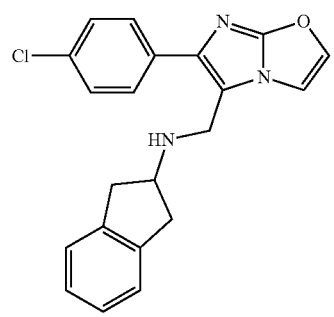

Yield 27%, $^1$H NMR (400 MHz, CDCl$_3$): δ(ppm) 7.58 (d, J=7.6 Hz, 2H), 7.46 (s, 1H), 7.37 (d, J=8.0 Hz, 2H), 7.30 (d, J=1.6 Hz, 1H), 7.21-7.14 (m, 4H), 4.13 (s, 2H), 3.67-3.60 (m, 1H), 3.14 (dd, J=6.8 Hz, J=8.8 Hz, 2H), 2.77 (dd, J=6.4 Hz, J=10.0 Hz, 2H); $^{13}$C NMR (100 MHz, CDCl$_3$): δ(ppm) 154.8, 141.4, 139.3, 137.2, 133.3, 132.8, 128.8, 128.6, 126.5, 124.7, 116.3, 112.1, 59.0, 42.4, 39.9. HRMS (ESI): Exact mass calcd for C$_{21}$H$_{19}$ClN$_3$O [M+H]$^+$ 364.1217, found 364.1227.

Example 79. 1-(2,3-dihydro-1H-inden-2-yl)-N-((6-(naphthalen-2-yl)imidazo[2,1-b]oxazol-5-yl)methyl)methanamine

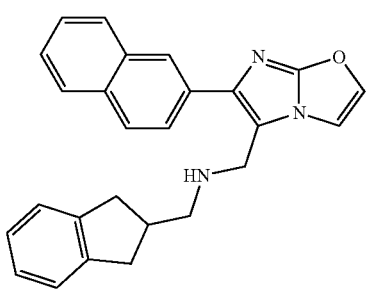

$^1$H NMR (400 MHz, CDCl$_3$): δ(ppm) 8.08 (s, 1H), 7.90-7.81 (m, 4H), 7.57 (s, 1H), 7.51-7.45 (m, 2H), 7.35 (s, 1H), 7.18-7.12 (m, 4H), 4.23 (s, 2H), 3.76 (br s, 1H), 3.09-3.03 (m, 2H), 2.77 (d, J=5.6 Hz, 2H), 2.67 (d, J=8.0 Hz, 3H); $^{13}$CNMR (100 MHz, CDCl$_3$): δ(ppm) 155.0, 142.6, 140.9, 137.2, 133.5, 132.5, 132.1, 128.11, 128.08, 127.6, 126.3, 126.2, 125.9, 125.8, 124.5, 115.9, 112.1, 54.2, 44.1, 39.4, 37.4. HRMS (ESI): Exact mass calcd for C$_{26}$H$_{24}$N$_3$O$_2$ [M+H]$^+$ 394.1919, found 394.1914.

Example 80. N-((6-(4-chlorophenyl)imidazo[2,1-b]thiazol-5-yl)methyl)-2-(3,4-dichlorophenyl)-N-methylethan-1-amine

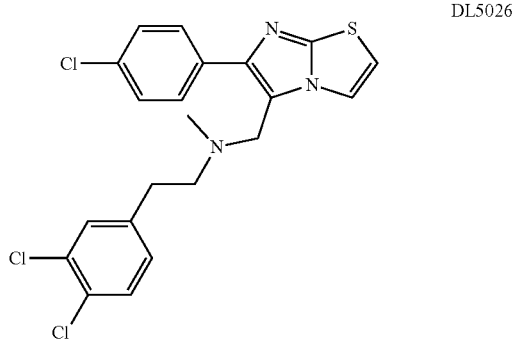 [SMILES: CN(CCc1ccc(Cl)c(Cl)c1)Cc1c(-c2ccc(Cl)cc2)nc2sccn12]

Yield 61%, ¹H NMR (400 MHz, CDCl₃): δ(ppm) 7.61 (d, J=8.8 Hz, 2H), 7.37 (d, J=8.8 Hz, 2H), 7.26 (d, J=8.0 Hz, 1H), 7.16 (d, J=1.6 Hz, 1H), 7.08 (d, J=4.0 Hz, 1H), 6.87 (d, J=8.8 Hz, 1H), 6.62 (d, J=4.0 Hz, 1H), 3.79 (s, 2H), 2.69 (t, J=6.0 Hz, 2H), 2.62 (t, J=5.6 Hz, 2H), 2.26 (s, 3H); ¹³C NMR (100 MHz, CDCl₃): δ(ppm) 149.1, 144.2, 140.7, 133.2, 133.0, 132.1, 130.6, 130.2, 129.9, 129.2, 128.6, 128.0, 119.4, 118.7, 111.6, 57.6, 52.4, 41.2, 32.6. HRMS (ESI): Exact mass calcd for $C_{21}H_{19}Cl_3N_3S$ $[M+H]^+$ 450.0365, found 450.0351.

Example 81. N-((6-(4-chlorophenyl)imidazo[2,1-b]thiazol-5-yl)methyl)-2-(3,4-dichlorophenyl)-N-ethyl-ethan-1-amine

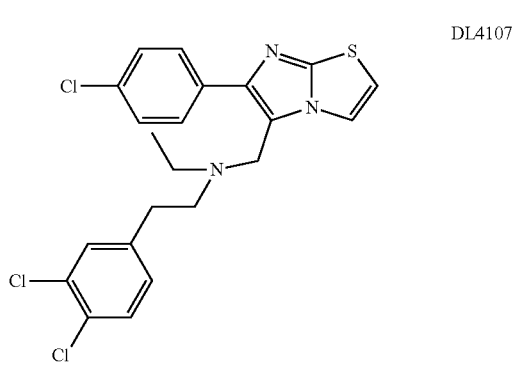 [SMILES: CCN(CCc1ccc(Cl)c(Cl)c1)Cc1c(-c2ccc(Cl)cc2)nc2sccn12]

Yield 40%, ¹H NMR (400 MHz, CDCl₃): δ(ppm) 7.61 (d, J=8.4 Hz, 2H), 7.39 (d, J=8.4 Hz, 2H), 7.21 (d, J=8.4 Hz, 2H), 7.07 (d, J=1.6 Hz, 1H), 6.76 (d, J=8.0 Hz, 1H), 6.64 (d, J=4.0 Hz, 1H), 3.90 (s, 2H), 2.65-2.61 (m, 6H), 1.07 (t, J=6.8 Hz, 3H); ¹³C NMR (100 MHz, CDCl₃): δ(ppm) 147.9, 144.3, 140.6, 133.2, 133.1, 130.6, 130.1, 129.8, 129.2, 128.6, 127.8, 119.6, 118.7, 111.5, 53.7, 48.3, 47.1, 32.3, 11.6. HRMS (ESI): Exact mass calcd for $C_{22}H_{21}Cl_3N_3S$ $[M+H]^+$ 464.0522, found 464.0538.

Example 82. N-benzyl-N-((6-(4-chlorophenyl)imidazo[2,1-b]thiazol-5-yl)methyl)-2-(3,4-dichlorophenyl)ethan-1-amine

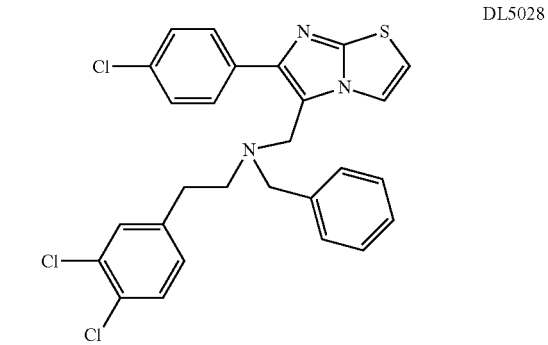 [SMILES: Clc1ccc(-c2nc3sccn3c2CN(CCc2ccc(Cl)c(Cl)c2)Cc2ccccc2)cc1]

Yield 72%, ¹H NMR (400 MHz, CDCl₃): δ(ppm) 7.61 (d, J=8.4 Hz, 2H), 7.40 (d, J=8.4 Hz, 2H), 7.36-7.28 (m, 3H), 7.20-7.18 (m, 3H), 7.03 (d, J=1.6 Hz, 1H), 6.94 (d, J=4.8 Hz, 1H), 6.68 (d, J=8.0 Hz, 1H), 6.20 (d, J=4.0 Hz, 1H), 3.85 (s, 2H), 3.60 (s, 2H), 2.70-2.64 (m, 4H); ¹³C NMR (100 MHz, CDCl₃): δ(ppm) 149.1, 144.6, 140.4, 138.2, 133.2, 133.1, 132.0, 130.6, 130.1, 129.9, 129.24, 129.20, 128.7, 128.5, 127.7, 127.5, 119.3, 118.5, 111.6, 58.7, 54.2, 48.2, 32.2. HRMS (ESI): Exact mass calcd for $C_{27}H_{23}Cl_3N_3S$ $[M+H]^+$ 526.0678, found 526.0672.

Example 83. N-((6-(4-chlorophenyl)imidazo[2,1-b]oxazol-5-yl)methyl)-2-(3,4-dichlorophenyl)ethan-1-amine Yield 57%, ¹H NMR (400 MHz, CDCl₃): δ(ppm) 7.53 (d, J=7.6 Hz, 2H), 7.35-7.24 (m, 6H), 6.96 (d, J=8.0 Hz, 2H), 4.03 (s, 2H), 2.84 (t, J=7.2 Hz, 2H), 2.69 (t, J=6.8 Hz, 2H); ¹³C NMR (100 MHz, CDCl₃): δ(ppm) 154.8, 140.2, 139.5, 137.1, 133.3, 132.8, 132.2, 130.6, 130.3, 130.1, 128.8, 128.6, 128.2, 116.1, 111.8, 49.7, 43.9, 35.4. HRMS (ESI): Exact mass calcd for $C_{20}H_{17}Cl_3N_3O$ $[M+H]^+$ 420.0437, found 420.0445.

Example 84. N-(2-(4-chlorophenyl)imidazo[1,2-a]pyrimidin-3-yl)methyl)-2-(3,4-dichlorophenyy)ethan-1-amine

A. 2-(4-chlorophenyl)imidazo[1,2-a]pyrimidine-3-carbaldehyde

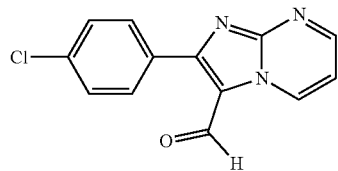 [SMILES: O=Cc1c(-c2ccc(Cl)cc2)nc2ncccn12]

$^1$H NMR (400 MHz, CDCl$_3$): δ(ppm) 10.1 (s, 1H), 9.87 (d, J=5.2 Hz, 1H), 8.84 (d, J=1.6 Hz, 1H), 7.85 (d, J=8.4 Hz, 2H), 7.52 (d, J=7.6 Hz, 2H), 7.22-7.19 (m, 1H); $^{13}$C NMR (100 MHz, CDCl$_3$): δ(ppm) 179.7, 157.8, 154.7, 150.3, 136.8, 136.4, 131.1, 130.2, 129.3, 118.9, 111.5.

B. N-(2-(4-chlorophenyl)imidazo[1,2-a]pyrimidin-3-yl)methyl)-2-(3,4-dichlorophenyy)ethan-1-amine

DL4167

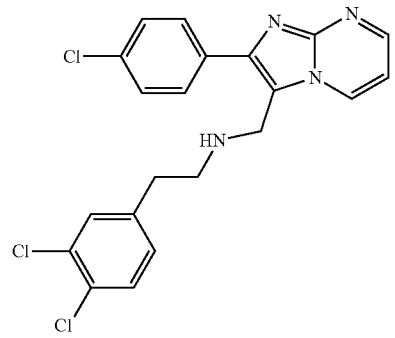

Yield 48%, $^1$H NMR (400 MHz, CDCl$_3$): δ(ppm) 8.54-8.51 (m, 2H), 7.70 (d, J=8.8 Hz, 2H), 7.44-7.41 (m, 2H), 7.31-7.24 (m, 2H), 6.93 (d, J=7.6 Hz, 1H), 6.78 (d, J=4.4 Hz, 1H), 4.24 (s, 2H), 2.89 (t, J=6.4 Hz, 2H), 2.71 (t, J=6.4 Hz, 2H); $^{13}$C NMR (100 MHz, CDCl$_3$): δ(ppm) 150.0, 148.1, 144.2, 140.1, 134.2, 132.9, 132.3, 132.2, 130.7, 130.3, 130.2, 130.0, 128.8, 128.1, 116.4, 108.1, 49.6, 43.0, 35.3. HRMS (ESI): Exact mass calcd for C$_{21}$H$_{18}$Cl$_3$N$_4$ [M+H]$^+$ 431.0597, found 431.0588.

4. Synthesis of phenethoxy methylimidazo[2,1-b]thiazole Analogs

General procedure: NaBH$_4$ (15 mmol, 3 equiv) was added in portion to a solution of Intermediate 3 (5 mmol) in methanol (200 mL) in an ice bath. The resulting mixture was then warmed to room temperature and stirred for 1 hour. Most of the solvent was evaporated under reduced pressure. Saturated aqueous Na$_2$CO$_3$ (50 mL) was added and then the mixture was extracted with EtOAc (3×50 mL). Purified from chromatographic column to give alcohol 6 (Scheme 4). The alcohol 6 (0.5 mmol) in DCM (10 mol) was put in ice bath. TEA (0.55 mmol, 1.1 equiv) was added, then methanesulfonyl chloride (0.55 mmol, 1.1 equiv) was added again. The mixture was stirred at 0° C. for 2 hours. Removed the DCM and provided crude compound 7 without purification. To a solution of alcohol 4' (0.5 mmol) and K$_2$CO$_3$ (1 mmol, 2 equiv) in DMF was added mesylate 7 (0.5 mmol). The mixture was stirred overnight at 60° C. Cooled to room temperature and added 50 mL of water. Extracted with EtOAc (2×50 mL), Combined the EtOAc layers and washed with brine. Dried (Na$_2$SO$_4$), filtered, and concentrated in vacuo. Purified by silica gel chromatography and got the final product II.

Scheme 4

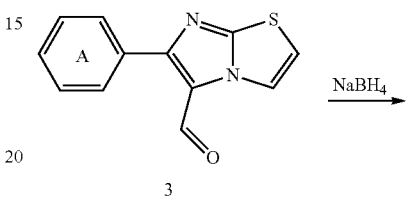

3

NaBH$_4$ →

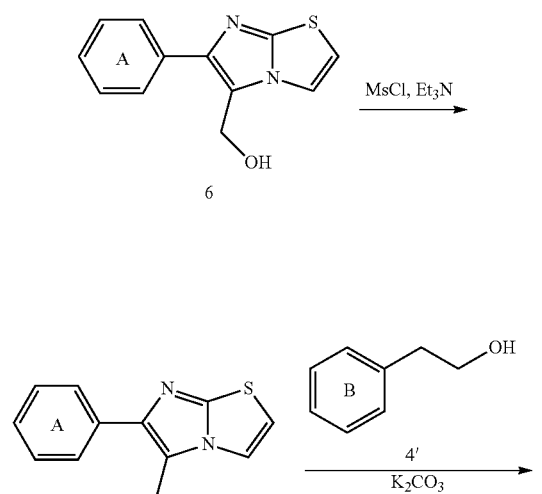

II

Example 85. 6-(4-chlorophenyl)-5-((3,4-dichloro-phenethoxy)methyl)imidazo[2,1-b]thiazole

A. (6-(4-chlorophenyl)imidazo[2,1-b]thiazol-5-yl)methanol

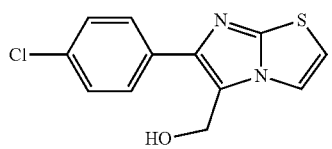 [SMILES: OCc1c(-c2ccc(Cl)cc2)nc2sccn12]

$^1$H NMR (400 MHz, CDCl$_3$): δ(ppm) 7.95 (d, J=8.8 Hz, 1H), 7.78 (d, J=8.8 Hz, 2H), 7.50 (d, J=8.0 Hz, 2H), 5.51 (br s, 1H), 4.80 (s, 2H); $^{13}$C NMR (100 MHz, CDCl$_3$): δ(ppm) 153.2, 147.4, 138.6, 136.9, 133.9, 133.7, 128.5, 124.3, 118.4, 58.1.

B. 6-(4-chlorophenyl)-5-((3,4-dichlorophenethoxy)methyl)imidazo[2,1-b]thiazole

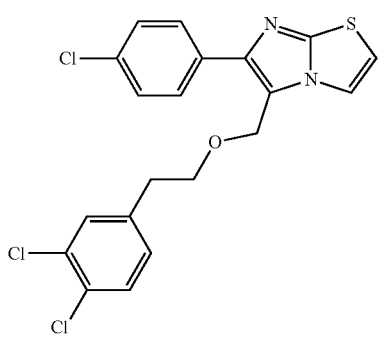

DL4082

Yield 28%, $^1$H NMR (400 MHz, CDCl$_3$): δ(ppm) 7.78 (d, J=8.0 Hz, 2H), 7.60 (d, J=8.0 Hz, 2H), 7.53 (d, J=8.0 Hz, 1H), 7.48 (d, J=3.6 Hz, 1H), 7.38 (d, J=3.6 Hz, 1H), 7.20 (d, J=8.4 Hz, 1H), 7.01 (d, J=3.6 Hz, 1H), 4.97 (s, 214), 3.88 (t, J=5.6 Hz, 2H), 3.04 (t, J=5.6 Hz, 2H); $^{13}$C NMR (100 MHz, CDCl$_3$): δ(ppm) 149.6, 145.0, 139.3, 133.6, 132.5, 132.2, 130.8, 130.3, 130.2, 129.0, 128.8, 128.3, 118.7, 117.8, 112.7, 70.0, 62.7, 35.3; HRMS (ESI): Exact mass calcd for C$_{20}$H$_{16}$Cl$_3$N$_2$OS [M+H]$^+$ 437.0049, found 437.0051.

Example 86: 5-(((2,3-dihydro-1H-inden-2-yl)oxy)methyl)-6-(naphthalen-2-yl)imidazo[2,1-b]oxazole

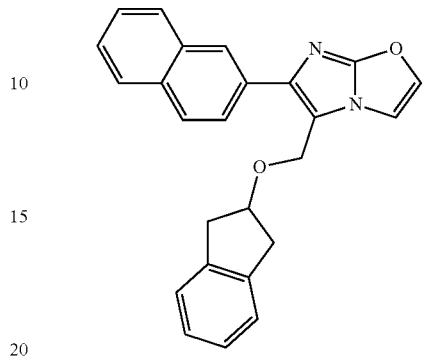

DL5161/DL5016D $^1$H NMR (400 MHz, CDCl$_3$): δ(ppm) 8.17 (s, 1H), 7.89-7.77 (m, 4H), 7.52-7.47 (m, 2H), 7.36 (d, J=7.2 Hz, 2H), 7.18-7.13 (m, 4H), 5.52-5.49 (m, 1H), 4.71 (s, 2H), 3.26-3.11 (m, 4H); $^{13}$CNMR (100 MHz, CDCl$_3$): δ(ppm) 155.8, 145.6, 138.9, 137.7, 133.3, 132.9, 130.7, 128.5, 128.4, 127.6, 127.2, 126.8, 126.4, 125.8, 124.6, 111.9, 104.6, 83.9, 48.9, 40.2, 29.7. HRMS (ESI): Exact mass calcd for C$_{25}$H$_{21}$N$_2$O$_2$ [M+H]$^+$ 381.1603, found 381.1601.

II. Biological Evaluations and Results

Figure 4A:
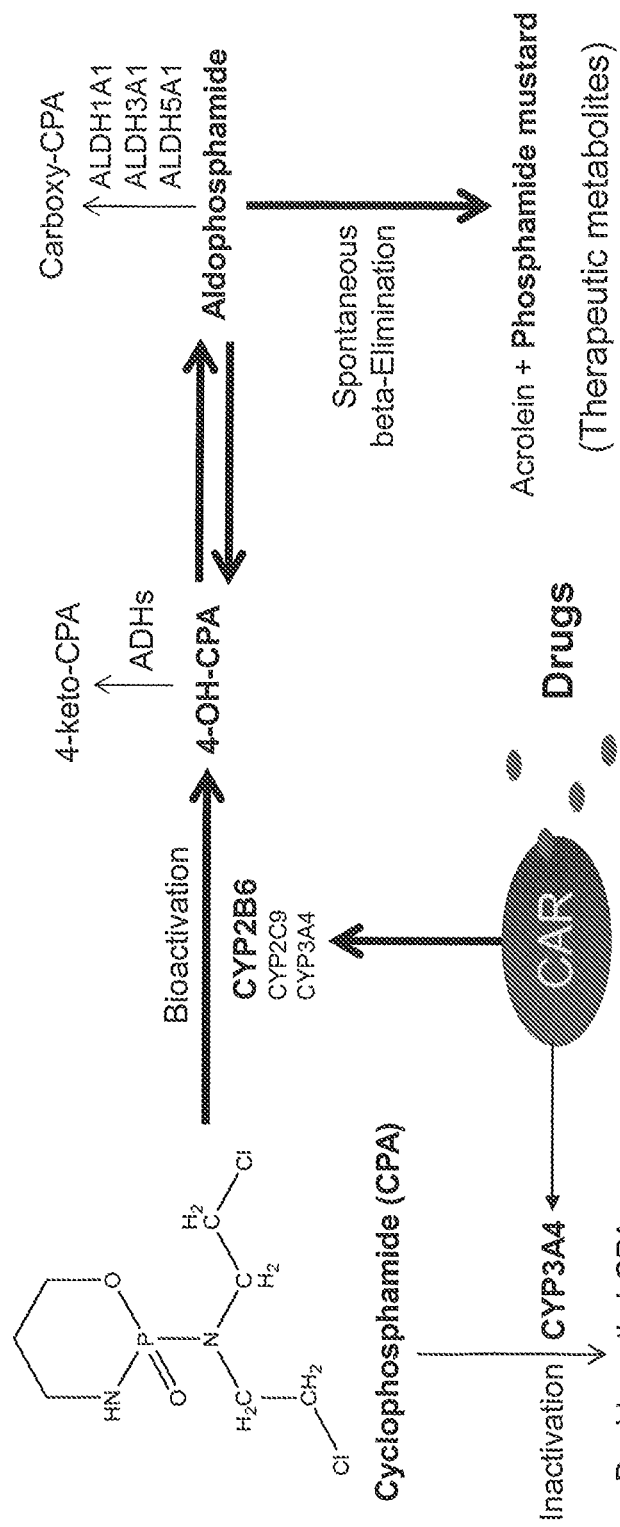
FIG. 4A. Schematic illustration of cyclophosphamide (CPA) metabolism and the proposed role of CAR in CPA bioactivation.
Figure 4B:
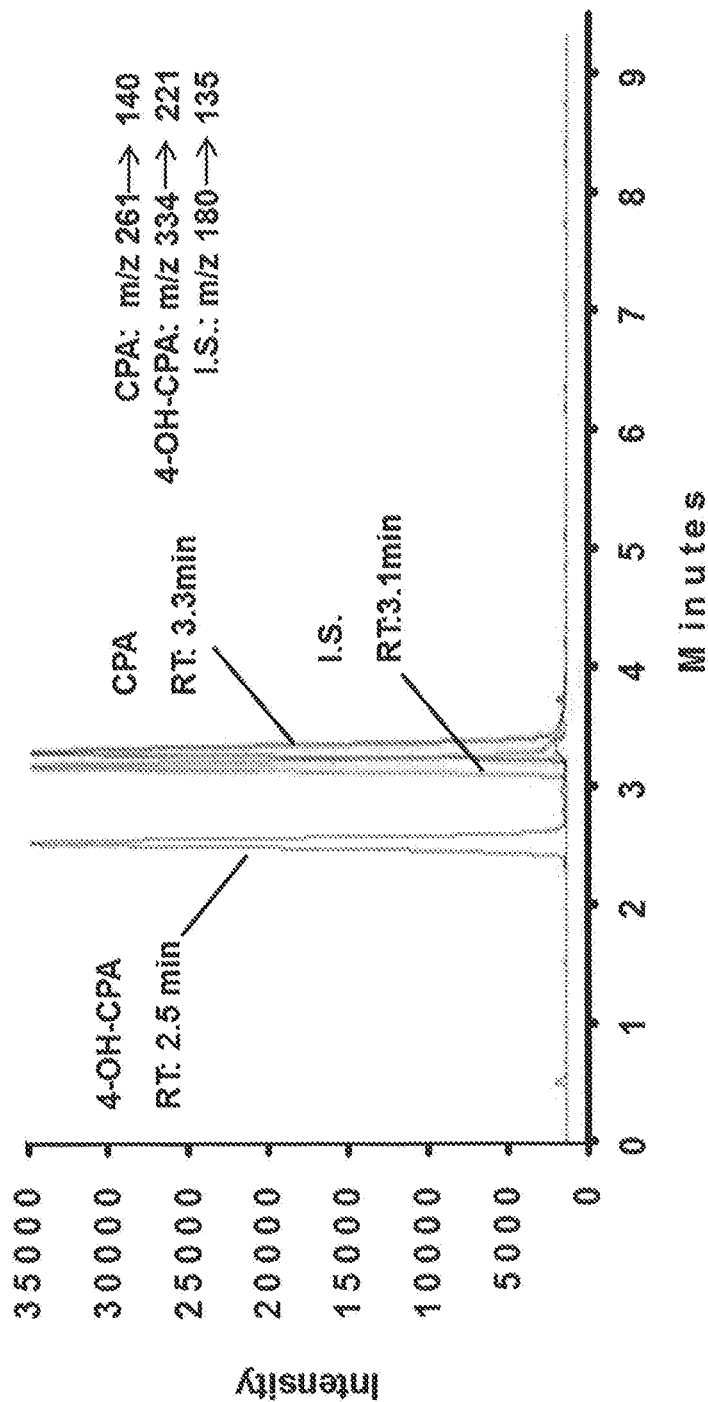
FIG. 4B. The multiple-reaction monitoring chromatogram demonstrates separation and retention of 4-OH-CPA, CPA, and the internal standard from LC-MS/MS detection.
Figure 9:
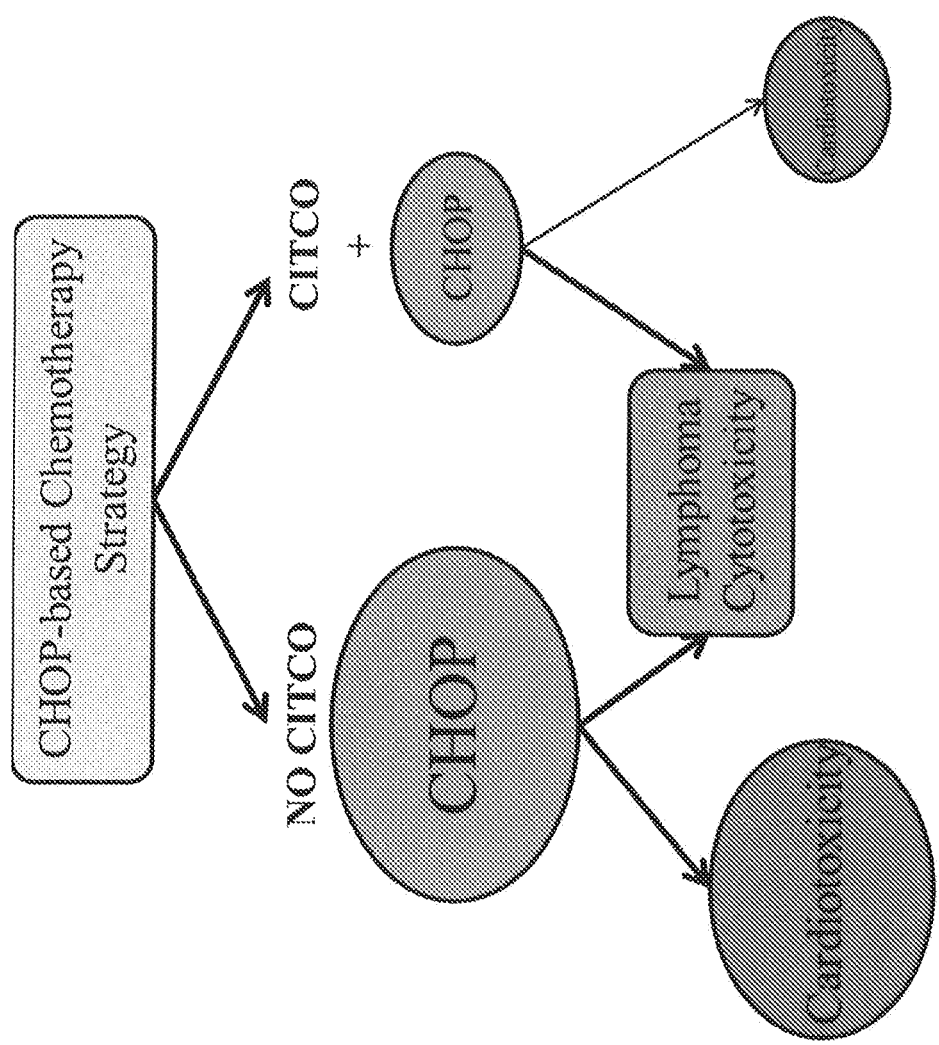
FIG. 9. Schematic illustration of CITCO-mediated enhancement of CHOP antineoplastic activity in targeted (SU-DHL-4) but not side-toxic (H9c2) cells.

CYP2B6 is selectively unregulated by hCAR, proving an attractive approach for improve CPA-based therapies (FIG. 4A). CHOP regimen (CPA, doxorubicin, vincristine, and prednisone) is the first line chemotherapy for non-Hodgkin's lymphoma and a number of other hematologic malignancies (FIG. 9). The CYP2B6 enzyme expressed in hepatocytes converts CPA to pharmacologically active 4-hydroxy-CPA94-OH-CPA) (FIGS. 4A-D). The activation of hCAR preferentially induces the expression of CYP2B6 in the liver, without concurrent augmentation of its nontherapeutic metabolites. The activation of hCAR can selectively enhance systemic exposure to the pharmacological active 4-OH-CPA and increase the efficacy: toxicity ratio of CPA in chemotherapy (FIG. 4B).

Figure 5B:
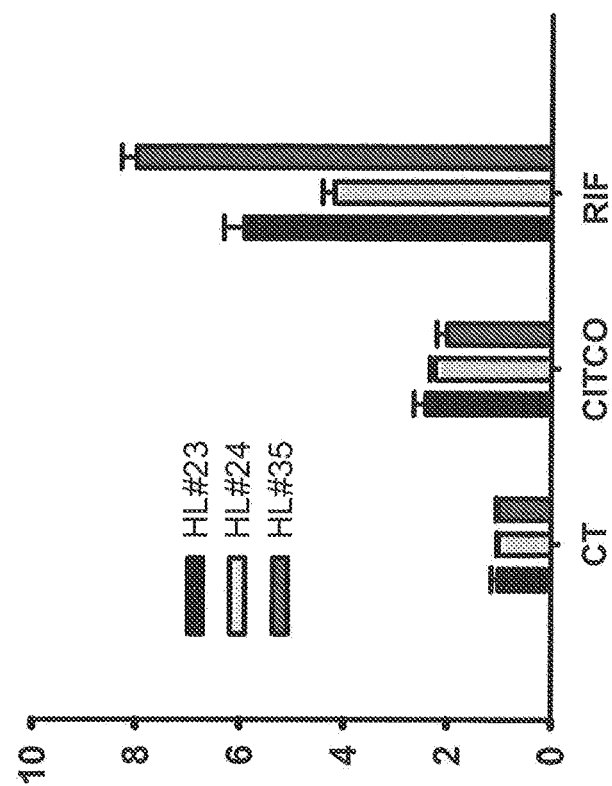
FIGS. 5A-5C. CAR-mediated induction of CYP2B6 and CYP3A4 in human primary hepatocytes. CYP2B6 and CYP3A4 mRNA and protein were measured in human primary hepatocytes prepared from 3 donors treated with CITCO (1 μM), RIF (10 μM), or vehicle control (0.1% DMSO).
Figure 5A:
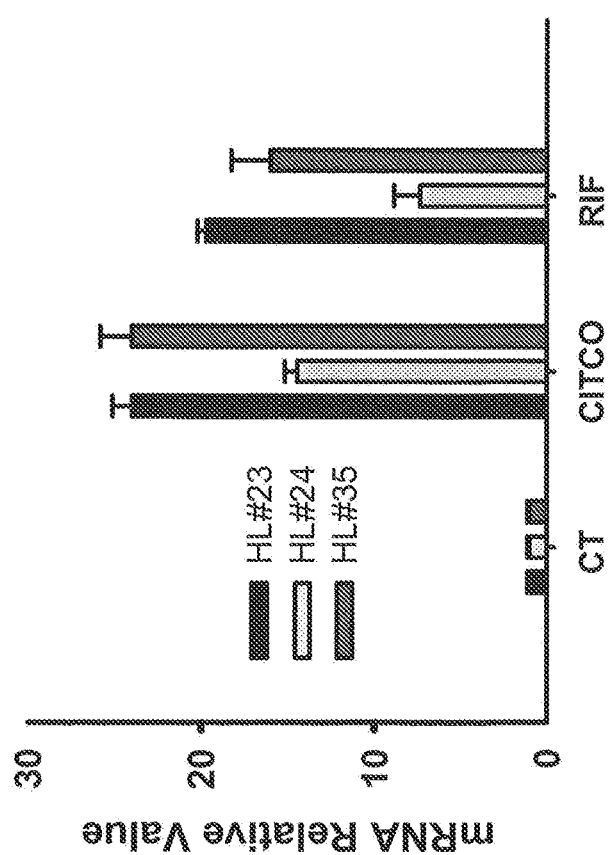
Figure 5C:
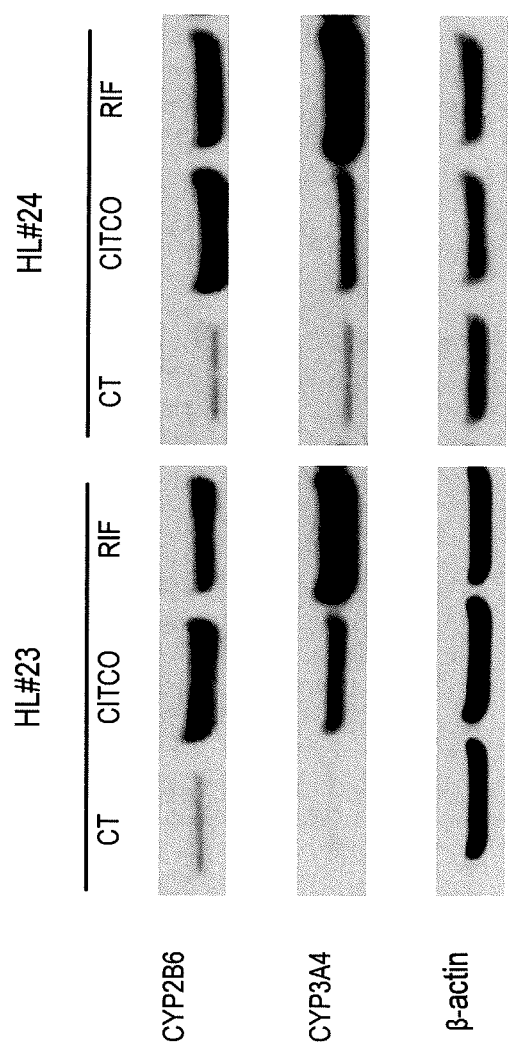
Figure 5D:
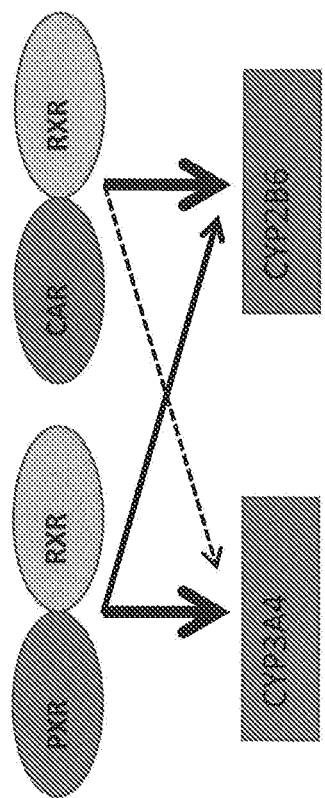
FIG. 5D: diagram of selective induction of CYP2B6.
Figure 6A:
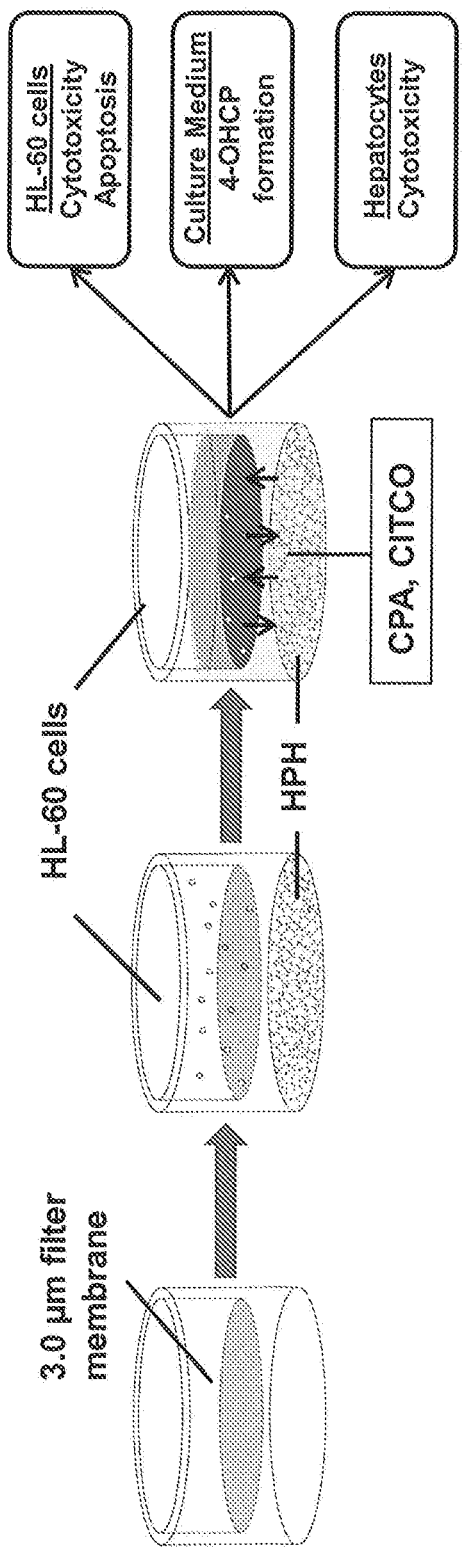

Using CITCO as a model compound, the biological activity of CITCO has been evaluated for its selective activation of hCAR vs. hPXR in luciferase reporter assays, and its effects on CYP2B6 expression at both mRNA and protein levels in cultured human primary hepatocytes (See FIGS. 5A-B). The beneficial effects of hCAR activation has been demonstrated (FIGS. 6A-D).

Figure 2:
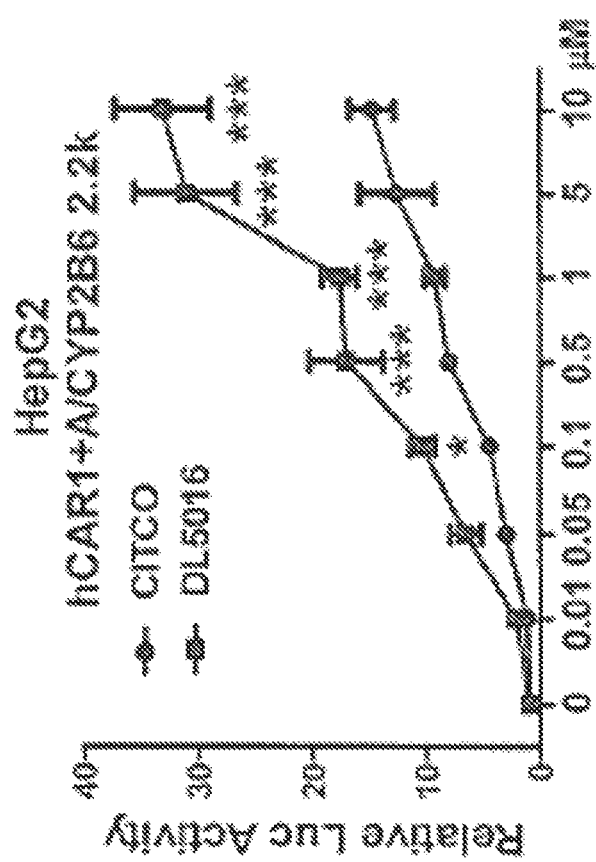
FIG. 2. DL5016 exhibits higher hCAR activity than CITCO.
Figure 7B:
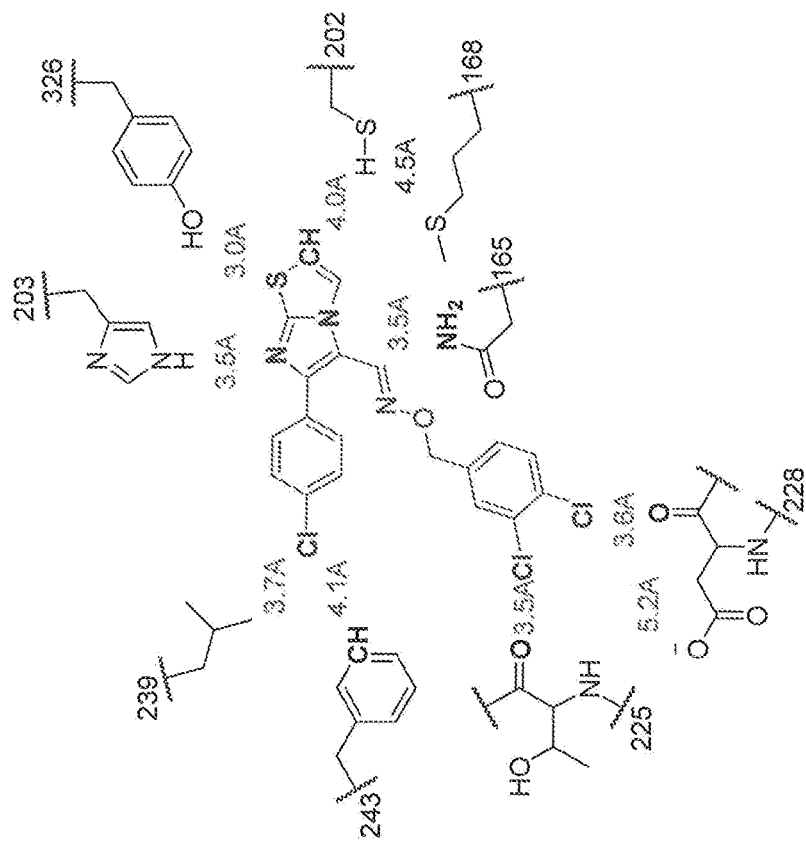
FIGS. 7A-7B. Computer simulation based optimization of lead compound CITCO based on docking of CITCO to the hCAR protein catalytic site.
Figure 7A:
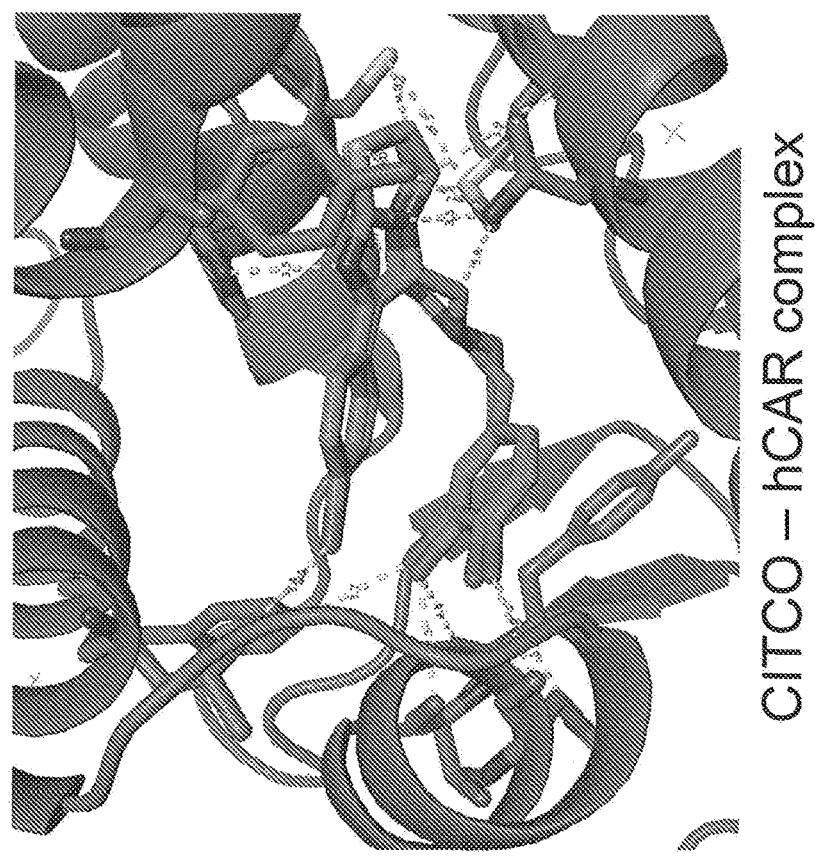
Figure 8A:
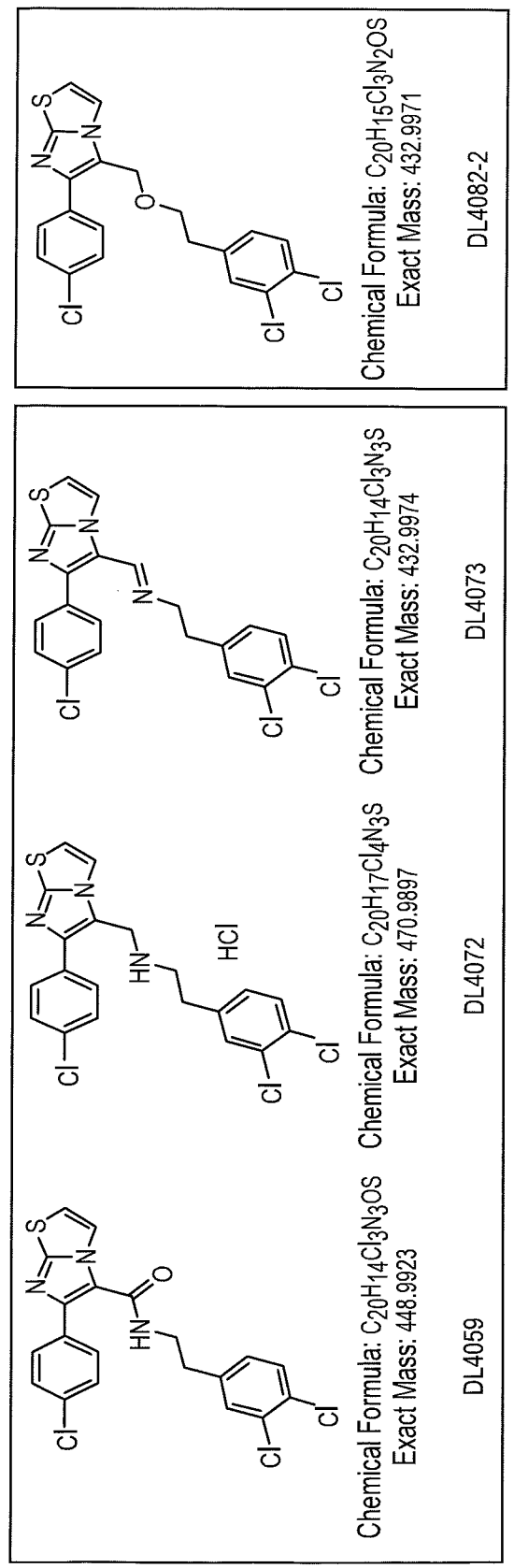
FIGS. 8A-8B. The development of structure activity relationship (SAR) based on docking model of CITCO-hCAR complex.
Figure 8B:
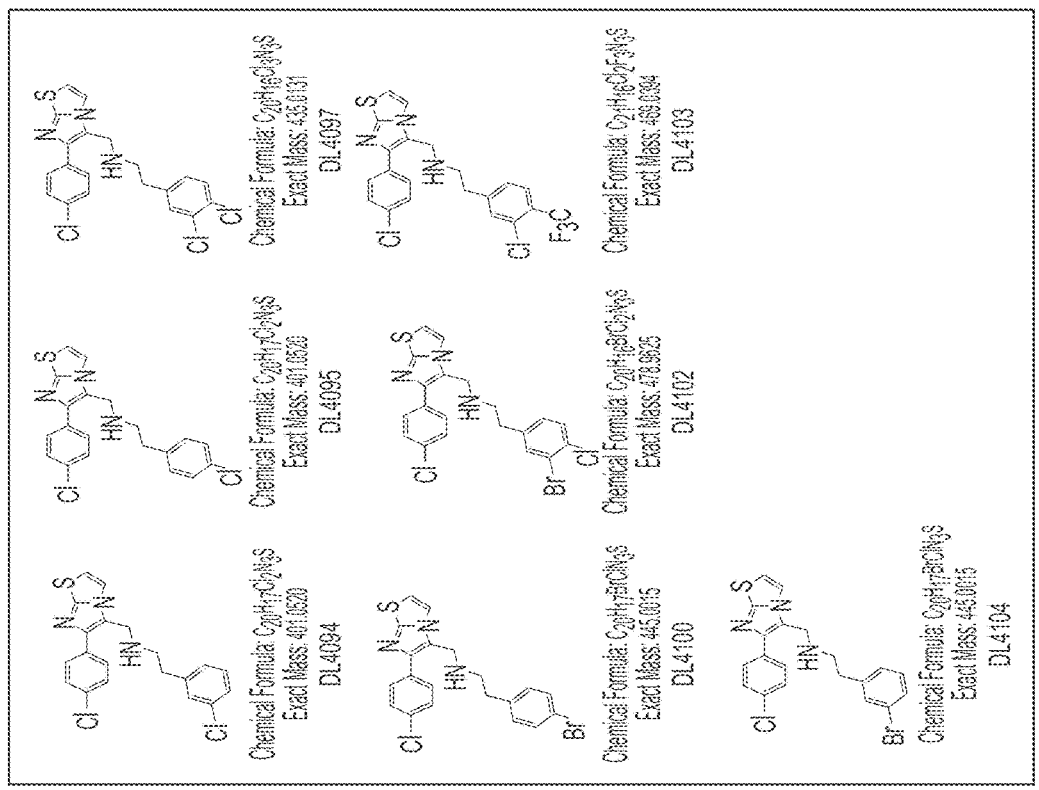
Figure 8B:
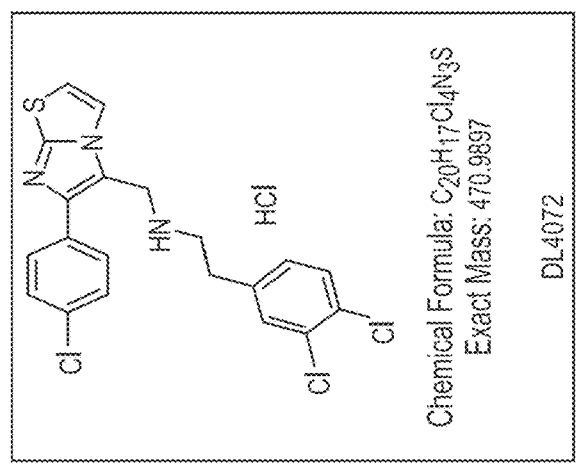

Through the integrated computational simulation guided chemical structural activity optimization based on docking modeling on CITCO-hCAR complex (FIG. 7) in combined with guidance of biological activities of the new compounds obtained by in vitro biological assay, a potent and selective hCAR activator, DL5016 is identified as a potent and selective small molecule hCAR activator (See FIG. 2). DL5016 exhibits higher hCAR-inducing activity than CITCO (FIG. 2), as well as improved aqueous solubility. A series of new analogs of CITCO as those from Table 1 above were also developed.

Biological Assay Protocols

Chemicals and Reagents for Biological Activity Determinations

CPA, doxorubicin, vincristine, prednisone, and 20,70-dichlorofluorescein diacetate (DFDA) were purchased from Sigma-Aldrich. (6-(4-chlorophenyl)imidazo[2,1-b][1,3]thiazole-5-carbaldehyde-O-(3,4-dichlorobenzyl)oxime) (CITCO) (see FIG. 1) was acquired from BIOMOL research laboratories. DL5016 (See FIG. 1) is obtained from the synthetic method as described above. Oligoniclueotide primers were synthesized by and purchased from Integrated DNA Technologies. Insulin, Matrigel, and ITS$^+$ culture supplies were obtained from BD Biosciences.

Human Primary Hepatocytes and HepaRG Cells

HPHs were obtained from Bioreclamation, IVT. Hepatocytes with viability over 90% were seeded at $1.5 \times 10^6$ or $7.5 \times 10^5$ cells per well in 6- or 12-well collagen-coated plates. After 4 hours of attachment, cells were overlaid with Matrigel (0.25 mg/mL) in serum-free Williams E medium to form the sandwich culture. Following incubation for 36 hours, HPH were treated with DMSO (0.1%) or hCAR activator (i.e. CITCO or DL 5016) (1 mmol/L) for 24 or 72 hours for mRNA and protein detection, respectively. In separate experiments, wild-type (WT) and CAR-knockout (KO) HepaRG cells obtained from Sigma-Aldrich were cultured in 6- or 12-well collagen-coated plates. Cells were further treated with DMSO or hCAR activator.

Culture and Treatment of Lymphoma Cells

Immortalized lymphoma cell lines SU-DHL-4 and SU-DHL-6 were obtained from the ATCC between 2012 and 2013. The OCILY-3 cell line was kindly provided by Dr. Ronald Gartenhaus (Department of Medicine, University of Maryland) in 2012. All cell lines were cultured in RPMI-1640 medium containing 10% FBS and 1% penicillin/streptomycin. The cell lines were used for less than 40 passages. The authenticity of the cell lines were confirmed by short tandem repeat polymorphism profiling (DDC Medical, Fairfield, Ohio). Cells were treated with DMSO (0.1%) or hCAR activator (1 mmol/L) for 24 hours before harvesting for total RNA extraction.

Quantitative PCR Analysis

Total RNA from HPH and lymphoma cells was isolated with TRizol Reagent (Life Technologies) and reverse transcribed using a High Capacity cDNA Archive kit (Applied Biosystems) following the manufacturers' instructions. mRNA expression of CYP2B6, CYP3A4, was normalized against that of GAPDH. Real-time PCR assays were performed in 96-well optical plates on a StepOnePlus Real-Time PCR System with SYBR Green PCR Master Mix (Applied Biosystems). The primer sequences used for real-time PCR analyses included: CYP2B6: 50-AGACGCCTT-CAATCCTGACC-30 and 50-CCTTCACCAA-GACAAATC-CGC-30; CYP3A4: 50-GTGGGGCTTTTATGATGGTCA-30 and 50GCGTCA-GATTTCTCACCAACACA-30. Fold induction of genes over control was determined as 2DDCt, where DCt is representative of the cycle threshold number difference between the target gene and GAPDH and DDCt represents the relative change in the intergroup variations.

Hepatocyte/SU-DHL-4 Coculture

HPH were cultured in collagen-coated 12-well plates and pretreated with vehicle control (0.1% DMSO) or hCAR activator (1 mmol/L) for 24 hours. The wells were then separated with 3.0 mm polycarbonate membrane inserts (Sigma-Aldrich). A total of $0.5 \times 10^6$ SU-DHL-4 cells suspended in supplemented Williams' Medium E were transferred into the insert chamber with a final volume of 2 mL/well. In separate coculture experiments, HPH were replaced with either WT or CAR-KO HepaRG cells. The cocultures were exposed to designated concentrations of the chemotherapy drugs in CHOP in the presence or absence of hCAR activator for various time intervals, as indicated.

Western Blotting Analysis

Homogenate proteins from treated HPH, H9c2 or HepaRG cells were resolved on NuPAGE Novex Bis-Tris 4% to 12% gels (Life Technologies) and electrophoretically transferred onto immobilon-P polyvinylidene difluoride membranes. Membranes were incubated with specific antibodies against human CAR (Perseus Proteomics), cleaved caspase-3 (Cell Signaling Technology), or g-H2AX (Millipore), diluted 1:1,000, 1:1,000, and 1:400, respectively. b-Actin was used to normalize protein loading. Following incubation with horseradish peroxidase goat antimouse or anti-rabbit IgG antibody, membranes were developed using SuperSignal West Pico Chemiluminescent Substrate (Thermo Scientific). Western blot signals were quantified by densitometry using ImageJ software from the National Institutes of Health.

Cell Viability Assays

HPHs and H9c2 rat cardiomyocytes were seeded at $7.5 \times 10^4$ cells per well in 96-well plates. HPH were cultured for 24 hours before treatment with hCAR activator (1 mmol/L) or vehicle control (0.1% DMSO), followed by treatment with the chemotherapy drugs included in CHOP at a range of concentrations. Culture medium containing CHOP drugs and metabolites was exchanged between the cell types at pre-determined time points. A typical 3-[4,5-dimethylthiazol-2-yl]-2,5 diphenyl tetrazolium bromide (MTT) assay was carried out as described previously (21). Cell viability was expressed as the percentage of vehicle control (0.1% DMSO). Cocultured cells were assembled and treated as described above. The viability of the SU-DHL-4 cells was determined at selected time points with a Cellometer Auto T4 (Nexcelom Biosciences) using trypan blue exclusion.

Effects of DL 5016 on hCAR-mediated CYP2B6 Reported Gene Activation

HepG2 cells were transfected with hCAR1+A expression plasmid and CYP2B6-2.2k firely luciferase reporter construct. Transfected cells were treated with vehicle control (0.1% DMSO), CITCO and DL5016 at indicated concentrations for 24 h, CYP2B6 reported activities were normalized as folds over vehicle control and are expressed as means±SD (n=3). * $p<0.05$; ***, $p<0.001$. The results for the effects of DL 5016 compared with CITCO on hCAR-mediated CYP2B6 reported gene activation are shown in FIG. 2. DL5016 is more effective than CITCO in activating genes that are downstream of hCAR (FIG. 2).

Effects of hCAR Activators of Table 1 on Induction of CYP2B6 Expression and Formation of 4-OH-CPA in Human Primary Hepatocytes (HPHs)

The human primary hepatocytes from human donor were treated with vehicle control (0.1% DMSO) or DL5016 at a concentration ranging from 0.1 μM to 1 μM for 24 h and 72 h. The expression mRNA for CYP2B6 and CYP3A4 and CYP2B6 and CYP3A4 protein were analyzed at the time point of 24 h and 72 h respectively.

Figure 3A:
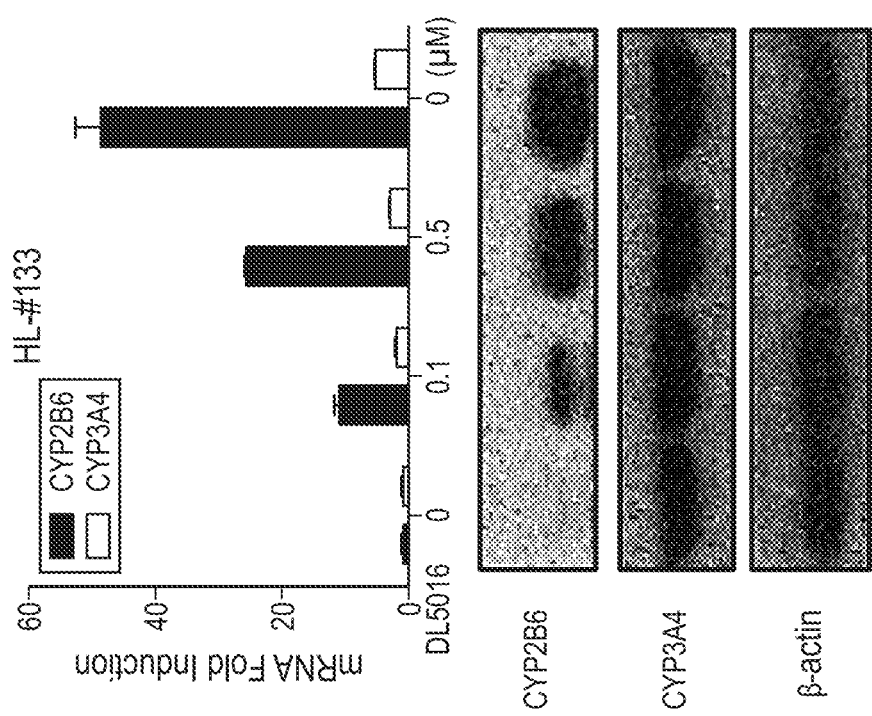
FIG. 3A. Comparative DL5016 dose dependent selective activation of CYP2B6 and CYP3A4, including RT-PCR and SDS-PAGE/Western blot analyses.
Figure 3B:
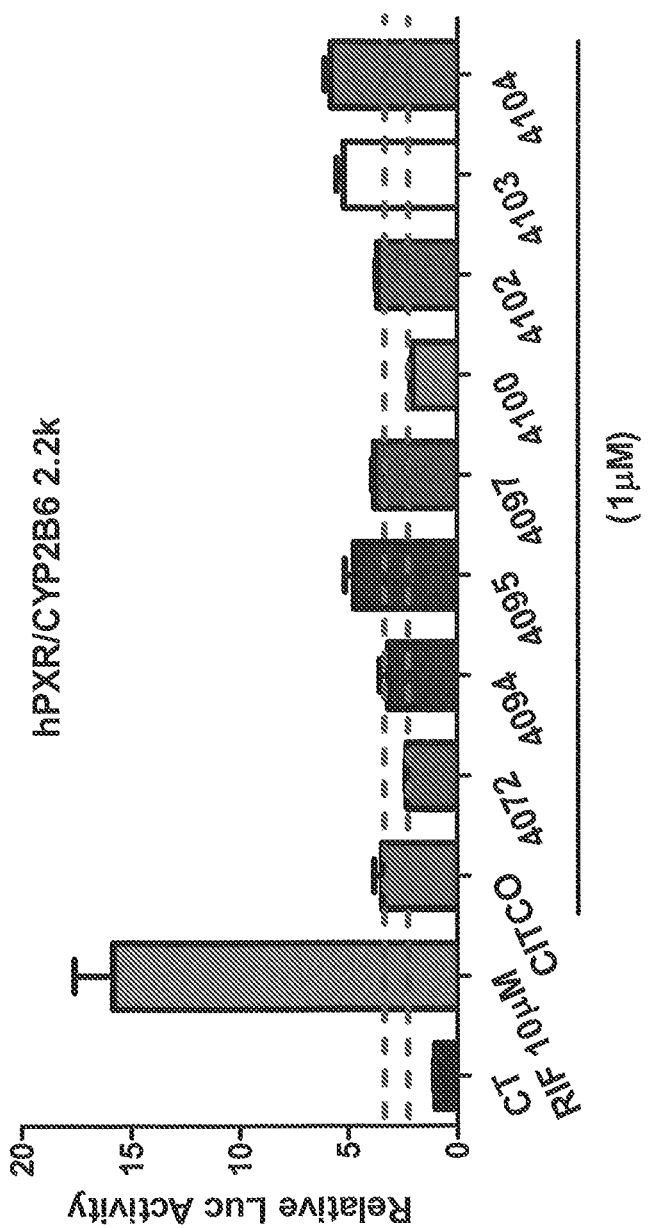
FIG. 3B. Luciferase report assay results for the effects of compounds DL4072, DL4094, DL4095, DL4097, DL4100, DL4102, DL4103 and DL4104 on activation of hPXR.
Figure 3C:
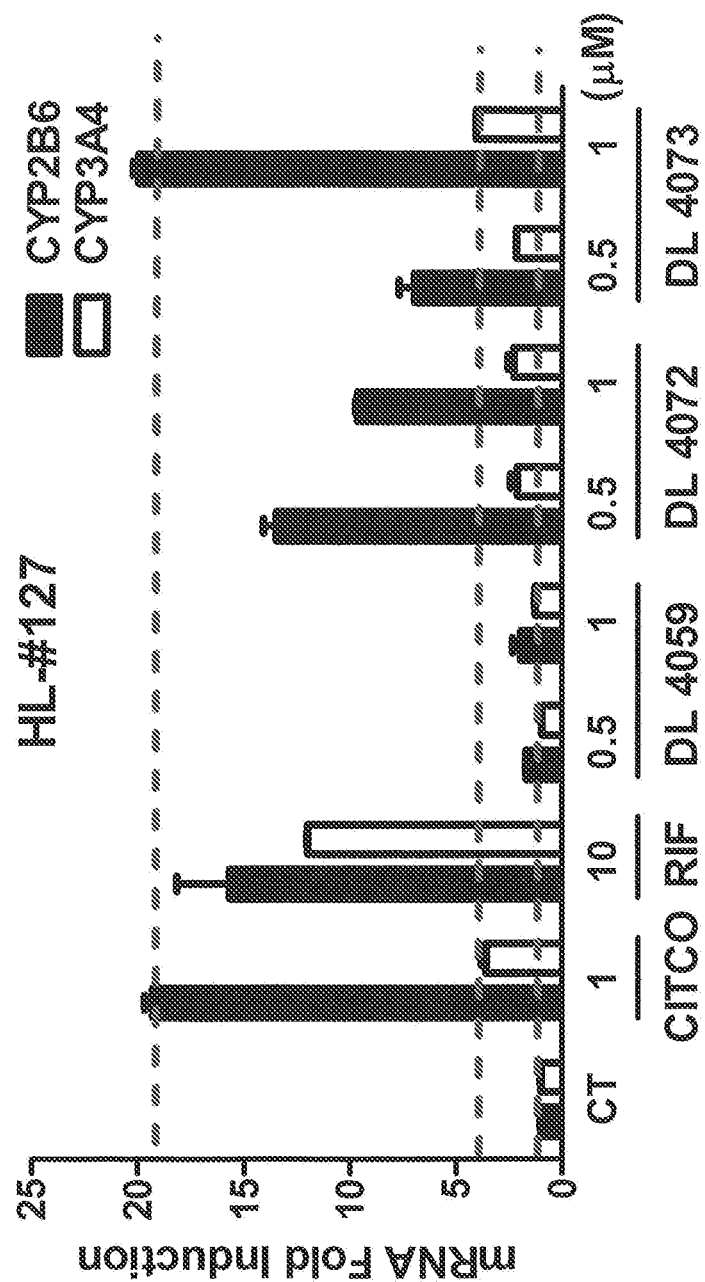
FIG. 3C. RT-PCR results for the effects of DL4059, DL4072, and DL4073 on the mRNA expression of CYP2B6 and CYP3A4.
Figure 3D:
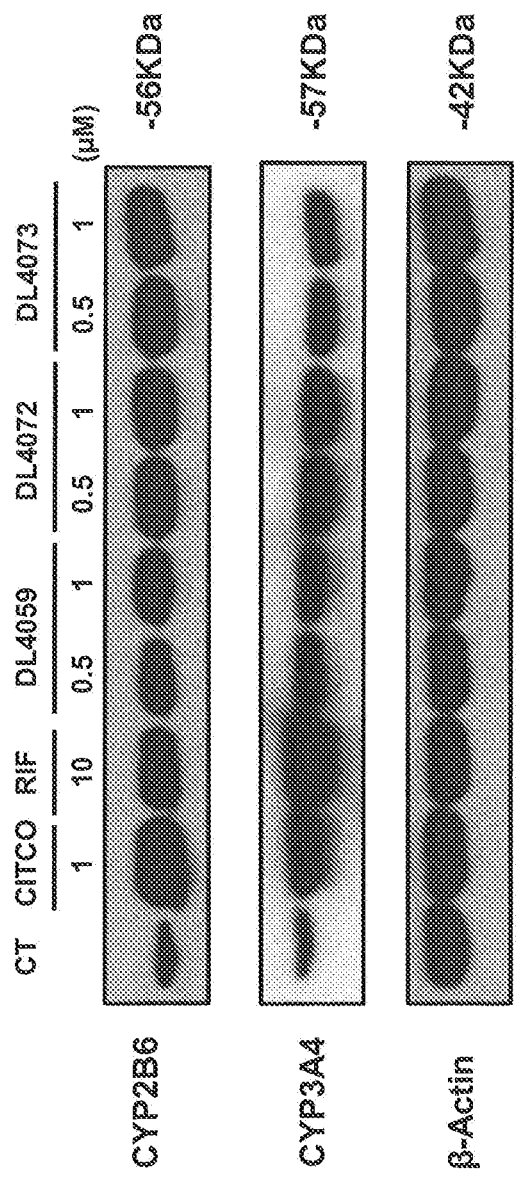
FIG. 3D. Western blot analysis results for the effects of DL4059, DL4072, and DL4073 on the protein expression of CYP2B6 and CYP3A4.
Figure 4D:
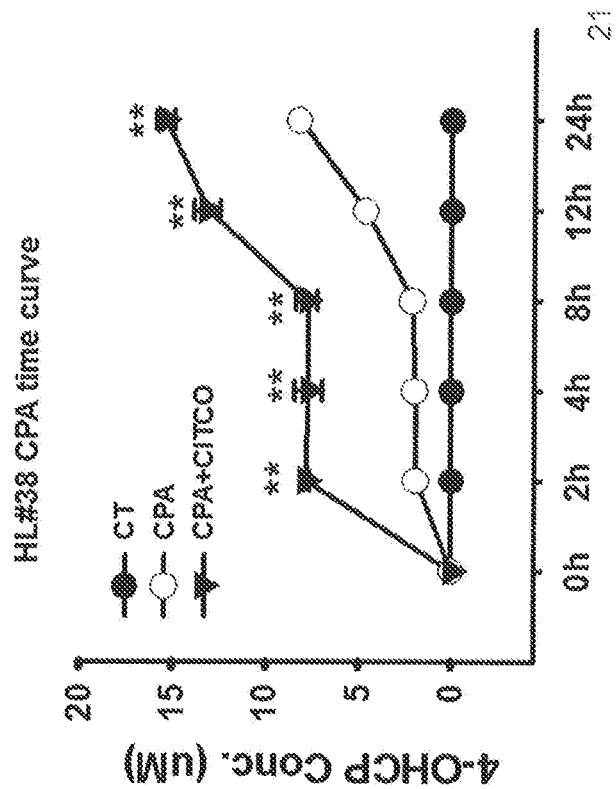
FIG. 4D. Time course for the generation of active metabolite of 4-OH-CAP by co-incubating compound CITCO with CAP in the presence of human hepatocytes (HPH). Effects of CAR activation on the temporal changes of 4-OH-CPA formation in cocultures under the treatment. 4-OH-CPA concentrations represent mean±SD of 3 LC-MS measurements (**P<0.01).
Figure 4C:
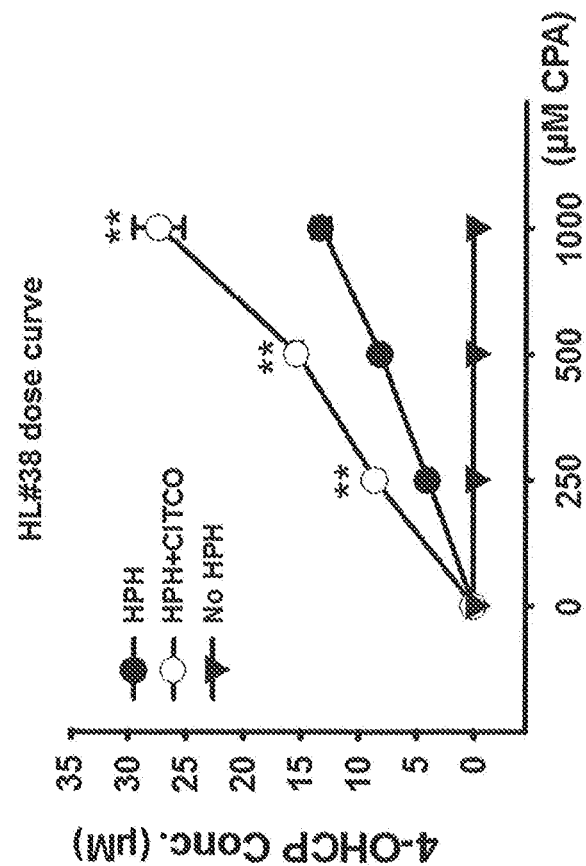
FIG. 4C. Effects of CAR activation on the concentration dependent formation of 4-OH-CPA in the coculture under the treatment.

In cultured human primary hepatocytes (HPHs), DL5016 exhibits potent and selective induction of CYP2B6 over CYP3A4 at both mRNA and protein levels (FIG. 3A). Compounds DL 4059, DL 4072, DL4073, DL4094, DL4095, DL4097, DL 4100, DL 4102, DL4103 and DL4104 from Table 1 also were found to activate hCAR resulted preferred expression of CYP2B6 protein (See FIGS. 3B-3D). Activation of hCAR increases the formation of 4-OH-CPA (FIGS. 4C-D).

Figure 10A:
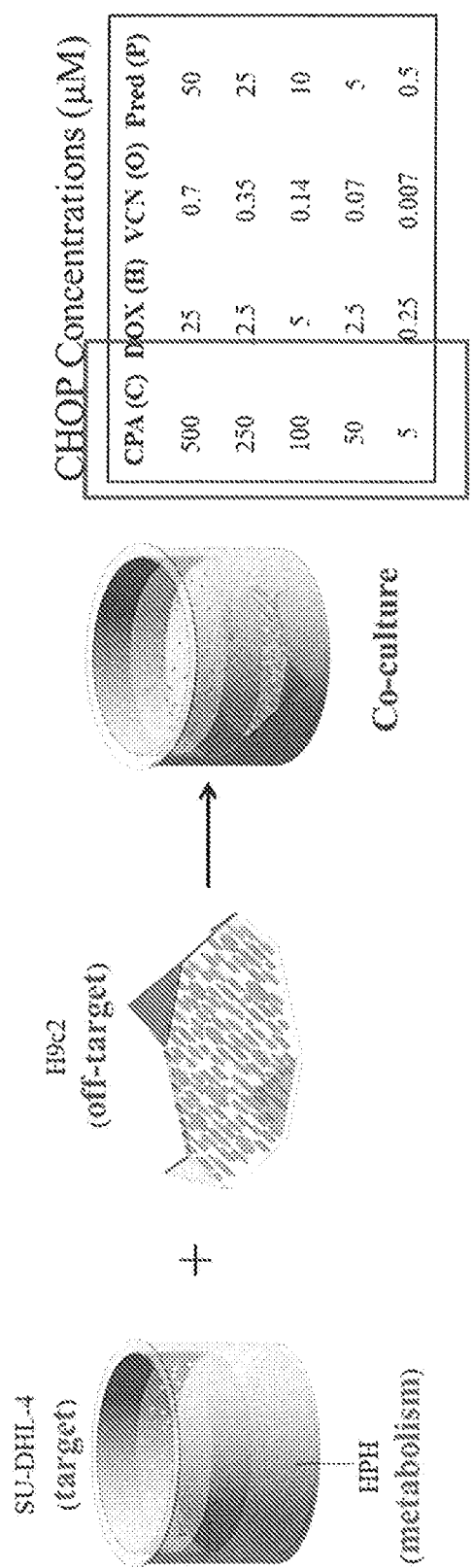
FIGS. 10A-10C. CITCO enhances CHOP-mediated cytoxicity in SU-DHL-4 but not H9c2 lymphoma cells.
Figure 10C:
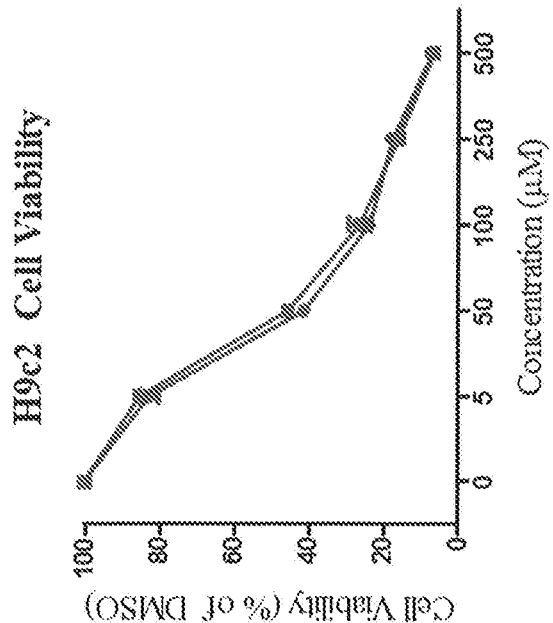
Figure 10B:
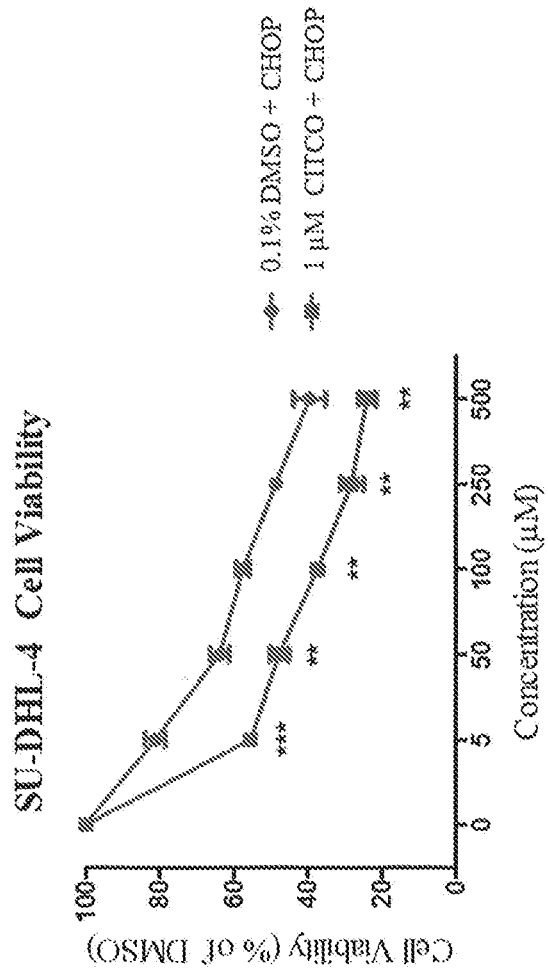
Figures 11A, 11B:
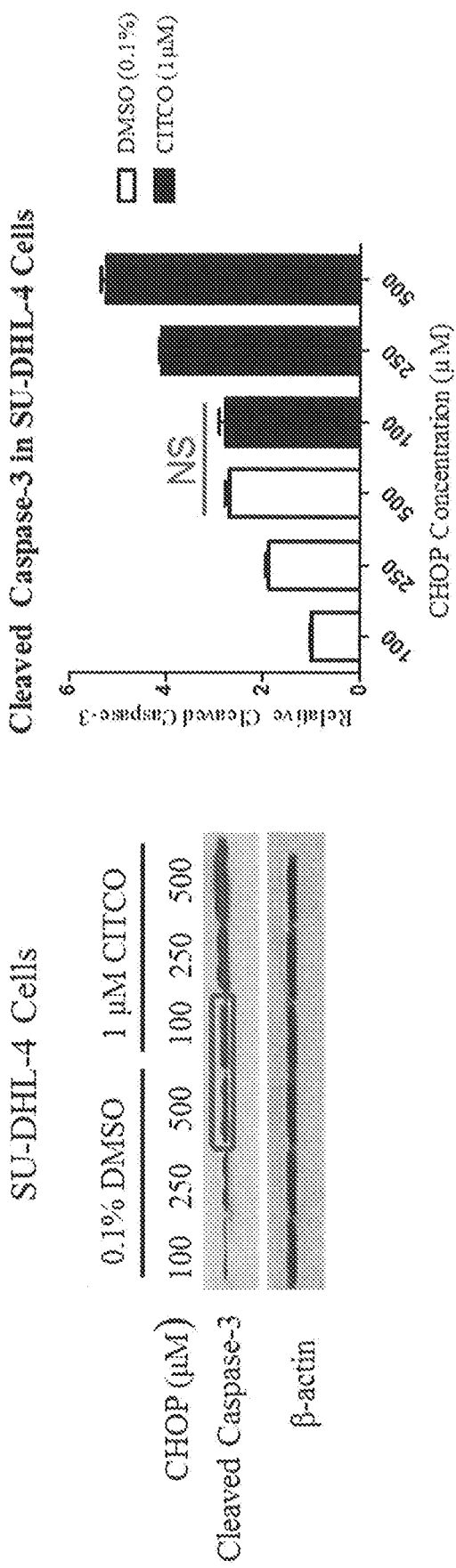
FIGS. 11A-11F. The synergistic effects of CITCO on increasing CHOP cytoxicity in lymphoma but not H9c2 cells by the induction of apoptosis protein caspase-3 by SDS-PAGE analysis.

Effects of CITCO on CPA Based Treatment of Lymphoma Cells (FIGS. 9-11)

In a hepatocyte/lymphoma co-culture model, DL 5016 potentiate the beneficial effects of CHOP in causing cancer cell death (indicated by caspase-3 protein expression), the addition of DL5016 to CHOP clearly enhanced the regimen's anticancer activity in a dose dependent and time dependent manner (See FIGS. 10B-C).

In a hepatocyte/lymphoma co-culture model, CITCO potentiates the beneficial effects of CHOP in causing cancer cell death (FIGS. 10B-C; 11(a)-(f)) as well as DL5016.

Figures 11C, 11D:
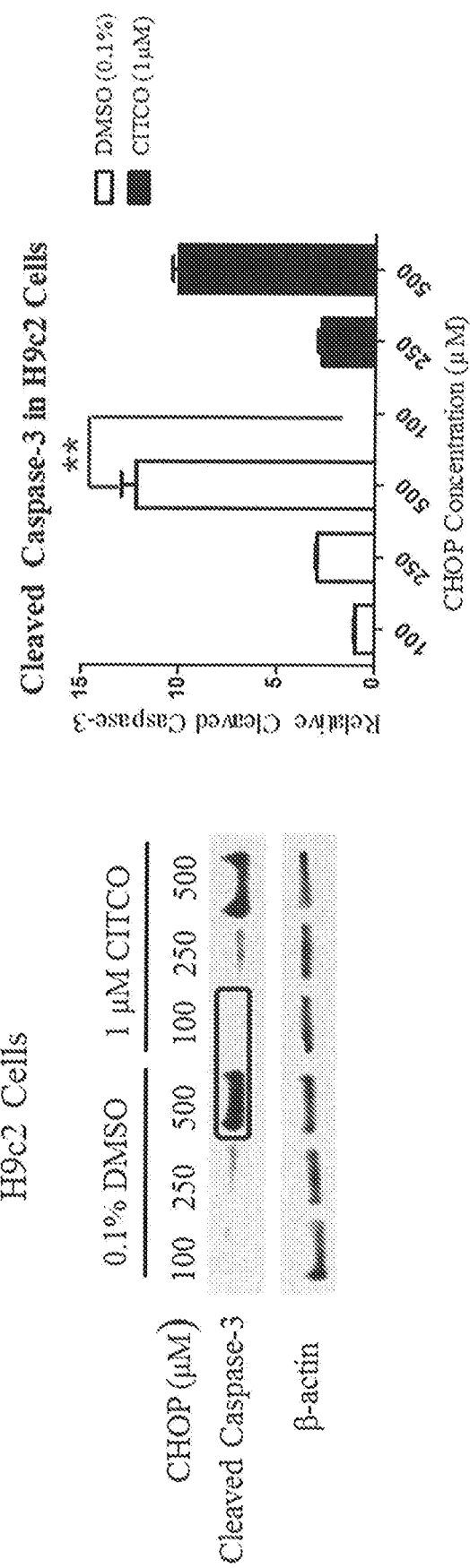
Figures 11E, 11F:
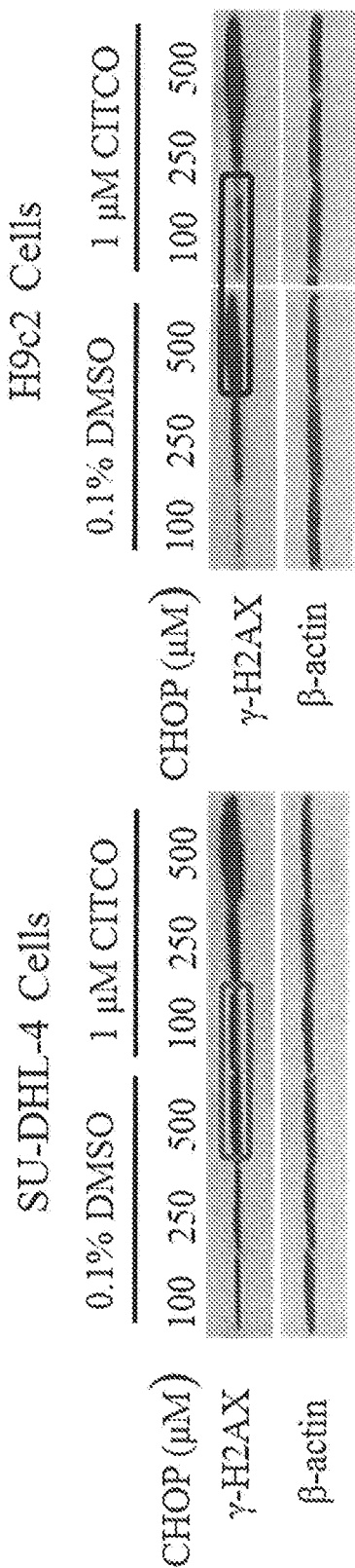

Co-administration of CPA with an hCAR activator leads to enhanced apoptosis of lymphoma cells without increasing off-target cytotoxicity (See FIG. 11(d)-(e) which shows dose dependent response of Caspase-3 expression to the addition of CITCO to CHOP). The Caspase-3 protein is a member of the cysteine-aspartic acid protease (caspase) family. Sequential activation of caspases plays a central role in the execution-phase of cell apoptosis (Alnemri E S et al., Human ICE/CED-3 protease nomenclature, Cell. 1996, vol. 87, p. 171).

Effects of CITCO and DL5016 on CPA Based Treatment of Lymphoma in EL4-Derived Xenografted Mouse Model (FIGS. 12-15)

Figure 12:
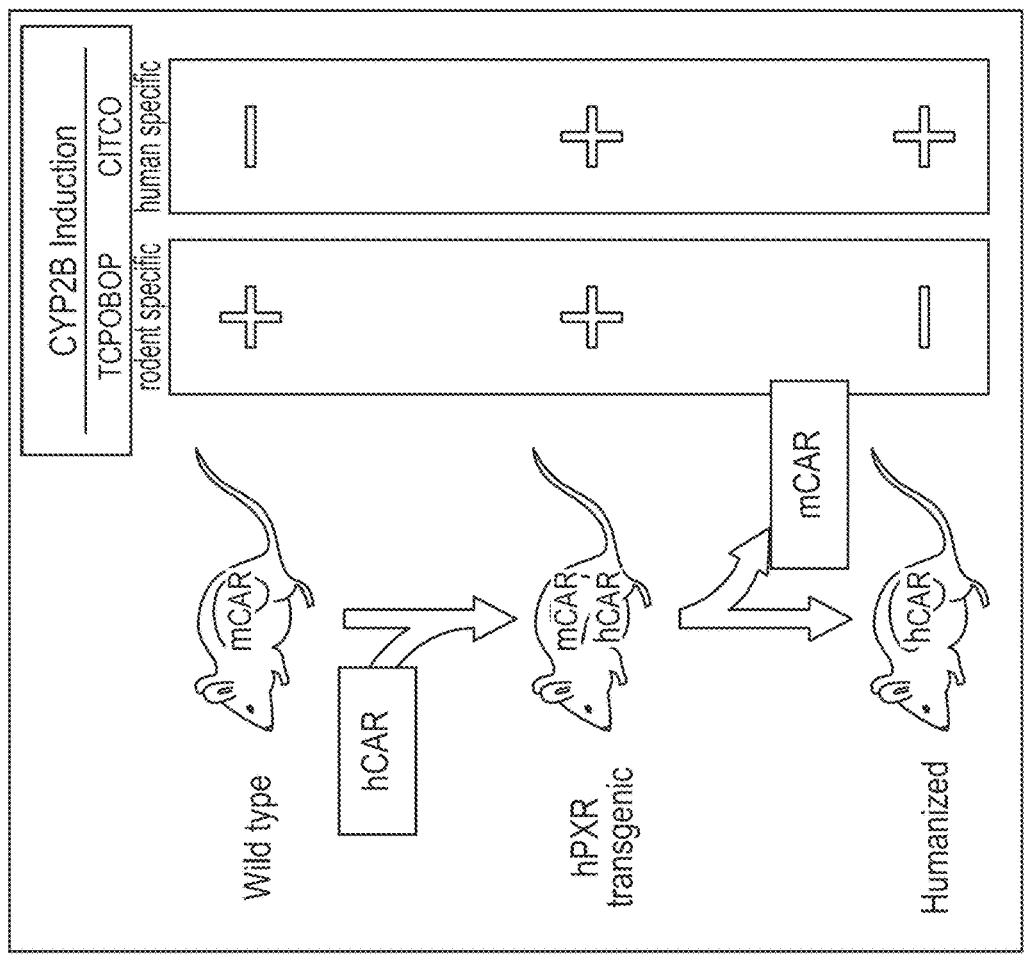
FIG. 12. Transgenic mouse models for evaluation of the CITCO's effects on potentiating CHOP therapeutic effects.
Figure 12:
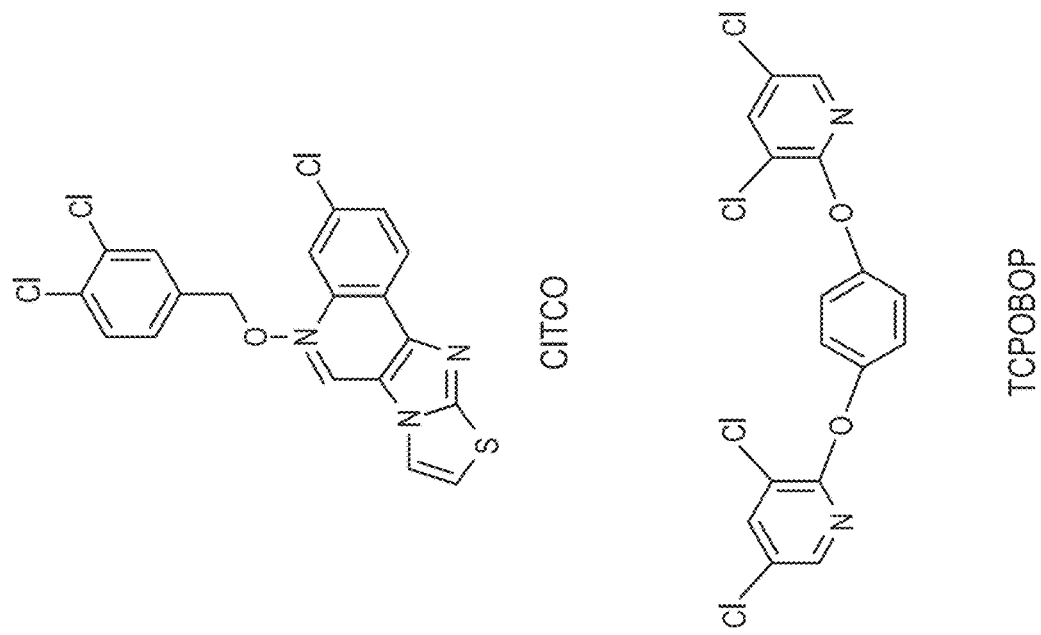
Figure 13:
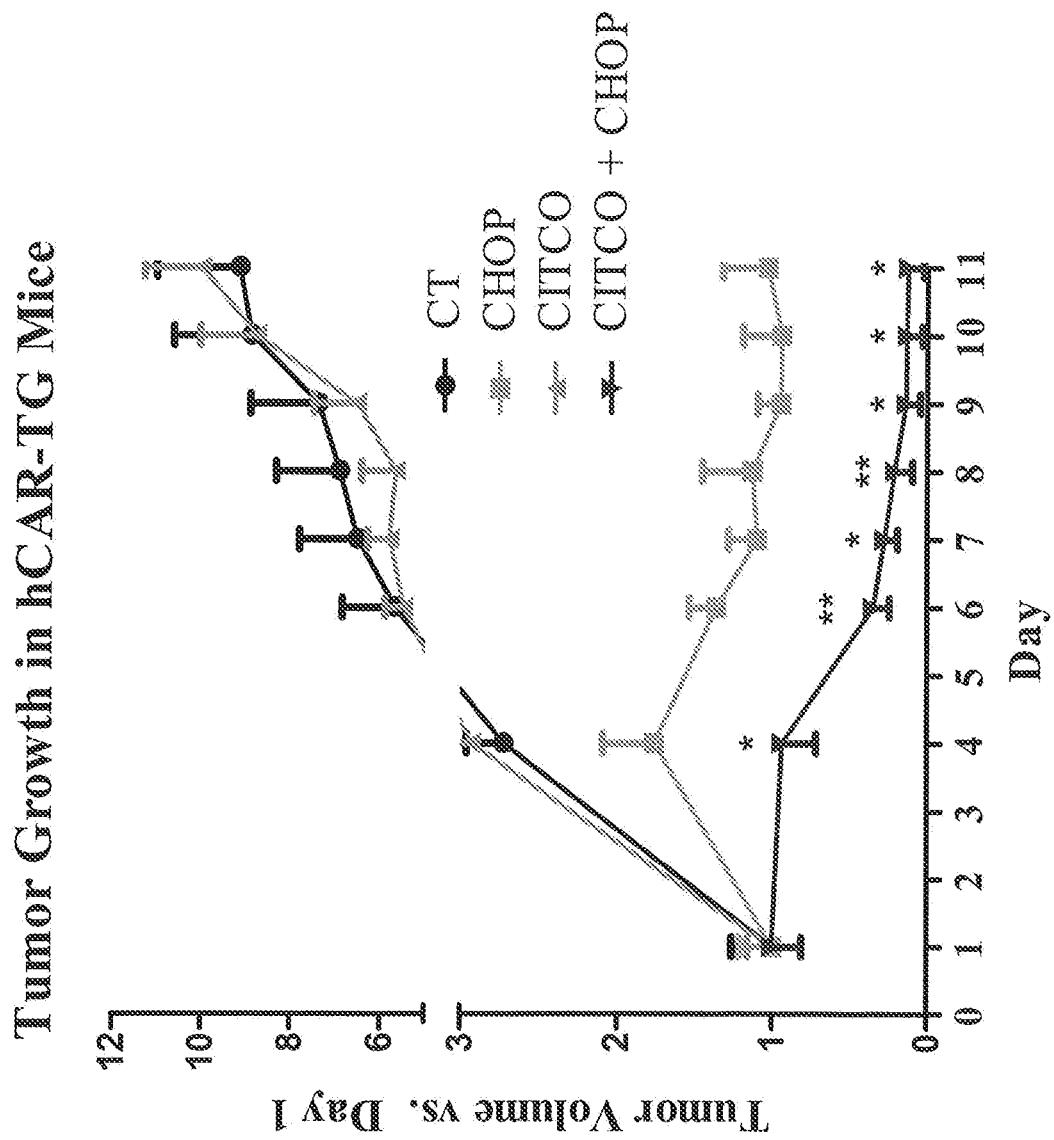
FIG. 13. Tumor growth diagram for the enhanced CHOP-based anticancer activity by CITCO in EL4-derived xenograft model, hCAR-TG mice.
Figure 14:
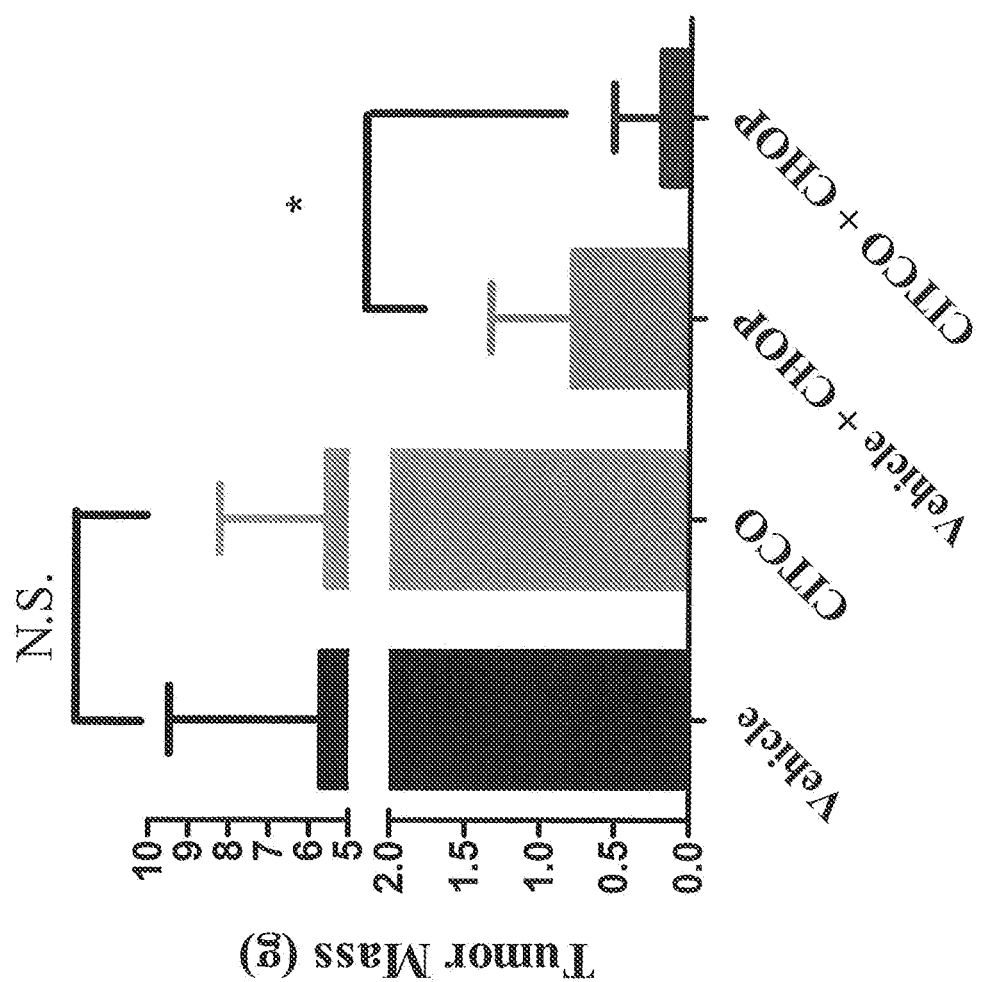
FIG. 14. The effects of CITCO on CHOP in hCAR-TG mice measured by isolated tumor mass.
Figures 15C, 15D:
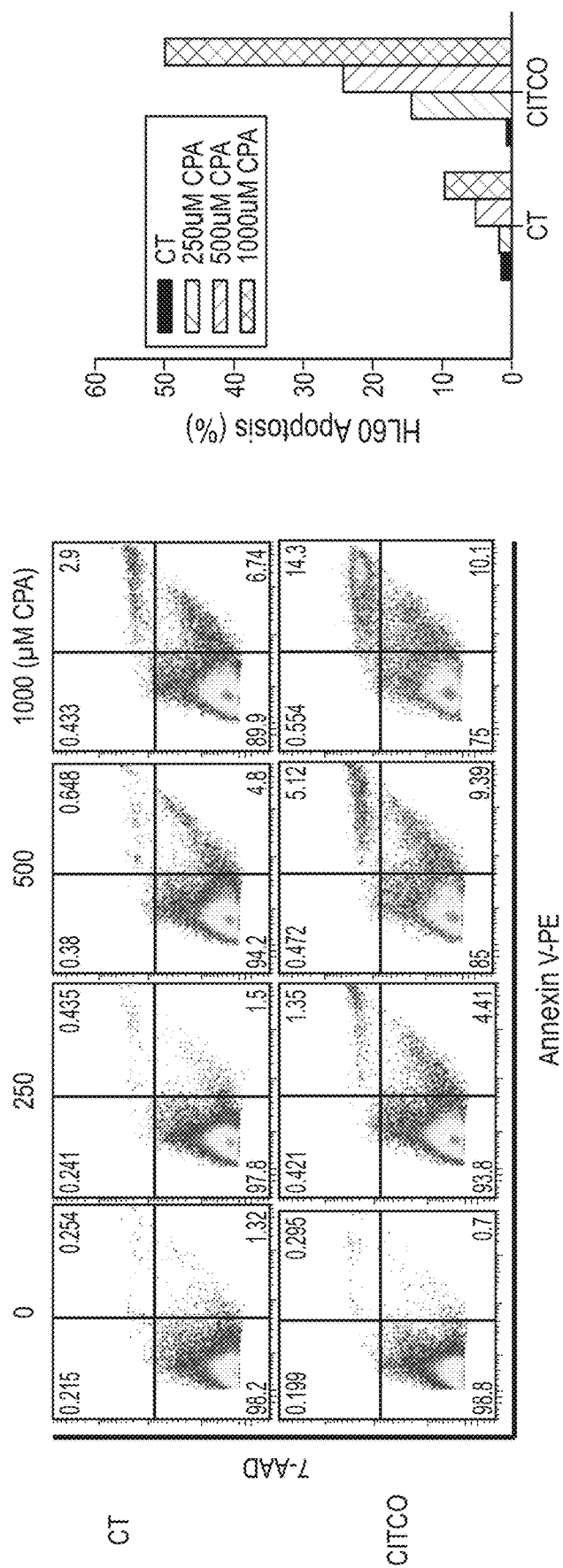

The effects of the novel hCAR activator e.g. CITCO on the CHOP based anticancer therapy has been examined in EL4-derived xenograft hCAR transgenic mouse model (FIG. 12). The tumor volume reduction was measured to determine the effects of hCAR activator on the CHOP treatment upon xenograft tumor model in mouse. The hCAR activator (e.g. CITCO) potentiate the therapeutic effects of the CHOP regimen as compared with vehicle, CITCO, and CHOP controls (See FIGS. 13-14).

Inclusion of an hCAR activator in the CHOP regimen can significantly lower the overall chemo-dose and associated side toxicity without sacrificing the target anticancer activity.

The addition of DL5016 to CHOP clearly enhanced the regimen's anticancer activity in a dose dependent and time dependent manner.

The invention claimed is:

1. A compound of Formula (II), or a pharmaceutically acceptable salt, solvate, hydrate, cocrystal, or prodrug thereof:

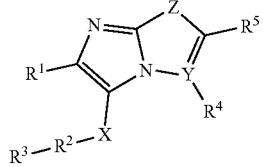

Formula (II)

wherein in Formula (II):

Z is O or S;

Y is C, $R^4$ is H or $C_{1-6}$-alkyl;

$R^1$ is selected from the group consisting of

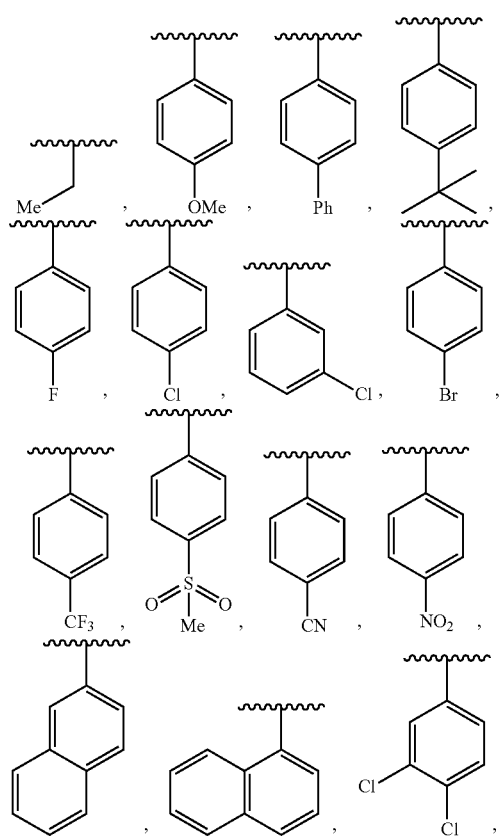

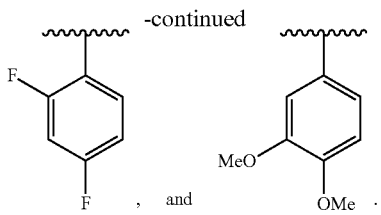

X is a linker moiety selected from the group consisting of —C(O)—$R^8$—, —CH$_2$—NH—C(O)—, —CH=N—, —$R^{10}$—NH—, —$R^{10}$—NR$^{11}$—, and —NH—C(O)—;

$R^2$ is selected from the group consisting of a bond, —C(O)—, $C_{1-6}$-alkyl, and $C_{3-8}$-heterocycloalkylamine;

$R^3$ is selected from the group consisting of aryl, heteroaryl, $C_{3-8}$-cycloalkyl, and $C_{3-8}$-heterocycloalkyl, wherein $R^3$ is optionally substituted with one or more substituents selected from the group consisting of non-substituted aryl, hydroxy, halo, cyano, trifluoromethyl, trifluoromethoxy, nitro, oxo, trimethylsilanyl, —OR$^a$, —SR$^a$, —OC(O)R$^a$, —N(R$^a$)R$^b$, —C(O)R$^a$, —C(O)OR$^a$, —OC(O)N(R$^a$)R$^b$, —C(O)N(R$^a$)R$^b$, —N(R$^a$)C(O)OR$^a$, —N(R$^a$)C(O)R$^a$, —N(R$^a$)C(O)N(R$^a$)R$^b$, —N(R$^a$)C(NR$^a$)N(R$^a$)R$^b$, —N(R$^a$)S(O)$_t$R$^a$, —S(O)$_t$OR$^a$, —S(O)$_t$N(R$^a$)R$^b$, or —P(O)(OR$^a$)(OR$^b$);

$R^5$ is selected from the group consisting of hydrogen, halogen, $C_{1-6}$-alkyl, —C(O)R$^a$, —C(O)OR$^a$, and —C(O)N(R$^a$)R$^b$;

$R^8$ is selected from the group consisting of a bond, $C_{1-3}$-alkenyl, O, —NH—, and —NH—O—;

$R^{10}$ is non-substituted $C_{1-3}$-alkyl or substituted or non-substituted $C_{2-3}$-alkenyl;

$R^{11}$ is substituted or non-substituted $C_{1-3}$-alkyl or $C_{2-3}$-alkenyl;

$R^a$ and $R^b$ are each independently selected from the group consisting of hydrogen, alkyl, fluoroalkyl, cycloalkyl, carbocyclyl, carbocyclylalkyl, aryl, aralkyl, heterocycloalkyl, heterocycloalkylalkyl, heteroaryl, heteroarylalkyl, halogen, —O-alkyl, —O-aryl, cyano, nitro, —OH, —NH$_2$, —NH-alkyl, and —NH-aryl;

and t is 1 or 2.

2. The compound of Formula (II), or a pharmaceutically acceptable salt, solvate, hydrate, cocrystal, or prodrug thereof, according to claim 1, wherein Z is O, Y is C, and $R^4$ is H.

3. The compound of Formula (II), or a pharmaceutically acceptable salt, solvate, hydrate, cocrystal, or prodrug thereof, according to claim 1, wherein Z is S, Y is C, and $R^4$ is H.

4. The compound of Formula (II), or a pharmaceutically acceptable salt, solvate, hydrate, cocrystal, or prodrug thereof, according to claim 1, wherein X is —CH═N—, —CH$_2$—NH—, —C(O)—, —C(O)—NH—, or —NH—C(O)—.
5. The compound of Formula (II), or a pharmaceutically acceptable salt, solvate, hydrate, cocrystal, or prodrug thereof, according to claim 1, wherein —R$^2$-R$^3$ is selected from the group consisting of:
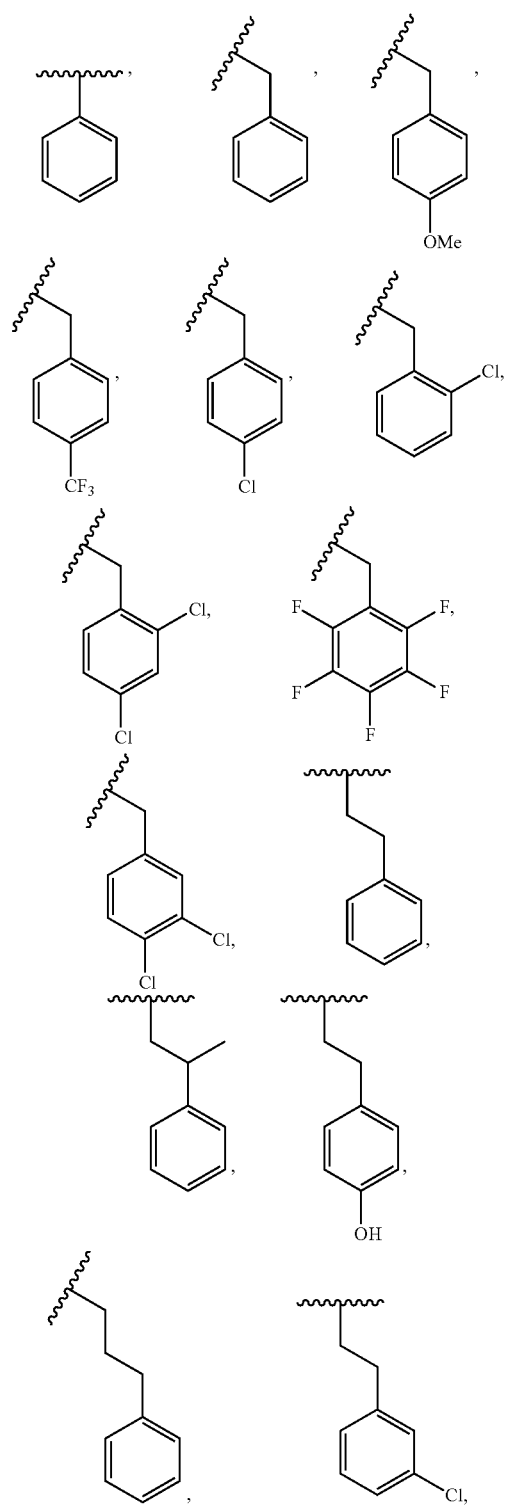
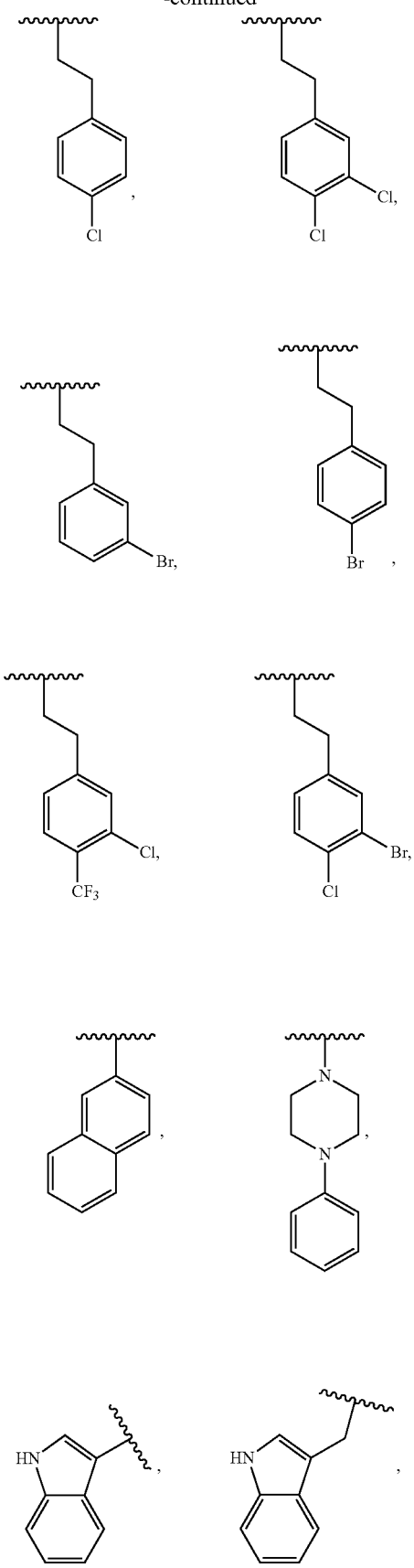

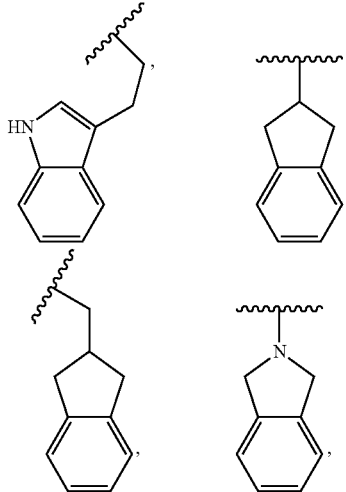

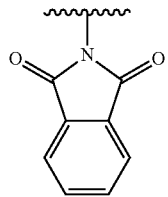 and 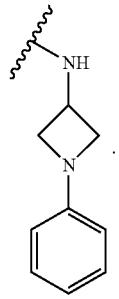

6. The compound of Formula (II), or a pharmaceutically acceptable salt, solvate, hydrate, cocrystal, or prodrug thereof, according to claim 1, wherein the compound is selected from:

| Compound | Chemical Name |
|---|---|
|  | N-((6-(naphthalen-2-yl)imidazo[2,1-b]oxazol-5-yl)methyl)-2,3-dihydro-1H-inden-2-amine |
|  | N-((6-(naphthalen-1-yl)imidazo[2,1-b]thiazol-5-yl)methyl)-2,3-dihydro-1H-inden-2-amine |
|  | N-((6-(naphthalen-1-yl)imididazo[2,1-b]thiazol-5-yl)methyl)-2,3-dihydro-1H-inden-2-amine |

| Compound | Chemical Name |
|---|---|
| 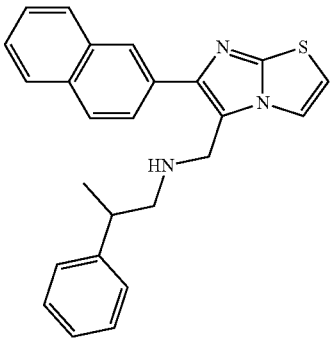 [SMILES: CC(CNCc1c(-c2ccc3ccccc3c2)nc2sccn12)c1ccccc1] | N-((6-(naphthalen-2-yl)imidazo[2,1-b]thiazol-5-yl)methyl)-2-phenylpropan-1-amine |
| 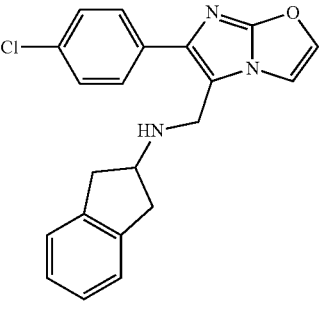 [SMILES: Clc1ccc(-c2nc3occn3c2CNC2Cc3ccccc3C2)cc1] | N-((6-(4-chlorophenyl)imidazo[2,1-b]oxazol-5-yl)methyl)-2,3-dihydro-1H-inden-2-amine |
| 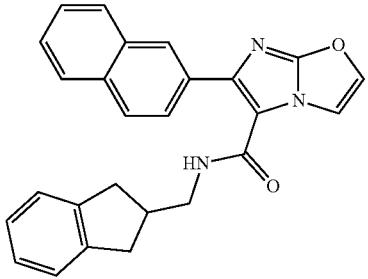 [SMILES: O=C(NCC1Cc2ccccc2C1)c1c(-c2ccc3ccccc3c2)nc2occn12] | N-((2,3-dihydro-1H-inden-2-yl)methyl)-6-(naphthalen-2-yl)imidazo[2,1-b]oxazole-5-carboxamide |
| 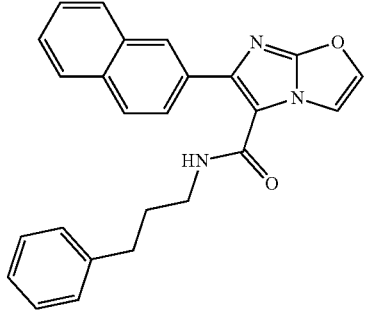 [SMILES: O=C(NCCCc1ccccc1)c1c(-c2ccc3ccccc3c2)nc2occn12] | 6-(naphthalen-2-yl)-N-(3-phenylpropyl)imidazo[2,1-b]oxazole-5-carboxamide |

| Compound | Chemical Name |
|---|---|
| | N-((3,4-dichlorobenzyl)oxy)-6-(naphthalen-2-yl)imidazo[2,1-b]oxazole-5-carboxamide |
| | N-(benzyloxy)-6-(naphthalen-2-yl)imidazo[2,1-b]oxazole-5-carboxamide |
| | (6-(naphthalen-2-yl)imidazo[2,1-b]oxazol-5-yl)(4-phenylpiperazin-1-yl)methanone |
| | 6-(naphthalen-2-yl)-N-(1-phenylazetidin-3-yl)imidazo[2,1-b]oxazole-5-carboxamide |

| Compound | Chemical Name |
|---|---|
|  | N-(3,4-dichlorophenethyl)-6-(naphthalen-2-yl)imidazo[2,1-b]oxazole-5-carboxamide |
|  | 6-(2,4-difluorophenyl)-N-(2,3-dihydro-1H-inden-2-yl)imidazo[2,1-b]oxazole-5-carboxamide |
|  | 6-(4-chlorophenyl)-N-(3,4-dichlorophenethyl)imidazo[2,1-b]oxazole-5-carboxamide |
|  | 6-(2,4-difluorophenyl)-N-((2,3-dihydro-1H-inden-2-yl)methyl)imidazo[2,1-b]oxazole-5-carboxamide |

| Compound | Chemical Name |
|---|---|
| | N-(2,3-dihydro-1H-inden-2-yl)-6-(4-fluorophenyl)imidazo[2,1-b]oxazole-5-carboxamide |
| | N-(3,4-dichlorophenethyl)-6-(4-fluorophenyl)imidazo[2,1-b]oxazole-5-carboxamide |
| | 6-(4-chlorophenyl)-N-(2,3-dihydro-1H-inden-2-yl)imidazo[2,1-b]oxazole-5-carboxamide |
| | 6-(4-chlorophenyl)-N-((2,3-dihydro-1H-inden-2-yl)methyl)imidazo[2,1-b]oxazole-5-carboxamide |
| | 2-(2-(6-naphthalen-2-yl)imidazo[2,1-b]oxazol-5-yl)-2-oxoethyl)isoindoline-1,3-dione |

| Compound | Chemical Name |
|---|---|
| | (E)-N-(isoindolin-2-yl)-1-(6-(naphthalen-2-yl)imidazo[2,1-b]oxazol-5-yl)methanimine |
| | (E)-1-(6-(4-chlorophenyl)imidazo[2,1-b]thiazol-5-yl)-N-(3,4-dichlorophenethyl)methanimine |
| | N-((6-(4-chlorophenyl)imidazo[2,1-b]thiazol-5-yl)methyl)-2-(3,4-dichlorophenyl)ethan-1-amine |
| | N-((6-(4-chlorophenyl)imidzo[2,1-b]thiazol-5-yl)methyl)-2-(3,4-dichlorophenyl)ethan-1-amine hydrochloride |

| Compound | Chemical Name |
|---|---|
| | 6-(4-chlorophenyl)-N-(3,4-dichlorophenethyl)imidazo[2,1-b]thiazole-5-carboxamide |
| | 2-(3-chlorophenyl)-N-((6-(4-chlorophenyl)imidazo[2,1-b]thiazol-5-yl)methyl)ethan-1-amine |
| | 2-(4-chlorophenyl)-N-((6-(4-chlorophenyl)imidazo[2,1-b]thiazol-5-yl)methyl)ethan-1-amine |
| | 2-(4-bromophenyl)-N-((6-(4-chlorophenyl)imidazo[2,1-b]thiazol-5-yl)methyl)ethan-1-amine |
| | 2-(3-bromo-4-chlorophenyl)-N-((6-(4-chlorophenyl)imidazo[2,1-b]thiazol-5-yl)methyl)ethan-1-amine |

| Compound | Chemical Name |
|---|---|
| | 2-(3-chloro-4-(trifluoromethyl)phenyl)-N-((6-(4-chlorophenyl)imidazo[2,1-b]thiazol-5-yl)methyl)ethan-1-amine |
| | 2-(3-bromophenyl)-N-((6-(4-chlorophenyl)imidazo[2,1-b]thiazol-5-yl)methyl)ethan-1-amine |
| | N-((6-(4-chlorophenyl)imidazo[2,1-b]thiazol-5-yl)methyl)-2-phenylethan-1-amine |
| | N-((6-(4-chlorophenyl)imidazo[2,1-b]thiazol-5-yl)methyl)-2-(4-fluorophenyl)ethan-1-amine |
| | 4-(2-((6-(4-chlorophenyl)imidazo[2,1-b]thiazol-5-yl)methyl)amino)ethyl)phenol |

| Compound | Chemical Name |
|---|---|
| | N-((6-(4-chlorophenyl)imidazo[2,1-b]thiazol-5-yl)methyl)-2-(1H-indol-3-yl)ethan-1-amine |
| | N-((6-(4-chlorophenyl)imidazo[2,1-b]thiazol-5-yl)methyl)-2,3-dihydro-1H-inden-2-amine |
| | N-((6-(4-chlorophenyl)imidazo[2,1-b]thiazol-5-yl)methyl)naphthalen-2-amine |
| | N-benzyl-1-(6-(4-chlorophenyl)imidazo[2,1-b]thiazol-5-yl)methanamine |
| | N-((6-(4-chlorophenyl)imidazo[2,1-b]thiazol-5-yl)methyl)-2-(3,4-dichlorophenyl)-N-methylethan-1-amine |

| Compound | Chemical Name |
|---|---|
| | N-((6-(4-chlorophenyl)imidazo[2,1-b]thiazol-5-yl)methyl)-2-(3,4-dichlorophenyl)-N-ethylethan-1-amine |
| | N-benzyl-N-((6-(4-chlorophenyl)imidazo[2,1-b]thiazol-5-yl)methyl)-2-(3,4-dichlorophenyl)ethan-1-amine |
| | 2-(3,4-dichlorophenyl)-N-((6-(4-methoxyphenyl)imidazo[2,1-b]thiazol-5-yl)methyl)ethan-1-amine |
| | N-((6-(3-chlorophenyl)imidazo[2,1-b]thiazol-5-yl)methyl)-2-(3,4-dichlorophenyl)ethan-1-amine |

| Compound | Chemical Name |
|---|---|
|  | N-((6-(4-bromophenyl)imidazo[2,1-b]thiazol-5-yl)methyl)-2-(3,4-dichlorophenyl)ethan-1-amine |
|  | 2-(3,4-dichlorophenyl)-N-((6-(4-isocyanophenyl)imidazo[2,1-b]thiazol-5-yl)methyl)ethan-1-amine |
|  | 2-(3,4-dichlorophenyl)-N-((6-(naphthalen-2-yl)imidazo[2,1-b]thiazol-5-yl)methyl)ethan-1-amine |
|  | N-((6-(4-(tert-butyl)phenyl)imidazo[2,1-b]thiazol-5-yl)methyl)-2-(3,4-dichlorophenyl)ethan-1-amine |

| Compound | Chemical Name |
|---|---|
| | 2-(3,4-dichlorophenyl)-N-((6-(4-fluorophenyl)imidazo[2,1-b]thiazol-5-yl)methyl)ethan-1-amine |
| | 2-(3,4-dichlorophenyl)-N-((6-(4-(trifluoromethyl)phenyl)imidazo[2,1-b]thiazol-5-yl)methyl)ethan-1-amine |
| | 2-(3,4-dichlorophenyl)-N-((6-ethylimidazo[2,1-b]thiazol-5-yl)methyl)ethan-1-amine |
| | 6-(4-chlorophenyl)-N-(3,4-dichlorophenethyl)imidazo[2,1-b]thiazole-5-carboxamide |

-continued

| Compound | Chemical Name |
|---|---|
| | N-(3-bromo-4-chlorophenethyl)-6-(4-chlorophenyl)imidazo[2,1-b]thiazole-5-carboxamide |
| | N-(2,3-dihydro-1H-inden-2-yl)-6-(naphthalen-2-yl)imidazo[2,1-b]thiazole-5-carboxamide |
| | N-((6-(naphthalen-2-yl)imidazo[2,1-b]thiazol-5-yl)methyl)-2,3-dihydro-1H-inden-2-amine |
| | N-((6-(4-chlorophenyl)-2-methylimidazo[2,1-b]thiazol-5-yl)methyl)-2-(3,4-dichlorophenyl)ethan-1-amine |

| Compound | Chemical Name |
|---|---|
| 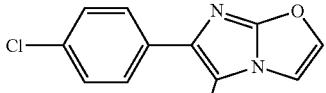 | N-((6-(4-chlorophenyl)imidazo[2,1-b]oxazol-5-yl)methyl)-2-(3,4-dichlorophenyl)ethan-1-amine |
| 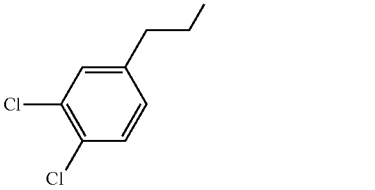 | 1-(2,3-dihydro-1H-inden-2-yl)-N-((6-(naphthalen-2-yl)imidazo[2,1-b]oxazol-5-yl)methyl)methanamine |
| 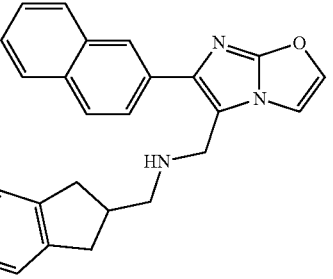 | N-((6-(naphthalen-2-yl)imidazo[2,1-b]thiazol-5-yl)methyl)-2,3-dihydro-1H-inden-2-amine |
| 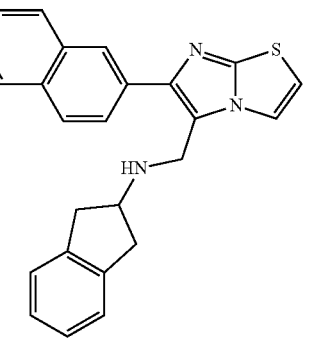 | N-((6-(4-chlorophenyl)imidazo[2,1-b]thiazol-5-yl)methyl)-2-(3,4-dichlorophenyl)ethan-1-amine |
| 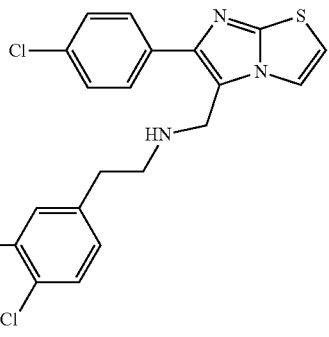 [SMILES: Clc1ccc(CCNCc2c(-c3ccc(Cl)cc3)nc3sccn23)cc1] | N-((6-(naphthalen-2-yl)imidazo[2,1-b]oxazol-5-yl)methyl)-2,3-dihydro-1H-indene-2-carboxamide |

-continued

| Compound | Chemical Name |
|---|---|
| | (6-(naphthalen-2-yl)imidazo[2,1-b]oxazol-5-yl)(4-phenylpiperazin-1-yl)methanone |
| | N-(2,3-dihydro-1H-inden-2-yl)-6-(4-fluorophenyl)imidazo[2,1-b]oxazole-5-carboxamide |
| | N-((3,4-dichlorobenzyl)oxy)-6-(naphthalen-2-yl)imidazo[2,1-b]oxazole-5-carboxamide |
| | N-(3,4-dichlorophenethyl)-6-(4-fluorophenyl)imidazo[2,1-b]oxazole-5-carboxamide |

| Compound | Chemical Name |
|---|---|
| | N-(benzyloxy)-6-(naphthalen-2-yl)imidazo[2,1-b]oxazole-5-carboxamide |
| | 6-(naphthalen-2-yl)-N-(1-phenylazetidin-3-yl)imidazo[2,1-b]oxazole-5-carboxamide |
| | 6-(4-chlorophenyl)-N-((2,3-dihydro-1H-inden-2-yl)methyl)imidazo[2,1-b]oxazole-5-carboxamide |
| | N-((2,3-dihydro-1H-inden-2-yl)methyl)-6-(naphthalen-2-yl)imidazo[2,1-b]oxazole-5-carboxamide |
| | 6-(2,4-difluorophenyl)-N-((2,3-dihydro-1H-inden-2-yl)methyl)imidazo[2,1-b]oxazole-5-carboxamide |

| Compound | Chemical Name |
|---|---|
| | 6-(naphthalen-2-yl)-N-(3-phenylpropyl)imidazo[2,1-b]oxazole-5-carboxamide |
| | 6-(4-chlorophenyl)-N-(2,3-dihydro-1H-inden-2-yl)imidazo[2,1-b]oxazole-5-carboxamide |
| | 6-(2,4-difluorophenyl)-N-(2,3-dihydro-1H-inden-2-yl)imidazo[2,1-b]oxazole-5-carboxamide |
| | N-(3,4-dichlorophenethyl)-6-(naphthalen-2-yl)imidazo[2,1-b]oxazole-5-carboxamide |

| Compound | Chemical Name |
|---|---|
| | 2-(isoindolin-2-yl)-1-(6-(naphthalen-2-yl)imidazo[2,1-b]oxazol-5-yl)ethan-1-one |
| | 2,3-dihydro-1H-inden-2-yl 6-(naphthalen-2-yl)imidazo[2,1-b]oxazole-5-carboxylate |
| | N-(2,3-dihydro-1H-inden-2-yl)-6-(naphthalen-2-yl)imidazo[2,1-b]oxazole-5-carboxamide |
| | N-((2,3-dihydro-1H-inden-2-yl)oxy)-6-(naphthalen-2-yl)imidazo[2,1-b]oxazole-5-carboxamide |

| Compound | Chemical Name |
|---|---|
| | 2-(3,4-dichlorophenyl)-N-((6-(3,4-dimethoxyphenyl)imidazo[2,1-b]thiazol-5-yl)methyl)ethan-1-amine |
| | 2-(3,4-dichlorophenyl)-N-((6-(3,4-dichlorophenyl)imidazo[2,1-b]thiazol-5-yl)methyl)ethan-1-amine |
| | 2-(3,4-dichlorophenyl)-N-((6-(4-nitrophenyl)imidazo[2,1-b]thiazol-5-yl)methyl)ethan-1-amine |
| | 2-(3,4-dichlorophenyl)-N-((6-(4-(methylsulfonyl)phenyl)imidazo[2,1-b]thiazol-5-yl)methyl)ethan-1-amine |

| Compound | Chemical Name |
|---|---|
| 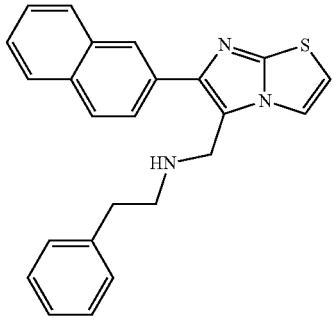 [SMILES: c1ccc(CCNCc2c(-c3ccc4ccccc4c3)nc3sccn23)cc1] | N-((6-(naphthalen-2-yl)imidazo[2,1-b]thiazol-5-yl)methyl)-2-phenylethan-1-amine |
| 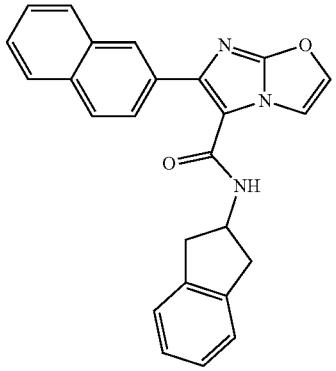 [SMILES: O=C(NC1Cc2ccccc2C1)c1c(-c2ccc3ccccc3c2)nc2occn12] | N-(2,3-dihydro-1H-inden-2-yl)-6-(naphthalen-2-yl)imidazo[2,1-b]oxazole-5-carboxamide |

7. The compound of Formula (II), or a pharmaceutically acceptable salt, solvate, hydrate, cocrystal, or prodrug thereof, according to claim 1, wherein the compound is formulated in a physiologically compatible carrier medium.

8. A method of controlling a disease alleviated by activating hCAR in a patient in need thereof, the method comprising administering to the patient a therapeutically effective amount of a compound of Formula (II), or a pharmaceutically acceptable salt, solvate, hydrate, cocrystal, or prodrug thereof, according to claim 1.

9. A method of controlling a disease alleviated by selective induction of CYP2B6 in a patient in need thereof, the method comprising administering to the patient a therapeutically effective amount of a compound of Formula (II), or a pharmaceutically acceptable salt, solvate, hydrate, cocrystal, or prodrug thereof, according to claim 1.

10. The method of claim 9, wherein CYP2B6 is selectively induced over CYP3A4.

11. The method of claim 8, the method further comprising co-administering to the patient a therapeutically effective amount of cyclophosphamide (CPA), or a pharmaceutically acceptable salt, solvate, hydrate, cocrystal, or prodrug thereof.

12. The method of claim 11, wherein CPA is administered as part of the CHOP regimen (CPA, doxorubicin, vincristine, and prednisone).

13. The method of claim 11, wherein the co-administration promotes the formation of therapeutically active CPA metabolite 4-OH-CPA.

14. The method of claim 8, wherein the compound of Formula (II), or pharmaceutically acceptable salt, solvate, hydrate, cocrystal, or prodrug thereof, is administered in a dosage unit form.

15. The method of claim 14, wherein the dosage unit form comprises a physiologically compatible carrier medium.

16. The method of claim 8, wherein the disease is cancer.

17. The method of claim 16, wherein the cancer is selected from the group consisting of bladder cancer, squamous cell carcinoma, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thymoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, esophageal cancer, testicular cancer, gynecological cancer, thyroid cancer, acquired immune deficiency syndrome (AIDS)-related cancers, lymphoma, Kaposi's sarcoma, viral-induced cancer, glioblastoma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus induced cancer, hepatocellular carcinoma, Hodgkin's disease, metastatic colon cancer, multiple myeloma, non-Hodgkin's lymphoma, indolent non-Hodgkin's lymphoma, ovary tumor, pancreas tumor, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

* * * * *